(12) United States Patent
Mao et al.

(10) Patent No.: US 11,535,851 B2
(45) Date of Patent: Dec. 27, 2022

(54) REAGENTS FOR TREATMENT OF HEPATITIS B VIRUS (HBV) INFECTION AND USE THEREOF

(71) Applicant: BENITEC BIOPHARMA LIMITED, North Sydney (AU)

(72) Inventors: Tin Mao, San Bruno, CA (US); David Suhy, San Ramon, CA (US)

(73) Assignee: Benitec IP Holdings Inc., New Castle, DE (US)

( * ) Notice: Subject to any disclaimer, the term of this patent is extended or adjusted under 35 U.S.C. 154(b) by 498 days.

(21) Appl. No.: 16/098,759

(22) PCT Filed: May 5, 2017

(86) PCT No.: PCT/AU2017/050413
§ 371 (c)(1),
(2) Date: Nov. 2, 2018

(87) PCT Pub. No.: WO2017/190197
PCT Pub. Date: Nov. 9, 2017

(65) Prior Publication Data
US 2019/0338285 A1 Nov. 7, 2019

Related U.S. Application Data

(60) Provisional application No. 62/332,245, filed on May 5, 2016.

(51) Int. Cl.
*C12N 15/113* (2010.01)
*A61K 31/513* (2006.01)
(Continued)

(52) U.S. Cl.
CPC ........ *C12N 15/1131* (2013.01); *A61K 31/513* (2013.01); *A61K 31/522* (2013.01);
(Continued)

(58) Field of Classification Search
CPC ................ A61K 31/513; A61K 31/522; C12N 15/1131; C12N 2310/141
See application file for complete search history.

(56) References Cited

U.S. PATENT DOCUMENTS 10,898,505 B2 * 1/2021 Mao ..................... A61K 31/713
2012/0035240 A1 2/2012 Pachuk et al.

FOREIGN PATENT DOCUMENTS

CN 101603042 A 12/2009
CN 103088026 A 5/2013
(Continued)

OTHER PUBLICATIONS

PCT International Search Report and Written Opinion, PCT Application No. PCT/AU2017/050413, dated Jun. 9, 2017, 30 pages.
(Continued)

*Primary Examiner* — Terra C Gibbs
(74) *Attorney, Agent, or Firm* — Goodwin Procter LLP

(57) ABSTRACT

This disclosure relates to RNA interference (RNAi) reagents for treatment of hepatitis B virus (HBV) infection, compositions comprising same, and use thereof to treat individuals
(Continued)

infected with HBV. The reagents are artificial miRNA (shmiRNA) used alone or in combination with additional shmiRNA or shRNA.

23 Claims, 21 Drawing Sheets

Specification includes a Sequence Listing.

(51) Int. Cl.
    *A61K 31/522*     (2006.01)
    *A61K 31/675*     (2006.01)
    *A61K 38/21*     (2006.01)

(52) U.S. Cl.
    CPC ............ *A61K 31/675* (2013.01); *A61K 38/21* (2013.01); *C12N 2310/141* (2013.01); *C12N 2310/531* (2013.01); *C12N 2330/51* (2013.01)

(56) References Cited

FOREIGN PATENT DOCUMENTS

| WO | WO 2004/078181 A1 | 9/2004 |
|---|---|---|
| WO | 2006/069064 A2 | 6/2006 |
| WO | WO 2008/147430 A2 | 12/2008 |
| WO | WO 2012/055362 A1 | 5/2012 |
| WO | 2013/159109 A1 | 10/2013 |
| WO | WO 2016/176745 A1 | 11/2016 |

OTHER PUBLICATIONS

Chen, Y. et al., "siRNA Pool Targeting Different Sites of Human Hepatitis B Surface Antigen Efficiently Inhibits HBV Infection," HHS Author Manuscript, 2009, [Online] [Retrieved on May 29, 2017] Retrieved from the Internet<URL:htts://www.ncbi.nlm.nih.gov/pmc/articles/PMC2778861/pdf/nihms157546..pdf>. Published in final form in Journal of Drug Targeting, Feb. 2008, pp. 140-148, vol. 16, No. 2.

Ely, A. et al., "Efficient Silencing of Gene Expression with Modular Trimeric Pol II Expression Cassettes Comprising microRNA Shuttles," Nucleic Acids Research, 2009, vol. 37, No. 13:e91.

Gao, Y.F. et al, "Inhibition of Hepatitis B Virus Gene Expression and Replication by Artificial MicroRNA," World Journal of Gastroenterology, Aug. 7, 2008, pp. 4684-4689, vol. 14, No. 29.

Pu, C. et al, "Optimized Tandem amiRNA Mediates Stronger Inhibitory Effects on Hepatitis B Virus Infection," Journal of Gastrointestinal and Liver Diseases, 2011, pp. 271-278, vol. 20, No. 3.

McBride, J.L. et al., "Artificial miRNAs Mitigate shRNA-Mediated Toxicity in the Brain: Implications for the Therapeutic Development of RNAi," Proceedings of the National Academy of Sciences, Apr. 15, 2008, pp. 5868-5873, vol. 105, No. 15.

\* cited by examiner

REAGENTS FOR TREATMENT OF HEPATITIS B VIRUS (HBV) INFECTION AND USE THEREOF

RELATED APPLICATION DATA

The present application claims priority from U.S. Provisional Application No. 62/332,245 filed on 5 May 2016, the full contents of which is incorporated herein by reference.

SEQUENCE LISTING

The instant application contains a Sequence Listing which has been filed electronically in ASCII format and is hereby incorporated by reference in its entirety. Said ASCII copy, created on Apr. 11, 2019, is named 33214-41901_US_SL.txt and is 69,741 bytes in size.

TECHNICAL FIELD

The present disclosure relates to RNA interference (RNAi) reagents for treatment of hepatitis B virus (HBV) infection, compositions comprising same, and use thereof to treat individuals infected with HBV.

BACKGROUND

Hepatitis B virus (HBV) is a serious and common infectious disease of the liver, affecting millions of people throughout the world. HBV is a hepatotrophic DNA virus belonging to the Hepadnaviridae. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene". More than 2 billion people worldwide have been infected with HBV at some time in their lives, and of these about 350-400 million remain chronically infected and are carriers of the virus. HBV infection can cause acute and chronic type B hepatitis, and may eventually lead to the development of chronic hepatic insufficiency, cirrhosis, and hepatocellular carcinoma. In addition, HBV carriers can transmit the disease for many years. Persons with chronic HBV infection i.e., carriers, have at least 12 times higher risk of developing hepatocellular carcinoma than non-carriers, and HBV causes 60-80% of the world's primary liver cancers. As a consequence, HBV ranks second only to tobacco as a known human carcinogen.

Although vaccines against HBV are available, the rate of HBV infection in the population remains high. Furthermore, current therapies for chronic HBV infection have only limited inhibitory effects on viral gene expression and replication in the majority of chronically infected patients. Another limitation of existing therapies for chronic HBV infection is the development of viral resistance to drugs.

For these reasons, there remains a need for a new therapeutic agents to treat HBV infection.

SUMMARY

The present disclosure is based, in part, on the recognition that existing vaccines and therapeutic agents for treatment and/or prevention of HBV infection are limited in their efficacy, such as where long term treatment is necessary e.g., due to the development of viral resistance to therapy and/or variation in responsiveness to therapy between genotypes of HBV. The present disclosure provides DNA-directed RNA interference (ddRNAi) constructs for expressing one or more short hairpin micro-RNAs (shmiRs) targeting conserved regions of RNA transcripts produced by the HBV genome i.e., regions conserved among different genotypes of HBV. Exemplary shmiRs of the disclosure comprise effector sequences capable of inhibiting or reducing expression of HBV gene transcripts in HepG2.2.15 cells harbouring active HBV. Exemplary shmiRs of the disclosure comprise effector sequences capable of inhibiting or reducing expression of HBV gene transcripts, reducing intracellular and extracellular HBV DNA, and reducing HBV covalently-closed circular DNA (cccDNA) in a PXB chimeric mouse infected with HBV. Thus, the inventors provide new compounds that inhibit or reduce expression of a nucleic acid and/or protein expressed by HBV and uses of such compounds e.g., to treat a HBV infection in a subject.

Accordingly, the present disclosure provides a nucleic acid comprising a DNA sequence which encodes a short hairpin micro-RNA (shmiR), said shmiR comprising:
 an effector sequence of at least 17 nucleotides in length;
 an effector complement sequence;
 a stemloop sequence; and
 primary micro RNA (pri-miRNA) backbone;
wherein the effector sequence is substantially complementary to a RNA transcript set forth in any one of SEQ ID NOs: 1-10, 38, 40, 42, 111, 113, 115, 117, 119, 121, 123, 125, 127, 129, 131 and 133. Preferably, the effector sequence will be less than 30 nucleotides in length. For example, a suitable effector sequence may be in the range of 17-29 nucleotides in length. Preferably, the effector sequence will be 20 nucleotides in length. More preferably, the effector sequence will be 21 nucleotides in length and the effector complement sequence will be 20 nucleotides in length.

The effector sequence may comprise 6 base pair mismatches relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In another example, the effector sequence comprises 5 base pair mismatches relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In another example, the effector sequence comprises 4 base pair mismatches relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In another example, the effector sequence comprises 3 base pair mismatches relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In another example, the effector sequence comprises 2 base pair mismatches relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In another example, the effector sequence comprises 1 base pair mismatch relative to the sequence set forth in any one of SEQ ID NOs: 1-10, 38, 40, 42, 111, 113, 115, 117, 119, 121, 123, 125, 127, 129, 131 and 133 to which the effector sequence is substantially complementary. In yet another example, the effector sequence is 100% complementary to a region of equivalent length within a sequence set forth in any one of SEQ ID NOs: 1-10, 38, 40, 42, 111, 113, 115, 117, 119, 121, 123, 125, 127, 129, 131 and 133. Where mismatches are present, it is preferred that they are not located within the region corresponding to the seed region of the shmiR i.e., nucleotides 2-8 of the effector sequence.

In one example, the nucleic acid described herein may comprise a DNA sequence encoding a shmiR selected from the group consisting of:

a shmiR comprising: (i) an effector sequence which is substantially complementary to the sequence set forth in SEQ ID NO:12 with the exception of 1, 2, 3, 4, 5 or 6 base mismatches, provided that the effector sequence is capable of forming a duplex with a sequence set forth in SEQ ID NO:12; and (ii) an effector complement sequence comprising a sequence which is substantially complementary to the effector sequence;

a shmiR comprising: (i) an effector sequence which is substantially complementary to the sequence set forth in SEQ ID NO:14 with the exception of 1, 2, 3, 4, 5 or 64 base mismatches, provided that the effector sequence is capable of forming a duplex with a sequence set forth in SEQ ID NO:14; and (ii) an effector complement sequence comprising a sequence which is substantially complementary to the effector sequence;

a shmiR comprising: (i) an effector sequence which is substantially complementary to the sequence set forth in SEQ ID NO:16 with the exception of 1, 2, 3, 4, 5 or 6 base mismatches, provided that the effector sequence is capable of forming a duplex with a sequence set forth in SEQ ID NO:16; and (ii) an effector complement sequence comprising a sequence which is substantially complementary to the effector sequence;

a shmiR comprising: (i) an effector sequence which is substantially complementary to the sequence set forth in SEQ ID NO:18 with the exception of 1, 2, 3, 4, 5 or 6 base mismatches, provided that the effector sequence is capable of forming a duplex with a sequence set forth in SEQ ID NO:18; and (ii) an effector complement sequence comprising a sequence which is substantially complementary to the effector sequence;

a shmiR comprising: (i) an effector sequence which is substantially complementary to the sequence set forth in SEQ ID NO:20 with the exception of 1, 2, 3, 4, 5 or 6 base mismatches, provided that the effector sequence is capable of forming a duplex with a sequence set forth in SEQ ID NO:20; and (ii) an effector complement sequence comprising a sequence which is substantially complementary to the effector sequence;

a shmiR comprising: (i) an effector sequence which is substantially complementary to the sequence set forth in SEQ ID NO:22 with the exception of 1, 2, 3, 4, 5 or 6 base mismatches, provided that the effector sequence is capable of forming a duplex with a sequence set forth in SEQ ID NO:22; and (ii) an effector complement sequence comprising a sequence which is substantially complementary to the effector sequence;

a shmiR comprising: (i) an effector sequence which is substantially complementary to the sequence set forth in SEQ ID NO:24 with the exception of 1, 2, 3, 4, 5 or 6 base mismatches, provided that the effector sequence is capable of forming a duplex with a sequence set forth in SEQ ID NO:24; and (ii) an effector complement sequence comprising a sequence which is substantially complementary to the effector sequence;

a shmiR comprising: (i) an effector sequence which is substantially complementary to the sequence set forth in SEQ ID NO:26 with the exception of 1, 2, 3, 4, 5 or 6 base mismatches, provided that the effector sequence is capable of forming a duplex with a sequence set forth in SEQ ID NO:26; and (ii) an effector complement sequence comprising a sequence which is substantially complementary to the effector sequence;

a shmiR comprising: (i) an effector sequence which is substantially complementary to the sequence set forth in SEQ ID NO:28 with the exception of 1, 2, 3, 4, 5 or 6 base mismatches, provided that the effector sequence is capable of forming a duplex with a sequence set forth in SEQ ID NO:28; and (ii) an effector complement sequence comprising a sequence which is substantially complementary to the effector sequence;

a shmiR comprising: (i) an effector sequence which is substantially complementary to the sequence set forth in SEQ ID NO:30 with the exception of 1, 2, 3, 4, 5 or 6 base mismatches, provided that the effector sequence is capable of forming a duplex with a sequence set forth in SEQ ID NO:30; and (ii) an effector complement sequence comprising a sequence which is substantially complementary to the effector sequence;

a shmiR comprising: (i) an effector sequence which is substantially complementary to the sequence set forth in SEQ ID NO:32 with the exception of 1, 2, 3, 4, 5 or 6 base mismatches, provided that the effector sequence is capable of forming a duplex with a sequence set forth in SEQ ID NO:32; and (ii) an effector complement sequence comprising a sequence which is substantially complementary to the effector sequence;

a shmiR comprising: (i) an effector sequence which is substantially complementary to the sequence set forth in SEQ ID NO:34 with the exception of 1, 2, 3, 4, 5 or 6 base mismatches, provided that the effector sequence is capable of forming a duplex with a sequence set forth in SEQ ID NO:34; and (ii) an effector complement sequence comprising a sequence which is substantially complementary to the effector sequence;

a shmiR comprising: (i) an effector sequence which is substantially complementary to the sequence set forth in SEQ ID NO:36 with the exception of 1, 2, 3, 4, 5 or 6 base mismatches, provided that the effector sequence is capable of forming a duplex with a sequence set forth in SEQ ID NO:36; and (ii) an effector complement sequence comprising a sequence which is substantially complementary to the effector sequence;

a shmiR comprising: (i) an effector sequence which is substantially complementary to the sequence set forth in SEQ ID NO:38 with the exception of 1, 2, 3, 4, 5 or 6 base mismatches, provided that the effector sequence is capable of forming a duplex with a sequence set forth in SEQ ID NO:38; and (ii) an effector complement sequence comprising a sequence which is substantially complementary to the effector sequence;

a shmiR comprising: (i) an effector sequence which is substantially complementary to the sequence set forth in SEQ ID NO:40 with the exception of 1, 2, 3, 4, 5 or 6 base mismatches, provided that the effector sequence is capable of forming a duplex with a sequence set forth in SEQ ID NO:40; and (ii) an effector complement sequence comprising a sequence which is substantially complementary to the effector sequence;

a shmiR comprising: (i) an effector sequence which is substantially complementary to the sequence set forth in SEQ ID NO:42 with the exception of 1, 2, 3, 4, 5 or 6 base mismatches, provided that the effector sequence is capable of forming a duplex with a sequence set forth in SEQ ID NO:42; and (ii) an effector complement sequence comprising a sequence which is substantially complementary to the effector sequence;

a shmiR comprising: (i) an effector sequence which is substantially complementary to the sequence set forth in SEQ ID NO:111 with the exception of 1, 2, 3, 4, 5, or 6 base mismatches, provided that the effector sequence is capable of forming a duplex with a sequence set forth in SEQ ID NO:111; and (ii) an effector complement sequence comprising a sequence which is substantially complementary to the effector sequence;

a shmiR comprising: (i) an effector sequence which is substantially complementary to the sequence set forth in SEQ ID NO:113 with the exception of 1, 2, 3, 4, 5, or 6 base mismatches, provided that the effector sequence is capable of forming a duplex with a sequence set forth in SEQ ID NO:113; and (ii) an effector complement sequence comprising a sequence which is substantially complementary to the effector sequence;

a shmiR comprising: (i) an effector sequence which is substantially complementary to the sequence set forth in SEQ ID NO:115 with the exception of 1, 2, 3, 4, 5, or 6 base mismatches, provided that the effector sequence is capable of forming a duplex with a sequence set forth in SEQ ID NO:115; and (ii) an effector complement sequence comprising a sequence which is substantially complementary to the effector sequence;

a shmiR comprising: (i) an effector sequence which is substantially complementary to the sequence set forth in SEQ ID NO:117 with the exception of 1, 2, 3, 4, 5, or 6 base mismatches, provided that the effector sequence is capable of forming a duplex with a sequence set forth in SEQ ID NO:117; and (ii) an effector complement sequence comprising a sequence which is substantially complementary to the effector sequence;

a shmiR comprising: (i) an effector sequence which is substantially complementary to the sequence set forth in SEQ ID NO:119 with the exception of 1, 2, 3, 4, 5, or 6 base mismatches, provided that the effector sequence is capable of forming a duplex with a sequence set forth in SEQ ID NO:119; and (ii) an effector complement sequence comprising a sequence which is substantially complementary to the effector sequence;

a shmiR comprising: (i) an effector sequence which is substantially complementary to the sequence set forth in SEQ ID NO:121 with the exception of 1, 2, 3, 4, 5, or 6 base mismatches, provided that the effector sequence is capable of forming a duplex with a sequence set forth in SEQ ID NO:121; and (ii) an effector complement sequence comprising a sequence which is substantially complementary to the effector sequence;

a shmiR comprising: (i) an effector sequence which is substantially complementary to the sequence set forth in SEQ ID NO:123 with the exception of 1, 2, 3, 4, 5, or 6 base mismatches, provided that the effector sequence is capable of forming a duplex with a sequence set forth in SEQ ID NO:123; and (ii) an effector complement sequence comprising a sequence which is substantially complementary to the effector sequence;

a shmiR comprising: (i) an effector sequence which is substantially complementary to the sequence set forth in SEQ ID NO:125 with the exception of 1, 2, 3, 4, 5, or 6 base mismatches, provided that the effector sequence is capable of forming a duplex with a sequence set forth in SEQ ID NO:125; and (ii) an effector complement sequence comprising a sequence which is substantially complementary to the effector sequence;

a shmiR comprising: (i) an effector sequence which is substantially complementary to the sequence set forth in SEQ ID NO:127 with the exception of 1, 2, 3, 4, 5, or 6 base mismatches, provided that the effector sequence is capable of forming a duplex with a sequence set forth in SEQ ID NO:127; and (ii) an effector complement sequence comprising a sequence which is substantially complementary to the effector sequence;

a shmiR comprising: (i) an effector sequence which is substantially complementary to the sequence set forth in SEQ ID NO:129 with the exception of 1, 2, 3, 4, 5, or 6 base mismatches, provided that the effector sequence is capable of forming a duplex with a sequence set forth in SEQ ID NO:129; and (ii) an effector complement sequence comprising a sequence which is substantially complementary to the effector sequence;

a shmiR comprising: (i) an effector sequence which is substantially complementary to the sequence set forth in SEQ ID NO:131 with the exception of 1, 2, 3, 4, 5, or 6 base mismatches, provided that the effector sequence is capable of forming a duplex with a sequence set forth in SEQ ID NO:131; and (ii) an effector complement sequence comprising a sequence which is substantially complementary to the effector sequence; and a shmiR comprising: (i) an effector sequence which is substantially complementary to the sequence set forth in SEQ ID NO:133 with the exception of 1, 2, 3, 4, 5, or 6 base mismatches, provided that the effector sequence is capable of forming a duplex with a sequence set forth in SEQ ID NO:133; and (ii) an effector complement sequence comprising a sequence which is substantially complementary to the effector sequence.

In another example, the nucleic acid described herein may comprise a DNA sequence encoding a shmiR selected from the group consisting of:

a shmiR comprising an effector sequence set forth in SEQ ID NO:11 and an effector complement sequence which is substantially complementary to the sequence set forth in SEQ ID NO:11 and capable of forming a duplex therewith;

a shmiR comprising an effector sequence set forth in SEQ ID NO:13 and an effector complement sequence which is substantially complementary to the sequence set forth in SEQ ID NO:13 and capable of forming a duplex therewith;

a shmiR comprising an effector sequence set forth in SEQ ID NO:15 and an effector complement sequence which is substantially complementary to the sequence set forth in SEQ ID NO:15 and capable of forming a duplex therewith;

a shmiR comprising an effector sequence set forth in SEQ ID NO:17 and an effector complement sequence which is substantially complementary to the sequence set forth in SEQ ID NO:17 and capable of forming a duplex therewith;

a shmiR comprising an effector sequence set forth in SEQ ID NO:19 and an effector complement sequence which is substantially complementary to the sequence set forth in SEQ ID NO:19 and capable of forming a duplex therewith;

a shmiR comprising an effector sequence set forth in SEQ ID NO:21 and an effector complement sequence which is substantially complementary to the sequence set forth in SEQ ID NO:21 and capable of forming a duplex therewith;

a shmiR comprising an effector sequence set forth in SEQ ID NO:23 and an effector complement sequence which is substantially complementary to the sequence set forth in SEQ ID NO:23 and capable of forming a duplex therewith;

a shmiR comprising an effector sequence set forth in SEQ ID NO:25 and an effector complement sequence which is substantially complementary to the sequence set forth in SEQ ID NO:25 and capable of forming a duplex therewith;

a shmiR comprising an effector sequence set forth in SEQ ID NO:27 and an effector complement sequence which is substantially complementary to the sequence set forth in SEQ ID NO:27 and capable of forming a duplex therewith;

a shmiR comprising an effector sequence set forth in SEQ ID NO:29 and an effector complement sequence which is substantially complementary to the sequence set forth in SEQ ID NO:29 and capable of forming a duplex therewith;

a shmiR comprising an effector sequence set forth in SEQ ID NO:31 and an effector complement sequence which is substantially complementary to the sequence set forth in SEQ ID NO:31 and capable of forming a duplex therewith;

a shmiR comprising an effector sequence set forth in SEQ ID NO:33 and an effector complement sequence which is substantially complementary to the sequence set forth in SEQ ID NO:33 and capable of forming a duplex therewith;

a shmiR comprising an effector sequence set forth in SEQ ID NO:35 and an effector complement sequence which is substantially complementary to the sequence set forth in SEQ ID NO:35 and capable of forming a duplex therewith;

a shmiR comprising an effector sequence set forth in SEQ ID NO:37 and an effector complement sequence which is substantially complementary to the sequence set forth in SEQ ID NO:37 and capable of forming a duplex therewith;

a shmiR comprising an effector sequence set forth in SEQ ID NO:39 and an effector complement sequence which is substantially complementary to the sequence set forth in SEQ ID NO:39 and capable of forming a duplex therewith;

a shmiR comprising an effector sequence set forth in SEQ ID NO:41 and an effector complement sequence which is substantially complementary to the sequence set forth in SEQ ID NO:41 and capable of forming a duplex therewith;

a shmiR comprising an effector sequence set forth in SEQ ID NO:110 and an effector complement sequence which is substantially complementary to the sequence set forth in SEQ ID NO:110 and capable of forming a duplex therewith;

a shmiR comprising an effector sequence set forth in SEQ ID NO:112 and an effector complement sequence which is substantially complementary to the sequence set forth in SEQ ID NO:112 and capable of forming a duplex therewith;

a shmiR comprising an effector sequence set forth in SEQ ID NO:114 and an effector complement sequence which is substantially complementary to the sequence set forth in SEQ ID NO:114 and capable of forming a duplex therewith;

a shmiR comprising an effector sequence set forth in SEQ ID NO:116 and an effector complement sequence which is substantially complementary to the sequence set forth in SEQ ID NO:116 and capable of forming a duplex therewith;

a shmiR comprising an effector sequence set forth in SEQ ID NO:118 and an effector complement sequence which is substantially complementary to the sequence set forth in SEQ ID NO:118 and capable of forming a duplex therewith;

a shmiR comprising an effector sequence set forth in SEQ ID NO:120 and an effector complement sequence which is substantially complementary to the sequence set forth in SEQ ID NO:120 and capable of forming a duplex therewith;

a shmiR comprising an effector sequence set forth in SEQ ID NO:122 and an effector complement sequence which is substantially complementary to the sequence set forth in SEQ ID NO:122 and capable of forming a duplex therewith;

a shmiR comprising an effector sequence set forth in SEQ ID NO:124 and an effector complement sequence which is substantially complementary to the sequence set forth in SEQ ID NO:124 and capable of forming a duplex therewith;

a shmiR comprising an effector sequence set forth in SEQ ID NO:126 and an effector complement sequence which is substantially complementary to the sequence set forth in SEQ ID NO:126 and capable of forming a duplex therewith;

a shmiR comprising an effector sequence set forth in SEQ ID NO:128 and an effector complement sequence which is substantially complementary to the sequence set forth in SEQ ID NO:128 and capable of forming a duplex therewith;

a shmiR comprising an effector sequence set forth in SEQ ID NO:130 and an effector complement sequence which is substantially complementary to the sequence set forth in SEQ ID NO:130 and capable of forming a duplex therewith; and a shmiR comprising an effector sequence set forth in SEQ ID NO:132 and an effector complement sequence which is substantially complementary to the sequence set forth in SEQ ID NO:132 and capable of forming a duplex therewith.

For example, the shmiR encoded by the nucleic acid described herein may comprise an effector complement sequence comprising 1, 2, 3 or 4 mismatches relative to the corresponding effector sequence, provided that the cognate effector and effector complement sequences are capable of forming a duplex region.

In another example, the nucleic acid described herein may comprise a DNA sequence encoding a shmiR selected from the group consisting of:

a shmiR comprising an effector sequence set forth in SEQ ID NO:11 and an effector complement sequence set forth in SEQ ID NO:12;

a shmiR comprising an effector sequence set forth in SEQ ID NO:13 and an effector complement sequence set forth in SEQ ID NO:14;

a shmiR comprising an effector sequence set forth in SEQ ID NO:15 and an effector complement sequence set forth in SEQ ID NO:16;

a shmiR comprising an effector sequence set forth in SEQ ID NO:17 and an effector complement sequence set forth in SEQ ID NO:18;

a shmiR comprising an effector sequence set forth in SEQ ID NO:19 and an effector complement sequence set forth in SEQ ID NO: 20;

a shmiR comprising an effector sequence set forth in SEQ ID NO:21 and an effector complement sequence set forth in SEQ ID NO:22;

a shmiR comprising an effector sequence set forth in SEQ ID NO:23 and an effector complement sequence set forth in SEQ ID NO:24;

a shmiR comprising an effector sequence set forth in SEQ ID NO:25 and an effector complement sequence set forth in SEQ ID NO:26;

a shmiR comprising an effector sequence set forth in SEQ ID NO:27 and an effector complement sequence set forth in SEQ ID NO:28;

a shmiR comprising an effector sequence set forth in SEQ ID NO:29 and an effector complement sequence set forth in SEQ ID NO:30;

a shmiR comprising an effector sequence set forth in SEQ ID NO:31 and an effector complement sequence set forth in SEQ ID NO:32;

a shmiR comprising an effector sequence set forth in SEQ ID NO:33 and an effector complement sequence set forth in SEQ ID NO:34;

a shmiR comprising an effector sequence set forth in SEQ ID NO:35 and an effector complement sequence set forth in SEQ ID NO:36;

a shmiR comprising an effector sequence set forth in SEQ ID NO:37 and an effector complement sequence set forth in SEQ ID NO:38;

a shmiR comprising an effector sequence set forth in SEQ ID NO:39 and an effector complement sequence set forth in SEQ ID NO:40; and a shmiR comprising an effector sequence set forth in SEQ ID NO:41 and an effector complement sequence set forth in SEQ ID NO:42;
a shmiR comprising an effector sequence set forth in SEQ ID NO:110 and an effector complement sequence set forth in SEQ ID NO:111;
a shmiR comprising an effector sequence set forth in SEQ ID NO:112 and an effector complement sequence set forth in SEQ ID NO:113;
a shmiR comprising an effector sequence set forth in SEQ ID NO:114 and an effector complement sequence set forth in SEQ ID NO:115;
a shmiR comprising an effector sequence set forth in SEQ ID NO:116 and an effector complement sequence set forth in SEQ ID NO:117;
a shmiR comprising an effector sequence set forth in SEQ ID NO:118 and an effector complement sequence set forth in SEQ ID NO:119;
a shmiR comprising an effector sequence set forth in SEQ ID NO:120 and an effector complement sequence set forth in SEQ ID NO:121;
a shmiR comprising an effector sequence set forth in SEQ ID NO:122 and an effector complement sequence set forth in SEQ ID NO:123;
a shmiR comprising an effector sequence set forth in SEQ ID NO:124 and an effector complement sequence set forth in SEQ ID NO:125;
a shmiR comprising an effector sequence set forth in SEQ ID NO:126 and an effector complement sequence set forth in SEQ ID NO:127;
a shmiR comprising an effector sequence set forth in SEQ ID NO:128 and an effector complement sequence set forth in SEQ ID NO:129;
a shmiR comprising an effector sequence set forth in SEQ ID NO:130 and an effector complement sequence set forth in SEQ ID NO:131; and
a shmiR comprising an effector sequence set forth in SEQ ID NO:132 and an effector complement sequence set forth in SEQ ID NO:133.

The shmiR encoded by the nucleic acid of the disclosure may comprise, in a 5' to 3' direction:
a 5' flanking sequence of the pri-miRNA backbone;
the effector complement sequence;
the stemloop sequence;
the effector sequence; and
a 3' flanking sequence of the pri-miRNA backbone.

Suitable loop sequences may be selected from those known in the art. However, an exemplary stemloop sequence is set forth in SEQ ID NO: 75.

Suitable primary micro RNA (pri-miRNA or pri-R) backbones for use in a nucleic acid of the disclosure may be selected from those known in the art. For example, the pri-miRNA backbone may be selected from a pri-miR-30a backbone, a pri-miR-155 backbone, a pri-miR-21 backbone and a pri-miR-136 backbone. Preferably, however, the pri-miRNA backbone is a pri-miR-30a backbone. In accordance with an example in which the pri-miRNA backbone is a pri-miR-30a backbone, the 5' flanking sequence of the pri-miRNA backbone is set forth in SEQ ID NO: 76 and the 3' flanking sequence of the pri-miRNA backbone is set forth in SEQ ID NO: 77.

In one example, the nucleic acid described herein comprises a DNA sequence selected from the sequence set forth in any one of SEQ ID NOs: 59-74 and 146-157. In accordance with this example, a shmiR encoded by the nucleic acid of the disclosure may comprise a sequence set forth in any one of SEQ ID NOs: 43-58 and 134-145.

It will be understood by a person of skill in the art that a nucleic acid in accordance with the present disclosure may be combined or used in conjunction with other therapeutic agents for treating HBV. Accordingly, the present disclosure provides a nucleic acid comprising a DNA sequence encoding a shmiR as described herein in combination with one or more other agents for treating HBV. In one example, a plurality of nucleic acids are provided comprising:
(a) at least one nucleic acid as described herein; and
(b) at least one further nucleic acid selected from:
   (i) a nucleic acid in accordance with the nucleic acids described herein; or
   (ii) a nucleic acid comprising a DNA sequence encoding a short hairpin RNA (shRNA) comprising an effector sequence of at least 17 nucleotides in length and a effector complement sequence, wherein the effector sequence is substantially complementary to a RNA sequence set forth in any one of SEQ ID NOs: 1-10, 38, 40, 42, 111, 113, 115, 117, 119, 121, 123, 125, 127, 129, 131 and 133;
wherein the shmiR encoded by the nucleic acid at (a) and the shmiR or shRNA encoded by the nucleic acid at (b) comprise different effector sequences.

Preferably, the effector sequence of the shRNA at (b)(ii) which is substantially complementary to a RNA sequence set forth in any one of SEQ ID NOs: 1-10, 38, 40, 42, 111, 113, 115, 117, 119, 121, 123, 125, 127, 129, 131 and 133 will be less than 30 nucleotides in length. For example, a suitable effector sequence of the shRNA may be in the range of 17-29 nucleotides in length.

In accordance with an example in which at least one of the nucleic acids in the plurality encodes a shRNA, the shRNA may be selected from the group consisting of:
a shRNA comprising: (i) an effector sequence which is substantially complementary to the sequence set forth in SEQ ID NO:12 with the exception of 1, 2, 3, 4, 5 or 6 base mismatches, provided that the effector sequence is capable of forming a duplex with a sequence set forth in SEQ ID NO:12; and (ii) an effector complement sequence comprising a sequence which is substantially complementary to the effector sequence;
a shRNA comprising: (i) an effector sequence which is substantially complementary to the sequence set forth in SEQ ID NO:14 with the exception of 1, 2, 3, 4, 5 or 6 base mismatches, provided that the effector sequence is capable of forming a duplex with a sequence set forth in SEQ ID NO:14; and (ii) an effector complement sequence comprising a sequence which is substantially complementary to the effector sequence;
a shRNA comprising: (i) an effector sequence which is substantially complementary to the sequence set forth in SEQ ID NO:16 with the exception of 1, 2, 3, 4, 5 or 6 base mismatches, provided that the effector sequence is capable of forming a duplex with a sequence set forth in SEQ ID NO:16; and (ii) an effector complement sequence comprising a sequence which is substantially complementary to the effector sequence;
a shRNA comprising: (i) an effector sequence which is substantially complementary to the sequence set forth in SEQ ID NO:18 with the exception of 1, 2, 3, 4, 5 or 6 base mismatches, provided that the effector sequence is capable of forming a duplex with a sequence set forth in SEQ ID NO:18; and (ii) an effector complement sequence comprising a sequence which is substantially complementary to the effector sequence;
a shRNA comprising: (i) an effector sequence which is substantially complementary to the sequence set forth in SEQ ID NO:20 with the exception of 1, 2, 3, 4, 5 or 6 base mismatches, provided that the effector sequence is capable of forming a duplex with a sequence set forth in SEQ ID NO:20; and (ii) an effector complement sequence comprising a sequence which is substantially complementary to the effector sequence;

a shRNA comprising: (i) an effector sequence which is substantially complementary to the sequence set forth in SEQ ID NO:22 with the exception of 1, 2, 3, 4, 5 or 6 base mismatches, provided that the effector sequence is capable of forming a duplex with a sequence set forth in SEQ ID NO:22; and (ii) an effector complement sequence comprising a sequence which is substantially complementary to the effector sequence;

a shRNA comprising: (i) an effector sequence which is substantially complementary to the sequence set forth in SEQ ID NO:24 with the exception of 1, 2, 3, 4, 5 or 6 base mismatches, provided that the effector sequence is capable of forming a duplex with a sequence set forth in SEQ ID NO:24; and (ii) an effector complement sequence comprising a sequence which is substantially complementary to the effector sequence;

a shRNA comprising: (i) an effector sequence which is substantially complementary to the sequence set forth in SEQ ID NO:26 with the exception of 1, 2, 3, 4, 5 or 6 base mismatches, provided that the effector sequence is capable of forming a duplex with a sequence set forth in SEQ ID NO:26; and (ii) an effector complement sequence comprising a sequence which is substantially complementary to the effector sequence;

a shRNA comprising: (i) an effector sequence which is substantially complementary to the sequence set forth in SEQ ID NO:28 with the exception of 1, 2, 3, 4, 5 or 6 base mismatches, provided that the effector sequence is capable of forming a duplex with a sequence set forth in SEQ ID NO:28; and (ii) an effector complement sequence comprising a sequence which is substantially complementary to the effector sequence;

a shRNA comprising: (i) an effector sequence which is substantially complementary to the sequence set forth in SEQ ID NO:30 with the exception of 1, 2, 3, 4, 5 or 6 base mismatches, provided that the effector sequence is capable of forming a duplex with a sequence set forth in SEQ ID NO:30; and (ii) an effector complement sequence comprising a sequence which is substantially complementary to the effector sequence;

a shRNA comprising: (i) an effector sequence which is substantially complementary to the sequence set forth in SEQ ID NO:32 with the exception of 1, 2, 3, 4, 5 or 6 base mismatches, provided that the effector sequence is capable of forming a duplex with a sequence set forth in SEQ ID NO:32; and (ii) an effector complement sequence comprising a sequence which is substantially complementary to the effector sequence;

a shRNA comprising: (i) an effector sequence which is substantially complementary to the sequence set forth in SEQ ID NO:34 with the exception of 1, 2, 3, 4, 5 or 6 base mismatches, provided that the effector sequence is capable of forming a duplex with a sequence set forth in SEQ ID NO:34; and (ii) an effector complement sequence comprising a sequence which is substantially complementary to the effector sequence;

a shRNA comprising: (i) an effector sequence which is substantially complementary to the sequence set forth in SEQ ID NO:36 with the exception of 1, 2, 3, 4, 5 or 6 base mismatches, provided that the effector sequence is capable of forming a duplex with a sequence set forth in SEQ ID NO:36; and (ii) an effector complement sequence comprising a sequence which is substantially complementary to the effector sequence;

a shRNA comprising: (i) an effector sequence which is substantially complementary to the sequence set forth in SEQ ID NO:38 with the exception of 1, 2, 3, 4, 5 or 6 base mismatches, provided that the effector sequence is capable of forming a duplex with a sequence set forth in SEQ ID NO:38; and (ii) an effector complement sequence comprising a sequence which is substantially complementary to the effector sequence;

a shRNA comprising: (i) an effector sequence which is substantially complementary to the sequence set forth in SEQ ID NO:40 with the exception of 1, 2, 3, 4, 5 or 6 base mismatches, provided that the effector sequence is capable of forming a duplex with a sequence set forth in SEQ ID NO:40; and (ii) an effector complement sequence comprising a sequence which is substantially complementary to the effector sequence;

a shRNA comprising: (i) an effector sequence which is substantially complementary to the sequence set forth in SEQ ID NO:42 with the exception of 1, 2, 3, 4, 5 or 6 base mismatches, provided that the effector sequence is capable of forming a duplex with a sequence set forth in SEQ ID NO:42; and (ii) an effector complement sequence comprising a sequence which is substantially complementary to the effector sequence;

a shRNA comprising: (i) an effector sequence which is substantially complementary to the sequence set forth in SEQ ID NO:111 with the exception of 1, 2, 3, 4, 5 or 6 base mismatches, provided that the effector sequence is capable of forming a duplex with a sequence set forth in SEQ ID NO:111; and (ii) an effector complement sequence comprising a sequence which is substantially complementary to the effector sequence;

a shRNA comprising: (i) an effector sequence which is substantially complementary to the sequence set forth in SEQ ID NO:113 with the exception of 1, 2, 3, 4, 5 or 6 base mismatches, provided that the effector sequence is capable of forming a duplex with a sequence set forth in SEQ ID NO:113; and (ii) an effector complement sequence comprising a sequence which is substantially complementary to the effector sequence;

a shRNA comprising: (i) an effector sequence which is substantially complementary to the sequence set forth in SEQ ID NO:115 with the exception of 1, 2, 3, 4, 5 or 6 base mismatches, provided that the effector sequence is capable of forming a duplex with a sequence set forth in SEQ ID NO:115; and (ii) an effector complement sequence comprising a sequence which is substantially complementary to the effector sequence;

a shRNA comprising: (i) an effector sequence which is substantially complementary to the sequence set forth in SEQ ID NO:117 with the exception of 1, 2, 3, 4, 5 or 6 base mismatches, provided that the effector sequence is capable of forming a duplex with a sequence set forth in SEQ ID NO:117; and (ii) an effector complement sequence comprising a sequence which is substantially complementary to the effector sequence;

a shRNA comprising: (i) an effector sequence which is substantially complementary to the sequence set forth in SEQ ID NO:119 with the exception of 1, 2, 3, 4, 5 or 6 base mismatches, provided that the effector sequence is capable of forming a duplex with a sequence set forth in SEQ ID NO:119; and (ii) an effector complement sequence comprising a sequence which is substantially complementary to the effector sequence;

a shRNA comprising: (i) an effector sequence which is substantially complementary to the sequence set forth in SEQ ID NO:121 with the exception of 1, 2, 3, 4, 5 or 6 base mismatches, provided that the effector sequence is capable of forming a duplex with a sequence set forth in SEQ ID NO:121; and (ii) an effector complement sequence comprising a sequence which is substantially complementary to the effector sequence;

a shRNA comprising: (i) an effector sequence which is substantially complementary to the sequence set forth in SEQ ID NO:123 with the exception of 1, 2, 3, 4, 5 or 6 base mismatches, provided that the effector sequence is capable of forming a duplex with a sequence set forth in SEQ ID NO:123; and (ii) an effector complement sequence comprising a sequence which is substantially complementary to the effector sequence;

a shRNA comprising: (i) an effector sequence which is substantially complementary to the sequence set forth in SEQ ID NO:125 with the exception of 1, 2, 3, 4, 5 or 6 base mismatches, provided that the effector sequence is capable of forming a duplex with a sequence set forth in SEQ ID NO:125; and (ii) an effector complement sequence comprising a sequence which is substantially complementary to the effector sequence;

a shRNA comprising: (i) an effector sequence which is substantially complementary to the sequence set forth in SEQ ID NO:127 with the exception of 1, 2, 3, 4, 5 or 6 base mismatches, provided that the effector sequence is capable of forming a duplex with a sequence set forth in SEQ ID NO:127; and (ii) an effector complement sequence comprising a sequence which is substantially complementary to the effector sequence;

a shRNA comprising: (i) an effector sequence which is substantially complementary to the sequence set forth in SEQ ID NO:129 with the exception of 1, 2, 3, 4, 5 or 6 base mismatches, provided that the effector sequence is capable of forming a duplex with a sequence set forth in SEQ ID NO:129; and (ii) an effector complement sequence comprising a sequence which is substantially complementary to the effector sequence;

a shRNA comprising: (i) an effector sequence which is substantially complementary to the sequence set forth in SEQ ID NO:131 with the exception of 1, 2, 3, 4, 5 or 6 base mismatches, provided that the effector sequence is capable of forming a duplex with a sequence set forth in SEQ ID NO:131; and (ii) an effector complement sequence comprising a sequence which is substantially complementary to the effector sequence; and a shRNA comprising: (i) an effector sequence which is substantially complementary to the sequence set forth in SEQ ID NO:133 with the exception of 1, 2, 3, 4, 5 or 6 base mismatches, provided that the effector sequence is capable of forming a duplex with a sequence set forth in SEQ ID NO:133; and (ii) an effector complement sequence comprising a sequence which is substantially complementary to the effector sequence.

In accordance with another example in which at least one of the nucleic acids in the plurality encodes a shRNA, the shRNA may be selected from the group consisting of:

a shRNA comprising an effector sequence set forth in SEQ ID NO:11 and an effector complement sequence which is substantially complementary to the sequence set forth in SEQ ID NO:11 and capable of forming a duplex therewith;

a shRNA comprising an effector sequence set forth in SEQ ID NO:13 and an effector complement sequence which is substantially complementary to the sequence set forth in SEQ ID NO:13 and capable of forming a duplex therewith;

a shRNA comprising an effector sequence set forth in SEQ ID NO:15 and an effector complement sequence which is substantially complementary to the sequence set forth in SEQ ID NO:15 and capable of forming a duplex therewith;

a shRNA comprising an effector sequence set forth in SEQ ID NO:17 and an effector complement sequence which is substantially complementary to the sequence set forth in SEQ ID NO:17 and capable of forming a duplex therewith;

a shRNA comprising an effector sequence set forth in SEQ ID NO:19 and an effector complement sequence which is substantially complementary to the sequence set forth in SEQ ID NO:19 and capable of forming a duplex therewith;

a shRNA comprising an effector sequence set forth in SEQ ID NO:21 and an effector complement sequence which is substantially complementary to the sequence set forth in SEQ ID NO:21 and capable of forming a duplex therewith;

a shRNA comprising an effector sequence set forth in SEQ ID NO:23 and an effector complement sequence which is substantially complementary to the sequence set forth in SEQ ID NO:23 and capable of forming a duplex therewith;

a shRNA comprising an effector sequence set forth in SEQ ID NO:25 and an effector complement sequence which is substantially complementary to the sequence set forth in SEQ ID NO:25 and capable of forming a duplex therewith;

a shRNA comprising an effector sequence set forth in SEQ ID NO:27 and an effector complement sequence which is substantially complementary to the sequence set forth in SEQ ID NO:27 and capable of forming a duplex therewith;

a shRNA comprising an effector sequence set forth in SEQ ID NO:29 and an effector complement sequence which is substantially complementary to the sequence set forth in SEQ ID NO:29 and capable of forming a duplex therewith;

a shRNA comprising an effector sequence set forth in SEQ ID NO:31 and an effector complement sequence which is substantially complementary to the sequence set forth in SEQ ID NO:31 and capable of forming a duplex therewith;

a shRNA comprising an effector sequence set forth in SEQ ID NO:33 and an effector complement sequence which is substantially complementary to the sequence set forth in SEQ ID NO:33 and capable of forming a duplex therewith;

a shRNA comprising an effector sequence set forth in SEQ ID NO:35 and an effector complement sequence which is substantially complementary to the sequence set forth in SEQ ID NO:35 and capable of forming a duplex therewith;

a shRNA comprising an effector sequence set forth in SEQ ID NO:37 and an effector complement sequence which is substantially complementary to the sequence set forth in SEQ ID NO:37 and capable of forming a duplex therewith;

a shRNA comprising an effector sequence set forth in SEQ ID NO:39 and an effector complement sequence which is substantially complementary to the sequence set forth in SEQ ID NO:39 and capable of forming a duplex therewith;

a shRNA comprising an effector sequence set forth in SEQ ID NO:41 and an effector complement sequence which is substantially complementary to the sequence set forth in SEQ ID NO:41 and capable of forming a duplex therewith;

a shRNA comprising an effector sequence set forth in SEQ ID NO:110 and an effector complement sequence which is substantially complementary to the sequence set forth in SEQ ID NO:110 and capable of forming a duplex therewith;

a shRNA comprising an effector sequence set forth in SEQ ID NO:112 and an effector complement sequence which is substantially complementary to the sequence set forth in SEQ ID NO:112 and capable of forming a duplex therewith;

a shRNA comprising an effector sequence set forth in SEQ ID NO:114 and an effector complement sequence which is substantially complementary to the sequence set forth in SEQ ID NO:114 and capable of forming a duplex therewith;

a shRNA comprising an effector sequence set forth in SEQ ID NO:116 and an effector complement sequence which is substantially complementary to the sequence set forth in SEQ ID NO:116 and capable of forming a duplex therewith;

a shRNA comprising an effector sequence set forth in SEQ ID NO:118 and an effector complement sequence which is substantially complementary to the sequence set forth in SEQ ID NO:118 and capable of forming a duplex therewith;

a shRNA comprising an effector sequence set forth in SEQ ID NO:120 and an effector complement sequence which is substantially complementary to the sequence set forth in SEQ ID NO:120 and capable of forming a duplex therewith;

a shRNA comprising an effector sequence set forth in SEQ ID NO:122 and an effector complement sequence which is substantially complementary to the sequence set forth in SEQ ID NO:122 and capable of forming a duplex therewith;

a shRNA comprising an effector sequence set forth in SEQ ID NO:124 and an effector complement sequence which is substantially complementary to the sequence set forth in SEQ ID NO:124 and capable of forming a duplex therewith;

a shRNA comprising an effector sequence set forth in SEQ ID NO:126 and an effector complement sequence which is substantially complementary to the sequence set forth in SEQ ID NO:126 and capable of forming a duplex therewith;

a shRNA comprising an effector sequence set forth in SEQ ID NO:128 and an effector complement sequence which is substantially complementary to the sequence set forth in SEQ ID NO:128 and capable of forming a duplex therewith;

a shRNA comprising an effector sequence set forth in SEQ ID NO:130 and an effector complement sequence which is substantially complementary to the sequence set forth in SEQ ID NO:130 and capable of forming a duplex therewith; and a shRNA comprising an effector sequence set forth in SEQ ID NO:132 and an effector complement sequence which is substantially complementary to the sequence set forth in SEQ ID NO:132 and capable of forming a duplex therewith.

For example, the shRNA encoded by the nucleic acid in the plurality of nucleic acids described herein may comprise an effector complement sequence comprising 1, 2, 3, 4, 5 or 6 base mismatches relative to the corresponding effector sequence, provided that the cognate effector and effector complement sequences are capable of forming a duplex region.

In another example in which at least one of the nucleic acids in the plurality encodes a shRNA, the shRNA may be selected from the group consisting of:

a shRNA comprising an effector sequence set forth in SEQ ID NO:11 and an effector complement sequence set forth in SEQ ID NO:12;

a shRNA comprising an effector sequence set forth in SEQ ID NO:13 and an effector complement sequence set forth in SEQ ID NO:14;

a shRNA comprising an effector sequence set forth in SEQ ID NO:15 and an effector complement sequence set forth in SEQ ID NO:16;

a shRNA comprising an effector sequence set forth in SEQ ID NO:17 and an effector complement sequence set forth in SEQ ID NO:18;

a shRNA comprising an effector sequence set forth in SEQ ID NO:19 and an effector complement sequence set forth in SEQ ID NO: 20;

a shRNA comprising an effector sequence set forth in SEQ ID NO:21 and an effector complement sequence set forth in SEQ ID NO:22;

a shRNA comprising an effector sequence set forth in SEQ ID NO:23 and an effector complement sequence set forth in SEQ ID NO:24;

a shRNA comprising an effector sequence set forth in SEQ ID NO:25 and an effector complement sequence set forth in SEQ ID NO:26;

a shRNA comprising an effector sequence set forth in SEQ ID NO:27 and an effector complement sequence set forth in SEQ ID NO:28;

a shRNA comprising an effector sequence set forth in SEQ ID NO:29 and an effector complement sequence set forth in SEQ ID NO:30;

a shRNA comprising an effector sequence set forth in SEQ ID NO:31 and an effector complement sequence set forth in SEQ ID NO:32;

a shRNA comprising an effector sequence set forth in SEQ ID NO:33 and an effector complement sequence set forth in SEQ ID NO:34;

a shRNA comprising an effector sequence set forth in SEQ ID NO:35 and an effector complement sequence set forth in SEQ ID NO:36;

a shRNA comprising an effector sequence set forth in SEQ ID NO:37 and an effector complement sequence set forth in SEQ ID NO:38;

a shRNA comprising an effector sequence set forth in SEQ ID NO:39 and an effector complement sequence set forth in SEQ ID NO:40;

a shRNA comprising an effector sequence set forth in SEQ ID NO:41 and an effector complement sequence set forth in SEQ ID NO:42;

a shRNA comprising an effector sequence set forth in SEQ ID NO:110 and an effector complement sequence set forth in SEQ ID NO:111;

a shRNA comprising an effector sequence set forth in SEQ ID NO:112 and an effector complement sequence set forth in SEQ ID NO:113;

a shRNA comprising an effector sequence set forth in SEQ ID NO:114 and an effector complement sequence set forth in SEQ ID NO:115;

a shRNA comprising an effector sequence set forth in SEQ ID NO:116 and an effector complement sequence set forth in SEQ ID NO:117;

a shRNA comprising an effector sequence set forth in SEQ ID NO:118 and an effector complement sequence set forth in SEQ ID NO:119;

a shRNA comprising an effector sequence set forth in SEQ ID NO:120 and an effector complement sequence set forth in SEQ ID NO:121;

a shRNA comprising an effector sequence set forth in SEQ ID NO:122 and an effector complement sequence set forth in SEQ ID NO:123;

a shRNA comprising an effector sequence set forth in SEQ ID NO:124 and an effector complement sequence set forth in SEQ ID NO:125;

a shRNA comprising an effector sequence set forth in SEQ ID NO:126 and an effector complement sequence set forth in SEQ ID NO:127;

a shRNA comprising an effector sequence set forth in SEQ ID NO:128 and an effector complement sequence set forth in SEQ ID NO:129;

a shRNA comprising an effector sequence set forth in SEQ ID NO:130 and an effector complement sequence set forth in SEQ ID NO:131; and a shRNA comprising an effector sequence set forth in SEQ ID NO:132 and an effector complement sequence set forth in SEQ ID NO:133.

According to any example in which a nucleic acid of the disclosure encodes a shRNA, the shRNA may comprise a stem loop sequence positioned between the effector sequence and the effector complement sequence. Suitable loop sequences may be selected from those known in the art. Alternatively, suitable stem loops may be developed de novo. In one example, a nucleic acid of the plurality described herein encoding a shRNA may comprise a DNA sequence encoding a stem loop positioned between the DNA sequences encoding the effector sequence and the effector complement sequence. For example, a shRNA encoded by a nucleic acid of the disclosure may comprise a sequence set forth in any one of SEQ ID NOs:78-93. Thus, a nucleic acid in the plurality of nucleic acids described herein may comprise or consist of a DNA sequence set forth in in any one of SEQ ID NOs:94-109.

A plurality of nucleic acids in accordance with the present disclosure may comprise up to 10 nucleic acids, each encoding a shmiR as described herein, such as two nucleic acids or three nucleic acids or four nucleic acids or five nucleic acids or six nucleic acids or seven nucleic acids or eight nucleic acids or nine nucleic acids or ten nucleic acids. In one example, the plurality of nucleic acids comprises two nucleic acids of the disclosure, each encoding a shmiR as described herein. In another example, the plurality of nucleic acids comprises three nucleic acids of the disclosure, each encoding a shmiR as described herein. In one example, the plurality of nucleic acids comprises four nucleic acids of the disclosure, each encoding a shmiR as described herein. In one example, the plurality of nucleic acids comprises five nucleic acids of the disclosure, each encoding a shmiR as described herein. In one example, the plurality of nucleic acids comprises six nucleic acids of the disclosure, each encoding a shmiR as described herein. In one example, the plurality of nucleic acids comprises seven nucleic acids of the disclosure, each encoding a shmiR as described herein. In one example, the plurality of nucleic acids comprises eight nucleic acids of the disclosure, each encoding a shmiR as described herein. In one example, the plurality of nucleic acids comprises nine nucleic acids of the disclosure, each encoding a shmiR as described herein. In one example, the plurality of RNAs comprises ten nucleic acids of the disclosure, each encoding a shmiR as described herein. In accordance with any of the examples described herein, one or more of the nucleic acids in the plurality may encode a shRNA as described herein.

In accordance with an example in which a plurality of nucleic acids is provided, two or more of the nucleic acids may form separate parts of the same polynucleotide. In another example, two or more of the nucleic acids in the plurality form parts of different polynucleotides, respectively.

The or each nucleic acid in accordance with the present disclosure may comprise, or be in operable linkage with, one or more transcriptional terminator sequences. For example, the or each nucleic acid may comprise a transcriptional terminator sequence at the 3' terminus of the sequence encoding the shmiR or shRNA. Such sequences will depend on the choice of promoter and will be known to a person of skill in the art. For example, where a nucleic acid of the disclosure is in operable linkage with a RNA pol III promoter, a transcriptional terminator sequence may include 'TTTTT' or 'TTTTTT'.

Alternatively, or in addition, the or each nucleic acid in accordance with the present disclosure may comprise, or be in operable linkage with, a transcription initiator sequence. For example, the or each nucleic acid may comprise a transcription initiator sequence at the 5' terminus of the sequence encoding the shmiR or shRNA. Such sequences will be known to a person of skill in the art, but may include 'G'.

Alternatively, or in addition, the or each nucleic acid in accordance with the present disclosure may comprise one or more restriction sites e.g., to facilitate cloning of the nucleic acid(s) into cloning or expression vectors. For example, the nucleic acids described herein may include a restriction site upstream and/or downstream of the sequence encoding a shmiR or shRNA of the disclosure. Suitable restriction enzyme recognition sequences will be known to a person of skill in the art. However, in one example, the nucleic acid(s) of the disclosure may include a BamH1 restriction site (GGATCC) at the 5' terminus i.e., upstream of the sequence encoding the shmiR or shRNA, and a EcoR1 restriction site (GAATTC) at the 3' terminus i.e., downstream of the sequence encoding the shmiR or shRNA.

A nucleic acid in accordance with the present disclosure may also be provided in the form of, or be comprised in, a DNA-directed RNA interference (ddRNAi) construct which is capable of expressing one or more shmiRs which is/are encoded by the nucleic acid(s) of the present disclosure. In this regard, one or more ddRNAi constructs comprising a nucleic acid of the disclosure is also provided.

In another example, a plurality of ddRNAi constructs, each comprising a nucleic acid encoding a shmiR as described herein is provided, wherein:

(a) at least one of the plurality of ddRNAi constructs comprises a first nucleic acid of the plurality of nucleic acids as described herein; and (b) at least one of the plurality of ddRNAi constructs comprises a second nucleic acid of the plurality of nucleic acids described herein; and wherein the first and second nucleic acids encode shmiRs that are different to one another.

The plurality of ddRNAi constructs described herein may comprise up to 10 ddRNAi constructs, each comprising one or more nucleic acids encoding a shmiR as described herein, such as two ddRNAi constructs or three ddRNAi constructs or four ddRNAi constructs or five ddRNAi constructs or six ddRNAi constructs or seven ddRNAi constructs or eight ddRNAi constructs or nine ddRNAi constructs or ten ddRNAi constructs of the disclosure.

In yet another example, a ddRNAi construct of the disclosure comprises a plurality of nucleic acids as described herein, such that the ddRNAi construct encodes a plurality of shmiRs targeting HBV, wherein each of the shmiRs are different to one another.

In one example, the ddRNAi construct comprises at least two nucleic acids of the disclosure, such that the ddRNAi construct encodes at least two shmiRs targeting HBV, each of which is different to one another.

An exemplary ddRNAi construct comprising at least two nucleic acids of the disclosure may comprise:
(a) a nucleic acid encoding a shmiR comprising or consisting of the sequence set forth in SEQ ID NO:48; and
(b) a nucleic acid encoding a shmiR comprising or consisting of the sequence set forth in SEQ ID NO:54.

In another example, the ddRNAi construct of the disclosure comprises at least three nucleic acids described herein, such that the ddRNAi construct encodes at least three shmiRs targeting HBV, each of which is different to one another.

One example of a ddRNAi construct of the disclosure comprises:
(a) a nucleic acid encoding a shmiR comprising or consisting of the sequence set forth in SEQ ID NO:48:
(b) a nucleic acid comprising a DNA sequence encoding a shmiR or shRNA as described herein; and
(c) a nucleic acid encoding a shmiR comprising or consisting of the sequence set forth in SEQ ID NO:54;
wherein the nucleic acid at (b) encodes a shmiR or shRNA having an effector sequence which is different to that of the shmiRs encoded by the nucleic acid at (a) and (c).

In one example, a ddRNAi construct of the disclosure may comprise, preferably in a 5' to 3' direction:
(a) a nucleic acid encoding a shmiR comprising or consisting of the sequence set forth in SEQ ID NO:48:
(b) a nucleic acid encoding a shmiR comprising or consisting of the sequence set forth in SEQ ID NO:57; and
(c) a nucleic acid encoding a shmiR comprising or consisting of the sequence set forth in SEQ ID NO:54.

For example, a ddRNAi construct of the disclosure may comprise, preferably in a 5' to 3' direction:
(a) a nucleic acid comprising or consisting of the sequence set forth in SEQ ID NO:64:
(b) a nucleic acid comprising or consisting of the sequence set forth in SEQ ID NO:73; and
(c) a nucleic acid comprising or consisting of the sequence set forth in SEQ ID NO:70.

In one example, a ddRNAi construct of the disclosure may comprise, preferably in a 5' to 3' direction:
(a) a nucleic acid encoding a shmiR comprising or consisting of the sequence set forth in SEQ ID NO:48:
(b) a nucleic acid encoding a shmiR comprising or consisting of the sequence set forth in SEQ ID NO:49; and
(c) a nucleic acid encoding a shmiR comprising or consisting of the sequence set forth in SEQ ID NO:54.

For example, a ddRNAi construct of the disclosure may comprise, preferably in a 5' to 3' direction:
(a) a nucleic acid comprising or consisting of the sequence set forth in SEQ ID NO:64:
(b) a nucleic acid comprising or consisting of the sequence set forth in SEQ ID NO:65; and
(c) a nucleic acid comprising or consisting of the sequence set forth in SEQ ID NO:70.

According to another example of a ddRNAi construct of the disclosure which encodings three shmiRs, the ddRNAi construct comprises:
(a) a nucleic acid encoding a shmiR comprising or consisting of the sequence set forth in SEQ ID NO:48:
(b) a nucleic acid encoding a shmiR comprising or consisting of the sequence set forth in SEQ ID NO:137; and
(c) a nucleic acid encoding a shmiR comprising or consisting of the sequence set forth in SEQ ID NO:141. In one example, (a) to (c) are provided in a 5' to 3' direction in the ddRNAi construct.

For example, a ddRNAi construct of the disclosure may comprise, preferably in a 5' to 3' direction:
(a) a nucleic acid comprising or consisting of the sequence set forth in SEQ ID NO:64:
(b) a nucleic acid comprising or consisting of the sequence set forth in SEQ ID NO:149; and
(c) a nucleic acid comprising or consisting of the sequence set forth in SEQ ID NO:153.

In yet another example, a ddRNAi construct of the disclosure may comprise at least one nucleic acid encoding a shmiR as described herein and at least one nucleic acid encoding a shRNA targeting HBV as described herein, wherein the shmiR and shRNA encoded by the ddRNAi construct comprise different effector sequences. In accordance with this example, a ddRNAi construct of the disclosure may comprise, preferably in a 5' to 3' direction:
(a) a nucleic acid encoding a shmiR comprising or consisting of the sequence set forth in SEQ ID NO:48;
(b) a nucleic acid encoding a shRNA comprising an effector sequence set forth in SEQ ID NO: 39 and an effector complement sequence set forth in SEQ ID NO: 40; and
(c) a nucleic acid encoding a shmiR comprising or consisting of the sequence set forth in SEQ ID NO:54.

For example, a ddRNAi construct of the disclosure may comprise, preferably in a 5' to 3' direction:
(a) a nucleic acid encoding a shmiR comprising or consisting of the sequence set forth in SEQ ID NO:48:
(b) a nucleic acid encoding a shRNA consisting of the sequence set forth in SEQ ID NO: 92; and
(c) a nucleic acid encoding a shmiR comprising or consisting of the sequence set forth in SEQ ID NO:54.

For example, a ddRNAi construct of the disclosure may comprise, preferably in a 5' to 3' direction:
(a) a nucleic acid comprising or consisting of the sequence set forth in SEQ ID NO:64:
(b) a nucleic acid comprising or consisting of the sequence set forth in SEQ ID NO:108; and
(c) a nucleic acid comprising or consisting of the sequence set forth in SEQ ID NO:70.

In one example, a ddRNAi construct as described herein comprises a single promoter which is operably-linked to the or each nucleic acid encoding a shmiR or shRNA of the disclosure.

In another example, each nucleic acid encoding a shmiR or shRNA of the disclosure is operably-linked to a separate promoter.

For example, the promoter(s) is(are) positioned upstream of the respective nucleic acid(s) encoding the shmiR(s) or shRNA(s). In a ddRNAi construct comprising multiple promoters, the promoters may be the same or different. Exemplary promoters are RNA pol III promoters, such as for example, the U6 and H1 promoters. Exemplary U6 promoters are U6-1, U6-8 and U6-9 promoters.

In one example, a ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:73; and
(c) U6-8 promoter upstream of a nucleic acid comprising or consisting of the sequence set forth in SEQ ID NO:70.

In another example, a ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:65; and (c) U6-8 promoter upstream of a nucleic acid comprising or consisting of the sequence set forth in SEQ ID NO:70.

In another example, a ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:149; and
(c) U6-8 promoter upstream of a nucleic acid comprising or consisting of the sequence set forth in SEQ ID NO:153.

The present disclosure also provides an expression vector, comprising a ddRNAi construct of the disclosure.

The present disclosure also provides plurality of expression vectors each of which comprises a ddRNAi construct of the disclosure. For example, one or more of the plurality of expression vectors comprises a plurality of ddRNAi constructs as disclosed herein. In another example, each of the plurality of expression vectors comprises a plurality of ddRNAi constructs as disclosed herein. In a further example, each of the plurality of expression vectors comprises a single ddRNAi construct as described herein. In any of the foregoing ways in this paragraph, the plurality of expression vectors may collectively express a plurality of shmiRs in accordance with the present disclosure.

In one example, the or each expression vector is a plasmid or a minicircle.

In one example, the plasmid or minicircle or expression vector or ddRNAi construct is complexed with a cationic DNA binding polymer.

In another example, the or each expression vector is a viral vector. For example, the viral vector is selected from the group consisting of an adeno-associated viral (AAV) vector, a retroviral vector, an adenoviral vector (AdV) and a lentiviral (LV) vector.

The present disclosure also provides a composition comprising a ddRNAi construct and/or a plurality of ddRNAi constructs and/or expression vector and/or a plurality of expression vectors as described herein. In one example, the composition may also comprise one or more pharmaceutically acceptable carriers and/or diluents. In one example, the composition may further comprise another therapeutic agent known for treating HBV infection i.e., as an adjunctive therapy. For example, the other therapeutic agent known for treating HBV infection may be selected from entecavir, tenofovir, lamivudine, adefovir and/or pegylated interferon.

The present disclosure also provides a method of treating HBV infection in a subject, the method comprising administering a therapeutically effective amount of a nucleic acid, a plurality of nucleic acids, a ddRNAi construct, a plurality of ddRNAi constructs, an expression vector, a plurality of expression vectors and/or composition described herein to the subject.

The present disclosure also provides a method of reducing HBV viral load in a subject infected with HBV, the method comprising administering a therapeutically effective amount of a nucleic acid, a plurality of nucleic acids, a ddRNAi construct, a plurality of ddRNAi constructs, an expression vector, a plurality of expression vectors and/or composition described herein to the subject.

The present disclosure also provides a method of reducing severity of one or more symptoms associated with HBV infection in a subject suffering therefrom, the method comprising administering to the subject a therapeutically effective amount of a nucleic acid, a plurality of nucleic acids, a ddRNAi construct, a plurality of ddRNAi constructs, an expression vector, a plurality of expression vectors and/or composition described herein to the subject.

The present disclosure also provides a method of reducing the infectivity of HBV in a subject infected therewith, the method comprising administering to the subject a therapeutically effective amount of a nucleic acid, a plurality of nucleic acids, a ddRNAi construct, a plurality of ddRNAi constructs, an expression vector, a plurality of expression vectors and/or composition described herein to the subject.

The present disclosure also provides a method for reducing the risk of a subject suffering from a HBV infection developing chronic hepatic insufficiency, cirrhosis, and/or hepatocellular carcinoma, the method comprising administering to the subject a therapeutically effective amount of a nucleic acid, a plurality of nucleic acids, a ddRNAi construct, a plurality of ddRNAi constructs, an expression vector, a plurality of expression vectors and/or composition described herein to the subject.

In accordance with any method described herein, in one example, the subject is suffering from acute HBV infection. Alternatively, in one example, the subject is suffering from chronic HBV infection.

In one example, the methods described herein comprise inhibiting or reducing expression of one or more transcripts encoded by the HBV genome in the subject.

In one example, the subject to which the nucleic acid, a plurality of nucleic acids, a ddRNAi construct, a plurality of ddRNAi constructs, an expression vector, a plurality of expression vectors and/or composition of the disclosure is/are administered has already received treatment with another therapeutic agent for treating HBV infection. For example, the subject and/or the HBV is refractory or resistant to treatment with the other agent known for treating HBV infection.

In another example, the nucleic acid, a plurality of nucleic acids, a ddRNAi construct, a plurality of ddRNAi constructs, an expression vector, a plurality of expression vectors and/or composition of the disclosure is administered in combination with another therapeutic agent known for treating HBV infection i.e., as an adjunctive therapy. For example, the other therapeutic agent known for treating HBV infection may be selected from entecavir, tenofovir, lamivudine, adefovir and/or pegylated interferon. The other therapeutic agent known for treating HBV infection and the nucleic acid, a plurality of nucleic acids, a ddRNAi construct, a plurality of ddRNAi constructs, an expression vector, a plurality of expression vectors and/or composition of the disclosure may be administered separately or together. In accordance with one example in which administration is separate, the other therapeutic agent known for treating HBV infection may be administered simultaneously with the administration of the nucleic acid, a plurality of nucleic acids, a ddRNAi construct, a plurality of ddRNAi constructs, an expression vector, a plurality of expression vectors and/or composition of the disclosure. In accordance with another example in which administration is separate, the other therapeutic agent known for treating HBV infection may be administered consecutively with the administration of the nucleic acid, a plurality of nucleic acids, a ddRNAi construct, a plurality of ddRNAi constructs, an expression vector, a plurality of expression vectors and/or composition of the disclosure.

In one example, a composition of the present disclosure is provided in a kit. For example, a composition of the present disclosure is packaged together with one or more other therapeutic agents known for treating HBV infections. Such other therapeutic agents will be known to a person of skill in the art. For example, the other therapeutic agent known for treating HBV infection may be selected from entecavir, tenofovir, lamivudine, adefovir and/or pegylated interferon. In another example, the composition is packaged with instruction for use in a method of the disclosure.

The present disclosure also provides use of a nucleic acid, a plurality of nucleic acids, a ddRNAi construct, a plurality of ddRNAi constructs, an expression vector, a plurality of expression vectors and/or composition described herein in the preparation of a medicament, e.g., for treating HBV infection in a subject and/or in a method disclosed herein. In one example, the subject is suffering from acute HBV infection. In an alternative example, the subject is suffering from chronic HBV infection.

The present disclosure also provides a nucleic acid, a plurality of nucleic acids, a ddRNAi construct, a plurality of ddRNAi constructs, an expression vector, a plurality of expression vectors and/or composition described herein for use in therapy. For example, the nucleic acid, a plurality of nucleic acids, a ddRNAi construct, a plurality of ddRNAi constructs, an expression vector, a plurality of expression vectors and/or composition may be for use in treating HBV infection in a subject and/or in a method disclosed herein. The subject may be suffering from acute HBV infection. In an alternative example, the subject may be suffering from chronic HBV infection.

Treatment of HBV in accordance with any example described herein, may comprise one or more of reducing HBV viral load in the subject, reducing severity of symptoms associated with HBV infection and/or reducing the infectivity of HBV in a subject. In one example, the medicament will reduce HBV gene transcription products in the subject to which the medicament is administered.

KEY TO THE SEQUENCE LISTING

Figure 1A:
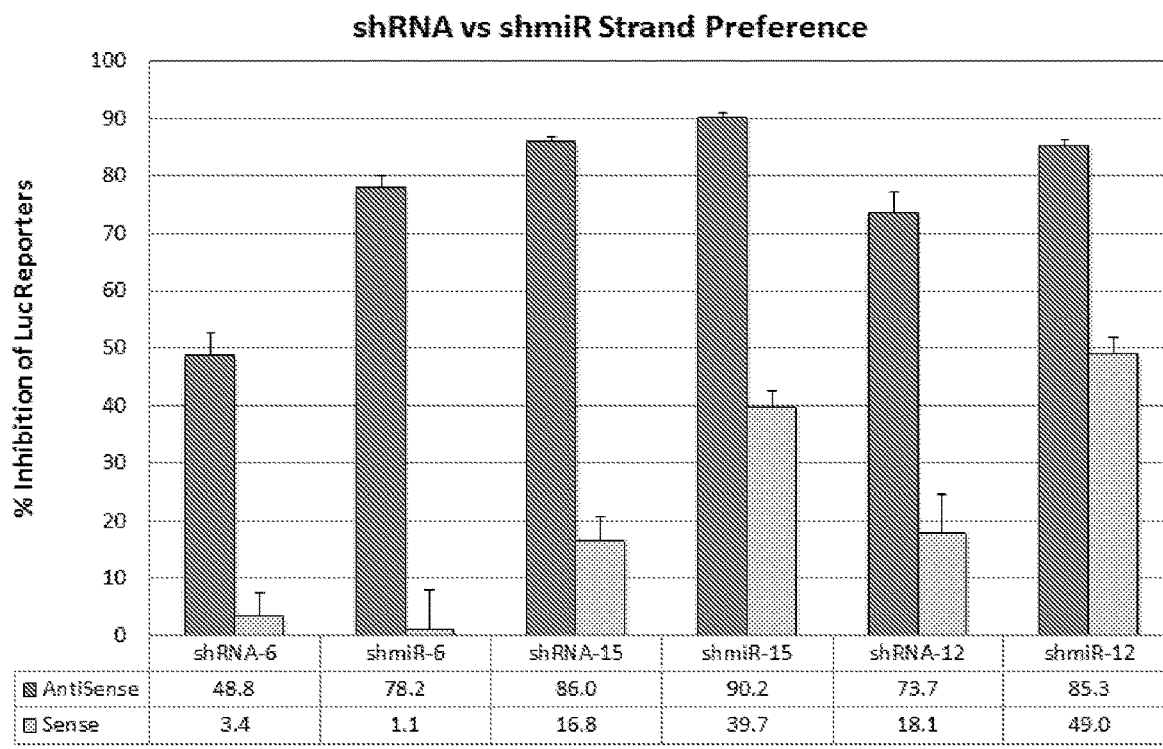
FIG. 1 illustrates the inhibitory activity of shmiRs designated shmiR-6, shmiR-15 and shmiR-12 relative to their shRNA counterparts (shRNA-6, shRNA-15 and shRNA-12 respectively) in Luciferase reporter assays: (A) illustrates sense and antisense strand preference inhibitory activity for shmiRs designated shmiR-6, shmiR-15 and shmiR-12 relative to their shRNA counterparts (shRNA-6, shRNA-15 and shRNA-12 respectively) in the Luciferase reporter assay; (B)-(D) illustrate and compare the abilities of shmiR-6, shmiR-15 and shmiR-12 respectively to inhibit luciferase protein expression in a Luciferase reporter assay system in a dose-dependent manner relative to their shRNA counterparts (shRNA-6, shRNA-15 and shRNA-12 respectively) at equivalent doses.
Figure 1B:
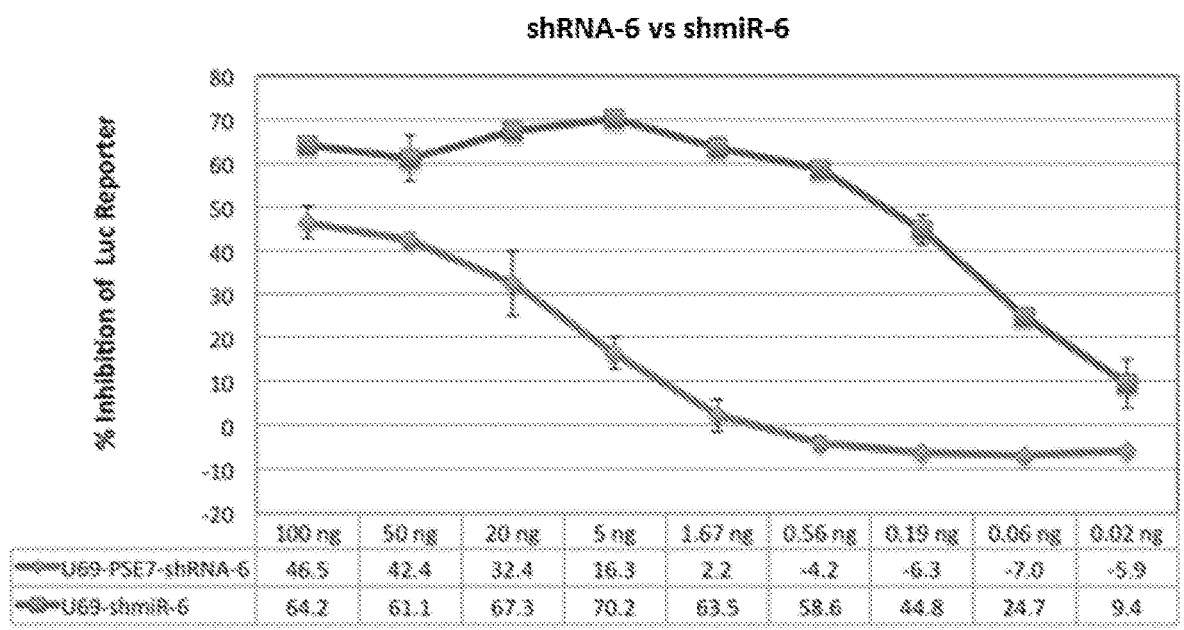
Figure 1C:
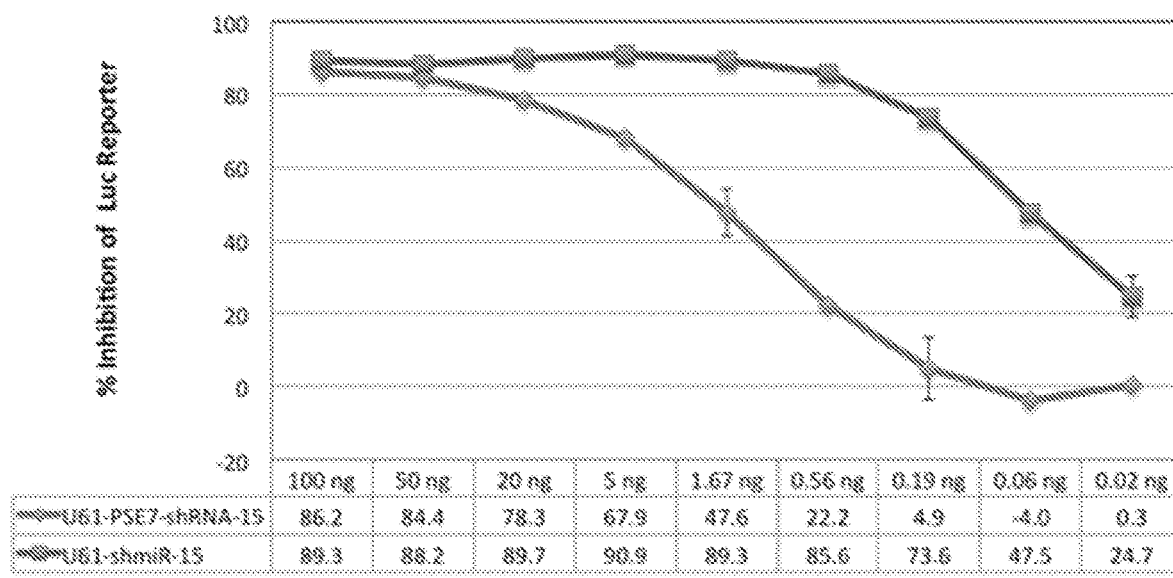
Figure 1D:
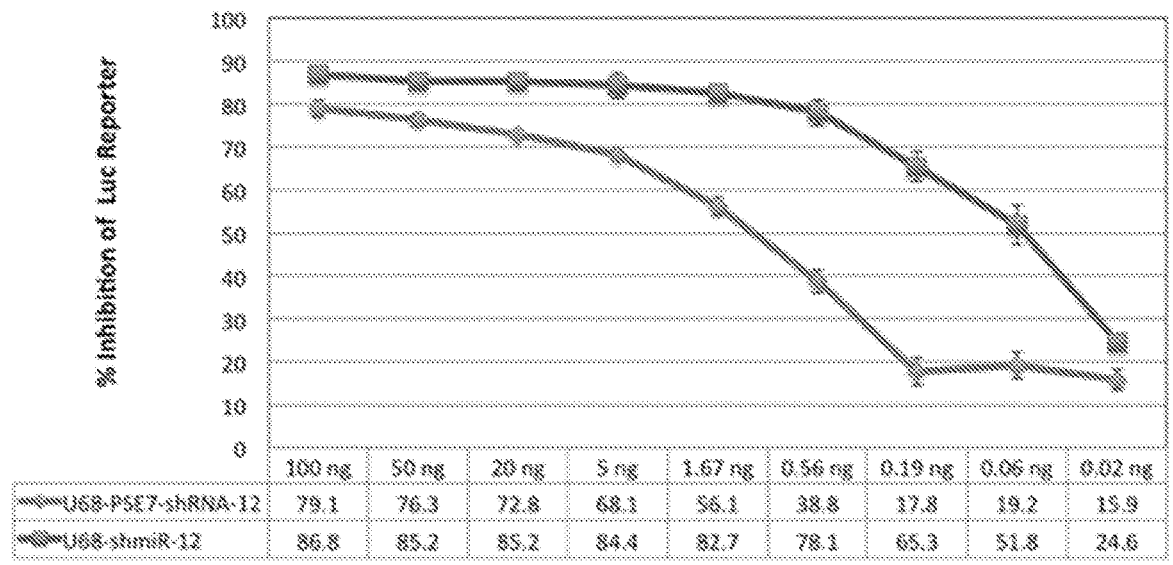

SEQ ID NO: 1: RNA transcript for target Region 1 within HBV genome.
SEQ ID NO: 2: RNA transcript for target Region 2 within HBV genome.
SEQ ID NO: 3: RNA transcript for target Region 3 within HBV genome.
SEQ ID NO: 4: RNA transcript for target Region 4 within HBV genome.
SEQ ID NO: 5: RNA transcript for target Region 5 within HBV genome.
SEQ ID NO: 6: RNA transcript for target Region 6 within HBV genome.
SEQ ID NO: 7: RNA transcript for target Region 7 within HBV genome.
SEQ ID NO: 8: RNA transcript for target Region 8 within HBV genome.
SEQ ID NO: 9: RNA transcript for target Region 9 within HBV genome.
SEQ ID NO: 10: RNA transcript for target Region 10 within HBV genome.
SEQ ID NO: 11: RNA effector sequence for shmiR-1.
SEQ ID NO: 12: RNA effector complement sequence for shmiR-1.
SEQ ID NO: 13: RNA effector sequence for shmiR-2.
SEQ ID NO: 14: RNA effector complement sequence for shmiR-2.
SEQ ID NO: 15: RNA effector sequence for shmiR-3.
SEQ ID NO: 16: RNA effector complement sequence for shmiR-3.
SEQ ID NO: 17: RNA effector sequence for shmiR-4.
SEQ ID NO: 18: RNA effector complement sequence for shmiR-4.
SEQ ID NO: 19: RNA effector sequence for shmiR-5.
SEQ ID NO: 20: RNA effector complement sequence for shmiR-5.
SEQ ID NO: 21: RNA effector sequence for shmiR-6.
SEQ ID NO: 22: RNA effector complement sequence for shmiR-6.
SEQ ID NO: 23: RNA effector sequence for shmiR-7.
SEQ ID NO: 24: RNA effector complement sequence for shmiR-7.
SEQ ID NO: 25: RNA effector sequence for shmiR-8.
SEQ ID NO: 26: RNA effector complement sequence for shmiR-8.
SEQ ID NO: 27: RNA effector sequence for shmiR-9.
SEQ ID NO: 28: RNA effector complement sequence for shmiR-9.
SEQ ID NO: 29: RNA effector sequence for shmiR-10.
SEQ ID NO: 30: RNA effector complement sequence for shmiR-10.
SEQ ID NO: 31: RNA effector sequence for shmiR-11.
SEQ ID NO: 32: RNA effector complement sequence for shmiR-11.
SEQ ID NO: 33: RNA effector sequence for shmiR-12
SEQ ID NO: 34: RNA effector complement sequence for shmiR-12.
SEQ ID NO: 35: RNA effector sequence for shmiR-13.
SEQ ID NO: 36: RNA effector complement sequence for shmiR-13.
SEQ ID NO: 37: RNA effector sequence for shmiR-14.
SEQ ID NO: 38: RNA effector complement sequence for shmiR-14.
SEQ ID NO: 39: RNA effector sequence for shmiR-15.
SEQ ID NO: 40: RNA effector complement sequence for shmiR-15.
SEQ ID NO: 41: RNA effector sequence for s shmiR-16.
SEQ ID NO: 42: RNA effector complement sequence for shmiR-16.
SEQ ID NO: 43: RNA sequence for shmiR-1.
SEQ ID NO: 44: RNA sequence for shmiR-2.
SEQ ID NO: 45: RNA sequence for shmiR-3.
SEQ ID NO: 46: RNA sequence for shmiR-4.
SEQ ID NO: 47: RNA sequence for shmiR-5.
SEQ ID NO: 48: RNA sequence for shmiR-6.
SEQ ID NO: 49: RNA sequence for shmiR-7.
SEQ ID NO: 50: RNA sequence for shmiR-8.
SEQ ID NO: 51: RNA sequence for shmiR-9.
SEQ ID NO: 52: RNA sequence for shmiR-10.
SEQ ID NO: 53: RNA sequence for shmiR-11.
SEQ ID NO: 54: RNA sequence for shmiR-12.
SEQ ID NO: 55: RNA sequence for shmiR-13.
SEQ ID NO: 56: RNA sequence for shmiR-14.
SEQ ID NO: 57: RNA sequence for shmiR-15.
SEQ ID NO: 58: RNA sequence for shmiR-16.
SEQ ID NO: 59: DNA sequence coding for shmiR-1.
SEQ ID NO: 60: DNA sequence coding for shmiR-2.
SEQ ID NO: 61: DNA sequence coding for shmiR-3.
SEQ ID NO: 62: DNA sequence coding for shmiR-4.
SEQ ID NO: 63: DNA sequence coding for shmiR-5.
SEQ ID NO: 64: DNA sequence coding for shmiR-6.
SEQ ID NO: 65: DNA sequence coding for shmiR-7.
SEQ ID NO: 66: DNA sequence coding for shmiR-8.
SEQ ID NO: 67: DNA sequence coding for shmiR-9.
SEQ ID NO: 68: DNA sequence coding for shmiR-10.
SEQ ID NO: 69: DNA sequence coding for shmiR-11.
SEQ ID NO: 70: DNA sequence coding for shmiR-12.
SEQ ID NO: 71: DNA sequence coding for shmiR-13.
SEQ ID NO: 72: DNA sequence coding for shmiR-14.
SEQ ID NO: 73: DNA sequence coding for shmiR-15.
SEQ ID NO: 74: DNA sequence coding for shmiR-16.
SEQ ID NO: 75: stemloop RNA sequence for shmiRs
SEQ ID NO: 76: 5' flanking sequence of pri-miR-30a backbone.
SEQ ID NO: 77: 3' flanking sequence of pri-miR-30a backbone.
SEQ ID NO: 78: RNA sequence for shRNA designated shRNA-1.
SEQ ID NO: 79: RNA sequence for shRNA designated shRNA-2.
SEQ ID NO: 80: RNA sequence for shRNA designated shRNA-3.

SEQ ID NO: 81: RNA sequence for shRNA designated shRNA-4.
SEQ ID NO: 82: RNA sequence for shRNA designated shRNA-5.
SEQ ID NO: 83: RNA sequence for shRNA designated shRNA-6.
SEQ ID NO: 84: RNA sequence for shRNA designated shRNA-7.
SEQ ID NO: 85: RNA sequence for shRNA designated shRNA-8.
SEQ ID NO: 86: RNA sequence for shRNA designated shRNA-9.
SEQ ID NO: 87: RNA sequence for shRNA designated shRNA-10.
SEQ ID NO: 88: RNA sequence for shRNA designated shRNA-11.
SEQ ID NO: 89: RNA sequence for shRNA designated shRNA-12.
SEQ ID NO: 90: RNA sequence for shRNA designated shRNA-13.
SEQ ID NO: 91: RNA sequence for shRNA designated shRNA-14.
SEQ ID NO: 92: RNA sequence for shRNA designated shRNA-15.
SEQ ID NO: 93: RNA sequence for shRNA designated shRNA-16.
SEQ ID NO: 94: DNA sequence coding for shRNA designated shRNA-1.
SEQ ID NO: 95: DNA sequence coding for shRNA designated shRNA-2.
SEQ ID NO: 96: DNA sequence coding for shRNA designated shRNA-3.
SEQ ID NO: 97: DNA sequence coding for shRNA designated shRNA-4.
SEQ ID NO: 98: DNA sequence coding for shRNA designated shRNA-5.
SEQ ID NO: 99: DNA sequence coding for shRNA designated shRNA-6.
SEQ ID NO: 100: DNA sequence coding for shRNA designated shRNA-7.
SEQ ID NO: 101: DNA sequence coding for shRNA designated shRNA-8.
SEQ ID NO: 102: DNA sequence coding for shRNA designated shRNA-9.
SEQ ID NO: 103: DNA sequence coding for shRNA designated shRNA-10.
SEQ ID NO: 104: DNA sequence coding for shRNA designated shRNA-11.
SEQ ID NO: 105: DNA sequence coding for shRNA designated shRNA-12.
SEQ ID NO: 106: DNA sequence coding for shRNA designated shRNA-13.
SEQ ID NO: 107: DNA sequence coding for shRNA designated shRNA-14.
SEQ ID NO: 108: DNA sequence coding for shRNA designated shRNA-15.
SEQ ID NO: 109: DNA sequence coding for shRNA designated shRNA-16.
SEQ ID NO: 110: RNA effector sequence for shmiR-17.
SEQ ID NO: 111: RNA effector complement sequence for shmiR-17.
SEQ ID NO: 112: RNA effector sequence for shmiR-18.
SEQ ID NO: 113: RNA effector complement sequence for shmiR-18.
SEQ ID NO: 114: RNA effector sequence for shmiR-19.
SEQ ID NO: 115: RNA effector complement sequence for shmiR-19.
SEQ ID NO: 116: RNA effector sequence for shmiR-20.
SEQ ID NO: 117: RNA effector complement sequence for shmiR-20.
SEQ ID NO: 118: RNA effector sequence for shmiR-21.
SEQ ID NO: 119: RNA effector complement sequence for shmiR-21.
SEQ ID NO: 120: RNA effector sequence for shmiR-22.
SEQ ID NO: 121: RNA effector complement sequence for shmiR-22.
SEQ ID NO: 122: RNA effector sequence for shmiR-23.
SEQ ID NO: 123: RNA effector complement sequence for shmiR-23.
SEQ ID NO: 124: RNA effector sequence for shmiR-24.
SEQ ID NO: 125: RNA effector complement sequence for shmiR-24.
SEQ ID NO: 126: RNA effector sequence for shmiR-25.
SEQ ID NO: 127: RNA effector complement sequence for shmiR-25.
SEQ ID NO: 128: RNA effector sequence for shmiR-26.
SEQ ID NO: 129: RNA effector complement sequence for shmiR-26.
SEQ ID NO: 130: RNA effector sequence for shmiR-27.
SEQ ID NO: 131: RNA effector complement sequence for shmiR-27.
SEQ ID NO: 132: RNA effector sequence for shmiR-28.
SEQ ID NO: 133: RNA effector complement sequence for shmiR-28.
SEQ ID NO: 134: RNA sequence for shmiR-17.
SEQ ID NO: 135: RNA sequence for shmiR-18.
SEQ ID NO: 136: RNA sequence for shmiR-19.
SEQ ID NO: 137: RNA sequence for shmiR-20.
SEQ ID NO: 138: RNA sequence for shmiR-21.
SEQ ID NO: 139: RNA sequence for shmiR-22.
SEQ ID NO: 140: RNA sequence for shmiR-23.
SEQ ID NO: 141: RNA sequence for shmiR-24.
SEQ ID NO: 142: RNA sequence for shmiR-25.
SEQ ID NO: 143: RNA sequence for shmiR-26.
SEQ ID NO: 144: RNA sequence for shmiR-27.
SEQ ID NO: 145: RNA sequence for shmiR-28.
SEQ ID NO: 146: DNA sequence coding for shmiR-17.
SEQ ID NO: 147: DNA sequence coding for shmiR-18.
SEQ ID NO: 148: DNA sequence coding for shmiR-19.
SEQ ID NO: 149: DNA sequence coding for shmiR-20.
SEQ ID NO: 150: DNA sequence coding for shmiR-21.
SEQ ID NO: 151: DNA sequence coding for shmiR-22.
SEQ ID NO: 152: DNA sequence coding for shmiR-23.
SEQ ID NO: 153: DNA sequence coding for shmiR-24.
SEQ ID NO: 154: DNA sequence coding for shmiR-25.
SEQ ID NO: 155: DNA sequence coding for shmiR-26.
SEQ ID NO: 156: DNA sequence coding for shmiR-27.
SEQ ID NO: 157: DNA sequence coding for shmiR-28.
SEQ ID NO: 158: DNA sequence for HBV forward primer.
SEQ ID NO: 159: DNA sequence for HBV reverse primer.
SEQ ID NO: 160: DNA sequence for HBV Taqman probe.
SEQ ID NO: 161: DNA sequence for HBV cccDNA forward primer.
SEQ ID NO: 162: DNA sequence for HBV cccDNA reverse primer.
SEQ ID NO: 163: DNA sequence for HBV cccDNA Taqman probe.
SEQ ID NO: 164: DNA sequence coding for shRNA-6, including flanking sequence.
SEQ ID NO: 165: DNA sequence corresponding to shRNA-6 effector species 1.
SEQ ID NO: 166: DNA sequence corresponding to shRNA-6 effector species 2.

SEQ ID NO: 167: DNA sequence corresponding to shRNA-6 effector species 3.
SEQ ID NO: 168: DNA sequence corresponding to shRNA-6 effector species 4.
SEQ ID NO: 169: DNA sequence corresponding to shRNA-6 effector species 5.
SEQ ID NO: 170: DNA sequence corresponding to shRNA-6 effector species 6.
SEQ ID NO: 171: DNA sequence corresponding to shRNA-6 effector species 7.
SEQ ID NO: 172: DNA sequence corresponding to shRNA-6 effector species 8.
SEQ ID NO: 173: DNA sequence corresponding to shRNA-6 effector species 9.
SEQ ID NO: 174: DNA sequence corresponding to shRNA-6 effector species 10.
SEQ ID NO: 175: DNA sequence corresponding to shRNA-6 effector species 11.
SEQ ID NO: 176: DNA sequence coding for shmiR-6, including flanking sequence of miRNA backbone.
SEQ ID NO: 177: DNA sequence corresponding to shmiR-6 effector species 1.
SEQ ID NO: 178: DNA sequence corresponding to shmiR-6 effector species 2.
SEQ ID NO: 179: DNA sequence corresponding to shmiR-6 effector species 3.
SEQ ID NO: 180: DNA sequence corresponding to shmiR-6 effector species 4.
SEQ ID NO: 181: DNA sequence corresponding to shmiR-6 effector species 5.
SEQ ID NO: 182: DNA sequence coding for shRNA-15, including flanking sequence.
SEQ ID NO: 183: DNA sequence corresponding to shRNA-15 effector species 1.
SEQ ID NO: 184: DNA sequence corresponding to shRNA-15 effector species 2.
SEQ ID NO: 185: DNA sequence corresponding to shRNA-15 effector species 3.
SEQ ID NO: 186: DNA sequence corresponding to shRNA-15 effector species 4.
SEQ ID NO: 187: DNA sequence corresponding to shRNA-15 effector species 5.
SEQ ID NO: 188: DNA sequence corresponding to shRNA-15 effector species 6.
SEQ ID NO: 189: DNA sequence corresponding to shRNA-15 effector species 7.
SEQ ID NO: 190: DNA sequence corresponding to shRNA-15 effector species 8.
SEQ ID NO: 191: DNA sequence corresponding to shRNA-15 effector species 9.
SEQ ID NO: 192: DNA sequence corresponding to shRNA-15 effector species 10.
SEQ ID NO: 193: DNA sequence corresponding to shRNA-15 effector species 11.
SEQ ID NO: 194: DNA sequence corresponding to shRNA-15 effector species 12.
SEQ ID NO: 195: DNA sequence corresponding to shRNA-15 effector species 13.
SEQ ID NO: 196: DNA sequence corresponding to shRNA-15 effector species 14.
SEQ ID NO: 197: DNA sequence corresponding to shRNA-15 effector species 15.
SEQ ID NO: 198: DNA sequence corresponding to shRNA-15 effector species 16.
SEQ ID NO: 199: DNA sequence corresponding to shRNA-15 effector species 17.
SEQ ID NO: 200: DNA sequence corresponding to shRNA-15 effector species 18.
SEQ ID NO: 201: DNA sequence corresponding to shRNA-15 effector species 19.
SEQ ID NO: 202: DNA sequence coding for shmiR-15, including flanking sequence of miRNA backbone.
SEQ ID NO: 203: DNA sequence corresponding to shmiR-15 effector species 1.
SEQ ID NO: 204: DNA sequence corresponding to shmiR-15 effector species 2.
SEQ ID NO: 205: DNA sequence corresponding to shmiR-15 effector species 3.
SEQ ID NO: 206: DNA sequence corresponding to shmiR-15 effector species 4.
SEQ ID NO: 207: DNA sequence corresponding to shmiR-15 effector species 5.
SEQ ID NO: 208: DNA sequence corresponding to shmiR-15 effector species 6.
SEQ ID NO: 209: DNA sequence coding for shRNA-12, including flanking sequence.
SEQ ID NO: 210: DNA sequence corresponding to shRNA-12 effector species 1.
SEQ ID NO: 211: DNA sequence corresponding to shRNA-12 effector species 2.
SEQ ID NO: 212: DNA sequence corresponding to shRNA-12 effector species 3.
SEQ ID NO: 213: DNA sequence corresponding to shRNA-12 effector species 4.
SEQ ID NO: 214: DNA sequence corresponding to shRNA-12 effector species 5.
SEQ ID NO: 215: DNA sequence corresponding to shRNA-12 effector species 6.
SEQ ID NO: 216: DNA sequence corresponding to shRNA-12 effector species 7.
SEQ ID NO: 217: DNA sequence corresponding to shRNA-12 effector species 8.
SEQ ID NO: 218: DNA sequence corresponding to shRNA-12 effector species 9.
SEQ ID NO: 219: DNA sequence corresponding to shRNA-12 effector species 10.
SEQ ID NO: 220: DNA sequence corresponding to shRNA-12 effector species 11.
SEQ ID NO: 221: DNA sequence corresponding to shRNA-12 effector species 12.
SEQ ID NO: 222: DNA sequence corresponding to shRNA-12 effector species 13.
SEQ ID NO: 223: DNA sequence corresponding to shRNA-12 effector species 14.
SEQ ID NO: 224: DNA sequence coding for shmiR-12, including flanking sequence of miRNA backbone.
SEQ ID NO: 225: DNA sequence corresponding to shmiR-12 effector species 1.
SEQ ID NO: 226: DNA sequence corresponding to shmiR-12 effector species 2.
SEQ ID NO: 227: DNA sequence corresponding to shmiR-12 effector species 3.
SEQ ID NO: 228: DNA sequence corresponding to shmiR-12 effector species 4.
SEQ ID NO: 229: DNA sequence corresponding to shmiR-12 effector species 5.

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNA interference" or "RNAi" refers generally to RNA-dependent silencing of gene expression initiated by double stranded RNA (dsRNA) molecules in a cell's cytoplasm. The dsRNA molecule reduces or inhibits transcription products of a target nucleic acid sequence, thereby silencing the gene or reducing expression of that gene.

As used herein, the term "double stranded RNA" or "dsRNA" refers to a RNA molecule having a duplex structure and comprising an effector sequence and an effector complement sequence which are of similar length to one another. The effector sequence and the effector complement sequence can be in a single RNA strand or in separate RNA strands. The "effector sequence" (often referred to as a "guide strand") is substantially complementary to a target sequence, which in the present case, is a region of a RNA transcription product of the HBV genome. The "effector sequence" can also be referred to as the "antisense sequence". The "effector complement sequence" will be of sufficient complementary to the effector sequence such that it can anneal to the effector sequence to form a duplex. In this regard, the effector complement sequence will be substantially homologous to a region of target sequence. As will be apparent to the skilled person, the term "effector complement sequence" can also be referred to as the "complement of the effector sequence" or the sense sequence.

As used herein, the term "duplex" refers to regions in two complementary or substantially complementary nucleic acids (e.g., RNAs), or in two complementary or substantially complementary regions of a single-stranded nucleic acid (e.g., RNA), that form base pairs with one another, either by Watson-Crick base pairing or any other manner that allows for a stabilized duplex between the nucleotide sequences that are complementary or substantially complementary. It will be understood by the skilled person that within a duplex region, 100% complementarity is not required; substantial complementarity is allowable. Substantial complementarity includes may include 69% or greater complementarity. For example, a single mismatch in a duplex region consisting of 19 base pairs (i.e., 18 base pairs and one mismatch) results in 94.7% complementarity, rendering the duplex region substantially complementary. In another example, two mismatches in a duplex region consisting of 19 base pairs (i.e., 17 base pairs and two mismatches) results in 89.5% complementarity, rendering the duplex region substantially complementary. In yet another example, three mismatches in a duplex region consisting of 19 base pairs (i.e., 16 base pairs and three mismatches) results in 84.2% complementarity, rendering the duplex region substantially complementary, and so on.

The dsRNA may be provided as a hairpin or stem loop structure, with a duplex region comprised of an effector sequence and effector complement sequence linked by at least 2 nucleotide sequence which is termed a stem loop. When a dsRNA is provided as a hairpin or stem loop structure it can be referred to as a "hairpin RNA" or "short hairpin RNAi agent" or "shRNA".

Other dsRNA molecules provided in, or which give rise to, a hairpin or stem loop structure include primary miRNA transcripts (pri-miRNA) and precursor microRNA (pre-miRNA). Pre-miRNA shRNAs can be naturally produced from pri-miRNA by the action of the enzymes Drosha and Pasha which recognize and release regions of the primary miRNA transcript which form a stem-loop structure. Alternatively, the pri-miRNA transcript can be engineered to replace the natural stem-loop structure with an artificial/recombinant stem-loop structure. That is, an artificial/recombinant stem-loop structure may be inserted or cloned into a pri-miRNA backbone sequence which lacks its natural stem-loop structure. In the case of stemloop sequences engineered to be expressed as part of a pri-miRNA molecule, Drosha and Pasha recognize and release the artificial shRNA. dsRNA molecules produced using this approach are known as "shmiRNAs", "shmiRs" or "microRNA framework shRNAs".

As used herein, the term "complementary" with regard to a sequence refers to a complement of the sequence by Watson-Crick base pairing, whereby guanine (G) pairs with cytosine (C), and adenine (A) pairs with either uracil (U) or thymine (T). A sequence may be complementary to the entire length of another sequence, or it may be complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "substantially complementary" is used to indicate a sufficient degree of complementarity or precise pairing such that stable and specific binding occurs between nucleic acid sequences e.g., between the effector sequence and the effector complement sequence or between the effector sequence and the target sequence. It is understood that the sequence of a nucleic acid need not be 100% complementary to that of its target or complement. The term encompasses a sequence complementary to another sequence with the exception of an overhang. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4 mismatches.

The term "encoded", as used in the context of a shRNA or shmiR of the disclosure, shall be understood to mean a shRNA or shmiR which is capable of being transcribed from a DNA template. Accordingly, a nucleic acid that encodes a shRNA or shmiR of the disclosure will comprise a DNA sequence which serves as a template for transcription of the respective shRNA or shmiR.

The term "DNA-directed RNAi construct" or "ddRNAi construct" refers to a nucleic acid comprising DNA sequence which, when transcribed produces a shRNA or shmiR molecule which elicits RNAi. The ddRNAi construct may comprise a nucleic acid which is transcribed as a single RNA that is capable of self-annealing into a hairpin structure with a duplex region linked by a stem loop of at least 2 nucleotides i.e., shRNA or shmiR, or as a single RNA with multiple shRNAs or shmiRs, or as multiple RNA transcripts each capable of folding as a single shRNA or shmiR respectively. The ddRNAi construct may be within an expression vector i.e., "ddRNAi expression construct", e.g., operably linked to a promoter.

As used herein, the term "operably-linked" or "operable linkage" (or similar) means that a coding nucleic acid sequence is linked to, or in association with, a regulatory sequence, e.g., a promoter, in a manner which facilitates expression of the coding sequence. Regulatory sequences include promoters, enhancers, and other expression control elements that are art-recognized and are selected to direct expression of the coding sequence.

A "vector" will be understood to mean a vehicle for introducing a nucleic acid into a cell. Vectors include, but are not limited to, plasmids, phagemids, viruses, bacteria, and vehicles derived from viral or bacterial sources. A "plasmid" is a circular, double-stranded DNA molecule. A useful type of vector for use in accordance with the present disclosure is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome. As used herein, the term "expression vector" will be understood to mean a vector capable of expressing a RNA molecule of the disclosure.

As used herein, the terms "treating", "treat" or "treatment" and variations thereof, refer to clinical intervention designed to alter the natural course of the individual or cell being treated during the course of clinical pathology. Desirable effects of treatment include decreasing the rate of disease progression, ameliorating or palliating the disease state, and remission or improved prognosis. It follows that treatment of HBV infection includes reducing HBV viral load in a subject infected with HBV, reducing severity of symptoms associated with HBV infection, and reducing the infectivity of HBV in a subject. An individual is successfully "treated", for example, if one or more of the above treatment outcomes is achieved.

A "therapeutically effective amount" is at least the minimum concentration or amount required to effect a measurable improvement of a particular disease (e.g., a HBV infection). A therapeutically effective amount herein may vary according to factors such as the disease state, age, sex, and weight of the patient, and the ability of the shRNA or shmiR, nucleic acid encoding same, ddRNAi or expression construct to elicit a desired response in the individual. A therapeutically effective amount is also one in which any toxic or detrimental effects of the shRNA or shmiR, nucleic acid encoding same, ddRNAi or expression construct are outweighed by the therapeutically beneficial effects.

As used herein, the "subject" or "patient" can be a human or non-human animal infected with HBV. The "non-human animal" may be a primate, livestock (e.g. sheep, horses, cattle, pigs, donkeys), companion animal (e.g. pets such as dogs and cats), laboratory test animal (e.g. mice, rabbits, rats, guinea pigs), performance animal (e.g. racehorses, camels, greyhounds) or captive wild animal. In one example, the subject or patient is a mammal. In one example, the subject or patient is a primate. In one example, the subject or patient is a human.

The terms "reduced expression", "reduction in expression" or similar, refer to the absence or an observable decrease in the level of protein and/or mRNA product from the target gene e.g., the HBV pol gene or other HBV gene. The decrease does not have to be absolute, but may be a partial decrease sufficient for there to a detectable or observable change as a result of the RNAi effected by the shmiR encoded by the nucleic acid of the disclosure. The decrease can be measured by determining a decrease in the level of mRNA and/or protein product from a target nucleic acid relative to a cell lacking the shmiR or shRNA, nucleic acid encoding same, ddRNAi construct or expression construct, and may be as little as 1%, 5% or 10%, or may be absolute i.e., 100% inhibition. The effects of the decrease may be determined by examination of the outward properties i.e., quantitative and/or qualitative phenotype of the cell or organism, and may also include an assessment of the viral load following administration of a ddRNAi construct of the disclosure.

Agents for RNAi

In one example, the present disclosure provides a nucleic acid comprising a DNA sequence which encodes a short hairpin micro-RNA (shmiR), said shmiR comprising:
- an effector sequence of at least 17 nucleotides in length;
- an effector complement sequence;
- a stemloop sequence; and
- primary micro RNA (pri-miRNA) backbone;

wherein the effector sequence is substantially complementary to a RNA transcript set forth in any one of SEQ ID NOs: 1-10, 38, 40, 42, 111, 113, 115, 117, 119, 121, 123, 125, 127, 129, 131 and 133. Preferably, the effector sequence will be less than 30 nucleotides in length. For example, a suitable effector sequence may be in the range of 17-29 nucleotides in length. In a particularly preferred example, the effector sequence will be 21 nucleotides in length. More preferably, the effector sequence will be 21 nucleotides in length and the effector complement sequence will be 20 nucleotides in length.

In one example, the shmiR comprises an effector sequence which is substantially complementary to a RNA transcript comprising or consisting of the sequence set forth in SEQ ID NO: 1. For example, the effector sequence may be substantially complementary to a RNA transcript comprising or consisting of the sequence set forth in SEQ ID NO: 1 and contain 6 mismatch bases relative thereto. For example, the effector sequence may be substantially complementary to a RNA transcript comprising or consisting of the sequence set forth in SEQ ID NO: 1 and contain 5 mismatch bases relative thereto. For example, the effector sequence may be substantially complementary to a RNA transcript comprising or consisting of the sequence set forth in SEQ ID NO: 1 and contain 4 mismatch bases relative thereto. For example, the effector sequence may be substantially complementary to a RNA transcript comprising or consisting of the sequence set forth in SEQ ID NO: 1 and contain 3 mismatch bases relative thereto. For example, the effector sequence may be substantially complementary to a RNA transcript comprising or consisting of the sequence set forth in SEQ ID NO: 1 and contain 2 mismatch bases relative thereto. For example, the effector sequence may be substantially complementary to a RNA transcript comprising or consisting of the sequence set forth in SEQ ID NO: 1 and contain 1 mismatch base relative thereto. For example, the effector sequence may be 100% complementary to a RNA transcript comprising or consisting of the sequence set forth in SEQ ID NO: 1.

In one example, the shmiR comprises an effector sequence which is substantially complementary to a RNA transcript comprising or consisting of the sequence set forth in SEQ ID NO: 2. For example, the effector sequence may be substantially complementary to a RNA transcript comprising or consisting of the sequence set forth in SEQ ID NO: 2 and contain 6 mismatch bases relative thereto. For example, the effector sequence may be substantially complementary to a RNA transcript comprising or consisting of the sequence set forth in SEQ ID NO: 2 and contain 5 mismatch bases relative thereto. For example, the effector sequence may be substantially complementary to a RNA transcript comprising or consisting of the sequence set forth in SEQ ID NO: 2 and contain 4 mismatch bases relative thereto. For example, the effector sequence may be substantially complementary to a RNA transcript comprising or consisting of the sequence set forth in SEQ ID NO: 2 and contain 3 mismatch bases relative thereto. For example, the effector sequence may be substantially complementary to a RNA transcript comprising or consisting of the sequence set forth in SEQ ID NO: 2 and contain 2 mismatch bases relative thereto. For example, the effector sequence may be substantially complementary to a RNA transcript comprising or consisting of the sequence set forth in SEQ ID NO: 2 and contain 1 mismatch base relative thereto. For example, the effector sequence may be 100% complementary to a RNA transcript comprising or consisting of the sequence set forth in SEQ ID NO: 2.

In one example, the shmiR comprises an effector sequence which is substantially complementary to a RNA transcript comprising or consisting of the sequence set forth in SEQ ID NO: 3. For example, the effector sequence may be substantially complementary to a RNA transcript comprising or consisting of the sequence set forth in SEQ ID NO: 3 and contain 6 mismatch bases relative thereto. For example, the effector sequence may be substantially complementary to a RNA transcript comprising or consisting of the sequence set forth in SEQ ID NO: 3 and contain 5 mismatch bases relative thereto. For example, the effector sequence may be substantially complementary to a RNA transcript comprising or consisting of the sequence set forth in SEQ ID NO: 3 and contain 4 mismatch bases relative thereto. For example, the effector sequence may be substantially complementary to a RNA transcript comprising or consisting of the sequence set forth in SEQ ID NO: 3 and contain 3 mismatch bases relative thereto. For example, the effector sequence may be substantially complementary to a RNA transcript comprising or consisting of the sequence set forth in SEQ ID NO: 3 and contain 2 mismatch bases relative thereto. For example, the effector sequence may be substantially complementary to a RNA transcript comprising or consisting of the sequence set forth in SEQ ID NO: 3 and contain 1 mismatch base relative thereto. For example, the effector sequence may be 100% complementary to a RNA transcript comprising or consisting of the sequence set forth in SEQ ID NO: 3.

In one example, the shmiR comprises an effector sequence which is substantially complementary to a RNA transcript comprising or consisting of the sequence set forth in SEQ ID NO: 4. For example, the effector sequence may be substantially complementary to a RNA transcript comprising or consisting of the sequence set forth in SEQ ID NO: 4 and contain 6 mismatch bases relative thereto. For example, the effector sequence may be substantially complementary to a RNA transcript comprising or consisting of the sequence set forth in SEQ ID NO: 4 and contain 5 mismatch bases relative thereto. For example, the effector sequence may be substantially complementary to a RNA transcript comprising or consisting of the sequence set forth in SEQ ID NO: 4 and contain 4 mismatch bases relative thereto. For example, the effector sequence may be substantially complementary to a RNA transcript comprising or consisting of the sequence set forth in SEQ ID NO: 4 and contain 3 mismatch bases relative thereto. For example, the effector sequence may be substantially complementary to a RNA transcript comprising or consisting of the sequence set forth in SEQ ID NO: 4 and contain 2 mismatch bases relative thereto. For example, the effector sequence may be substantially complementary to a RNA transcript comprising or consisting of the sequence set forth in SEQ ID NO: 4 and contain 1 mismatch base relative thereto. For example, the effector sequence may be 100% complementary to a RNA transcript comprising or consisting of the sequence set forth in SEQ ID NO: 4.

In one example, the shmiR comprises an effector sequence which is substantially complementary to a RNA transcript comprising or consisting of the sequence set forth in SEQ ID NO: 5. For example, the effector sequence may be substantially complementary to a RNA transcript comprising or consisting of the sequence set forth in SEQ ID NO: 5 and contain 6 mismatch bases relative thereto. For example, the effector sequence may be substantially complementary to a RNA transcript comprising or consisting of the sequence set forth in SEQ ID NO: 5 and contain 5 mismatch bases relative thereto. For example, the effector sequence may be substantially complementary to a RNA transcript comprising or consisting of the sequence set forth in SEQ ID NO: 5 and contain 4 mismatch bases relative thereto. For example, the effector sequence may be substantially complementary to a RNA transcript comprising or consisting of the sequence set forth in SEQ ID NO: 5 and contain 3 mismatch bases relative thereto. For example, the effector sequence may be substantially complementary to a RNA transcript comprising or consisting of the sequence set forth in SEQ ID NO: 5 and contain 2 mismatch bases relative thereto. For example, the effector sequence may be substantially complementary to a RNA transcript comprising or consisting of the sequence set forth in SEQ ID NO: 5 and contain 1 mismatch base relative thereto. For example, the effector sequence may be 100% complementary to a RNA transcript comprising or consisting of the sequence set forth in SEQ ID NO: 5.

In one example, the shmiR comprises an effector sequence which is substantially complementary to a RNA transcript comprising or consisting of the sequence set forth in SEQ ID NO: 6. For example, the effector sequence may be substantially complementary to a RNA transcript comprising or consisting of the sequence set forth in SEQ ID NO: 6 and contain 6 mismatch bases relative thereto. For example, the effector sequence may be substantially complementary to a RNA transcript comprising or consisting of the sequence set forth in SEQ ID NO: 6 and contain 5 mismatch bases relative thereto. For example, the effector sequence may be substantially complementary to a RNA transcript comprising or consisting of the sequence set forth in SEQ ID NO: 6 and contain 4 mismatch bases relative thereto. For example, the effector sequence may be substantially complementary to a RNA transcript comprising or consisting of the sequence set forth in SEQ ID NO: 6 and contain 3 mismatch bases relative thereto. For example, the effector sequence may be substantially complementary to a RNA transcript comprising or consisting of the sequence set forth in SEQ ID NO: 6 and contain 2 mismatch bases relative thereto. For example, the effector sequence may be substantially complementary to a RNA transcript comprising or consisting of the sequence set forth in SEQ ID NO: 6 and contain 1 mismatch base relative thereto. For example, the effector sequence may be 100% complementary to a RNA transcript comprising or consisting of the sequence set forth in SEQ ID NO: 6.

In one example, the shmiR comprises an effector sequence which is substantially complementary to a RNA transcript comprising or consisting of the sequence set forth in SEQ ID NO: 7. For example, the effector sequence may be substantially complementary to a RNA transcript comprising or consisting of the sequence set forth in SEQ ID NO: 7 and contain 6 mismatch bases relative thereto. For example, the effector sequence may be substantially complementary to a RNA transcript comprising or consisting of the sequence set forth in SEQ ID NO: 7 and contain 5 mismatch bases relative thereto. For example, the effector sequence may be substantially complementary to a RNA transcript comprising or consisting of the sequence set forth in SEQ ID NO: 7 and contain 4 mismatch bases relative thereto. For example, the effector sequence may be substantially complementary to a RNA transcript comprising or consisting of the sequence set forth in SEQ ID NO: 7 and contain 3 mismatch bases relative thereto. For example, the effector sequence may be substantially complementary to a RNA transcript comprising or consisting of the sequence set forth in SEQ ID NO: 7 and contain 2 mismatch bases relative thereto. For example, the effector sequence may be substantially complementary to a RNA transcript comprising or consisting of the sequence set forth in SEQ ID NO: 7 and contain 1 mismatch base relative thereto. For example, the effector sequence may be 100% complementary to a RNA transcript comprising or consisting of the sequence set forth in SEQ ID NO: 7.

In one example, the shmiR comprises an effector sequence which is substantially complementary to a RNA transcript comprising or consisting of the sequence set forth in SEQ ID NO: 8. For example, the effector sequence may be substantially complementary to a RNA transcript comprising or consisting of the sequence set forth in SEQ ID NO: 8 and contain 6 mismatch bases relative thereto. For example, the effector sequence may be substantially complementary to a RNA transcript comprising or consisting of the sequence set forth in SEQ ID NO: 8 and contain 5 mismatch bases relative thereto. For example, the effector sequence may be substantially complementary to a RNA transcript comprising or consisting of the sequence set forth in SEQ ID NO: 8 and contain 4 mismatch bases relative thereto. For example, the effector sequence may be substantially complementary to a RNA transcript comprising or consisting of the sequence set forth in SEQ ID NO: 8 and contain 3 mismatch bases relative thereto. For example, the effector sequence may be substantially complementary to a RNA transcript comprising or consisting of the sequence set forth in SEQ ID NO: 8 and contain 2 mismatch bases relative thereto. For example, the effector sequence may be substantially complementary to a RNA transcript comprising or consisting of the sequence set forth in SEQ ID NO: 8 and contain 1 mismatch base relative thereto. For example, the effector sequence may be 100% complementary to a RNA transcript comprising or consisting of the sequence set forth in SEQ ID NO: 8.

In one example, the shmiR comprises an effector sequence which is substantially complementary to a RNA transcript comprising or consisting of the sequence set forth in SEQ ID NO: 9. For example, the effector sequence may be substantially complementary to a RNA transcript comprising or consisting of the sequence set forth in SEQ ID NO: 9 and contain 6 mismatch bases relative thereto. For example, the effector sequence may be substantially complementary to a RNA transcript comprising or consisting of the sequence set forth in SEQ ID NO: 9 and contain 5 mismatch bases relative thereto. For example, the effector sequence may be substantially complementary to a RNA transcript comprising or consisting of the sequence set forth in SEQ ID NO: 9 and contain 4 mismatch bases relative thereto. For example, the effector sequence may be substantially complementary to a RNA transcript comprising or consisting of the sequence set forth in SEQ ID NO: 9 and contain 3 mismatch bases relative thereto. For example, the effector sequence may be substantially complementary to a RNA transcript comprising or consisting of the sequence set forth in SEQ ID NO: 9 and contain 2 mismatch bases relative thereto. For example, the effector sequence may be substantially complementary to a RNA transcript comprising or consisting of the sequence set forth in SEQ ID NO: 9 and contain 1 mismatch base relative thereto. For example, the effector sequence may be 100% complementary to a RNA transcript comprising or consisting of the sequence set forth in SEQ ID NO: 9.

In one example, the shmiR comprises an effector sequence which is substantially complementary to a RNA transcript comprising or consisting of the sequence set forth in SEQ ID NO: 10. For example, the effector sequence may be substantially complementary to a RNA transcript comprising or consisting of the sequence set forth in SEQ ID NO: 10 and contain 6 mismatch bases relative thereto. For example, the effector sequence may be substantially complementary to a RNA transcript comprising or consisting of the sequence set forth in SEQ ID NO: 10 and contain 5 mismatch bases relative thereto. For example, the effector sequence may be substantially complementary to a RNA transcript comprising or consisting of the sequence set forth in SEQ ID NO: 10 and contain 4 mismatch bases relative thereto. For example, the effector sequence may be substantially complementary to a RNA transcript comprising or consisting of the sequence set forth in SEQ ID NO: 10 and contain 3 mismatch bases relative thereto. For example, the effector sequence may be substantially complementary to a RNA transcript comprising or consisting of the sequence set forth in SEQ ID NO: 10 and contain 2 mismatch bases relative thereto. For example, the effector sequence may be substantially complementary to a RNA transcript comprising or consisting of the sequence set forth in SEQ ID NO: 10 and contain 1 mismatch base relative thereto. For example, the effector sequence may be 100% complementary to a RNA transcript comprising or consisting of the sequence set forth in SEQ ID NO: 10.

In one example, the shmiR comprises an effector sequence which is substantially complementary to a RNA transcript comprising or consisting of the sequence set forth in SEQ ID NO: 38. For example, the effector sequence may be substantially complementary to a RNA transcript comprising or consisting of the sequence set forth in SEQ ID NO: 38 and contain 6 mismatch bases relative thereto. For example, the effector sequence may be substantially complementary to a RNA transcript comprising or consisting of the sequence set forth in SEQ ID NO: 38 and contain 5 mismatch bases relative thereto. For example, the effector sequence may be substantially complementary to a RNA transcript comprising or consisting of the sequence set forth in SEQ ID NO: 38 and contain 4 mismatch bases relative thereto. For example, the effector sequence may be substantially complementary to a RNA transcript comprising or consisting of the sequence set forth in SEQ ID NO: 38 and contain 3 mismatch bases relative thereto. For example, the effector sequence may be substantially complementary to a RNA transcript comprising or consisting of the sequence set forth in SEQ ID NO: 38 and contain 2 mismatch bases relative thereto. For example, the effector sequence may be substantially complementary to a RNA transcript comprising or consisting of the sequence set forth in SEQ ID NO: 38 and contain 1 mismatch base relative thereto. For example, the effector sequence may be 100% complementary to a RNA transcript comprising or consisting of the sequence set forth in SEQ ID NO: 38.

In one example, the shmiR comprises an effector sequence which is substantially complementary to a RNA transcript comprising or consisting of the sequence set forth in SEQ ID NO: 40. For example, the effector sequence may be substantially complementary to a RNA transcript comprising or consisting of the sequence set forth in SEQ ID NO: 40 and contain 6 mismatch bases relative thereto. For example, the effector sequence may be substantially complementary to a RNA transcript comprising or consisting of the sequence set forth in SEQ ID NO: 40 and contain 5 mismatch bases relative thereto. For example, the effector sequence may be substantially complementary to a RNA transcript comprising or consisting of the sequence set forth in SEQ ID NO: 40 and contain 4 mismatch bases relative thereto. For example, the effector sequence may be substantially complementary to a RNA transcript comprising or consisting of the sequence set forth in SEQ ID NO: 40 and contain 3 mismatch bases relative thereto. For example, the effector sequence may be substantially complementary to a RNA transcript comprising or consisting of the sequence set forth in SEQ ID NO: 40 and contain 2 mismatch bases relative thereto. For example, the effector sequence may be substantially complementary to a RNA transcript comprising or consisting of the sequence set forth in SEQ ID NO: 40 and contain 1 mismatch base relative thereto. For example, the effector sequence may be 100% complementary to a RNA transcript comprising or consisting of the sequence set forth in SEQ ID NO: 40.

In one example, the shmiR comprises an effector sequence which is substantially complementary to a RNA transcript comprising or consisting of the sequence set forth in SEQ ID NO: 42. For example, the effector sequence may be substantially complementary to a RNA transcript comprising or consisting of the sequence set forth in SEQ ID NO: 42 and contain 6 mismatch bases relative thereto. For example, the effector sequence may be substantially complementary to a RNA transcript comprising or consisting of the sequence set forth in SEQ ID NO: 42 and contain 5 mismatch bases relative thereto. For example, the effector sequence may be substantially complementary to a RNA transcript comprising or consisting of the sequence set forth in SEQ ID NO: 42 and contain 4 mismatch bases relative thereto. For example, the effector sequence may be substantially complementary to a RNA transcript comprising or consisting of the sequence set forth in SEQ ID NO: 42 and contain 3 mismatch bases relative thereto. For example, the effector sequence may be substantially complementary to a RNA transcript comprising or consisting of the sequence set forth in SEQ ID NO: 42 and contain 2 mismatch bases relative thereto. For example, the effector sequence may be substantially complementary to a RNA transcript comprising or consisting of the sequence set forth in SEQ ID NO: 42 and contain 1 mismatch base relative thereto. For example, the effector sequence may be 100% complementary to a RNA transcript comprising or consisting of the sequence set forth in SEQ ID NO: 42.

In one example, the shmiR comprises an effector sequence which is substantially complementary to a RNA transcript comprising or consisting of the sequence set forth in SEQ ID NO: 111. For example, the effector sequence may be substantially complementary to a RNA transcript comprising or consisting of the sequence set forth in SEQ ID NO: 111 and contain 6 mismatch bases relative thereto. For example, the effector sequence may be substantially complementary to a RNA transcript comprising or consisting of the sequence set forth in SEQ ID NO: 111 and contain 5 mismatch bases relative thereto. For example, the effector sequence may be substantially complementary to a RNA transcript comprising or consisting of the sequence set forth in SEQ ID NO: 111 and contain 4 mismatch bases relative thereto. For example, the effector sequence may be substantially complementary to a RNA transcript comprising or consisting of the sequence set forth in SEQ ID NO: 111 and contain 3 mismatch bases relative thereto. For example, the effector sequence may be substantially complementary to a RNA transcript comprising or consisting of the sequence set forth in SEQ ID NO: 111 and contain 2 mismatch bases relative thereto. For example, the effector sequence may be substantially complementary to a RNA transcript comprising or consisting of the sequence set forth in SEQ ID NO: 111 and contain 1 mismatch base relative thereto. For example, the effector sequence may be 100% complementary to a RNA transcript comprising or consisting of the sequence set forth in SEQ ID NO: 111.

In one example, the shmiR comprises an effector sequence which is substantially complementary to a RNA transcript comprising or consisting of the sequence set forth in SEQ ID NO: 113. For example, the effector sequence may be substantially complementary to a RNA transcript comprising or consisting of the sequence set forth in SEQ ID NO: 113 and contain 6 mismatch bases relative thereto. For example, the effector sequence may be substantially complementary to a RNA transcript comprising or consisting of the sequence set forth in SEQ ID NO: 113 and contain 5 mismatch bases relative thereto. For example, the effector sequence may be substantially complementary to a RNA transcript comprising or consisting of the sequence set forth in SEQ ID NO: 113 and contain 4 mismatch bases relative thereto. For example, the effector sequence may be substantially complementary to a RNA transcript comprising or consisting of the sequence set forth in SEQ ID NO: 113 and contain 3 mismatch bases relative thereto. For example, the effector sequence may be substantially complementary to a RNA transcript comprising or consisting of the sequence set forth in SEQ ID NO: 113 and contain 2 mismatch bases relative thereto. For example, the effector sequence may be substantially complementary to a RNA transcript comprising or consisting of the sequence set forth in SEQ ID NO: 113 and contain 1 mismatch base relative thereto. For example, the effector sequence may be 100% complementary to a RNA transcript comprising or consisting of the sequence set forth in SEQ ID NO: 113.

In one example, the shmiR comprises an effector sequence which is substantially complementary to a RNA transcript comprising or consisting of the sequence set forth in SEQ ID NO: 115. For example, the effector sequence may be substantially complementary to a RNA transcript comprising or consisting of the sequence set forth in SEQ ID NO: 115 and contain 6 mismatch bases relative thereto. For example, the effector sequence may be substantially complementary to a RNA transcript comprising or consisting of the sequence set forth in SEQ ID NO: 115 and contain 5 mismatch bases relative thereto. For example, the effector sequence may be substantially complementary to a RNA transcript comprising or consisting of the sequence set forth in SEQ ID NO: 115 and contain 4 mismatch bases relative thereto. For example, the effector sequence may be substantially complementary to a RNA transcript comprising or consisting of the sequence set forth in SEQ ID NO: 115 and contain 3 mismatch bases relative thereto. For example, the effector sequence may be substantially complementary to a RNA transcript comprising or consisting of the sequence set forth in SEQ ID NO: 115 and contain 2 mismatch bases relative thereto. For example, the effector sequence may be substantially complementary to a RNA transcript comprising or consisting of the sequence set forth in SEQ ID NO: 115 and contain 1 mismatch base relative thereto. For example, the effector sequence may be 100% complementary to a RNA transcript comprising or consisting of the sequence set forth in SEQ ID NO: 115.

In one example, the shmiR comprises an effector sequence which is substantially complementary to a RNA transcript comprising or consisting of the sequence set forth in SEQ ID NO: 117. For example, the effector sequence may be substantially complementary to a RNA transcript comprising or consisting of the sequence set forth in SEQ ID NO: 117 and contain 6 mismatch bases relative thereto. For example, the effector sequence may be substantially complementary to a RNA transcript comprising or consisting of the sequence set forth in SEQ ID NO: 117 and contain 5 mismatch bases relative thereto. For example, the effector sequence may be substantially complementary to a RNA transcript comprising or consisting of the sequence set forth in SEQ ID NO: 117 and contain 4 mismatch bases relative thereto. For example, the effector sequence may be substantially complementary to a RNA transcript comprising or consisting of the sequence set forth in SEQ ID NO: 117 and contain 3 mismatch bases relative thereto. For example, the effector sequence may be substantially complementary to a RNA transcript comprising or consisting of the sequence set forth in SEQ ID NO: 117 and contain 2 mismatch bases relative thereto. For example, the effector sequence may be substantially complementary to a RNA transcript comprising or consisting of the sequence set forth in SEQ ID NO: 117 and contain 1 mismatch base relative thereto. For example, the effector sequence may be 100% complementary to a RNA transcript comprising or consisting of the sequence set forth in SEQ ID NO: 117.

In one example, the shmiR comprises an effector sequence which is substantially complementary to a RNA transcript comprising or consisting of the sequence set forth in SEQ ID NO: 119. For example, the effector sequence may be substantially complementary to a RNA transcript comprising or consisting of the sequence set forth in SEQ ID NO: 119 and contain 6 mismatch bases relative thereto. For example, the effector sequence may be substantially complementary to a RNA transcript comprising or consisting of the sequence set forth in SEQ ID NO: 119 and contain 5 mismatch bases relative thereto. For example, the effector sequence may be substantially complementary to a RNA transcript comprising or consisting of the sequence set forth in SEQ ID NO: 119 and contain 4 mismatch bases relative thereto. For example, the effector sequence may be substantially complementary to a RNA transcript comprising or consisting of the sequence set forth in SEQ ID NO: 119 and contain 3 mismatch bases relative thereto. For example, the effector sequence may be substantially complementary to a RNA transcript comprising or consisting of the sequence set forth in SEQ ID NO: 119 and contain 2 mismatch bases relative thereto. For example, the effector sequence may be substantially complementary to a RNA transcript comprising or consisting of the sequence set forth in SEQ ID NO: 119 and contain 1 mismatch base relative thereto. For example, the effector sequence may be 100% complementary to a RNA transcript comprising or consisting of the sequence set forth in SEQ ID NO: 119.

In one example, the shmiR comprises an effector sequence which is substantially complementary to a RNA transcript comprising or consisting of the sequence set forth in SEQ ID NO: 121. For example, the effector sequence may be substantially complementary to a RNA transcript comprising or consisting of the sequence set forth in SEQ ID NO: 121 and contain 6 mismatch bases relative thereto. For example, the effector sequence may be substantially complementary to a RNA transcript comprising or consisting of the sequence set forth in SEQ ID NO: 121 and contain 5 mismatch bases relative thereto. For example, the effector sequence may be substantially complementary to a RNA transcript comprising or consisting of the sequence set forth in SEQ ID NO: 121 and contain 4 mismatch bases relative thereto. For example, the effector sequence may be substantially complementary to a RNA transcript comprising or consisting of the sequence set forth in SEQ ID NO: 121 and contain 3 mismatch bases relative thereto. For example, the effector sequence may be substantially complementary to a RNA transcript comprising or consisting of the sequence set forth in SEQ ID NO: 121 and contain 2 mismatch bases relative thereto. For example, the effector sequence may be substantially complementary to a RNA transcript comprising or consisting of the sequence set forth in SEQ ID NO: 121 and contain 1 mismatch base relative thereto. For example, the effector sequence may be 100% complementary to a RNA transcript comprising or consisting of the sequence set forth in SEQ ID NO: 121.

In one example, the shmiR comprises an effector sequence which is substantially complementary to a RNA transcript comprising or consisting of the sequence set forth in SEQ ID NO: 123. For example, the effector sequence may be substantially complementary to a RNA transcript comprising or consisting of the sequence set forth in SEQ ID NO: 123 and contain 6 mismatch bases relative thereto. For example, the effector sequence may be substantially complementary to a RNA transcript comprising or consisting of the sequence set forth in SEQ ID NO: 123 and contain 5 mismatch bases relative thereto. For example, the effector sequence may be substantially complementary to a RNA transcript comprising or consisting of the sequence set forth in SEQ ID NO: 123 and contain 4 mismatch bases relative thereto. For example, the effector sequence may be substantially complementary to a RNA transcript comprising or consisting of the sequence set forth in SEQ ID NO: 123 and contain 3 mismatch bases relative thereto. For example, the effector sequence may be substantially complementary to a RNA transcript comprising or consisting of the sequence set forth in SEQ ID NO: 123 and contain 2 mismatch bases relative thereto. For example, the effector sequence may be substantially complementary to a RNA transcript comprising or consisting of the sequence set forth in SEQ ID NO: 123 and contain 1 mismatch base relative thereto. For example, the effector sequence may be 100% complementary to a RNA transcript comprising or consisting of the sequence set forth in SEQ ID NO: 123.

In one example, the shmiR comprises an effector sequence which is substantially complementary to a RNA transcript comprising or consisting of the sequence set forth in SEQ ID NO: 125. For example, the effector sequence may be substantially complementary to a RNA transcript comprising or consisting of the sequence set forth in SEQ ID NO: 125 and contain 6 mismatch bases relative thereto. For example, the effector sequence may be substantially complementary to a RNA transcript comprising or consisting of the sequence set forth in SEQ ID NO: 125 and contain 5 mismatch bases relative thereto. For example, the effector sequence may be substantially complementary to a RNA transcript comprising or consisting of the sequence set forth in SEQ ID NO: 125 and contain 4 mismatch bases relative thereto. For example, the effector sequence may be substantially complementary to a RNA transcript comprising or consisting of the sequence set forth in SEQ ID NO: 125 and contain 3 mismatch bases relative thereto. For example, the effector sequence may be substantially complementary to a RNA transcript comprising or consisting of the sequence set forth in SEQ ID NO: 125 and contain 2 mismatch bases relative thereto. For example, the effector sequence may be substantially complementary to a RNA transcript comprising or consisting of the sequence set forth in SEQ ID NO: 125 and contain 1 mismatch base relative thereto. For example, the effector sequence may be 100% complementary to a RNA transcript comprising or consisting of the sequence set forth in SEQ ID NO: 125.

In one example, the shmiR comprises an effector sequence which is substantially complementary to a RNA transcript comprising or consisting of the sequence set forth in SEQ ID NO: 127. For example, the effector sequence may be substantially complementary to a RNA transcript comprising or consisting of the sequence set forth in SEQ ID NO: 127 and contain 6 mismatch bases relative thereto. For example, the effector sequence may be substantially complementary to a RNA transcript comprising or consisting of the sequence set forth in SEQ ID NO: 127 and contain 5 mismatch bases relative thereto. For example, the effector sequence may be substantially complementary to a RNA transcript comprising or consisting of the sequence set forth in SEQ ID NO: 127 and contain 4 mismatch bases relative thereto. For example, the effector sequence may be substantially complementary to a RNA transcript comprising or consisting of the sequence set forth in SEQ ID NO: 127 and contain 3 mismatch bases relative thereto. For example, the effector sequence may be substantially complementary to a RNA transcript comprising or consisting of the sequence set forth in SEQ ID NO: 127 and contain 2 mismatch bases relative thereto. For example, the effector sequence may be substantially complementary to a RNA transcript comprising or consisting of the sequence set forth in SEQ ID NO: 127 and contain 1 mismatch base relative thereto. For example, the effector sequence may be 100% complementary to a RNA transcript comprising or consisting of the sequence set forth in SEQ ID NO: 127.

In one example, the shmiR comprises an effector sequence which is substantially complementary to a RNA transcript comprising or consisting of the sequence set forth in SEQ ID NO: 129. For example, the effector sequence may be substantially complementary to a RNA transcript comprising or consisting of the sequence set forth in SEQ ID NO: 129 and contain 6 mismatch bases relative thereto. For example, the effector sequence may be substantially complementary to a RNA transcript comprising or consisting of the sequence set forth in SEQ ID NO: 129 and contain 5 mismatch bases relative thereto. For example, the effector sequence may be substantially complementary to a RNA transcript comprising or consisting of the sequence set forth in SEQ ID NO: 129 and contain 4 mismatch bases relative thereto. For example, the effector sequence may be substantially complementary to a RNA transcript comprising or consisting of the sequence set forth in SEQ ID NO: 129 and contain 3 mismatch bases relative thereto. For example, the effector sequence may be substantially complementary to a RNA transcript comprising or consisting of the sequence set forth in SEQ ID NO: 129 and contain 2 mismatch bases relative thereto. For example, the effector sequence may be substantially complementary to a RNA transcript comprising or consisting of the sequence set forth in SEQ ID NO:

129 and contain 1 mismatch base relative thereto. For example, the effector sequence may be 100% complementary to a RNA transcript comprising or consisting of the sequence set forth in SEQ ID NO: 129.

In one example, the shmiR comprises an effector sequence which is substantially complementary to a RNA transcript comprising or consisting of the sequence set forth in SEQ ID NO: 131. For example, the effector sequence may be substantially complementary to a RNA transcript comprising or consisting of the sequence set forth in SEQ ID NO: 131 and contain 6 mismatch bases relative thereto. For example, the effector sequence may be substantially complementary to a RNA transcript comprising or consisting of the sequence set forth in SEQ ID NO: 131 and contain 5 mismatch bases relative thereto. For example, the effector sequence may be substantially complementary to a RNA transcript comprising or consisting of the sequence set forth in SEQ ID NO: 131 and contain 4 mismatch bases relative thereto. For example, the effector sequence may be substantially complementary to a RNA transcript comprising or consisting of the sequence set forth in SEQ ID NO: 131 and contain 3 mismatch bases relative thereto. For example, the effector sequence may be substantially complementary to a RNA transcript comprising or consisting of the sequence set forth in SEQ ID NO: 131 and contain 2 mismatch bases relative thereto. For example, the effector sequence may be substantially complementary to a RNA transcript comprising or consisting of the sequence set forth in SEQ ID NO: 131 and contain 1 mismatch base relative thereto. For example, the effector sequence may be 100% complementary to a RNA transcript comprising or consisting of the sequence set forth in SEQ ID NO: 131.

In one example, the shmiR comprises an effector sequence which is substantially complementary to a RNA transcript comprising or consisting of the sequence set forth in SEQ ID NO: 133. For example, the effector sequence may be substantially complementary to a RNA transcript comprising or consisting of the sequence set forth in SEQ ID NO: 133 and contain 6 mismatch bases relative thereto. For example, the effector sequence may be substantially complementary to a RNA transcript comprising or consisting of the sequence set forth in SEQ ID NO: 133 and contain 5 mismatch bases relative thereto. For example, the effector sequence may be substantially complementary to a RNA transcript comprising or consisting of the sequence set forth in SEQ ID NO: 133 and contain 4 mismatch bases relative thereto. For example, the effector sequence may be substantially complementary to a RNA transcript comprising or consisting of the sequence set forth in SEQ ID NO: 133 and contain 3 mismatch bases relative thereto. For example, the effector sequence may be substantially complementary to a RNA transcript comprising or consisting of the sequence set forth in SEQ ID NO: 133 and contain 2 mismatch bases relative thereto. For example, the effector sequence may be substantially complementary to a RNA transcript comprising or consisting of the sequence set forth in SEQ ID NO: 133 and contain 1 mismatch base relative thereto. For example, the effector sequence may be 100% complementary to a RNA transcript comprising or consisting of the sequence set forth in SEQ ID NO: 133.

In accordance with an example in which the effector sequence of a shmiR of the disclosure is substantially complementary to a HBV RNA transcript described herein and contains 1, 2, 3, 4, 5 or 6 mismatch base(s) relative thereto, it is preferred that the mismatch(es) are not located within the region corresponding to the seed region of the shmiR i.e., nucleotides 2-8 of the effector sequence.

In one example, the nucleic acid described herein may comprise a DNA sequence encoding a shmiR comprising: (i) an effector sequence which is substantially complementary to the sequence set forth in SEQ ID NO:12 with the exception of 1, 2, 3, 4, 5 or 6 base mismatches, provided that the effector sequence is capable of forming a duplex with a sequence set forth in SEQ ID NO:12; and (ii) an effector complement sequence comprising a sequence which is substantially complementary to the effector sequence. For example, the shmiR encoded by the nucleic acid may comprise an effector sequence set forth in SEQ ID NO:11 and an effector complement sequence which is substantially complementary to the sequence set forth in SEQ ID NO:11 and capable of forming a duplex therewith. The effector complement sequence which is substantially complementary to the sequence set forth in SEQ ID NO:11 may be the sequence set forth in SEQ ID NO:12. A shmiR in accordance with this example is hereinafter designated "shmiR-1".

In one example, the nucleic acid described herein may comprise a DNA sequence encoding a shmiR comprising: (i) an effector sequence which is substantially complementary to the sequence set forth in SEQ ID NO:14 with the exception of 1, 2, 3, 4, 5 or 6 base mismatches, provided that the effector sequence is capable of forming a duplex with a sequence set forth in SEQ ID NO:14; and (ii) an effector complement sequence comprising a sequence which is substantially complementary to the effector sequence. For example, the shmiR encoded by the nucleic acid may comprise an effector sequence set forth in SEQ ID NO:13 and an effector complement sequence which is substantially complementary to the sequence set forth in SEQ ID NO:13 and capable of forming a duplex therewith. The effector complement sequence which is substantially complementary to the sequence set forth in SEQ ID NO:13 may be the sequence set forth in SEQ ID NO:14. A shmiR in accordance with this example is hereinafter designated "shmiR-2".

In one example, the nucleic acid described herein may comprise a DNA sequence encoding a shmiR comprising: (i) an effector sequence which is substantially complementary to the sequence set forth in SEQ ID NO:16 with the exception of 1, 2, 3, 4, 5 or 6 base mismatches, provided that the effector sequence is capable of forming a duplex with a sequence set forth in SEQ ID NO:16; and (ii) an effector complement sequence comprising a sequence which is substantially complementary to the effector sequence. For example, the shmiR encoded by the nucleic acid may comprise an effector sequence set forth in SEQ ID NO:15 and an effector complement sequence which is substantially complementary to the sequence set forth in SEQ ID NO:15 and capable of forming a duplex therewith. The effector complement sequence which is substantially complementary to the sequence set forth in SEQ ID NO:15 may be the sequence set forth in SEQ ID NO:16. A shmiR in accordance with this example is hereinafter designated "shmiR-3".

In one example, the nucleic acid described herein may comprise a DNA sequence encoding a shmiR comprising: (i) an effector sequence which is substantially complementary to the sequence set forth in SEQ ID NO:18 with the exception of 1, 2, 3, 4, 5 or 6 base mismatches, provided that the effector sequence is capable of forming a duplex with a sequence set forth in SEQ ID NO:18; and (ii) an effector complement sequence comprising a sequence which is substantially complementary to the effector sequence. For example, the shmiR encoded by the nucleic acid may comprise an effector sequence set forth in SEQ ID NO:17 and an effector complement sequence which is substantially complementary to the sequence set forth in SEQ ID NO:17 and capable of forming a duplex therewith. The effector complement sequence which is substantially complementary to the sequence set forth in SEQ ID NO:17 may be the sequence set forth in SEQ ID NO:18. A shmiR in accordance with this example is hereinafter designated "shmiR-4".

In one example, the nucleic acid described herein may comprise a DNA sequence encoding a shmiR comprising: (i) an effector sequence which is substantially complementary to the sequence set forth in SEQ ID NO:20 with the exception of 1, 2, 3, 4, 5 or 6 base mismatches, provided that the effector sequence is capable of forming a duplex with a sequence set forth in SEQ ID NO:20; and (ii) an effector complement sequence comprising a sequence which is substantially complementary to the effector sequence. For example, the shmiR encoded by the nucleic acid may comprise an effector sequence set forth in SEQ ID NO:19 and an effector complement sequence which is substantially complementary to the sequence set forth in SEQ ID NO:19 and capable of forming a duplex therewith. The effector complement sequence which is substantially complementary to the sequence set forth in SEQ ID NO:19 may be the sequence set forth in SEQ ID NO:20. A shmiR in accordance with this example is hereinafter designated "shmiR-5".

In one example, the nucleic acid described herein may comprise a DNA sequence encoding a shmiR comprising: (i) an effector sequence which is substantially complementary to the sequence set forth in SEQ ID NO:22 with the exception of 1, 2, 3, 4, 5 or 6 base mismatches, provided that the effector sequence is capable of forming a duplex with a sequence set forth in SEQ ID NO:22; and (ii) an effector complement sequence comprising a sequence which is substantially complementary to the effector sequence. For example, the shmiR encoded by the nucleic acid may comprise an effector sequence set forth in SEQ ID NO:21 and an effector complement sequence which is substantially complementary to the sequence set forth in SEQ ID NO:21 and capable of forming a duplex therewith. The effector complement sequence which is substantially complementary to the sequence set forth in SEQ ID NO:21 may be the sequence set forth in SEQ ID NO:22. A shmiR in accordance with this example is hereinafter designated "shmiR-6".

In one example, the nucleic acid described herein may comprise a DNA sequence encoding a shmiR comprising: (i) an effector sequence which is substantially complementary to the sequence set forth in SEQ ID NO:24 with the exception of 1, 2, 3, 4, 5 or 6 base mismatches, provided that the effector sequence is capable of forming a duplex with a sequence set forth in SEQ ID NO:24; and (ii) an effector complement sequence comprising a sequence which is substantially complementary to the effector sequence. For example, the shmiR encoded by the nucleic acid may comprise an effector sequence set forth in SEQ ID NO:23 and an effector complement sequence which is substantially complementary to the sequence set forth in SEQ ID NO:23 and capable of forming a duplex therewith. The effector complement sequence which is substantially complementary to the sequence set forth in SEQ ID NO:23 may be the sequence set forth in SEQ ID NO:24. A shmiR in accordance with this example is hereinafter designated "shmiR-7".

In one example, the nucleic acid described herein may comprise a DNA sequence encoding a shmiR comprising: (i) an effector sequence which is substantially complementary to the sequence set forth in SEQ ID NO:26 with the exception of 1, 2, 3, 4, 5 or 6 base mismatches, provided that the effector sequence is capable of forming a duplex with a sequence set forth in SEQ ID NO:26; and (ii) an effector complement sequence comprising a sequence which is substantially complementary to the effector sequence. For example, the shmiR encoded by the nucleic acid may comprise an effector sequence set forth in SEQ ID NO:25 and an effector complement sequence which is substantially complementary to the sequence set forth in SEQ ID NO:25 and capable of forming a duplex therewith. The effector complement sequence which is substantially complementary to the sequence set forth in SEQ ID NO:25 may be the sequence set forth in SEQ ID NO:26. A shmiR in accordance with this example is hereinafter designated "shmiR-8".

In one example, the nucleic acid described herein may comprise a DNA sequence encoding a shmiR comprising: (i) an effector sequence which is substantially complementary to the sequence set forth in SEQ ID NO:28 with the exception of 1, 2, 3, 4, 5 or 6 base mismatches, provided that the effector sequence is capable of forming a duplex with a sequence set forth in SEQ ID NO:28; and (ii) an effector complement sequence comprising a sequence which is substantially complementary to the effector sequence. For example, the shmiR encoded by the nucleic acid may comprise an effector sequence set forth in SEQ ID NO:27 and an effector complement sequence which is substantially complementary to the sequence set forth in SEQ ID NO:27 and capable of forming a duplex therewith. The effector complement sequence which is substantially complementary to the sequence set forth in SEQ ID NO:27 may be the sequence set forth in SEQ ID NO:28. A shmiR in accordance with this example is hereinafter designated "shmiR-9".

In one example, the nucleic acid described herein may comprise a DNA sequence encoding a shmiR comprising: (i) an effector sequence which is substantially complementary to the sequence set forth in SEQ ID NO:30 with the exception of 1, 2, 3, 4, 5 or 6 base mismatches, provided that the effector sequence is capable of forming a duplex with a sequence set forth in SEQ ID NO:30; and (ii) an effector complement sequence comprising a sequence which is substantially complementary to the effector sequence. For example, the shmiR encoded by the nucleic acid may comprise an effector sequence set forth in SEQ ID NO:29 and an effector complement sequence which is substantially complementary to the sequence set forth in SEQ ID NO:29 and capable of forming a duplex therewith. The effector complement sequence which is substantially complementary to the sequence set forth in SEQ ID NO:29 may be the sequence set forth in SEQ ID NO:30. A shmiR in accordance with this example is hereinafter designated "shmiR-10".

In one example, the nucleic acid described herein may comprise a DNA sequence encoding a shmiR comprising: (i) an effector sequence which is substantially complementary to the sequence set forth in SEQ ID NO:32 with the exception of 1, 2, 3, 4, 5 or 6 base mismatches, provided that the effector sequence is capable of forming a duplex with a sequence set forth in SEQ ID NO:32; and (ii) an effector complement sequence comprising a sequence which is substantially complementary to the effector sequence. For example, the shmiR encoded by the nucleic acid may comprise an effector sequence set forth in SEQ ID NO:31 and an effector complement sequence which is substantially complementary to the sequence set forth in SEQ ID NO:31 and capable of forming a duplex therewith. The effector complement sequence which is substantially complementary to the sequence set forth in SEQ ID NO:31 may be the sequence set forth in SEQ ID NO:32. A shmiR in accordance with this example is hereinafter designated "shmiR-11".

In one example, the nucleic acid described herein may comprise a DNA sequence encoding a shmiR comprising: (i) an effector sequence which is substantially complementary to the sequence set forth in SEQ ID NO:34 with the exception of 1, 2, 3, 4, 5 or 6 base mismatches, provided that the effector sequence is capable of forming a duplex with a sequence set forth in SEQ ID NO:34; and (ii) an effector complement sequence comprising a sequence which is substantially complementary to the effector sequence. For example, the shmiR encoded by the nucleic acid may comprise an effector sequence set forth in SEQ ID NO:33 and an effector complement sequence which is substantially complementary to the sequence set forth in SEQ ID NO:33 and capable of forming a duplex therewith. The effector complement sequence which is substantially complementary to the sequence set forth in SEQ ID NO:33 may be the sequence set forth in SEQ ID NO:34. A shmiR in accordance with this example is hereinafter designated "shmiR-12".

In one example, the nucleic acid described herein may comprise a DNA sequence encoding a shmiR comprising: (i) an effector sequence which is substantially complementary to the sequence set forth in SEQ ID NO:36 with the exception of 1, 2, 3, 4, 5 or 6 base mismatches, provided that the effector sequence is capable of forming a duplex with a sequence set forth in SEQ ID NO:36; and (ii) an effector complement sequence comprising a sequence which is substantially complementary to the effector sequence. For example, the shmiR encoded by the nucleic acid may comprise an effector sequence set forth in SEQ ID NO:35 and an effector complement sequence which is substantially complementary to the sequence set forth in SEQ ID NO:35 and capable of forming a duplex therewith. The effector complement sequence which is substantially complementary to the sequence set forth in SEQ ID NO:35 may be the sequence set forth in SEQ ID NO:36. A shmiR in accordance with this example is hereinafter designated "shmiR-13".

In one example, the nucleic acid described herein may comprise a DNA sequence encoding a shmiR comprising: (i) an effector sequence which is substantially complementary to the sequence set forth in SEQ ID NO:38 with the exception of 1, 2, 3, 4, 5 or 6 base mismatches, provided that the effector sequence is capable of forming a duplex with a sequence set forth in SEQ ID NO:38; and (ii) an effector complement sequence comprising a sequence which is substantially complementary to the effector sequence. For example, the shmiR encoded by the nucleic acid may comprise an effector sequence set forth in SEQ ID NO:37 and an effector complement sequence which is substantially complementary to the sequence set forth in SEQ ID NO:37 and capable of forming a duplex therewith. The effector complement sequence which is substantially complementary to the sequence set forth in SEQ ID NO:37 may be the sequence set forth in SEQ ID NO:38. A shmiR in accordance with this example is hereinafter designated "shmiR-14".

In one example, the nucleic acid described herein may comprise a DNA sequence encoding a shmiR comprising: (i) an effector sequence which is substantially complementary to the sequence set forth in SEQ ID NO:40 with the exception of 1, 2, 3, 4, 5 or 6 base mismatches, provided that the effector sequence is capable of forming a duplex with a sequence set forth in SEQ ID NO:40; and (ii) an effector complement sequence comprising a sequence which is substantially complementary to the effector sequence. For example, the shmiR encoded by the nucleic acid may comprise an effector sequence set forth in SEQ ID NO:39 and an effector complement sequence which is substantially complementary to the sequence set forth in SEQ ID NO:39 and capable of forming a duplex therewith. The effector complement sequence which is substantially complementary to the sequence set forth in SEQ ID NO:39 may be the sequence set forth in SEQ ID NO:40. A shmiR in accordance with this example is hereinafter designated "shmiR-15".

In one example, the nucleic acid described herein may comprise a DNA sequence encoding a shmiR comprising: (i) an effector sequence which is substantially complementary to the sequence set forth in SEQ ID NO:42 with the exception of 1, 2, 3, 4, 5 or 6 base mismatches, provided that the effector sequence is capable of forming a duplex with a sequence set forth in SEQ ID NO:42; and (ii) an effector complement sequence comprising a sequence which is substantially complementary to the effector sequence. For example, the shmiR encoded by the nucleic acid may comprise an effector sequence set forth in SEQ ID NO:41 and an effector complement sequence which is substantially complementary to the sequence set forth in SEQ ID NO:41 and capable of forming a duplex therewith. The effector complement sequence which is substantially complementary to the sequence set forth in SEQ ID NO:41 may be the sequence set forth in SEQ ID NO:42. A shmiR in accordance with this example is hereinafter designated "shmiR-16".

In one example, the nucleic acid described herein may comprise a DNA sequence encoding a shmiR comprising: (i) an effector sequence which is substantially complementary to the sequence set forth in SEQ ID NO:111 with the exception of 1, 2, 3, 4, 5 or 6 base mismatches, provided that the effector sequence is capable of forming a duplex with a sequence set forth in SEQ ID NO:111; and (ii) an effector complement sequence comprising a sequence which is substantially complementary to the effector sequence. For example, the shmiR encoded by the nucleic acid may comprise an effector sequence set forth in SEQ ID NO:112 and an effector complement sequence which is substantially complementary to the sequence set forth in SEQ ID NO:112 and capable of forming a duplex therewith. The effector complement sequence which is substantially complementary to the sequence set forth in SEQ ID NO:112 may be the sequence set forth in SEQ ID NO:111. A shmiR in accordance with this example is hereinafter designated "shmiR-17".

In one example, the nucleic acid described herein may comprise a DNA sequence encoding a shmiR comprising: (i) an effector sequence which is substantially complementary to the sequence set forth in SEQ ID NO:113 with the exception of 1, 2, 3, 4, 5 or 6 base mismatches, provided that the effector sequence is capable of forming a duplex with a sequence set forth in SEQ ID NO:113; and (ii) an effector complement sequence comprising a sequence which is substantially complementary to the effector sequence. For example, the shmiR encoded by the nucleic acid may comprise an effector sequence set forth in SEQ ID NO:114 and an effector complement sequence which is substantially complementary to the sequence set forth in SEQ ID NO:114 and capable of forming a duplex therewith. The effector complement sequence which is substantially complementary to the sequence set forth in SEQ ID NO:114 may be the sequence set forth in SEQ ID NO:113. A shmiR in accordance with this example is hereinafter designated "shmiR-18".

In one example, the nucleic acid described herein may comprise a DNA sequence encoding a shmiR comprising: (i) an effector sequence which is substantially complementary to the sequence set forth in SEQ ID NO:115 with the exception of 1, 2, 3, 4, 5 or 6 base mismatches, provided that the effector sequence is capable of forming a duplex with a sequence set forth in SEQ ID NO:115; and (ii) an effector complement sequence comprising a sequence which is substantially complementary to the effector sequence. For example, the shmiR encoded by the nucleic acid may comprise an effector sequence set forth in SEQ ID NO:116 and an effector complement sequence which is substantially complementary to the sequence set forth in SEQ ID NO:116 and capable of forming a duplex therewith. The effector complement sequence which is substantially complementary to the sequence set forth in SEQ ID NO:116 may be the sequence set forth in SEQ ID NO:115. A shmiR in accordance with this example is hereinafter designated "shmiR-19".

In one example, the nucleic acid described herein may comprise a DNA sequence encoding a shmiR comprising: (i) an effector sequence which is substantially complementary to the sequence set forth in SEQ ID NO:117 with the exception of 1, 2, 3, 4, 5 or 6 base mismatches, provided that the effector sequence is capable of forming a duplex with a sequence set forth in SEQ ID NO:117; and (ii) an effector complement sequence comprising a sequence which is substantially complementary to the effector sequence. For example, the shmiR encoded by the nucleic acid may comprise an effector sequence set forth in SEQ ID NO:118 and an effector complement sequence which is substantially complementary to the sequence set forth in SEQ ID NO:118 and capable of forming a duplex therewith. The effector complement sequence which is substantially complementary to the sequence set forth in SEQ ID NO:118 may be the sequence set forth in SEQ ID NO:117. A shmiR in accordance with this example is hereinafter designated "shmiR-20".

In one example, the nucleic acid described herein may comprise a DNA sequence encoding a shmiR comprising: (i) an effector sequence which is substantially complementary to the sequence set forth in SEQ ID NO:119 with the exception of 1, 2, 3, 4, 5 or 6 base mismatches, provided that the effector sequence is capable of forming a duplex with a sequence set forth in SEQ ID NO:119; and (ii) an effector complement sequence comprising a sequence which is substantially complementary to the effector sequence. For example, the shmiR encoded by the nucleic acid may comprise an effector sequence set forth in SEQ ID NO:120 and an effector complement sequence which is substantially complementary to the sequence set forth in SEQ ID NO:120 and capable of forming a duplex therewith. The effector complement sequence which is substantially complementary to the sequence set forth in SEQ ID NO:120 may be the sequence set forth in SEQ ID NO:119. A shmiR in accordance with this example is hereinafter designated "shmiR-21".

In one example, the nucleic acid described herein may comprise a DNA sequence encoding a shmiR comprising: (i) an effector sequence which is substantially complementary to the sequence set forth in SEQ ID NO:121 with the exception of 1, 2, 3, 4, 5 or 6 base mismatches, provided that the effector sequence is capable of forming a duplex with a sequence set forth in SEQ ID NO:121; and (ii) an effector complement sequence comprising a sequence which is substantially complementary to the effector sequence. For example, the shmiR encoded by the nucleic acid may comprise an effector sequence set forth in SEQ ID NO:122 and an effector complement sequence which is substantially complementary to the sequence set forth in SEQ ID NO:122 and capable of forming a duplex therewith. The effector complement sequence which is substantially complementary to the sequence set forth in SEQ ID NO:122 may be the sequence set forth in SEQ ID NO:121. A shmiR in accordance with this example is hereinafter designated "shmiR-22".

In one example, the nucleic acid described herein may comprise a DNA sequence encoding a shmiR comprising: (i) an effector sequence which is substantially complementary to the sequence set forth in SEQ ID NO:123 with the exception of 1, 2, 3, 4, 5 or 6 base mismatches, provided that the effector sequence is capable of forming a duplex with a sequence set forth in SEQ ID NO:123; and (ii) an effector complement sequence comprising a sequence which is substantially complementary to the effector sequence. For example, the shmiR encoded by the nucleic acid may comprise an effector sequence set forth in SEQ ID NO:124 and an effector complement sequence which is substantially complementary to the sequence set forth in SEQ ID NO:124 and capable of forming a duplex therewith. The effector complement sequence which is substantially complementary to the sequence set forth in SEQ ID NO:124 may be the sequence set forth in SEQ ID NO:123. A shmiR in accordance with this example is hereinafter designated "shmiR-23".

In one example, the nucleic acid described herein may comprise a DNA sequence encoding a shmiR comprising: (i) an effector sequence which is substantially complementary to the sequence set forth in SEQ ID NO:125 with the exception of 1, 2, 3, 4, 5 or 6 base mismatches, provided that the effector sequence is capable of forming a duplex with a sequence set forth in SEQ ID NO:125; and (ii) an effector complement sequence comprising a sequence which is substantially complementary to the effector sequence. For example, the shmiR encoded by the nucleic acid may comprise an effector sequence set forth in SEQ ID NO:126 and an effector complement sequence which is substantially complementary to the sequence set forth in SEQ ID NO:126 and capable of forming a duplex therewith. The effector complement sequence which is substantially complementary to the sequence set forth in SEQ ID NO:126 may be the sequence set forth in SEQ ID NO:125. A shmiR in accordance with this example is hereinafter designated "shmiR-24".

In one example, the nucleic acid described herein may comprise a DNA sequence encoding a shmiR comprising: (i) an effector sequence which is substantially complementary to the sequence set forth in SEQ ID NO:127 with the exception of 1, 2, 3, 4, 5 or 6 base mismatches, provided that the effector sequence is capable of forming a duplex with a sequence set forth in SEQ ID NO:127; and (ii) an effector complement sequence comprising a sequence which is substantially complementary to the effector sequence. For example, the shmiR encoded by the nucleic acid may comprise an effector sequence set forth in SEQ ID NO:128 and an effector complement sequence which is substantially complementary to the sequence set forth in SEQ ID NO:128 and capable of forming a duplex therewith. The effector complement sequence which is substantially complementary to the sequence set forth in SEQ ID NO:128 may be the sequence set forth in SEQ ID NO:127. A shmiR in accordance with this example is hereinafter designated "shmiR-25".

In one example, the nucleic acid described herein may comprise a DNA sequence encoding a shmiR comprising: (i) an effector sequence which is substantially complementary to the sequence set forth in SEQ ID NO:129 with the exception of 1, 2, 3, 4, 5 or 6 base mismatches, provided that the effector sequence is capable of forming a duplex with a sequence set forth in SEQ ID NO:129; and (ii) an effector complement sequence comprising a sequence which is substantially complementary to the effector sequence. For example, the shmiR encoded by the nucleic acid may comprise an effector sequence set forth in SEQ ID NO:130 and an effector complement sequence which is substantially complementary to the sequence set forth in SEQ ID NO:130 and capable of forming a duplex therewith. The effector complement sequence which is substantially complementary to the sequence set forth in SEQ ID NO:130 may be the sequence set forth in SEQ ID NO:129. A shmiR in accordance with this example is hereinafter designated "shmiR-26".

In one example, the nucleic acid described herein may comprise a DNA sequence encoding a shmiR comprising: (i) an effector sequence which is substantially complementary to the sequence set forth in SEQ ID NO:131 with the exception of 1, 2, 3, 4, 5 or 6 base mismatches, provided that the effector sequence is capable of forming a duplex with a sequence set forth in SEQ ID NO:131; and (ii) an effector complement sequence comprising a sequence which is substantially complementary to the effector sequence. For example, the shmiR encoded by the nucleic acid may comprise an effector sequence set forth in SEQ ID NO:132 and an effector complement sequence which is substantially complementary to the sequence set forth in SEQ ID NO:132 and capable of forming a duplex therewith. The effector complement sequence which is substantially complementary to the sequence set forth in SEQ ID NO:132 may be the sequence set forth in SEQ ID NO:131. A shmiR in accordance with this example is hereinafter designated "shmiR-27".

In one example, the nucleic acid described herein may comprise a DNA sequence encoding a shmiR comprising: (i) an effector sequence which is substantially complementary to the sequence set forth in SEQ ID NO:133 with the exception of 1, 2, 3, 4, 5 or 6 base mismatches, provided that the effector sequence is capable of forming a duplex with a sequence set forth in SEQ ID NO:133; and (ii) an effector complement sequence comprising a sequence which is substantially complementary to the effector sequence. For example, the shmiR encoded by the nucleic acid may comprise an effector sequence set forth in SEQ ID NO:134 and an effector complement sequence which is substantially complementary to the sequence set forth in SEQ ID NO:134 and capable of forming a duplex therewith. The effector complement sequence which is substantially complementary to the sequence set forth in SEQ ID NO:134 may be the sequence set forth in SEQ ID NO:133. A shmiR in accordance with this example is hereinafter designated "shmiR-28".

In any of the examples described herein, the shmiR encoded by the nucleic acid of the disclosure may comprise, in a 5' to 3' direction:
 a 5' flanking sequence of the pri-miRNA backbone;
 the effector complement sequence;
 the stemloop sequence;
 the effector sequence; and
 a 3' flanking sequence of the pri-miRNA backbone.

Suitable loop sequences may be selected from those known in the art. However, an exemplary stemloop sequence is set forth in SEQ ID NO: 75.

Suitable primary micro RNA (pri-miRNA or pri-R) backbones for use in a nucleic acid of the disclosure may be selected from those known in the art. For example, the pri-miRNA backbone may be selected from a pri-miR-30a backbone, a pri-miR-155 backbone, a pri-miR-21 backbone and a pri-miR-136 backbone. Preferably, however, the pri-miRNA backbone is a pri-miR-30a backbone. In accordance with an example in which the pri-miRNA backbone is a pri-miR-30a backbone, the 5' flanking sequence of the pri-miRNA backbone is set forth in SEQ ID NO: 76 and the 3' flanking sequence of the pri-miRNA backbone is set forth in SEQ ID NO: 77. Thus, the nucleic acid encoding the shmiRs of the disclosure (e.g., shmiR-1 to shmiR-16 described herein) may comprise DNA sequence encoding the sequence set forth in SEQ ID NO: 76 and DNA sequence encoding the sequence set forth in SEQ ID NO: 77.

In one example, the nucleic acid described herein may comprise a DNA sequence selected from the sequence set forth in any one of SEQ ID NOs: 59-74 and 146-157.

In one example, the nucleic acid described herein comprises or consists of a DNA sequence set forth in SEQ ID NO: 59 and encodes a shmiR (shmiR-1) comprising or consisting of the sequence set forth in SEQ ID NO: 43.

In one example, the nucleic acid described herein comprises or consists of a DNA sequence set forth in SEQ ID NO: 60 and encodes a shmiR (shmiR-2) comprising or consisting of the sequence set forth in SEQ ID NO: 44.

In one example, the nucleic acid described herein comprises or consists of a DNA sequence set forth in SEQ ID NO: 61 and encodes a shmiR (shmiR-3) comprising or consisting of the sequence set forth in SEQ ID NO: 45.

In one example, the nucleic acid described herein comprises or consists of a DNA sequence set forth in SEQ ID NO: 62 and encodes a shmiR (shmiR-4) comprising or consisting of the sequence set forth in SEQ ID NO: 46.

In one example, the nucleic acid described herein comprises or consists of a DNA sequence set forth in SEQ ID NO: 63 and encodes a shmiR (shmiR-5) comprising or consisting of the sequence set forth in SEQ ID NO: 47.

In one example, the nucleic acid described herein comprises or consists of a DNA sequence set forth in SEQ ID NO: 64 and encodes a shmiR (shmiR-6) comprising or consisting of the sequence set forth in SEQ ID NO: 48.

In one example, the nucleic acid described herein comprises or consists of a DNA sequence set forth in SEQ ID NO: 65 and encodes a shmiR (shmiR-7) comprising or consisting of the sequence set forth in SEQ ID NO: 49.

In one example, the nucleic acid described herein comprises or consists of a DNA sequence set forth in SEQ ID NO: 66 and encodes a shmiR (shmiR-8) comprising or consisting of the sequence set forth in SEQ ID NO: 50.

In one example, the nucleic acid described herein comprises or consists of a DNA sequence set forth in SEQ ID NO: 67 and encodes a shmiR (shmiR-9) comprising or consisting of the sequence set forth in SEQ ID NO: 51.

In one example, the nucleic acid described herein comprises or consists of a DNA sequence set forth in SEQ ID NO: 68 and encodes a shmiR (shmiR-10) comprising or consisting of the sequence set forth in SEQ ID NO: 52.

In one example, the nucleic acid described herein comprises or consists of a DNA sequence set forth in SEQ ID NO: 69 and encodes a shmiR (shmiR-11) comprising or consisting of the sequence set forth in SEQ ID NO: 53.

In one example, the nucleic acid described herein comprises or consists of a DNA sequence set forth in SEQ ID NO: 70 and encodes a shmiR (shmiR-12) comprising or consisting of the sequence set forth in SEQ ID NO: 54.

In one example, the nucleic acid described herein comprises or consists of a DNA sequence set forth in SEQ ID NO: 71 and encodes a shmiR (shmiR-13) comprising or consisting of the sequence set forth in SEQ ID NO: 55.

In one example, the nucleic acid described herein comprises or consists of a DNA sequence set forth in SEQ ID NO: 72 and encodes a shmiR (shmiR-14) comprising or consisting of the sequence set forth in SEQ ID NO: 56.

In one example, the nucleic acid described herein comprises or consists of a DNA sequence set forth in SEQ ID NO: 73 and encodes a shmiR (shmiR-15) comprising or consisting of the sequence set forth in SEQ ID NO: 57.

In one example, the nucleic acid described herein comprises or consists of a DNA sequence set forth in SEQ ID NO: 74 and encodes a shmiR (shmiR-16) comprising or consisting of the sequence set forth in SEQ ID NO: 58.

In one example, the nucleic acid described herein comprises or consists of a DNA sequence set forth in SEQ ID NO: 146 and encodes a shmiR (shmiR-17) comprising or consisting of the sequence set forth in SEQ ID NO: 134.

In one example, the nucleic acid described herein comprises or consists of a DNA sequence set forth in SEQ ID NO: 147 and encodes a shmiR (shmiR-18) comprising or consisting of the sequence set forth in SEQ ID NO: 135.

In one example, the nucleic acid described herein comprises or consists of a DNA sequence set forth in SEQ ID NO: 148 and encodes a shmiR (shmiR-19) comprising or consisting of the sequence set forth in SEQ ID NO: 136.

In one example, the nucleic acid described herein comprises or consists of a DNA sequence set forth in SEQ ID NO: 149 and encodes a shmiR (shmiR-20) comprising or consisting of the sequence set forth in SEQ ID NO: 137.

In one example, the nucleic acid described herein comprises or consists of a DNA sequence set forth in SEQ ID NO: 150 and encodes a shmiR (shmiR-21) comprising or consisting of the sequence set forth in SEQ ID NO: 138.

In one example, the nucleic acid described herein comprises or consists of a DNA sequence set forth in SEQ ID NO: 151 and encodes a shmiR (shmiR-22) comprising or consisting of the sequence set forth in SEQ ID NO: 139.

In one example, the nucleic acid described herein comprises or consists of a DNA sequence set forth in SEQ ID NO: 152 and encodes a shmiR (shmiR-23) comprising or consisting of the sequence set forth in SEQ ID NO: 140.

In one example, the nucleic acid described herein comprises or consists of a DNA sequence set forth in SEQ ID NO: 153 and encodes a shmiR (shmiR-24) comprising or consisting of the sequence set forth in SEQ ID NO: 141.

In one example, the nucleic acid described herein comprises or consists of a DNA sequence set forth in SEQ ID NO: 154 and encodes a shmiR (shmiR-25) comprising or consisting of the sequence set forth in SEQ ID NO: 142.

In one example, the nucleic acid described herein comprises or consists of a DNA sequence set forth in SEQ ID NO: 155 and encodes a shmiR (shmiR-26) comprising or consisting of the sequence set forth in SEQ ID NO: 143.

In one example, the nucleic acid described herein comprises or consists of a DNA sequence set forth in SEQ ID NO: 156 and encodes a shmiR (shmiR-27) comprising or consisting of the sequence set forth in SEQ ID NO: 144.

In one example, the nucleic acid described herein comprises or consists of a DNA sequence set forth in SEQ ID NO: 157 and encodes a shmiR (shmiR-28) comprising or consisting of the sequence set forth in SEQ ID NO: 145.

Exemplary nucleic acids of the disclosure encode a shmiR selected from shmiR-6, shmiR-7, shmiR-12 and shmiR-15 as described herein. Further exemplary nucleic acids of the disclosure encode variants of shmiR-12 selected from shmiR-23, shmiR-24, shmiR-25, shmiR-26, shmiR-27 and shmiR-28, or encode variants of shmiR-15 selected from shmiR-17, shmiR-18, shmiR-19, shmiR-20, shmiR-21 and shmiR-22.

It will be understood by a person of skill in the art that a nucleic acid in accordance with the present disclosure may be combined or used in conjunction with other therapeutic agents for treating HBV. Accordingly, the present disclosure provides a nucleic acid comprising a DNA sequence encoding a shmiR as described herein (e.g., one or shmiRs designated shmiR1-shmiR-28 described herein) in combination with one or more other agents for treating HBV. In one example, a plurality of nucleic acids are provided comprising:

(a) at least one nucleic acid as described herein; and
(b) at least one further nucleic acid selected from:
 (i) a nucleic acid comprising a DNA sequence encoding a shmiR as described herein; or
 (ii) a nucleic acid comprising a DNA sequence encoding a short hairpin RNA (shRNA) comprising an effector sequence of at least 17 nucleotides in length and a effector complement sequence, wherein the effector sequence is substantially complementary to a RNA sequence set forth in any one of SEQ ID NOs: 1-10, 38, 40, 42, 111, 113, 115, 117, 119, 121, 123, 125, 127, 129, 131 and 133;

wherein the shmiR encoded by the nucleic acid at (a) and the shmiR or shRNA encoded by the nucleic acid at (b) comprise different effector sequences. Preferably, the effector sequence of the shRNA at (b)(ii) which is substantially complementary to a RNA sequence set forth in any one of SEQ ID NOs: 1-10, 38, 40, 42, 111, 113, 115, 117, 119, 121, 123, 125, 127, 129, 131 and 133 will be less than 30 nucleotides in length. For example, a suitable effector sequence of the shRNA may be in the range of 17-29 nucleotides in length.

Accordingly, in one example the plurality of nucleic acids of the disclosure may comprise two or more nucleic acids encoding shmiRs as described herein, such as two, or three, or four, or five, or six, or seven, or eight, or nine, or ten nucleic acids encoding shmiRs as described herein.

In another example, the plurality of nucleic acids of the disclosure comprises at least one nucleic acid encoding a shmiR as described herein and at least one nucleic acid comprising a DNA sequence encoding a shRNA comprising an effector of at least 17 nucleotides in length and a effector complement sequence, wherein the effector sequence is substantially complementary to a RNA sequence set forth in any one of SEQ ID NOs: 1-10, 38, 40, 42, 111, 113, 115, 117, 119, 121, 123, 125, 127, 129, 131 and 133.

In one example, the shRNA encoded by a nucleic acid in the plurality comprises: (i) an effector sequence which is substantially complementary to the sequence set forth in SEQ ID NO:12 with the exception of 1, 2, 3, 4, 5 or 6 base mismatches, provided that the effector sequence is capable of forming a duplex with a sequence set forth in SEQ ID NO:12; and (ii) an effector complement sequence comprising a sequence which is substantially complementary to the effector sequence. For example, the shRNA encoded by the nucleic acid may comprise an effector sequence set forth in SEQ ID NO:11 and an effector complement sequence which is substantially complementary to the sequence set forth in SEQ ID NO:11 and capable of forming a duplex therewith. The effector complement sequence which is substantially complementary to the sequence set forth in SEQ ID NO:11 may be the sequence set forth in SEQ ID NO:12. A shRNA in accordance with this example is hereinafter designated "shRNA-1".

In one example, the shRNA encoded by a nucleic acid in the plurality comprises: (i) an effector sequence which is substantially complementary to the sequence set forth in SEQ ID NO:14 with the exception of 1, 2, 3, 4, 5 or 6 base mismatches, provided that the effector sequence is capable of forming a duplex with a sequence set forth in SEQ ID NO:14; and (ii) an effector complement sequence comprising a sequence which is substantially complementary to the effector sequence. For example, the shRNA encoded by the nucleic acid may comprise an effector sequence set forth in SEQ ID NO:13 and an effector complement sequence which is substantially complementary to the sequence set forth in SEQ ID NO:13 and capable of forming a duplex therewith. The effector complement sequence which is substantially complementary to the sequence set forth in SEQ ID NO:13 may be the sequence set forth in SEQ ID NO:14. A shRNA in accordance with this example is hereinafter designated "shRNA-2".

In one example, the shRNA encoded by a nucleic acid in the plurality comprises: (i) an effector sequence which is substantially complementary to the sequence set forth in SEQ ID NO:16 with the exception of 1, 2, 3, 4, 5 or 6 base mismatches, provided that the effector sequence is capable of forming a duplex with a sequence set forth in SEQ ID NO:16; and (ii) an effector complement sequence comprising a sequence which is substantially complementary to the effector sequence. For example, the shRNA encoded by the nucleic acid may comprise an effector sequence set forth in SEQ ID NO:15 and an effector complement sequence which is substantially complementary to the sequence set forth in SEQ ID NO:15 and capable of forming a duplex therewith. The effector complement sequence which is substantially complementary to the sequence set forth in SEQ ID NO:15 may be the sequence set forth in SEQ ID NO:16. A shRNA in accordance with this example is hereinafter designated "shRNA-3".

In one example, the shRNA encoded by a nucleic acid in the plurality comprises: (i) an effector sequence which is substantially complementary to the sequence set forth in SEQ ID NO:18 with the exception of 1, 2, 3, 4, 5 or 6 base mismatches, provided that the effector sequence is capable of forming a duplex with a sequence set forth in SEQ ID NO:18; and (ii) an effector complement sequence comprising a sequence which is substantially complementary to the effector sequence. For example, the shRNA encoded by the nucleic acid may comprise an effector sequence set forth in SEQ ID NO:17 and an effector complement sequence which is substantially complementary to the sequence set forth in SEQ ID NO:17 and capable of forming a duplex therewith. The effector complement sequence which is substantially complementary to the sequence set forth in SEQ ID NO:17 may be the sequence set forth in SEQ ID NO:18. A shRNA in accordance with this example is hereinafter designated "shRNA-4".

In one example, the shRNA encoded by a nucleic acid in the plurality comprises: (i) an effector sequence which is substantially complementary to the sequence set forth in SEQ ID NO:20 with the exception of 1, 2, 3, 4, 5 or 6 base mismatches, provided that the effector sequence is capable of forming a duplex with a sequence set forth in SEQ ID NO:20; and (ii) an effector complement sequence comprising a sequence which is substantially complementary to the effector sequence. For example, the shRNA encoded by the nucleic acid may comprise an effector sequence set forth in SEQ ID NO:19 and an effector complement sequence which is substantially complementary to the sequence set forth in SEQ ID NO:19 and capable of forming a duplex therewith. The effector complement sequence which is substantially complementary to the sequence set forth in SEQ ID NO:19 may be the sequence set forth in SEQ ID NO:20. A shRNA in accordance with this example is hereinafter designated "shRNA-5".

In one example, the shRNA encoded by a nucleic acid in the plurality comprises: (i) an effector sequence which is substantially complementary to the sequence set forth in SEQ ID NO:22 with the exception of 1, 2, 3, 4, 5 or 6 base mismatches, provided that the effector sequence is capable of forming a duplex with a sequence set forth in SEQ ID NO:22; and (ii) an effector complement sequence comprising a sequence which is substantially complementary to the effector sequence. For example, the shRNA encoded by the nucleic acid may comprise an effector sequence set forth in SEQ ID NO:21 and an effector complement sequence which is substantially complementary to the sequence set forth in SEQ ID NO:21 and capable of forming a duplex therewith. The effector complement sequence which is substantially complementary to the sequence set forth in SEQ ID NO:21 may be the sequence set forth in SEQ ID NO:22. A shRNA in accordance with this example is hereinafter designated "shRNA-6".

In one example, the shRNA encoded by a nucleic acid in the plurality comprises: (i) an effector sequence which is substantially complementary to the sequence set forth in SEQ ID NO:24 with the exception of 1, 2, 3, 4, 5 or 6 base mismatches, provided that the effector sequence is capable of forming a duplex with a sequence set forth in SEQ ID NO:24; and (ii) an effector complement sequence comprising a sequence which is substantially complementary to the effector sequence. For example, the shRNA encoded by the nucleic acid may comprise an effector sequence set forth in SEQ ID NO:23 and an effector complement sequence which is substantially complementary to the sequence set forth in SEQ ID NO:23 and capable of forming a duplex therewith. The effector complement sequence which is substantially complementary to the sequence set forth in SEQ ID NO:23 may be the sequence set forth in SEQ ID NO:24. A shRNA in accordance with this example is hereinafter designated "shRNA-7".

In one example, the shRNA encoded by a nucleic acid in the plurality comprises: (i) an effector sequence which is substantially complementary to the sequence set forth in SEQ ID NO:26 with the exception of 1, 2, 3, 4, 5 or 6 base mismatches, provided that the effector sequence is capable of forming a duplex with a sequence set forth in SEQ ID NO:26; and (ii) an effector complement sequence comprising a sequence which is substantially complementary to the effector sequence. For example, the shRNA encoded by the nucleic acid may comprise an effector sequence set forth in SEQ ID NO:25 and an effector complement sequence which is substantially complementary to the sequence set forth in SEQ ID NO:25 and capable of forming a duplex therewith. The effector complement sequence which is substantially complementary to the sequence set forth in SEQ ID NO:25 may be the sequence set forth in SEQ ID NO:26. A shRNA in accordance with this example is hereinafter designated "shRNA-8".

In one example, the shRNA encoded by a nucleic acid in the plurality comprises: (i) an effector sequence which is substantially complementary to the sequence set forth in SEQ ID NO:28 with the exception of 1, 2, 3, 4, 5 or 6 base mismatches, provided that the effector sequence is capable of forming a duplex with a sequence set forth in SEQ ID NO:28; and (ii) an effector complement sequence comprising a sequence which is substantially complementary to the effector sequence. For example, the shRNA encoded by the nucleic acid may comprise an effector sequence set forth in SEQ ID NO:27 and an effector complement sequence which is substantially complementary to the sequence set forth in SEQ ID NO:27 and capable of forming a duplex therewith.

The effector complement sequence which is substantially complementary to the sequence set forth in SEQ ID NO:27 may be the sequence set forth in SEQ ID NO:28. A shRNA in accordance with this example is hereinafter designated "shRNA-9".

In one example, the shRNA encoded by a nucleic acid in the plurality comprises: (i) an effector sequence which is substantially complementary to the sequence set forth in SEQ ID NO:30 with the exception of 1, 2, 3, 4, 5 or 6 base mismatches, provided that the effector sequence is capable of forming a duplex with a sequence set forth in SEQ ID NO:30; and (ii) an effector complement sequence comprising a sequence which is substantially complementary to the effector sequence. For example, the shRNA encoded by the nucleic acid may comprise an effector sequence set forth in SEQ ID NO:29 and an effector complement sequence which is substantially complementary to the sequence set forth in SEQ ID NO:29 and capable of forming a duplex therewith. The effector complement sequence which is substantially complementary to the sequence set forth in SEQ ID NO:29 may be the sequence set forth in SEQ ID NO:30. A shRNA in accordance with this example is hereinafter designated "shRNA-10".

In one example, the shRNA encoded by a nucleic acid in the plurality comprises: (i) an effector sequence which is substantially complementary to the sequence set forth in SEQ ID NO:32 with the exception of 1, 2, 3, 4, 5 or 6 base mismatches, provided that the effector sequence is capable of forming a duplex with a sequence set forth in SEQ ID NO:32; and (ii) an effector complement sequence comprising a sequence which is substantially complementary to the effector sequence. For example, the shRNA encoded by the nucleic acid may comprise an effector sequence set forth in SEQ ID NO:31 and an effector complement sequence which is substantially complementary to the sequence set forth in SEQ ID NO:31 and capable of forming a duplex therewith. The effector complement sequence which is substantially complementary to the sequence set forth in SEQ ID NO:31 may be the sequence set forth in SEQ ID NO:32. A shRNA in accordance with this example is hereinafter designated "shRNA-11".

In one example, the shRNA encoded by a nucleic acid in the plurality comprises: (i) an effector sequence which is substantially complementary to the sequence set forth in SEQ ID NO:34 with the exception of 1, 2, 3, 4, 5 or 6 base mismatches, provided that the effector sequence is capable of forming a duplex with a sequence set forth in SEQ ID NO:34; and (ii) an effector complement sequence comprising a sequence which is substantially complementary to the effector sequence. For example, the shRNA encoded by the nucleic acid may comprise an effector sequence set forth in SEQ ID NO:33 and an effector complement sequence which is substantially complementary to the sequence set forth in SEQ ID NO:33 and capable of forming a duplex therewith. The effector complement sequence which is substantially complementary to the sequence set forth in SEQ ID NO:33 may be the sequence set forth in SEQ ID NO:34. A shRNA in accordance with this example is hereinafter designated "shRNA-12".

In one example, the shRNA encoded by a nucleic acid in the plurality comprises: (i) an effector sequence which is substantially complementary to the sequence set forth in SEQ ID NO:36 with the exception of 1, 2, 3, 4, 5 or 6 base mismatches, provided that the effector sequence is capable of forming a duplex with a sequence set forth in SEQ ID NO:36; and (ii) an effector complement sequence comprising a sequence which is substantially complementary to the effector sequence. For example, the shRNA encoded by the nucleic acid may comprise an effector sequence set forth in SEQ ID NO:35 and an effector complement sequence which is substantially complementary to the sequence set forth in SEQ ID NO:35 and capable of forming a duplex therewith. The effector complement sequence which is substantially complementary to the sequence set forth in SEQ ID NO:35 may be the sequence set forth in SEQ ID NO:36. A shRNA in accordance with this example is hereinafter designated "shRNA-13".

In one example, the shRNA encoded by a nucleic acid in the plurality comprises: (i) an effector sequence which is substantially complementary to the sequence set forth in SEQ ID NO:38 with the exception of 1, 2, 3, 4, 5 or 6 base mismatches, provided that the effector sequence is capable of forming a duplex with a sequence set forth in SEQ ID NO:38; and (ii) an effector complement sequence comprising a sequence which is substantially complementary to the effector sequence. For example, the shRNA encoded by the nucleic acid may comprise an effector sequence set forth in SEQ ID NO:37 and an effector complement sequence which is substantially complementary to the sequence set forth in SEQ ID NO:37 and capable of forming a duplex therewith. The effector complement sequence which is substantially complementary to the sequence set forth in SEQ ID NO:37 may be the sequence set forth in SEQ ID NO:38. A shRNA in accordance with this example is hereinafter designated "shRNA-14".

In one example, the shRNA encoded by a nucleic acid in the plurality comprises: (i) an effector sequence which is substantially complementary to the sequence set forth in SEQ ID NO:40 with the exception of 1, 2, 3, 4, 5 or 6 base mismatches, provided that the effector sequence is capable of forming a duplex with a sequence set forth in SEQ ID NO:40; and (ii) an effector complement sequence comprising a sequence which is substantially complementary to the effector sequence. For example, the shRNA encoded by the nucleic acid may comprise an effector sequence set forth in SEQ ID NO:39 and an effector complement sequence which is substantially complementary to the sequence set forth in SEQ ID NO:39 and capable of forming a duplex therewith. The effector complement sequence which is substantially complementary to the sequence set forth in SEQ ID NO:39 may be the sequence set forth in SEQ ID NO:40. A shRNA in accordance with this example is hereinafter designated "shRNA-15".

In one example, the shRNA encoded by a nucleic acid in the plurality comprises: (i) an effector sequence which is substantially complementary to the sequence set forth in SEQ ID NO:42 with the exception of 1, 2, 3, 4, 5 or 6 base mismatches, provided that the effector sequence is capable of forming a duplex with a sequence set forth in SEQ ID NO:42; and (ii) an effector complement sequence comprising a sequence which is substantially complementary to the effector sequence. For example, the shRNA encoded by the nucleic acid may comprise an effector sequence set forth in SEQ ID NO:41 and an effector complement sequence which is substantially complementary to the sequence set forth in SEQ ID NO:41 and capable of forming a duplex therewith. The effector complement sequence which is substantially complementary to the sequence set forth in SEQ ID NO:41 may be the sequence set forth in SEQ ID NO:42. A shRNA in accordance with this example is hereinafter designated "shRNA-16".

According to any example in which one or more of the nucleic acid in the plurality of nucleic acids described herein encodes a shRNA, the shRNA may comprise a stem loop sequence positioned between the effector sequence and the effector complement sequence. Suitable loop sequences may be selected from those known in the art. Alternatively, suitable stem loops may be developed de novo. In one example, a nucleic acid of the plurality described herein encoding a shRNA may comprise a DNA sequence encoding a stem loop positioned between the DNA sequences encoding the effector sequence and the effector complement sequence. For example, a shRNA encoded by a nucleic acid of the disclosure may comprise a sequence set forth in any one of SEQ ID NOs:78-93. Thus, a nucleic acid in the plurality of nucleic acids described herein may comprise or consist of a DNA sequence set forth in in any one of SEQ ID NOs: 94-109.

In one example, the plurality of nucleic acids described herein comprises a nucleic acid which comprises or consists of a DNA sequence set forth in SEQ ID NO: 59 and encodes a shmiR (shmiR-1) comprising or consisting of the sequence set forth in SEQ ID NO: 43, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 60 and encodes a shmiR (shmiR-2) comprising or consisting of the sequence set forth in SEQ ID NO: 44, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 61 and encodes a shmiR (shmiR-3) comprising or consisting of the sequence set forth in SEQ ID NO: 45, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 62 and encodes a shmiR (shmiR-4) comprising or consisting of the sequence set forth in SEQ ID NO: 46, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 63 and encodes a shmiR (shmiR-5) comprising or consisting of the sequence set forth in SEQ ID NO: 47, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 64 and encodes a shmiR (shmiR-6) comprising or consisting of the sequence set forth in SEQ ID NO: 48, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 65 and encodes a shmiR (shmiR-7) comprising or consisting of the sequence set forth in SEQ ID NO: 49, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 66 and encodes a shmiR (shmiR-8) comprising or consisting of the sequence set forth in SEQ ID NO: 50, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 67 and encodes a shmiR (shmiR-9) comprising or consisting of the sequence set forth in SEQ ID NO: 51, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 68 and encodes a shmiR (shmiR-10) comprising or consisting of the sequence set forth in SEQ ID NO: 52, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 69 and encodes a shmiR (shmiR-11) comprising or consisting of the sequence set forth in SEQ ID NO: 53, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 70 and encodes a shmiR (shmiR-12) comprising or consisting of the sequence set forth in SEQ ID NO: 54, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 71 and encodes a shmiR (shmiR-13) comprising or consisting of the sequence set forth in SEQ ID NO: 55, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 72 and encodes a shmiR (shmiR-14) comprising or consisting of the sequence set forth in SEQ ID NO: 56, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 73 and encodes a shmiR (shmiR-15) comprising or consisting of the sequence set forth in SEQ ID NO: 57, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 74 and encodes a shmiR (shmiR-16) comprising or consisting of the sequence set forth in SEQ ID NO: 58, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 146 and encodes a shmiR (shmiR-17) comprising or consisting of the sequence set forth in SEQ ID NO: 134, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 147 and encodes a shmiR (shmiR-18) comprising or consisting of the sequence set forth in SEQ ID NO: 135, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 148 and encodes a shmiR (shmiR-19) comprising or consisting of the sequence set forth in SEQ ID NO: 136, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 149 and encodes a shmiR (shmiR-20) comprising or consisting of the sequence set forth in SEQ ID NO: 137, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 150 and encodes a shmiR (shmiR-21) comprising or consisting of the sequence set forth in SEQ ID NO: 138, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 151 and encodes a shmiR (shmiR-22) comprising or consisting of the sequence set forth in SEQ ID NO: 139, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 152 and encodes a shmiR (shmiR-23) comprising or consisting of the sequence set forth in SEQ ID NO: 140, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 153 and encodes a shmiR (shmiR-24) comprising or consisting of the sequence set forth in SEQ ID NO: 141, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 154 and encodes a shmiR (shmiR-25) comprising or consisting of the sequence set forth in SEQ ID NO: 142, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 155 and encodes a shmiR (shmiR-26) comprising or consisting of the sequence set forth in SEQ ID NO: 143, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 156 and encodes a shmiR (shmiR-27) comprising or consisting of the sequence set forth in SEQ ID NO: 144, and at least one other nucleic acid of the disclosure which encodes a shmiR or shRNA targeting HBV.

In one example, the plurality of nucleic acids described herein comprises a nucleic acid which comprises or consists of a DNA sequence set forth in SEQ ID NO: 157 and encodes a shmiR (shmiR-28) comprising or consisting of the sequence set forth in SEQ ID NO: 145, and at least one other nucleic acid of the disclosure which encodes a shmiR or shRNA targeting HBV.

In accordance with any example of a plurality of nucleic acids as described herein, the plurality of nucleic acids may comprise two or more nucleic acids encoding shmiRs or shRNAs as described herein, such as two, or three, or four, or five, or six, or seven, or eight, or nine, or ten nucleic acids encoding shmiRs as described herein, provided at that at least one of the nucleic acids encodes a shmiRs of the disclosure.

In one example, the plurality of nucleic acids comprises two nucleic acids encoding a shmiR or shRNA described herein, with the proviso that at least one of the nucleic acids encodes a shmiR as described herein. In one example, the plurality of nucleic acids comprises three nucleic acids encoding a shmiR or shRNA described herein, with the proviso that at least one of the nucleic acids encodes a shmiR as described herein. In one example, the plurality of nucleic acids comprises four nucleic acids encoding a shmiR or shRNA described herein, with the proviso that at least one of the nucleic acids encodes a shmiR as described herein. In one example, the plurality of nucleic acids comprises five nucleic acids encoding a shmiR or shRNA described herein, with the proviso that at least one of the nucleic acids encodes a shmiR as described herein. In one example, the plurality of nucleic acids comprises six nucleic acids encoding a shmiR or shRNA described herein, with the proviso that at least one of the nucleic acids encodes a shmiR as described herein. In one example, the plurality of nucleic acids comprises seven nucleic acids encoding a shmiR or shRNA described herein, with the proviso that at least one of the nucleic acids encodes a shmiR as described herein. In one example, the plurality of nucleic acids comprises eight nucleic acids encoding a shmiR or shRNA described herein, with the proviso that at least one of the nucleic acids encodes a shmiR as described herein. In one example, the plurality of nucleic acids comprises nine nucleic acids encoding a shmiR or shRNA described herein, with the proviso that at least one of the nucleic acids encodes a shmiR as described herein. In one example, the plurality of nucleic acids comprises ten nucleic acids encoding a shmiR or shRNA described herein, with the proviso that at least one of the nucleic acids encodes a shmiR as described herein.

In one example, the effector sequence of a shmiR or shRNA encoded by one of the nucleic acids in the plurality is substantially complementary to a RNA transcript comprising or consisting of the sequence set forth in SEQ ID NO: 4. Suitable nucleic acids encoding a shmiR or shRNA having an effector sequence which is substantially complementary to a RNA transcript comprising or consisting of the sequence set forth in SEQ ID NO: 4 are described herein.

In one example, the effector sequence of a shmiR or shRNA encoded by one of the nucleic acids in the plurality is substantially complementary to a RNA transcript comprising or consisting of the sequence set forth in SEQ ID NO: 5. Suitable nucleic acids encoding a shmiR or shRNA having an effector sequence which is substantially complementary to a RNA transcript comprising or consisting of the sequence set forth in SEQ ID NO: 5 are described herein.

In one example, the effector sequence of a shmiR or shRNA encoded by one of the nucleic acids in the plurality is substantially complementary to a RNA transcript comprising or consisting of the sequence set forth in SEQ ID NO: 9. Suitable nucleic acids encoding a shmiR or shRNA having an effector sequence which is substantially complementary to a RNA transcript comprising or consisting of the sequence set forth in SEQ ID NO: 9 are described herein.

In one example, the effector sequence of a shmiR or shRNA encoded by one of the nucleic acids in the plurality is substantially complementary to a RNA transcript comprising or consisting of the sequence set forth in SEQ ID NO: 40. Suitable nucleic acids encoding a shmiR or shRNA having an effector sequence which is substantially complementary to a RNA transcript comprising or consisting of the sequence set forth in SEQ ID NO: 40 are described herein.

In one example, the effector sequence of a shmiR encoded by a nucleic acid in the plurality is substantially complementary to a RNA transcript comprising or consisting of the sequence set forth in SEQ ID NO: 4 and the effector sequence of a shmiR encoded by a nucleic acid in the plurality is substantially complementary to a RNA transcript comprising or consisting of the sequence set forth in SEQ ID NO: 9.

In one example, the effector sequence of a shmiR encoded by a nucleic acid in the plurality is substantially complementary to a RNA transcript comprising or consisting of the sequence set forth in SEQ ID NO: 4 and the effector sequence of a shmiR encoded by a nucleic acid in the plurality is substantially complementary to a RNA transcript comprising or consisting of the sequence set forth in SEQ ID NO: 9; and the effector sequence of a shmiR encoded by a nucleic acid in the plurality is substantially complementary to a RNA transcript comprising or consisting of the sequence set forth in SEQ ID NO: 5.

In one example, the effector sequence of a shmiR encoded by a nucleic acid in the plurality is substantially complementary to a RNA transcript comprising or consisting of the sequence set forth in SEQ ID NO: 4 and the effector sequence of a shmiR encoded by a nucleic acid in the plurality is substantially complementary to a RNA transcript comprising or consisting of the sequence set forth in SEQ ID NO: 9; and the effector sequence of a shmiR encoded by a nucleic acid in the plurality is substantially complementary to a RNA transcript comprising or consisting of the sequence set forth in SEQ ID NO: 40.

Exemplary nucleic acids of the disclosure encoding shmiRs which target HBV, including shmiRs comprising effector sequences which are substantially complementary to RNA transcripts set forth in SEQ ID NO: 4, 5, 9 or 40, are described herein and shall be taken to apply mutatis mutandis to each example in which a plurality of nucleic acids of the disclosure is described.

In one example, the plurality of nucleic acids of the disclosure comprises:
(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22; and
(ii) a nucleic acid comprising a DNA sequence encoding a shmiR comprising an effector sequence consisting of the sequence set forth in SEQ ID NO: 33 and an effector complement sequence consisting of the sequence set forth in SEQ ID NO: 34.

In one example, the plurality of nucleic acids of the disclosure comprises:
(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22;
(ii) a nucleic acid comprising a DNA sequence encoding a shmiR comprising an effector sequence consisting of the sequence set forth in SEQ ID NO: 33 and an effector complement sequence consisting of the sequence set forth in SEQ ID NO: 34; and
(iii) at least one other nucleic acid comprising a DNA sequence encoding a shmiR or shRNA comprising an effector sequence of at least 17 nucleotides in length which is substantially complimentary to a RNA transcript of the HBV genome.

In one example, the other nucleic acid of the disclosure is a nucleic acid described herein which encodes a shmiR or shRNA having an effector sequence which is different to that of the shmiRs encoded by the nucleic acids at (i) and (ii)

In one example, the plurality of nucleic acids of the disclosure comprises:
(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22;
(ii) a nucleic acid comprising a DNA sequence encoding a shmiR comprising an effector sequence consisting of the sequence set forth in SEQ ID NO: 39 and an effector complement sequence consisting of the sequence set forth in SEQ ID NO: 40; and
(iii) a nucleic acid comprising a DNA sequence encoding a shmiR comprising an effector sequence consisting of the sequence set forth in SEQ ID NO: 33 and an effector complement sequence consisting of the sequence set forth in SEQ ID NO: 34.

In one example, the plurality of nucleic acids of the disclosure comprises:
(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22;
(ii) a nucleic acid comprising a DNA sequence encoding a shmiR comprising an effector sequence consisting of the sequence set forth in SEQ ID NO: 23 and an effector complement sequence consisting of the sequence set forth in SEQ ID NO: 24; and
(iii) a nucleic acid comprising a DNA sequence encoding a shmiR comprising an effector sequence consisting of the sequence set forth in SEQ ID NO: 33 and an effector complement sequence consisting of the sequence set forth in SEQ ID NO: 34.

In one example, the plurality of nucleic acids of the disclosure comprises:
(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22;
(ii) a nucleic acid comprising a DNA sequence encoding a shRNA comprising an effector sequence consisting of the sequence set forth in SEQ ID NO: 39 and an effector complement sequence consisting of the sequence set forth in SEQ ID NO: 40; and (iii) a nucleic acid comprising a DNA sequence encoding a shmiR comprising an effector sequence consisting of the sequence set forth in SEQ ID NO: 33 and an effector complement sequence consisting of the sequence set forth in SEQ ID NO: 34.

In one example, the plurality of nucleic acids of the disclosure comprises:

(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22; and (ii) a nucleic acid comprising a DNA sequence encoding a shmiR comprising an effector sequence consisting of the sequence set forth in SEQ ID NO: 116 and an effector complement sequence consisting of the sequence set forth in SEQ ID NO: 117.

In one example, the plurality of nucleic acids of the disclosure comprises:

(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22; and (ii) a nucleic acid comprising a DNA sequence encoding a shmiR comprising an effector sequence consisting of the sequence set forth in SEQ ID NO: 124 and an effector complement sequence consisting of the sequence set forth in SEQ ID NO: 125.

In one example, the plurality of nucleic acids of the disclosure comprises:

(i) a nucleic acid comprising a DNA sequence encoding a shmiR comprising an effector sequence consisting of the sequence set forth in SEQ ID NO: 21 and an effector complement sequence consisting of the sequence set forth in SEQ ID NO: 22;

(ii) a nucleic acid comprising a DNA sequence encoding a shmiR comprising an effector sequence consisting of the sequence set forth in SEQ ID NO: 116 and an effector complement sequence consisting of the sequence set forth in SEQ ID NO: 117; and (iii) a nucleic acid comprising a DNA sequence encoding a shmiR comprising an effector sequence consisting of the sequence set forth in SEQ ID NO: 124 and an effector complement sequence consisting of the sequence set forth in SEQ ID NO: 125.

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48); and (ii) a nucleic acid comprising a DNA sequence comprising or consisting of the sequence set forth in SEQ ID NO: 70 (encoding a shmiR comprising or consisting of the sequence set forth in SEQ ID NO: 54).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48);

(ii) a nucleic acid comprising a DNA sequence comprising or consisting of the sequence set forth in SEQ ID NO: 73 (encoding a shmiR comprising or consisting of the sequence set forth in SEQ ID NO: 57); and (iii) a nucleic acid comprising a DNA sequence comprising or consisting of the sequence set forth in SEQ ID NO: 70 (encoding a shmiR comprising or consisting of the sequence set forth in SEQ ID NO: 54).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48);

(ii) a nucleic acid comprising a DNA sequence comprising or consisting of the sequence set forth in SEQ ID NO: 73 (encoding a shmiR comprising or consisting of the sequence set forth in SEQ ID NO: 57); and (iii) a nucleic acid comprising a DNA sequence comprising or consisting of the sequence set forth in SEQ ID NO: 70 (encoding a shmiR comprising or consisting of the sequence set forth in SEQ ID NO: 54).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48);

(ii) a nucleic acid comprising a DNA sequence comprising or consisting of the sequence set forth in SEQ ID NO: 99 (encoding a shRNA comprising or consisting of the sequence set forth in SEQ ID NO: 83); and (iii) a nucleic acid comprising a DNA sequence comprising or consisting of the sequence set forth in SEQ ID NO: 70 (encoding a shmiR comprising or consisting of the sequence set forth in SEQ ID NO: 54).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48); and (ii) a nucleic acid comprising a DNA sequence comprising or consisting of the sequence set forth in SEQ ID NO: 149 (encoding a shmiR comprising or consisting of the sequence set forth in SEQ ID NO: 137).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48); and (ii) a nucleic acid comprising a DNA sequence comprising or consisting of the sequence set forth in SEQ ID NO: 153 (encoding a shmiR comprising or consisting of the sequence set forth in SEQ ID NO: 141).

In one example, the plurality of nucleic acids of the disclosure comprises:

(i) a nucleic acid comprising a DNA sequence comprising or consisting of the sequence set forth in SEQ ID NO: 64 (encoding a shmiR comprising or consisting of the sequence set forth in SEQ ID NO: 48);

(ii) a nucleic acid comprising a DNA sequence comprising or consisting of the sequence set forth in SEQ ID NO: 149 (encoding a shmiR comprising or consisting of the sequence set forth in SEQ ID NO: 137); and (iii) a nucleic acid comprising a DNA sequence comprising or consisting of the sequence set forth in SEQ ID NO: 153 (encoding a shmiR comprising or consisting of the sequence set forth in SEQ ID NO: 141).

In accordance with an example in which a plurality of nucleic acids is provided, two or more of the nucleic acids may form separate parts of the same polynucleotide. In another example, two or more of the nucleic acids in the plurality form parts of different polynucleotides, respectively. In another example, the plurality of nucleic acids described herein are provided as multiple components e.g., multiple compositions. For example, each of the nucleic acids of the plurality may be provided separately. Alternatively, in an example where at least three nucleic acids of the disclosure are provided, at least one of the nucleic acids may be provided separately and two or more of the plurality provided together.

In some examples, the or each nucleic acid in accordance with the present disclosure may comprise, or be in operable linkage with, additional elements e.g., to facilitate transcription of the RNA. For example, the or each nucleic acid may comprise a promoter operably linked to the sequence encoding a shmiR or shRNA described herein. Other elements e.g., transcriptional terminators and initiators, are known in the art and/or described herein.

Alternatively, or in addition, the or each nucleic acid in accordance with the present disclosure may comprise one or more restriction sites e.g., to facilitate cloning of the nucleic acid(s) into cloning or expression vectors. For example, the nucleic acids described herein may include a restriction site upstream and/or downstream of the sequence encoding a shmiR or shRNA of the disclosure. Suitable restriction enzyme recognition sequences will be known to a person of skill in the art. However, in one example, the nucleic acid(s) of the disclosure may include a BamH1 restriction site (GGATCC) at the 5' terminus i.e., upstream of the sequence encoding the shmiR or shRNA, and a EcoR1 restriction site (GAATTC) at the 3' terminus i.e., downstream of the sequence encoding the shmiR or shRNA.

ddRNAi

In one example, the or each nucleic acid of the disclosure is provided in the form of, or is comprised in, a DNA-directed RNAi (ddRNAi) construct. Accordingly, in one example, the present disclosure provides a ddRNAi construct comprising a nucleic acid as described herein. In another example, the present disclosure provides a ddNAi construct comprising a plurality of nucleic acids described herein. Exemplary nucleic acids encoding shmiRs or shRNAs comprising effector sequences targeting HBV transcripts are described herein and shall be taken to apply mutatis mutandis to this example of the disclosure.

In one example, the ddRNAi construct comprises a nucleic acid of the disclosure operably linked to a promoter.

In accordance with an example in which the ddRNAi construct comprises a plurality of the nucleic acids described herein, each of the nucleic acids may be operably-linked to a promoter. In one example, the nucleic acids in the ddRNAi construct may be operably linked to the same promoter. In one example, the nucleic acids in the ddRNAi construct may be operably linked to different promoters.

In one example, a ddRNAi of the disclosure comprises a nucleic acid comprising or consisting of a DNA sequence set forth in SEQ ID NO: 59 and encodes a shmiR (shmiR-1) comprising or consisting of the sequence set forth in SEQ ID NO: 43. The ddRNAi construct may comprise one or more further nucleic acids of the disclosure, such as a nucleic acid comprising a DNA sequence selected from the sequences set forth in any one of SEQ ID NOs: 60-74 and 146-157.

In one example, a ddRNAi of the disclosure comprises a nucleic acid comprising or consisting of a DNA sequence set forth in SEQ ID NO: 60 and encodes a shmiR (shmiR-2) comprising or consisting of the sequence set forth in SEQ ID NO: 44. The ddRNAi construct may comprise one or more further nucleic acids of the disclosure, such as a nucleic acid comprising a DNA sequence selected from the sequences set forth in any one of SEQ ID NOs: 59, 61-74 and 146-157.

In one example, a ddRNAi of the disclosure comprises a nucleic acid comprising or consisting of a DNA sequence set forth in SEQ ID NO: 61 and encodes a shmiR (shmiR-3) comprising or consisting of the sequence set forth in SEQ ID NO: 45. The ddRNAi construct may comprise one or more further nucleic acids of the disclosure, such as a nucleic acid comprising a DNA sequence selected from the sequences set forth in any one of SEQ ID NOs: 59-60, 62-74 and 146-157.

In one example, a ddRNAi of the disclosure comprises a nucleic acid comprising or consisting of a DNA sequence set forth in SEQ ID NO: 62 and encodes a shmiR (shmiR-4) comprising or consisting of the sequence set forth in SEQ ID NO: 46. The ddRNAi construct may comprise one or more further nucleic acids of the disclosure, such as a nucleic acid comprising a DNA sequence selected from the sequences set forth in any one of SEQ ID NOs: 59-61, 63-74 and 146-157.

In one example, a ddRNAi of the disclosure comprises a nucleic acid comprising or consisting of a DNA sequence set forth in SEQ ID NO: 63 and encodes a shmiR (shmiR-5) comprising or consisting of the sequence set forth in SEQ ID NO: 47. The ddRNAi construct may comprise one or more further nucleic acids of the disclosure, such as a nucleic acid comprising a DNA sequence selected from the sequences set forth in any one of SEQ ID NOs: 59-62, 64-74 and 146-157.

In one example, a ddRNAi of the disclosure comprises a nucleic acid comprising or consisting of a DNA sequence set forth in SEQ ID NO: 64 and encodes a shmiR (shmiR-6) comprising or consisting of the sequence set forth in SEQ ID NO: 48. The ddRNAi construct may comprise one or more further nucleic acids of the disclosure, such as a nucleic acid comprising a DNA sequence selected from the sequences set forth in any one of SEQ ID NOs: 59-63, 65-74 and 146-157.

In one example, a ddRNAi of the disclosure comprises a nucleic acid comprising or consisting of a DNA sequence set forth in SEQ ID NO: 65 and encodes a shmiR (shmiR-7) comprising or consisting of the sequence set forth in SEQ ID NO: 49. The ddRNAi construct may comprise one or more further nucleic acids of the disclosure, such as a nucleic acid comprising a DNA sequence selected from the sequences set forth in any one of SEQ ID NOs: 59-64, 66-74 and 146-157.

In one example, a ddRNAi of the disclosure comprises a nucleic acid comprising or consisting of a DNA sequence set forth in SEQ ID NO: 66 and encodes a shmiR (shmiR-8) comprising or consisting of the sequence set forth in SEQ ID NO: 50. The ddRNAi construct may comprise one or more further nucleic acids of the disclosure, such as a nucleic acid comprising a DNA sequence selected from the sequences set forth in any one of SEQ ID NOs: 59-65, 67-74 and 146-157.

In one example, a ddRNAi of the disclosure comprises a nucleic acid comprising or consisting of a DNA sequence set forth in SEQ ID NO: 67 and encodes a shmiR (shmiR-9) comprising or consisting of the sequence set forth in SEQ ID NO: 51. The ddRNAi construct may comprise one or more further nucleic acids of the disclosure, such as a nucleic acid comprising a DNA sequence selected from the sequences set forth in any one of SEQ ID NOs: 59-66, 68-74 and 146-157.

In one example, a ddRNAi of the disclosure comprises a nucleic acid comprising or consisting of a DNA sequence set forth in SEQ ID NO: 68 and encodes a shmiR (shmiR-10) comprising or consisting of the sequence set forth in SEQ ID NO: 52. The ddRNAi construct may comprise one or more further nucleic acids of the disclosure, such as a nucleic acid comprising a DNA sequence selected from the sequences set forth in any one of SEQ ID NOs: 59-67, 69-74 and 146-157.

In one example, a ddRNAi of the disclosure comprises a nucleic acid comprising or consisting of a DNA sequence set forth in SEQ ID NO: 69 and encodes a shmiR (shmiR-11) comprising or consisting of the sequence set forth in SEQ ID NO: 53. The ddRNAi construct may comprise one or more further nucleic acids of the disclosure, such as a nucleic acid comprising a DNA sequence selected from the sequences set forth in any one of SEQ ID NOs: 59-68, 70-74 and 146-157.

In one example, a ddRNAi of the disclosure comprises a nucleic acid comprising or consisting of a DNA sequence set forth in SEQ ID NO: 70 and encodes a shmiR (shmiR-12) comprising or consisting of the sequence set forth in SEQ ID NO: 54. The ddRNAi construct may comprise one or more further nucleic acids of the disclosure, such as a nucleic acid comprising a DNA sequence selected from the sequences set forth in any one of SEQ ID NOs: 59-69, 71-74 and 146-157.

In one example, a ddRNAi of the disclosure comprises a nucleic acid comprising or consisting of a DNA sequence set forth in SEQ ID NO: 71 and encodes a shmiR (shmiR-13) comprising or consisting of the sequence set forth in SEQ ID NO: 55. The ddRNAi construct may comprise one or more further nucleic acids of the disclosure, such as a nucleic acid comprising a DNA sequence selected from the sequences set forth in any one of SEQ ID NOs: 59-70, 72-74 and 146-157.

In one example, a ddRNAi of the disclosure comprises a nucleic acid comprising or consisting of a DNA sequence set forth in SEQ ID NO: 72 and encodes a shmiR (shmiR-14) comprising or consisting of the sequence set forth in SEQ ID NO: 56. The ddRNAi construct may comprise one or more further nucleic acids of the disclosure, such as a nucleic acid comprising a DNA sequence selected from the sequences set forth in any one of SEQ ID NOs: 59-71, 73-74 and 146-157.

In one example, a ddRNAi of the disclosure comprises a nucleic acid comprising or consisting of a DNA sequence set forth in SEQ ID NO: 73 and encodes a shmiR (shmiR-15) comprising or consisting of the sequence set forth in SEQ ID NO: 57. The ddRNAi construct may comprise one or more further nucleic acids of the disclosure, such as a nucleic acid comprising a DNA sequence selected from the sequences set forth in any one of SEQ ID NOs: 59-72, 74 and 146-157.

In one example, a ddRNAi of the disclosure comprises a nucleic acid comprising or consisting of a DNA sequence set forth in SEQ ID NO: 74 and encodes a shmiR (shmiR-16) comprising or consisting of the sequence set forth in SEQ ID NO: 58. The ddRNAi construct may comprise one or more further nucleic acids of the disclosure, such as a nucleic acid comprising a DNA sequence selected from the sequences set forth in any one of SEQ ID NOs: 59-73 and 146-157.

In one example, a ddRNAi of the disclosure comprises a nucleic acid comprising or consisting of a DNA sequence set forth in SEQ ID NO: 146 and encodes a shmiR (shmiR-17) comprising or consisting of the sequence set forth in SEQ ID NO: 134. The ddRNAi construct may comprise one or more further nucleic acids of the disclosure, such as a nucleic acid comprising a DNA sequence selected from the sequences set forth in any one of SEQ ID NOs: 59-74 and 147-157.

In one example, a ddRNAi of the disclosure comprises a nucleic acid comprising or consisting of a DNA sequence set forth in SEQ ID NO: 147 and encodes a shmiR (shmiR-18) comprising or consisting of the sequence set forth in SEQ ID NO: 135. The ddRNAi construct may comprise one or more further nucleic acids of the disclosure, such as a nucleic acid comprising a DNA sequence selected from the sequences set forth in any one of SEQ ID NOs: 59-74, 146 and 148-157.

In one example, a ddRNAi of the disclosure comprises a nucleic acid comprising or consisting of a DNA sequence set forth in SEQ ID NO: 148 and encodes a shmiR (shmiR-19) comprising or consisting of the sequence set forth in SEQ ID NO: 136. The ddRNAi construct may comprise one or more further nucleic acids of the disclosure, such as a nucleic acid comprising a DNA sequence selected from the sequences set forth in any one of SEQ ID NOs: 59-74, 146, 147 and 149-157.

In one example, a ddRNAi of the disclosure comprises a nucleic acid comprising or consisting of a DNA sequence set forth in SEQ ID NO: 149 and encodes a shmiR (shmiR-20) comprising or consisting of the sequence set forth in SEQ ID NO: 137. The ddRNAi construct may comprise one or more further nucleic acids of the disclosure, such as a nucleic acid comprising a DNA sequence selected from the sequences set forth in any one of SEQ ID NOs: 59-74, 146-148 and 150-157.

In one example, a ddRNAi of the disclosure comprises a nucleic acid comprising or consisting of a DNA sequence set forth in SEQ ID NO: 150 and encodes a shmiR (shmiR-21) comprising or consisting of the sequence set forth in SEQ ID NO: 138. The ddRNAi construct may comprise one or more further nucleic acids of the disclosure, such as a nucleic acid comprising a DNA sequence selected from the sequences set forth in any one of SEQ ID NOs: 59-74, 146-149 and 151-157.

In one example, a ddRNAi of the disclosure comprises a nucleic acid comprising or consisting of a DNA sequence set forth in SEQ ID NO: 151 and encodes a shmiR (shmiR-22) comprising or consisting of the sequence set forth in SEQ ID NO: 139. The ddRNAi construct may comprise one or more further nucleic acids of the disclosure, such as a nucleic acid comprising a DNA sequence selected from the sequences set forth in any one of SEQ ID NOs: 59-74, 146-150 and 152-157.

In one example, a ddRNAi of the disclosure comprises a nucleic acid comprising or consisting of a DNA sequence set forth in SEQ ID NO: 152 and encodes a shmiR (shmiR-23) comprising or consisting of the sequence set forth in SEQ ID NO: 140. The ddRNAi construct may comprise one or more further nucleic acids of the disclosure, such as a nucleic acid comprising a DNA sequence selected from the sequences set forth in any one of SEQ ID NOs: 59-74, 146-151 and 153-157.

In one example, a ddRNAi of the disclosure comprises a nucleic acid comprising or consisting of a DNA sequence set forth in SEQ ID NO: 153 and encodes a shmiR (shmiR-24) comprising or consisting of the sequence set forth in SEQ ID NO: 141. The ddRNAi construct may comprise one or more further nucleic acids of the disclosure, such as a nucleic acid comprising a DNA sequence selected from the sequences set forth in any one of SEQ ID NOs: 59-74, 146-152 and 154-157.

In one example, a ddRNAi of the disclosure comprises a nucleic acid comprising or consisting of a DNA sequence set forth in SEQ ID NO: 154 and encodes a shmiR (shmiR-25) comprising or consisting of the sequence set forth in SEQ ID NO: 142. The ddRNAi construct may comprise one or more further nucleic acids of the disclosure, such as a nucleic acid comprising a DNA sequence selected from the sequences set forth in any one of SEQ ID NOs: 59-74, 146-153 and 155-157.

In one example, a ddRNAi of the disclosure comprises a nucleic acid comprising or consisting of a DNA sequence set forth in SEQ ID NO: 155 and encodes a shmiR (shmiR-26) comprising or consisting of the sequence set forth in SEQ ID NO: 143. The ddRNAi construct may comprise one or more further nucleic acids of the disclosure, such as a nucleic acid comprising a DNA sequence selected from the sequences set forth in any one of SEQ ID NOs: 59-74, 146-154 and 156-157.

In one example, a ddRNAi of the disclosure comprises a nucleic acid comprising or consisting of a DNA sequence set forth in SEQ ID NO: 156 and encodes a shmiR (shmiR-27) comprising or consisting of the sequence set forth in SEQ ID NO: 144. The ddRNAi construct may comprise one or more further nucleic acids of the disclosure, such as a nucleic acid comprising a DNA sequence selected from the sequences set forth in any one of SEQ ID NOs: 59-74, 146-155 and 157.

In one example, a ddRNAi of the disclosure comprises a nucleic acid comprising or consisting of a DNA sequence set forth in SEQ ID NO: 157 and encodes a shmiR (shmiR-28) comprising or consisting of the sequence set forth in SEQ ID NO: 145. The ddRNAi construct may comprise one or more further nucleic acids of the disclosure, such as a nucleic acid comprising a DNA sequence selected from the sequences set forth in any one of SEQ ID NOs: 59-74 and 146-156.

An exemplary ddRNAi construct comprising a plurality of nucleic acids of the discloses comprises:

(a) a nucleic acid encoding a shmiR comprising or consisting of the sequence set forth in SEQ ID NO:48 (shmiR-6); and (b) a nucleic acid encoding a shmiR comprising or consisting of the sequence set forth in SEQ ID NO:54 (shmiR-12).

An exemplary ddRNAi construct comprising a plurality of nucleic acids of the discloses comprises:

(a) a nucleic acid comprising or consisting of the sequence set forth in SEQ ID NO:64 (coding for shmiR-6); and (b) a nucleic acid comprising or consisting of the sequence set forth in SEQ ID NO:70 (coding for shmiR-12).

In another example, a ddRNAi construct comprising a plurality of nucleic acids of the discloses comprises:

(a) a nucleic acid encoding a shmiR comprising or consisting of the sequence set forth in SEQ ID NO:48 (shmiR-6); and (b) a nucleic acid encoding a shmiR comprising or consisting of the sequence set forth in SEQ ID NO:137 (shmiR-20).

For example, a ddRNAi construct comprising a plurality of nucleic acids of the discloses may comprise:

(a) a nucleic acid comprising or consisting of the sequence set forth in SEQ ID NO:64 (coding for shmiR-6); and (b) a nucleic acid comprising or consisting of the sequence set forth in SEQ ID NO:149 (coding for shmiR-20).

In another example, a ddRNAi construct comprising a plurality of nucleic acids of the discloses comprises:

(a) a nucleic acid encoding a shmiR comprising or consisting of the sequence set forth in SEQ ID NO:48 (shmiR-6); and (b) a nucleic acid encoding a shmiR comprising or consisting of the sequence set forth in SEQ ID NO:141 (shmiR-24).

For example, a ddRNAi construct comprising a plurality of nucleic acids of the discloses may comprise:

(a) a nucleic acid comprising or consisting of the sequence set forth in SEQ ID NO:64 (coding for shmiR-6); and (b) a nucleic acid comprising or consisting of the sequence set forth in SEQ ID NO:153 (coding for shmiR-24).

The present disclosure also provides a ddRNAi construct comprising at least three nucleic acids described herein, such that the ddRNAi construct encodes at least three shmiRs targeting HBV, each of which is different to one another.

In one example, the disclosure provides a ddRNAi construct comprising:

(a) a nucleic acid encoding a shmiR comprising or consisting of the sequence set forth in SEQ ID NO:48 (shmiR-6):

(b) a nucleic acid comprising a DNA sequence encoding a shmiR or shRNA as described herein; and (c) a nucleic acid encoding a shmiR comprising or consisting of the sequence set forth in SEQ ID NO:54 (shmiR-12);

wherein the nucleic acid at (b) encodes a shmiR or shRNA having an effector sequence which is different to that of the shmiRs encoded by the nucleic acid at (a) and (c).

In one example, the ddRNAi construct of the disclosure comprises, preferably in a 5' to 3' direction:

(a) a nucleic acid encoding a shmiR comprising or consisting of the sequence set forth in SEQ ID NO:48 (shmiR-6);

(b) a nucleic acid encoding a shmiR comprising or consisting of the sequence set forth in SEQ ID NO:57 (shmiR-15); and (c) a nucleic acid encoding a shmiR comprising or consisting of the sequence set forth in SEQ ID NO:54 (shmiR-12).

For example, a ddRNAi construct of the disclosure may comprise, in a 5' to 3' direction:

(a) a nucleic acid comprising or consisting of the sequence set forth in SEQ ID NO:64 (coding for shmiR-6);

(b) a nucleic acid comprising or consisting of the sequence set forth in SEQ ID NO:73 (coding for shmiR-15); and (c) a nucleic acid comprising or consisting of the sequence set forth in SEQ ID NO:70 (coding for shmiR-12).

In one example, a ddRNAi construct of the disclosure comprises, preferably in a 5' to 3' direction:

(a) a nucleic acid encoding a shmiR comprising or consisting of the sequence set forth in SEQ ID NO:48 (shmiR-6);

(b) a nucleic acid encoding a shmiR comprising or consisting of the sequence set forth in SEQ ID NO:49 (shmiR-7); and (c) a nucleic acid encoding a shmiR comprising or consisting of the sequence set forth in SEQ ID NO:54 (shmiR-12).

For example, a ddRNAi construct of the disclosure may comprise, in a 5' to 3' direction:

(a) a nucleic acid comprising or consisting of the sequence set forth in SEQ ID NO:64 (coding for shmiR-6):

(b) a nucleic acid comprising or consisting of the sequence set forth in SEQ ID NO:65 (coding for shmiR-7); and (c) a nucleic acid comprising or consisting of the sequence set forth in SEQ ID NO:70 (coding for shmiR-12). In one example, the disclosure provides a ddRNAi construct comprising:

(a) a nucleic acid encoding a shmiR comprising or consisting of the sequence set forth in SEQ ID NO:48 (shmiR-6):

(b) a nucleic acid comprising a DNA sequence encoding a shmiR or shRNA as described herein; and (c) a nucleic acid encoding a shmiR comprising or consisting of the sequence set forth in SEQ ID NO:141 (shmiR-24);

wherein the nucleic acid at (b) encodes a shmiR or shRNA having an effector sequence which is different to that of the shmiRs encoded by the nucleic acid at (a) and (c).

In one example, the disclosure provides a ddRNAi construct comprising:
(a) a nucleic acid encoding a shmiR comprising or consisting of the sequence set forth in SEQ ID NO:48 (shmiR-6):
(b) a nucleic acid comprising a DNA sequence encoding a shmiR or shRNA as described herein; and
(c) a nucleic acid encoding a shmiR comprising or consisting of the sequence set forth in SEQ ID NO:137 (shmiR-20);
wherein the nucleic acid at (b) encodes a shmiR or shRNA having an effector sequence which is different to that of the shmiRs encoded by the nucleic acid at (a) and (c).

In one example, the ddRNAi construct of the disclosure comprises, preferably in a 5' to 3' direction:
(a) a nucleic acid encoding a shmiR comprising or consisting of the sequence set forth in SEQ ID NO:48 (shmiR-6);
(b) a nucleic acid encoding a shmiR comprising or consisting of the sequence set forth in SEQ ID NO:137 (shmiR-20); and
(c) a nucleic acid encoding a shmiR comprising or consisting of the sequence set forth in SEQ ID NO:141 (shmiR-24).

For example, a ddRNAi construct of the disclosure may comprise, in a 5' to 3' direction:
(a) a nucleic acid comprising or consisting of the sequence set forth in SEQ ID NO:64 (coding for shmiR-6);
(b) a nucleic acid comprising or consisting of the sequence set forth in SEQ ID NO:149 (coding for shmiR-20); and
(c) a nucleic acid comprising or consisting of the sequence set forth in SEQ ID NO:153 (coding for shmiR-24).

In yet another example, a ddRNAi construct of the disclosure may comprise at least one nucleic acid encoding a shmiR as described herein and at least one nucleic acid encoding a shRNA targeting HBV as described herein, wherein the shmiR and shRNA encoded by the ddRNAi construct comprise different effector sequences. In accordance with this example, a ddRNAi construct of the disclosure may comprise, preferably in a 5' to 3' direction:
(a) a nucleic acid encoding a shmiR comprising or consisting of the sequence set forth in SEQ ID NO:48;
(b) a nucleic acid encoding a shRNA comprising an effector sequence set forth in SEQ ID NO: 39 and an effector complement sequence set forth in SEQ ID NO: 40; and
(c) a nucleic acid encoding a shmiR comprising or consisting of the sequence set forth in SEQ ID NO:54.

For example, a ddRNAi construct of the disclosure may comprise, preferably in a 5' to 3' direction:
(a) a nucleic acid encoding a shmiR comprising or consisting of the sequence set forth in SEQ ID NO:48:
(b) a nucleic acid encoding a shRNA consisting of the sequence set forth in SEQ ID NO: 92; and
(c) a nucleic acid encoding a shmiR comprising or consisting of the sequence set forth in SEQ ID NO:54.

For example, a ddRNAi construct of the disclosure may comprise, in a 5' to 3' direction:
(a) a nucleic acid comprising or consisting of the sequence set forth in SEQ ID NO:64:
(b) a nucleic acid comprising or consisting of the sequence set forth in SEQ ID NO:108; and
(c) a nucleic acid comprising or consisting of the sequence set forth in SEQ ID NO:70.

In each of the foregoing examples describing a ddRNAi construct of the disclosure, the or each nucleic acid comprised therein may be operably linked to a promoter. For example, the ddRNAi construct as described herein may comprise a single promoter which is operably-linked to the or each nucleic acid comprised therein e.g., to drive expression of one or more shmiRs and/or shRNAs from the ddRNAi construct.

In another example, each nucleic acid encoding a shmiR or shRNA of the disclosure comprised in the ddRNAi construct is operably-linked to a separate promoter.

According to an example in which multiple promoters are present, the promoters can be the same or different. For example, the construct may comprise multiple copies of the same promoter with each copy operably linked to a different nucleic acid of the disclosure. In another example, each promoter operably linked to a RNA of the disclosure is different. For example, in a ddRNAi construct encoding three shmiRs, the three nucleic acids encoding the shmiRs are each operably linked to a different promoter.

In a further example, in a ddRNAi construct encoding three or more shmiRs, two (or more) of the nucleic acids encoding the shmiRs are linked to the same promoter and one (or more) of the nucleic acids encoding the shmiR is linked to a different promoter.

In one example, the promoter is a constitutive promoter. The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe shmiRs or shRNAs from the nucleic acid(s) of the disclosure include promoters for ubiquitin, CMV, β-actin, histone H4, EF-1α or pgk genes controlled by RNA polymerase II, or promoter elements controlled by RNA polymerase I.

In one example, a Pol II promoter such as CMV, SV40, U1, β-actin or a hybrid Pol II promoter is employed.

In another example, a promoter controlled by RNA polymerase III is used, such as a U6 promoter (U6-1, U6-8, U6-9), H1 promoter, 7SL promoter, a human Y promoter (hY1, hY3, hY4 (see Maraia, et al., *Nucleic Acids Res* 22(15):3045-52(1994)) and hY5 (see Maraia, et al., *Nucleic Acids Res* 24(18):3552-59(1994)), a human MRP-7-2 promoter, an Adenovirus VA1 promoter, a human tRNA promoter, or a 5s ribosomal RNA promoter.

Suitable promoters for use in a ddRNAi construct of the disclosure are described in U.S. Pat. Nos. 8,008,468 and 8,129,510.

In one example, the promoter is a RNA pol III promoter. For example, the promoter is a U6 promoter (e.g., a U6-1, U6-8 or U6-9 promoter). In another example, the promoter is a H1 promoter.

In the case of a ddRNAi construct of the disclosure encoding a plurality of shmiRs, or encoding one or more shmiRs and a shRNA, as described herein, each of the nucleic acids in the ddRNAi construct is operably linked to a U6 promoter e.g., a separate U6 promoter.

In one example, the promoter in a construct is a U6 promoter. For example, the promoter is a U6-1 promoter. For example, the promoter is a U6-8 promoter. For example, the promoter is a U6-9 promoter.

In some examples, promoters of variable strength are employed. For example, use of two or more strong promoters (such as a Pol III-type promoter) may tax the cell, by, e.g., depleting the pool of available nucleotides or other cellular components needed for transcription. In addition, or alternatively, use of several strong promoters may cause a toxic level of expression of RNAi agents e.g., shmiRs or shRNAs, in the cell. Thus, in some examples one or more of the promoters in the multiple-promoter ddRNAi construct is weaker than other promoters in the construct, or all promoters in the construct may express the shmiRs or shRNAs at less than a maximum rate. Promoters may also be modified using various molecular techniques, or otherwise, e.g., through modification of various regulatory elements, to attain weaker levels or stronger levels of transcription. One means of achieving reduced transcription is to modify sequence elements within promoters known to control promoter activity. For example the Proximal Sequence Element (PSE) is known to effect the activity of human U6 promoters (see Domitrovich, et al., *Nucleic Acids Res* 31: 2344-2352 (2003). Replacing the PSE elements present in strong promoters, such as the human U6-1, U6-8 or U6-9 promoters, with the element from a weak promoter, such as the human U6-7 promoter, reduces the activity of the hybrid U6-1, U6-8 or U6-9 promoters. This approach has been used in the examples described in this application, but other means to achieve this outcome are known in the art.

Promoters useful in some examples of the present disclosure can be tissue-specific or cell-specific. The term "tissue specific" as it applies to a promoter refers to a promoter that is capable of directing selective transcription of a nucleic acid of interest to a specific type of tissue (e.g., liver tissue) in the relative absence of expression of the same nucleotide sequence of interest in a different type of tissue (e.g., muscle). The term "cell-specific" as applied to a promoter refers to a promoter which is capable of directing selective transcription of a nucleic acid of interest in a specific type of cell in the relative absence of expression of the same nucleotide sequence of interest in a different type of cell within the same tissue.

In one example, a ddRNAi construct of the disclosure may additionally comprise one or more enhancers to increase expression of the shmiRs or shRNAs encoded by the nucleic acids described herein. Enhancers appropriate for use in examples of the present disclosure include the Apo E HCR enhancer, a CMV enhancer (Xia et al, *Nucleic Acids Res* 31-17(2003)), and other enhancers known to those skilled in the art. Suitable enhancers for use in a ddRNAi construct of the disclosure are described in U.S. Pat. No. 8,008,468.

In a further example, a ddRNAi construct of the disclosure may comprise a transcriptional terminator linked to a nucleic acid encoding a shmiR or shRNA of the disclosure. In the case of a ddRNAi construct comprising a plurality of nucleic acids described herein i.e., encoding multiple shmiRs and/or shRNAs, the terminators linked to each nucleic acid can be the same or different. According to an example in which a RNA pol III promoter is employed, the terminator may be a contiguous stretch of 4 or more or 5 or more or 6 or more T residues.

In some examples, where different promoters are used, the terminators can be different and are matched to the promoter from the gene from which the terminator is derived. Such terminators include the SV40 poly A, the AdV VA1 gene, the 5S ribosomal RNA gene, and the terminators for human t-RNAs. In addition, promoters and terminators may be mixed and matched, as is commonly done with RNA pol II promoters and terminators.

In one example, the promoter and terminator combinations used for each nucleic acid in a ddRNAi construct comprising a plurality of nucleic acids is different to decrease the likelihood of DNA recombination events between components.

One exemplary ddRNAi construct of the disclosure comprises a nucleic acid encoding a shmiR comprising or consisting of the sequence set forth in SEQ ID NO:48 operably linked to a U6 promoter e.g., a U6-9 promoter. For example, the ddRNAi construct of the disclosure comprises a nucleic acid comprising or consisting of the sequence set forth in SEQ ID NO:64 operably linked to a U6 promoter e.g., a U6-9 promoter.

Another exemplary ddRNAi construct of the disclosure comprises a nucleic acid encoding a shmiR comprising or consisting of the sequence set forth in SEQ ID NO:57 operably linked to a U6 promoter e.g., a U6-1 promoter. For example, the ddRNAi construct of the disclosure comprises a nucleic acid comprising or consisting of the sequence set forth in SEQ ID NO:73 operably linked to a U6 promoter e.g., a U6-1 promoter.

Another exemplary ddRNAi construct of the disclosure comprises a nucleic acid encoding a shmiR comprising or consisting of the sequence set forth in SEQ ID NO:54 operably linked to a U6 promoter e.g., a U6-8 promoter. For example, the ddRNAi construct of the disclosure comprises a nucleic acid comprising or consisting of the sequence set forth in SEQ ID NO:70 operably linked to a U6 promoter e.g., a U6-8 promoter.

Another exemplary ddRNAi construct of the disclosure comprises a nucleic acid encoding a shmiR comprising or consisting of the sequence set forth in SEQ ID NO:49 operably linked to a U6 promoter e.g., a U6-1 promoter. For example, the ddRNAi construct of the disclosure comprises a nucleic acid comprising or consisting of the sequence set forth in SEQ ID NO:65 operably linked to a U6 promoter e.g., a U6-1 promoter.

Another exemplary ddRNAi construct of the disclosure comprises a nucleic acid encoding a shmiR comprising or consisting of the sequence set forth in SEQ ID NO:137 operably linked to a U6 promoter e.g., a U6-1 promoter. For example, the ddRNAi construct of the disclosure comprises a nucleic acid comprising or consisting of the sequence set forth in SEQ ID NO:149 operably linked to a U6 promoter e.g., a U6-1 promoter.

Another exemplary ddRNAi construct of the disclosure comprises a nucleic acid encoding a shmiR comprising or consisting of the sequence set forth in SEQ ID NO:141 operably linked to a U6 promoter e.g., a U6-1 promoter. For example, the ddRNAi construct of the disclosure comprises a nucleic acid comprising or consisting of the sequence set forth in SEQ ID NO:153 operably linked to a U6 promoter e.g., a U6-8 promoter.

According to one example in which the ddRNAi construct of the disclosure comprises a plurality of nucleic acids described herein, the ddRNAi construct may comprise:

(a) a nucleic acid encoding a shmiR comprising or consisting of the sequence set forth in SEQ ID NO:48 operably linked to a U6 promoter e.g., a U6-9 promoter; and (b) a nucleic acid encoding a shmiR comprising or consisting of the sequence set forth in SEQ ID NO:54 operably linked to a U6 promoter e.g., a U6-8 promoter.

For example, the ddRNAi construct may comprise:

(a) a nucleic acid comprising or consisting of the sequence set forth in SEQ ID NO:64 operably linked to a U6 promoter e.g., a U6-9 promoter; and (b) a nucleic acid comprising or consisting of the sequence set forth in SEQ ID NO:70 operably linked to a U6 promoter e.g., a U6-8 promoter.

According to another example in which the ddRNAi construct of the disclosure comprises a plurality of nucleic acids described herein, the ddRNAi construct may comprise:

(a) a nucleic acid encoding a shmiR comprising or consisting of the sequence set forth in SEQ ID NO:48 (shmiR-6) operably linked to a U6 promoter e.g., a U6-9 promoter; and (b) a nucleic acid encoding a shmiR comprising or consisting of the sequence set forth in SEQ ID NO:141 (shmiR-24) operably linked to a U6 promoter e.g., a U6-8 promoter.

For example, the ddRNAi construct may comprise:

(a) a nucleic acid comprising or consisting of the sequence set forth in SEQ ID NO:64 (coding for shmiR-6) operably linked to a U6 promoter e.g., a U6-9 promoter; and (b) a nucleic acid comprising or consisting of the sequence set forth in SEQ ID NO:153 (coding for shmiR-24) operably linked to a U6 promoter e.g., a U6-8 promoter.

According to yet another example in which the ddRNAi construct of the disclosure comprises a plurality of nucleic acids described herein, the ddRNAi construct may comprise:

(a) a nucleic acid encoding a shmiR comprising or consisting of the sequence set forth in SEQ ID NO:48 (shmiR-6) operably linked to a U6 promoter e.g., a U6-9 promoter; and (b) a nucleic acid encoding a shmiR comprising or consisting of the sequence set forth in SEQ ID NO:137 (shmiR-20) operably linked to a U6 promoter e.g., a U6-1 promoter.

For example, the ddRNAi construct may comprise:

(a) a nucleic acid comprising or consisting of the sequence set forth in SEQ ID NO:64 (coding for shmiR-6) operably linked to a U6 promoter e.g., a U6-9 promoter; and (b) a nucleic acid comprising or consisting of the sequence set forth in SEQ ID NO:149 (coding for shmiR-20) operably linked to a U6 promoter e.g., a U6-1 promoter.

According to an example in which the ddRNAi construct of the disclosure comprises three nucleic acids described herein, the ddRNAi construct comprises:

(a) a nucleic acid encoding a shmiR comprising or consisting of the sequence set forth in SEQ ID NO:48 (shmiR-6) operably linked to a U6 promoter e.g., a U6-9 promoter;

(b) a nucleic acid encoding a shmiR comprising or consisting of the sequence set forth in SEQ ID NO:57 (shmiR-15) operably linked to a U6 promoter e.g., a U6-1 promoter; and (c) a nucleic acid encoding a shmiR comprising or consisting of the sequence set forth in SEQ ID NO:54 (shmiR-12) operably linked to a U6 promoter e.g., a U6-8 promoter.

For example, the ddRNAi construct may comprise:

(a) a nucleic acid comprising or consisting of the sequence set forth in SEQ ID NO:64 (coding for shmiR-6) operably linked to a U6 promoter e.g., a U6-9 promoter;

(b) a nucleic acid comprising or consisting of the sequence set forth in SEQ ID NO:73 (coding for shmiR-15) operably linked to a U6 promoter e.g., a U6-1 promoter; and (c) a nucleic acid comprising or consisting of the sequence set forth in SEQ ID NO:70 (coding for shmiR-12) operably linked to a U6 promoter e.g., a U6-8 promoter.

According to another example in which the ddRNAi construct of the disclosure comprises three nucleic acids described herein, the ddRNAi construct comprises:

(a) a nucleic acid encoding a shmiR comprising or consisting of the sequence set forth in SEQ ID NO:48 (shmiR-6) operably linked to a U6 promoter e.g., a U6-9 promoter;

(b) a nucleic acid encoding a shmiR comprising or consisting of the sequence set forth in SEQ ID NO:137 (shmiR-20) operably linked to a U6 promoter e.g., a U6-1 promoter; and (c) a nucleic acid encoding a shmiR comprising or consisting of the sequence set forth in SEQ ID NO:141 (shmiR-24) operably linked to a U6 promoter e.g., a U6-8 promoter.

For example, the ddRNAi construct may comprise:

(a) a nucleic acid comprising or consisting of the sequence set forth in SEQ ID NO:64 (coding for shmiR-6) operably linked to a U6 promoter e.g., a U6-9 promoter;

(b) a nucleic acid comprising or consisting of the sequence set forth in SEQ ID NO:149 (coding for shmiR-20) operably linked to a U6 promoter e.g., a U6-1 promoter; and (c) a nucleic acid comprising or consisting of the sequence set forth in SEQ ID NO:153 (coding for shmiR-24) operably linked to a U6 promoter e.g., a U6-8 promoter.

According to yet another example in which the ddRNAi construct of the disclosure comprises three nucleic acids described herein, the ddRNAi construct comprises:

(a) a nucleic acid encoding a shmiR comprising or consisting of the sequence set forth in SEQ ID NO:48 (shmiR-6) operably linked to a U6 promoter e.g., a U6-9 promoter;

(b) a nucleic acid encoding a shmiR comprising or consisting of the sequence set forth in SEQ ID NO:49 (shmiR-7) operably linked to a U6 promoter e.g., a U6-1 promoter; and (c) a nucleic acid encoding a shmiR comprising or consisting of the sequence set forth in SEQ ID NO:54 (shmiR-12) operably linked to a U6 promoter e.g., a U6-8 promoter.

For example, the ddRNAi construct may comprise:

(a) a nucleic acid comprising or consisting of the sequence set forth in SEQ ID NO:64 (coding for shmiR-6) operably linked to a U6 promoter e.g., a U6-9 promoter;

(b) a nucleic acid comprising or consisting of the sequence set forth in SEQ ID NO:65 (coding for shmiR-7) operably linked to a U6 promoter e.g., a U6-1 promoter; and (c) a nucleic acid comprising or consisting of the sequence set forth in SEQ ID NO:70 (coding for shmiR-12) operably linked to a U6 promoter e.g., a U6-8 promoter.

An exemplary ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:73; and
(c) U6-8 promoter upstream of a nucleic acid comprising or consisting of the sequence set forth in SEQ ID NO:70.

An exemplary ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:149; and
(c) U6-8 promoter upstream of a nucleic acid comprising or consisting of the sequence set forth in SEQ ID NO: 159.

Yet another exemplary ddRNAi construct of the disclosure comprises, in a 5' to 3' direction:
(a) U6-9 promoter upstream of a nucleic acid comprising or consisting of the sequence set forth in SEQ ID NO:64:
(b) U6-1 promoter upstream of a nucleic acid comprising or consisting of the sequence set forth in SEQ ID NO:65; and
(c) U6-8 promoter upstream of a nucleic acid comprising or consisting of the sequence set forth in SEQ ID NO:70.

According to another example in which the ddRNAi construct of the disclosure comprises at least one nucleic acid encoding a shmiR as described herein and at least one nucleic acid encoding a shRNA targeting HBV as described herein, the ddRNAi construct of the disclosure may comprise:

(a) a nucleic acid encoding a shmiR comprising or consisting of the sequence set forth in SEQ ID NO:48 operably linked to a U6 promoter e.g., a U6-9 promoter;

(b) a nucleic acid encoding a shRNA comprising or consisting of the sequence set forth in SEQ ID NO: 92 operably linked to a U6 promoter e.g., a U6-1 promoter; and (c) a nucleic acid encoding a shmiR comprising or consisting of the sequence set forth in SEQ ID NO:54 operably linked to a U6 promoter e.g., a U6-8 promoter.

For example, the ddRNAi construct may comprise:

(a) a nucleic acid comprising or consisting of the sequence set forth in SEQ ID NO:64 operably linked to a U6 promoter e.g., a U6-9 promoter;

(b) a nucleic acid comprising or consisting of the sequence set forth in SEQ ID NO:108 operably linked to a U6 promoter e.g., a U6-1 promoter; and (c) a nucleic acid comprising or consisting of the sequence set forth in SEQ ID NO:70 operably linked to a U6 promoter e.g., a U6-8 promoter.

The present disclosure also provides a plurality of ddRNAi constructs comprising two or more ddRNAi constructs, each comprising nucleic acid encoding a shmiR of the disclosure operably linked to a suitable promoter as described herein.

In one example, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter; and (b) a ddRNAi construct comprising a nucleic acid encoding a shmiR comprising or consisting of the sequence set forth in SEQ ID NO:54 (shmiR-12) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter; and (b) a ddRNAi construct comprising a nucleic acid comprising or consisting of the sequence set forth in SEQ ID NO:70 (coding for shmiR-12) operably linked to a U6 promoter e.g., a U6-8 promoter.

In one example, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter; and (b) a ddRNAi construct comprising a nucleic acid encoding a shmiR comprising or consisting of the sequence set forth in SEQ ID NO:57 (shmiR-15) operably linked to a U6 promoter e.g., a U6-1 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter; and (b) a ddRNAi construct comprising a nucleic acid comprising or consisting of the sequence set forth in SEQ ID NO:73 (coding for shmiR-15) operably linked to a U6 promoter e.g., a U6-1 promoter.

In one example, the plurality of ddRNAi constructs comprises:

(a) a ddRNAi construct comprising a nucleic acid encoding a shmiR comprising or consisting of the sequence set forth in SEQ ID NO:54 (shmiR-12) operably linked to a U6 promoter e.g., a U6-8 promoter; and (b) a ddRNAi construct comprising a nucleic acid encoding a shmiR comprising or consisting of the sequence set forth in SEQ ID NO:57 (shmiR-15) operably linked to a U6 promoter e.g., a U6-1 promoter.

For example, the plurality of ddRNAi constructs may comprise:

(a) a ddRNAi construct comprising a nucleic acid encoding a shmiR comprising or consisting of the sequence set forth in SEQ ID NO:54 (shmiR-12) operably linked to a U6 promoter e.g., a U6-8 promoter; and (b) a ddRNAi construct comprising a nucleic acid comprising or consisting of the sequence set forth in SEQ ID NO:73 (coding for shmiR-15) operably linked to a U6 promoter e.g., a U6-1 promoter.

In one example, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter; and (b) a ddRNAi construct comprising a nucleic acid encoding a shmiR comprising or consisting of the sequence set forth in SEQ ID NO:137 (shmiR-20) operably linked to a U6 promoter e.g., a U6-1 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter; and (b) a ddRNAi construct comprising a nucleic acid comprising or consisting of the sequence set forth in SEQ ID NO:149 (coding for shmiR-20) operably linked to a U6 promoter e.g., a U6-1 promoter.

In one example, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter; and (b) a ddRNAi construct comprising a nucleic acid encoding a shmiR comprising or consisting of the sequence set forth in SEQ ID NO:141 (shmiR-24) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter; and (b) a ddRNAi construct comprising a nucleic acid comprising or consisting of the sequence set forth in SEQ ID NO:153 (coding for shmiR-24) operably linked to a U6 promoter e.g., a U6-8 promoter. According to an example in which the plurality of ddRNAi constructs comprises three ddRNAi constructs, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter;

(b) a ddRNAi construct comprising a nucleic acid encoding a shmiR comprising or consisting of the sequence set forth in SEQ ID NO:57 (shmiR-15) operably linked to a U6 promoter e.g., a U6-1 promoter; and (c) a ddRNAi construct comprising a nucleic acid encoding a shmiR comprising or consisting of the sequence set forth in SEQ ID NO:54 (shmiR-12) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter;

(b) a ddRNAi construct comprising a nucleic acid comprising or consisting of the sequence set forth in SEQ ID NO:73 (coding for shmiR-15) operably linked to a U6 promoter e.g., a U6-1 promoter; and (c) a ddRNAi construct comprising a nucleic acid comprising or consisting of the sequence set forth in SEQ ID NO:70 (coding for shmiR-12) operably linked to a U6 promoter e.g., a U6-8 promoter.

According to another example in which the plurality of ddRNAi constructs comprises three ddRNAi constructs, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter;

(b) a ddRNAi construct comprising a nucleic acid encoding a shmiR comprising or consisting of the sequence set forth in SEQ ID NO:49 (shmiR-7) operably linked to a U6 promoter e.g., a U6-1 promoter; and (c) a ddRNAi construct comprising a nucleic acid encoding a shmiR comprising or consisting of the sequence set forth in SEQ ID NO:54 (shmiR-12) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter;

(b) a ddRNAi construct comprising a nucleic acid comprising or consisting of the sequence set forth in SEQ ID NO:65 (coding for shmiR-7) operably linked to a U6 promoter e.g., a U6-1 promoter; and (c) a ddRNAi construct comprising a nucleic acid comprising or consisting of the sequence set forth in SEQ ID NO:70 (coding for shmiR-12) operably linked to a U6 promoter e.g., a U6-8 promoter.

According to another example, the plurality of ddRNAi constructs of the disclosure may comprise:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter;

(b) a ddRNAi construct comprising a nucleic acid encoding a shRNA comprising or consisting of the sequence set forth in SEQ ID NO: 92 (shRNA-15) operably linked to a U6 promoter e.g., a U6-1 promoter; and (c) a ddRNAi construct comprising a nucleic acid encoding a shmiR comprising or consisting of the sequence set forth in SEQ ID NO:54 (shmiR-12) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter;

(b) a ddRNAi construct comprising a nucleic acid comprising or consisting of the sequence set forth in SEQ ID NO:108 (coding for shRNA-15) operably linked to a U6 promoter e.g., a U6-1 promoter; and (c) a ddRNAi construct comprising a nucleic acid comprising or consisting of the sequence set forth in SEQ ID NO:70 (coding for shmiR-12) operably linked to a U6 promoter e.g., a U6-8 promoter.

According to another example in which the plurality of ddRNAi constructs comprises three ddRNAi constructs, the plurality of ddRNAi constructs comprises:

(a) a ddRNAi construct comprising a nucleic acid encoding a shmiR comprising or consisting of the sequence set forth in SEQ ID NO:48 (shmiR-6) operably linked to a U6 promoter e.g., a U6-9 promoter;

(b) a ddRNAi construct comprising a nucleic acid encoding a shmiR comprising or consisting of the sequence set forth in SEQ ID NO:137 (shmiR-20) operably linked to a U6 promoter e.g., a U6-1 promoter; and (c) a ddRNAi construct comprising a nucleic acid encoding a shmiR comprising or consisting of the sequence set forth in SEQ ID NO:141 (shmiR-24) operably linked to a U6 promoter e.g., a U6-8 promoter.

For example, the plurality of ddRNAi constructs may comprise:

(a) a ddRNAi construct comprising a nucleic acid comprising or consisting of the sequence set forth in SEQ ID NO:64 (coding for shmiR-6) operably linked to a U6 promoter e.g., a U6-9 promoter;

(b) a ddRNAi construct comprising a nucleic acid comprising or consisting of the sequence set forth in SEQ ID NO:149 (coding for shmiR-20) operably linked to a U6 promoter e.g., a U6-1 promoter; and (c) a ddRNAi construct comprising a nucleic acid comprising or consisting of the sequence set forth in SEQ ID NO:153 (coding for shmiR-24) operably linked to a U6 promoter e.g., a U6-8 promoter.

In addition, the or each ddRNAi construct can comprise one or more multiple cloning sites and/or unique restriction sites that are located strategically, such that the promoter, nucleic acid encoding the shmiR or shRNA and/or other regulator elements are easily removed or replaced. The or each ddRNAi construct can be assembled from smaller oligonucleotide components using strategically located restriction sites and/or complementary sticky ends. The base vector for one approach according to the present disclosure comprises plasmids with a multilinker in which all sites are unique (though this is not an absolute requirement). Sequentially, each promoter is inserted between its designated unique sites resulting in a base cassette with one or more promoters, all of which can have variable orientation. Sequentially, again, annealed primer pairs are inserted into the unique sites downstream of each of the individual promoters, resulting in a single-, double- or multiple-expression cassette construct. The insert can be moved into, e.g. an AdV backbone or an AAV backbone using two unique restriction enzyme sites (the same or different ones) that flank the single-, double- or multiple-expression cassette insert.

Generation of the or each construct can be accomplished using any suitable genetic engineering techniques known in the art, including without limitation, the standard techniques of PCR, oligonucleotide synthesis, restriction endonuclease digestion, ligation, transformation, plasmid purification, and DNA sequencing. If the or each construct is a viral construct, the construct comprises, for example, sequences necessary to package the ddRNAi construct into viral particles and/or sequences that allow integration of the ddRNAi construct into the target cell genome. In some examples, the or each viral construct additionally contains genes that allow for replication and propagation of virus, however such genes will be supplied in trans. Additionally, the or each viral construct cam contain genes or genetic sequences from the genome of any known organism incorporated in native form or modified. For example, a viral construct may comprise sequences useful for replication of the construct in bacteria.

The or each construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines.

Other genetic elements that may find use in embodiments of the present disclosure include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the or each construct, an internal ribosomal entry site (IRES) sequence can be included. In one example, the additional genetic elements are operably linked with and controlled by an independent promoter/enhancer. In addition a suitable origin of replication for propagation of the construct in bacteria may be employed. The sequence of the origin of replication generally is separated from the ddRNAi construct and other genetic sequences. Such origins of replication are known in the art and include the pUC, ColE1, 2-micron or SV40 origins of replication.

Expression Vectors

In one example, a ddRNAi construct of the disclosure is included within an expression vector.

In one example, the expression vector is a plasmid, e.g., as is known in the art. In one example, a suitable plasmid expression vector is a pSsh vector e.g., with a U6 promoter and proximal sequence element 7 (PSE7).

In one example, the expression vector is mini-circle DNA. Mini-circle DNA is described in U.S. Patent Publication No. 2004/0214329. Mini-circle DNA are useful for persistently high levels of nucleic acid transcription. The circular vectors are characterized by being devoid of expression-silencing bacterial sequences. For example, mini-circle vectors differ from bacterial plasmid vectors in that they lack an origin of replication, and lack drug selection markers commonly found in bacterial plasmids, e.g. β-lactamase, tet, and the like. Consequently, minicircle DNA becomes smaller in size, allowing more efficient delivery.

In one example, the expression vector is a viral vector.

A viral vector based on any appropriate virus may be used to deliver a ddRNAi of the disclosure. In addition, hybrid viral systems may be of use. The choice of viral delivery system will depend on various parameters, such as the tissue targeted for delivery, transduction efficiency of the system, pathogenicity, immunological and toxicity concerns, and the like.

Commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). In one example, a viral vector of the disclosure integrates into a host cell's chromatin. In another example, a viral vector of the disclosure persists in a host cell's nucleus as an extrachomosomal episome.

In one example, a viral vector is an adenoviral (AdV) vector. Adenoviruses are medium-sized double-stranded, non-enveloped DNA viruses with linear genomes that is between 26-48 Kbp. Adenoviruses gain entry to a target cell by receptor-mediated binding and internalization, penetrating the nucleus in both non-dividing and dividing cells. Adenoviruses are heavily reliant on the host cell for survival and replication and are able to replicate in the nucleus of vertebrate cells using the host's replication machinery.

In one example, a viral vector is from the Parvoviridae family. The Parvoviridae is a family of small single-stranded, non-enveloped DNA viruses with genomes approximately 5000 nucleotides long. Included among the family members is adeno-associated virus (AAV). In one example, a viral vector of the disclosure is an AAV. AAV is a dependent parvovirus that generally requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells. Because progeny virus is not produced from AAV infection in the absence of helper virus, the extent of transduction is restricted only to the initial cells that are infected with the virus. It is this feature which makes AAV a desirable vector for the present disclosure. Furthermore, unlike retrovirus, adenovirus, and herpes simplex virus, AAV appears to lack human pathogenicity and toxicity (Kay, et al., *Nature*. 424: 251 (2003)). Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as shmiRs and shRNAs.

Another viral delivery system useful with the ddRNAi constructs of the disclosure is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some examples, a viral vector is a lentivirus. Lentivirus vectors are often pseudotyped with vesicular steatites virus glycoprotein (VSV-G), and have been derived from the human immunodeficiency virus (HIV); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. One of the main advantages to the use of lentiviral vectors is that gene transfer is persistent in most tissues or cell types, even following cell division of the transduced cell.

A lentiviral-based construct used to express shmiRs and/or shRNAs from the nucleic acids and ddRNAi constructs of the disclosure comprises sequences from the 5' and 3' long terminal repeats (LTRs) of a lentivirus. In one example, the viral construct comprises an inactivated or self-inactivating 3' LTR from a lentivirus. The 3' LTR may be made self-inactivating by any method known in the art. For example, the U3 element of the 3' LTR contains a deletion of its enhancer sequence, e.g., the TATA box, Sp1 and NF-kappa B sites. As a result of the self-inactivating 3' LTR, the provirus that is integrated into the host genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Other viral or non-viral systems known to those skilled in the art may be used to deliver the ddRNAi or nucleic acid of the present invention to cells of interest, including but not limited to gene-deleted adenovirus-transposon vectors (see Yant, et al., *Nature Biotech.* 20:999-1004 (2002)); systems derived from Sindbis virus or Semliki forest virus (see Perri, et al, *J. Virol.* 74(20):9802-07 (2002)); systems derived from Newcastle disease virus or Sendai virus.

Testing Nucleic Acids and ddRNAi Constructs of the Disclosure

Cell Culture Models

HBV does not infect cells in culture. However, transfection of HBV DNA (either as a head-to-tail dimer or as an "overlength" genome of >100%) into HuH7 or Hep G2 hepatocytes results in viral gene expression and production of HBV virions released into the media. An example of such a cell line is HepG2.2.15, which is a sub-cell line of the HepG2 human hepatocellular carcinoma cell line which stably harbors the complete HBV genome (serotype ayw, genotype D). HepG2.2.15 expresses all HBV viral RNA and proteins, produce viral genomes, and secretes virus-like particles. As exemplified herein, activity shmiR expressed from a nucleic acid or ddRNAi construct of the disclosure can be determined by administering the nucleic acid or ddRNAi construct to the cell and subsequently measuring the level of expression of a RNA or protein encoded by the HBV genome. Intracellular HBV gene expression can be assayed either by a Taqman™ assay or other real time PCR assay for HBV RNA or by ELISA for HBV protein. Extracellular virus can be assayed either by PCR for DNA or ELISA for protein. Antibodies are commercially available for HBV surface antigen and core protein. Various means for normalizing differences in transfection efficiency and sample recovery are known in the art. Recent advances in cell culture systems using primary human hepatocytes show promise for determining the activity of HBV therapeutics.

A shmiR and/or shRNA expressed from a nucleic acid or ddRNAi construct of the disclosure that reduces expression of a RNA or protein encoded by the HBV genome by at least 50% compared to in the absence of the nucleic acid or ddRNAi construct of the disclosure is considered to be useful in a method of the disclosure.

Animal Models

There are several small animal models available to study HBV replication. One is the transplantation of HBV-infected liver tissue into irradiated mice. Viremia (as evidenced by measuring HBV DNA by PCR) is first detected 8 days after transplantation and peaks between 18-25 days (Ilan et al., 1999, Hepatology, 29, 553-562).

Transgenic mice that express HBV have also been used as a model to evaluate potential anti-virals. HBV DNA is detectable in both liver and serum of the transgenic mice (Money et al., *Antiviral Res.,* 42, 97-108, 1999).

An additional model is to establish subcutaneous tumors in nude mice with Hep G2 cells transfected with HBV. Tumors develop in about 2 weeks after inoculation and express HBV surface and core antigens. HBV DNA and surface antigen are also detected in the circulation of tumor-bearing mice (Yao et al., *J. Viral Hepat.,* 3, 19-22, 1996).

An additional model is to use is the PXB mouse as described herein, which is a chimeric group of mice in which immunodeficient mice that have liver disease (uPA/SCID) have been transplanted with human hepatocytes. Because the uPA/SCID mice exhibit significant liver toxicity, transplanting healthy human cells can result in the production of a mouse with a healthy and functional liver that has been 70 to 90 percent repopulated by human hepatocytes. Because PXB mice exhibit normal histological structures in the liver and exhibit many of the hallmark of human liver cells, the mice can sustain active HBV infection in the chimeric hepatic tissues.

An additional model is the use of the Quantum B model which is a 3 dimensional cell culture platform in which the human hepatocytes supplied into the model, assemble in such a way that mimics the architecture and physiology of the human liver. Because the model is solely comprised of liver hepatocytes, it is thought to be the first long term stable fully human full viral lifecycle model of Hepatitis B and recapitulates some critical features of the HBV infectious life cycle.

Any of the foregoing animal models can be used to determine the efficacy of nucleic acid or ddRNAi construct of the disclosure in treating or reducing a HBV infection.

Carriers

In some examples, one or more of the nucleic acids or ddRNAi constructs or expression vectors of the disclosure is/are provided in a composition with a carrier.

In some examples, the carrier is a lipid-based carrier, cationic lipid, or liposome nucleic acid complex, a liposome, a micelle, a virosome, a lipid nanoparticle or a mixture thereof.

In some examples, the carrier is a polymer-based carrier such as a cationic polymer-nucleic acid complex.

In a further example, the carrier is a cyclodextrin-based carrier such as a cyclodextrin polymer-nucleic acid complex.

In a further example, the carrier is a protein-based carrier such as a cationic peptide-nucleic acid complex.

In another example, the carrier is a lipid nanoparticle. Exemplary nanoparticles are described, for example, in U.S. Pat. No. 7,514,099.

In some examples, one or more of the nucleic acids or ddRNAi constructs or expression vectors of the disclosure is/are formulated with a lipid nanoparticle composition comprising a cationic lipid/Cholesterol/PEG-C-DMA/DSPC (e.g., in a 40/48/2/10 ratio), a cationic lipid/Cholesterol/PEG-DMG/DSPC (e.g., in a 40/48/2/10 ratio), or a cationic lipid/Cholesterol/PEG-DMG (e.g., in a 60/38/2 ratio). In some examples, the cationic lipid is Octyl CL in DMA, DL in DMA, L-278, DLinKC2DMA, or MC3.

In another example, one or more of the nucleic acids or ddRNAi constructs or expression vectors of the disclosure is/are formulated with any of the cationic lipid formulations described in WO 2010/021865; WO 2010/080724; WO 2010/042877; WO 2010/105209 or WO 2011/022460.

In another example, one or more of the nucleic acids or ddRNAi constructs or expression vectors of the disclosure is/are conjugated to or complexed with another compound, e.g., to facilitate delivery of the RNA or ddRNAi or expression construct. Non-limiting, examples of such conjugates are described in US 2008/0152661 and US 2004/0162260 (e.g., CDM-LBA, CDM-Pip-LBA, CDM-PEG, CDM-NAG, etc.).

In another example, polyethylene glycol (PEG) is covalently attached to a nucleic acid or ddRNAi construct or expression construct of the disclosure. The attached PEG can be any molecular weight, e.g., from about 100 to about 50,000 daltons (Da).

In yet other example, one or more of the nucleic acids or ddRNAi constructs or expression vectors of the disclosure is/are formulated with a carrier comprising surface-modified liposomes containing poly(ethylene glycol) lipids (PEG-modified, or long-circulating liposomes or stealth liposomes), such as is disclosed in for example, WO 96/10391; WO 96/10390; or WO 96/10392.

In some examples, the nucleic acids or ddRNAi constructs or expression constructs of the disclosure can also be formulated or complexed with polyethyleneimine or a derivative thereof, such as polyethyleneimine-polyethyleneglycol-N-acetylgalactosamine (PEI-PEG-GAL) or poly-ethyleneimine-polyethyleneglycol-tri-N-acetylgalactosamine (PEI-PEG-triGAL) derivatives. In one example, a RNA or ddRNAi or expression construct of the disclosure is formulated as described in U.S. Patent Application Publication No. 2003/0077829.

In other examples, one or more of the nucleic acids or ddRNAi constructs or expression vectors of the disclosure is/are complexed with membrane disruptive agents such as those described in U.S. Patent Application Publication No. 2001/0007666.

Other carriers include cyclodextrins (see for example, Gonzalez et al., 1999, *Bioconjugate Chem.*, 10, 1068-1074; or WO 03/46185), poly(lactic-co-glycolic) acid (PLGA) and PLCA microspheres (see for example US 2002130430).

Compositions and Methods of Treatment

One or more nucleic acids, ddRNAi constructs or expression vectors of the disclosure may be used in compositions for preventing or treating HBV infection. The therapeutic compositions of the invention may be used alone or in combination with one or more materials, including other antiviral agents. Currently, entecavir, tenofovir, lamivudine, adefovir dipivoxil, and interferon alpha (e.g., pegylated interferon alpha) have been approved for treatment of HBV. Since the nucleic acids, ddRNAi constructs or expression vectors of the disclosure act against HBV through a different mechanism to other approved drugs, combination therapy of the agents of the invention and other antivirals is expected to significantly increase the efficacy of therapy while substantially reducing the development of drug resistance, e.g., the development of lamivudine resistance, a problem of major concern with long term lamivudine therapy.

Compositions will desirably include materials that increase the biological stability of the nucleic acids, ddRNAi constructs or expression vectors of the disclosure and/or materials that increase the ability of the compositions to penetrate hepatocytes selectively. The therapeutic compositions of the disclosure may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises one or more nucleic acids, ddRNAi constructs or expression vectors of the disclosure. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some examples, a vasoconstriction agent is added to the formulation. The compositions according to the present disclosure are provided sterile and pyrogen free. Suitable pharmaceutical carriers, as well as pharmaceutical necessities for use in pharmaceutical formulations, are described in Remington: The Science and Practice of Pharmacy (formerly Remington's Pharmaceutical Sciences), Mack Publishing Co., a standard reference text in this field, and in the USP/NF.

Routes of administration include, but are not limited to, intramuscular, intraperitoneal, intradermal, subcutaneous, intravenous, intrathecal, intraarterially, intraocularly and oral as well as transdermal or by inhalation or suppository. Exemplary routes of administration include intravenous, intramuscular, oral, intraperitoneal, intradermal, intraarterial and subcutaneous injection. Targeted transfection of hepatocytes in vivo for delivery of nucleic acids, ddRNAi constructs or expression vectors of the disclosure may be accomplished through IV injection with a composition comprising one or more nucleic acids, ddRNAi constructs or expression vectors as described herein complexed with a mixture (e.g., a 35%/65% ratio) of a lactosyl spermine (mono or trilactosylated) and cholesteryl spermine (containing spermine to DNA at a charge ratio of 0.8). Such compositions are useful for pharmaceutical applications and may readily be formulated in a suitable sterile, non-pyrogenic vehicle, e.g., buffered saline for injection, for parenteral administration, e.g., IV (including IV infusion), IM, SC, and for intraperitoneal administration. In certain compositions, a nucleic acid, ddRNAi construct or expression vector of the disclosure is complexed with an endosomolytic spermine such cholesteryl spermine alone, without a targeting spermine; some routes of administration, such as intraperitoneal injection or infusion, may achieve effective hepatic delivery and transfection of the nucleic acid, ddRNAi construct or expression vector.

Intraperitoneal administration (e.g., ultrasound guided intraperitoneal injection) of a sterile pharmaceutical composition comprising one or more nucleic acids, ddRNAi constructs or expression vectors of the disclosure in a specially formulated delivery vehicle may be an advantageous route of delivery to promote uptake by liver cells, including hepatocytes.

The volume, concentration, and formulation of the pharmaceutical composition as well as the dosage regimen may be tailored specifically to maximize cellular delivery while minimizing toxicity such as an inflammatory response. E.g, relatively large volumes (5, 10, 20, 50 ml or more) with corresponding low concentrations of active ingredients, as well as the inclusion of an anti-inflammatory compound such as a corticosteroid, may be utilized if desired.

In HBV infected individuals it is anticipated that a nucleic acid, ddRNAi construct or expression vector of the disclosure is useful as a pre-treatment in conjunction with therapeutic vaccination protocols designed to boost immunity against the virus. It is also anticipated that the nucleic acids, ddRNAi constructs or expression vectors of the disclosure is/are useful for prophylaxis in a regimen of periodic administrations to individuals who because of occupational or other potential for exposure are considered at high risk of exposure to HBV.

Kits

The present disclosure also provides the nucleic acids, ddRNAi constructs and/or expression vectors of the disclosure in a kit form. The kit may comprise a container. The kit typically contains one or more nucleic acids, ddRNAi constructs or expression vectors of the disclosure with instructions for its administration. In some examples, the kit contains more than one nucleic acids, ddRNAi constructs or expression vectors of the disclosure and/or another nucleic acid, ddRNAi construct or expression vector of the disclosure. In some examples, the kit contains more than one nucleic acids, ddRNAi constructs or expression vectors of the disclosure packed together with another compound for treatment of HBV infection (as described herein). For example, the other therapeutic agent known for treating HBV infection may be selected from entecavir, tenofovir, lamivudine, adefovir and/or pegylated interferon.

EXAMPLES

Example 1—Preparation of ddRNAi Expression Constructs Expressing shmiRs

To produce ddRNAi constructs capable of expressing single shmiRs of the disclosure, DNA sequences encoding the shmiRs are synthesized and cloned downstream of a U6 promoter (e.g., U6-1, U6-8, or U6-9). The ddRNAi constructs are designated HBV-shmiR1 to HBV-shmiR16, respectively.

ddRNAi constructs capable of expressing single shRNAs which correspond to the shmiRs of the disclosure are also produced. Briefly, DNA sequences encoding the shRNAs are synthesized and cloned downstream of a U6 promoter (e.g., U6-1, U6-8, or U6-9) with a proximal sequence element 7 (PSE7). The ddRNAi constructs are designated HBV-shRNA1 to HBV-shRNA16, respectively.

In addition, ddRNAi constructs comprising triple HBV shmiR expression cassettes and capable of expressing three shmiRs of the disclosure are prepared. A first triple HBV shmiR ddRNAi construct (designated HBV-shmiRx3-v1) is synthesized comprising, in a 5'-3' direction, DNA sequence coding for a U6-9 promoter, shmiR6 (SEQ ID NO: 64), a U6-1 promoter, shmiR15 (SEQ ID NO: 73), a U6-8 promoter, and shmiR12 (SEQ ID NO: 70). A second triple HBV shmiR ddRNAi construct (designated HBV-shmiRx3-v2) is also synthesized comprising, in a 5'-3' direction, DNA sequences coding for a U6-9 promoter, shmiR6 (SEQ ID NO: 64), a U6-1 promoter, shmiR7 (SEQ ID NO: 65), a U6-8 promoter, and shmiR12 (SEQ ID NO: 70).

A ddRNAi construct comprising a triple HBV shRNA expression cassette which is capable of expressing three shRNAs corresponding to the three shmiRs expressed by the construct designated HBV-shmiRx3-v1 is also prepared. Specifically, a triple HBV shRNA ddRNAi construct (designated HBV-shRNAx3-v1) is synthesized comprising, in a 5'-3' direction, DNA sequence coding for a U6-9 promoter and PSE7, shRNA6 (SEQ ID NO: 99), a U6-1 promoter and PSE7, shRNA15 (SEQ ID NO: 108), a U6-8 promoter and PSE7, and shRNA12 (SEQ ID NO: 105).

Example 2—Activity of ddRNAi Expression Constructs in Dual-Luciferase Reporter Assay Efficacy of the ddRNAi constructs expressing shmiRs or shRNAs of the disclosure to knockdown HBV transcripts is determined using dual-luciferase reporter assays in HEK293 cells.

Plasmid reporter constructs based on the pGL3 Luciferase Reporter Vector are constructed for effector and effector complement sequences from each of the shmiRs and shRNAs of the disclosure. Luciferase reporter constructs e.g., firefly luciferase reporter constructs, are generated by inserting the respective effector sequence or effector complement sequence of the shmiRs or shRNAs (as appropriate) with 20 bp flanking sequences at each end into the pGL3-control vector (Promega, Madison, Wis.). The inserts are subcloned using FseI and XbaI restriction enzyme sites following the luciferase reporter gene.

The dual-luciferase reporter assays are performed in HEK293 cells (ATCC). The HEK293 cells are cultured in DMEM medium containing 10% fetal bovine serum, 2 mM glutamine, penicillin (100 U/mL), and streptomycin (100 µg/mL) at 37° C. humid incubator with 5% $CO_2$. The HEK293 cell are seeded at a density of $2\times10^4$ cells per well into 96-well culture plate one day prior to transfection.

ddRNAi expression constructs described in Example 1 (i.e., ddRNAi constructs designated HBV-shmiR1 to HBV-shmiR16, HBV-shmiRx3-v1 and HBV-shmiRx3-v2) are synthesized and inserted into an appropriate plasmid vector e.g., a pSsh vector, optionally with a proximal sequence element 7 (PSE7) for constructs expressing shRNAs.

Expression vectors comprising the ddRNAi expression constructs are co-transfected into HEK293 cells with a Luciferase reporter construct e.g., a firefly luciferase reporter construct, expressing an effector sequence or effector complement sequence of the corresponding shmiR or shRNA (as appropriate) at a ratio of 10:1 (ddRNAi expression construct: Luciferase reporter construct) using 0.3 uL of Lipofectamine 2000 reagent (Life Technologies, Carlsbad, Calif.) according to manufacturer's instructions. Cells are also transfected with 1 ng of a *Renilla* reporter construct (serving as a transfection control). 48 hour post-transfection, cell lysates are collected and analyzed using Dual Luciferase Reporter Assay System (Promega, Madison, Wis.). The firefly/*Renilla* activity ratios are determined for each transfection. Percentage inhibition of reporter expression is calculated relative to a negative control e.g., a construct expressing a random non-targeting sequence. The experiment is performed in replicate.

The ability of ddRNAi expression constructs to express shmiRs of the disclosure and inhibit expression of luciferase protein from the respective Luciferase reporter constructs is determined.

In addition, the three ddRNAi shmiR constructs (i.e., the ddRNAi shmiR constructs expressing shmiR6, shmiR15 and shmiR12 respectively) were compared for strand preference activity relative to their shRNA expressing counterparts. The data presented in FIG. 1A show that shmiRs display higher antisense (effector) strand activity relative to the corresponding shRNAs.

Example 3—Hyperfunctional Properties of ddRNAi Constructs Expressing shmiRs

The hyperfunctional properties of three ddRNAi constructs (i.e., the ddRNAi shmiR constructs expressing shmiR6, shmiR15 and shmiR12 respectively) were assessed in HEK293 cells.

For each of the three ddRNAi expression constructs, a well containing HEK293 cells was co-transfected with (i) 100 ng, 50 ng, 20 ng, 5 ng, 1.67 ng, 0.56 ng, 0.19 ng, 0.06 ng, or 0.03 ng of the respective ddRNAi expression construct, (ii) various amounts of filler plasmid to adjust the final DNA content to 100 ng, and (iii) 10 ng of the corresponding Firefly luciferase reporter construct, using 0.3 uL of Lipofectamine 2000 reagent (Life Technologies, Carlsbad, Calif.) according to manufacturer's instructions. The cells were also transfected with 1 ng of a *Renilla* reporter construct (serving as a loading control). 48 hour post-transfection, cell lysates were collected and analyzed using Dual Luciferase Reporter Assay System (Promega, Madison, Wis.). The firefly/*Renilla* activity ratios were determined for each well, and the inhibition efficiency of ddRNAi expression constructs were calculated.

The activity of constructs expressing shmiR6, shmiR15 or shmiR12 (SEQ ID NO: 64, SEQ ID NO: 73, or SEQ ID NO: 70 respectively) was determined and compared directly to corresponding constructs expressing shRNA6, shRNA15 and shRNA12 (SEQ ID NO: 99, SEQ ID NO: 108, or SEQ ID NO: 105, respectively) as shown in FIG. 1. These data show that shmiR constructs were more effective than the corresponding shRNA constructs under these experimental conditions (FIG. 1A).

Relative activities of constructs were further characterised using hyperfunctionality assays. Hyperfunctional assays were performed by titrating down the amounts of constructs expressing shmiRs (100 ng to 0.02 ng) co-transfected with a fixed amount of Firefly reporter. These data (FIGS. 1B-1D) show that all three of the ddRNAi shmiR constructs were highly active at low concentrations compared to the corresponding constructs expressing shRNAs, which is indicative of increased biological activity.

Example 4—Design and Testing of ddRNAi Constructs Expressing shmiR Variants

To improve on the strand preference activity of shmiR-12 (SEQ ID NO: 54) and shmiR-15 (SEQ ID NO: 57), variants of shmiR-12 and shmiR-15 were produced by shifting the effector complement (sense) sequence by 1 or 2 nucleotides either upstream or downstream. The variants of shmiR-15 are designated shmiR-17 to shmiR-22 (SEQ ID NOs: 134-139 respectively) and the variants of shmiR-12 are designated shmiR-23 to shmiR-28 (SEQ ID NOs: 140-145 respectively).

The influence of addition of an 'A' nucleotide at the 3' end or a 'G' nucleotide at the 5' end of the sense sequence on thermodynamics of the shmiR variant was also assessed. The idea is to allow for the antisense (or effector) strand to be preferentially loaded into the RISC complex for functional RNAi activity.

Figure 2A:
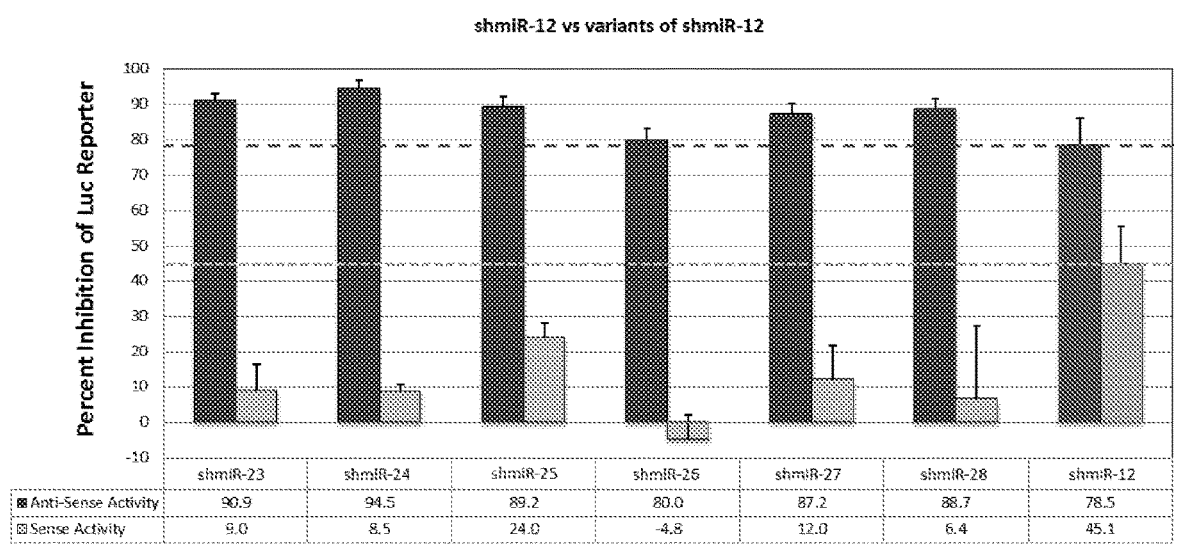
FIG. 2 illustrates sense and antisense strand preference inhibitory activity for variants of shmiR-12 and shmiR-15 relative to the respective parental shmiRs (shmiR-12 and shmiR-15 respectively) in the Luciferase reporter assay: (A) shows that all six variants of shmiR-12 have better strand preference to the parental shmiR; and (B) shows that four of the six variants of shmiR-15 have better strand preference to the parental shmiR.
Figure 2B:
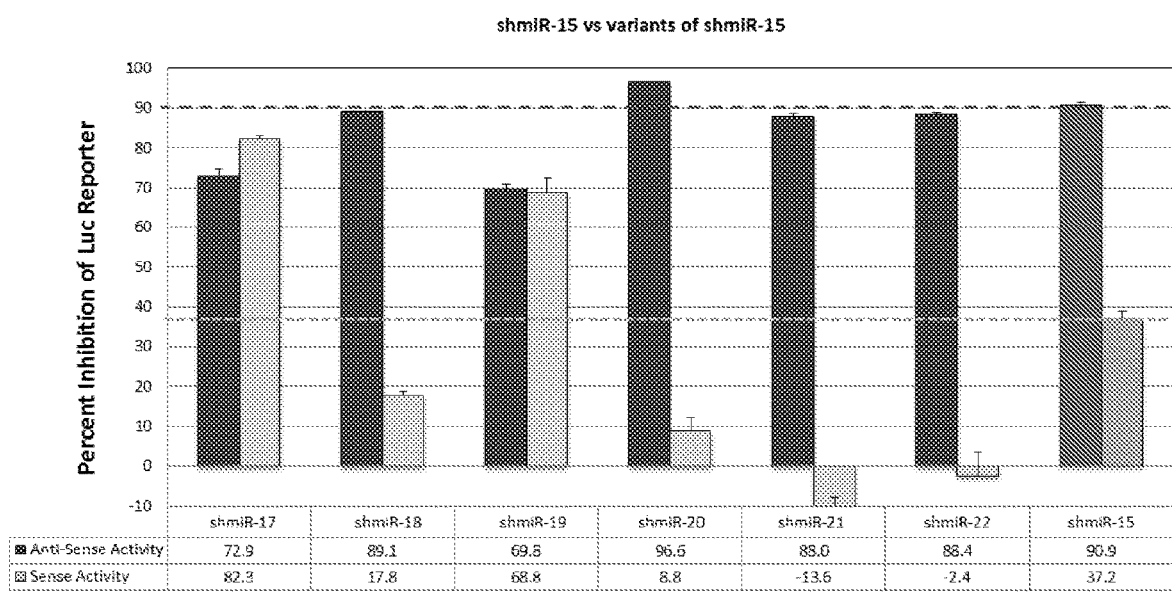

For variants of shmiR-12 (i.e., shmiR-23 to shmiR28), all six shmiR variants demonstrated better strand preference than the parental shmiR-12 (FIG. 2A). For variants of shmiR-15 (i.e., shmiR-17 to shmiR-22), four of the six variants demonstrated better strand preference than the parental shmiR-15 (FIG. 2B). Based on these results, a further triple HBV shmiR ddRNAi construct was designed by substituting the sequences in HBV-shmiRx3-v1 coding for shmiR-12 and shmiR-15 with sequences coding for shmiR-24 (SEQ ID NO: 153) and shmiR-20 (SEQ ID NO: 149), respectively, to form a third triple HBV shmiR ddRNAi construct (designated HBV-shmiRx3-v3).

Example 5—Knockdown of HBV Transcripts in HepG2.2.15 Cells Using HBV shmiR AdV Vectors Single and triple shmiR AdV vectors are prepared by subcloning the ddRNAi expression constructs described in Example 1 (i.e., ddRNAi constructs designated HBV-shmiR1 to HBV-shmiR16, HBV-shmiRx3-v1 and HBV-shmiRx3-v2) into a adenovirus (AdV) construct for virus production (Vector Biolabs, Malvern Pa.).

To test the efficacy of shmiR AdV vectors described herein to knockdown expression of HBV genes, HepG2.2.15 are infected with shmiR AdV vectors of the disclosure and inhibition of HBV gene expression is assayed.

HepG2.2.15 is a sub-cell line of the HepG2 human hepatocellular carcinoma cell line which stably harbors the complete HBV genome (serotype ayw, genotype D). HepG2.2.15 cells express all HBV viral RNA and proteins, produces viral genomes, and secrete virus-like particles. HepG2.2.15 cells are maintained in the RPMI1640 medium supplemented with 4% fetal bovine serum, 4 mM glutamine, penicillin (100 U/mL), and streptomycin (100 µg/mL) and propagated in a 37° C. humid incubator in an atmosphere of 5% $CO_2$.

HepG2.2.15 cells are infected with the HBV shmiR AdV vectors in cell suspension and cultured on multi-well plates. Each well contains a suspension of approximately $1.0 \times 10^5$ HepG2.2.15 cells and one of the single or triple HBV shmiR AdV vectors of the disclosure at one of the following MOIs: 6, 15, 30, 60, 90, or 120. Following transduction, cells are cultured at 37° C. at 5% $CO_2$ for 72 h before being harvested for RNA and DNA extraction using Qiagen miRNeasy mini kit and QiAmp DNA mini kit, respectively (Valencia, Calif.).

Total RNA is isolated using miRNeasy Mini Kit (Qiagen, Valencia, Calif.). Total RNA is quantified using the Nano-Drop 1000 Spectrophotometer (Thermo Scientific) and diluted to a working concentration of 10 ng/µl.

shmiR copies per cell are determined for each shmiR of the disclosure when expressed in HepG2.2.15 cells from single or triple HBV shmiR AdV vector(s) at the various MOIs using Qiagen's miScript PCR system. For each RT-qPCR analysis, 50 ng of total RNA is converted into cDNA using Qiagen's miScript II RT kit. Quantitative PCR of shmiRs is carried out using Qiagen miScript SYBR green PCR kit with custom primers designed for the respective shmiRs and the following real-time PCR conditions: initial denaturation at 95° C. for 15 min followed by 40 cycles of 94° C. for 15 sec, 55° C. for 30 sec and 70° C. for 30 sec.

Levels of inhibition of HBV transcripts at regions corresponding to HBV antigens HBsAg, HBcAg and HbxAg, relative to levels of GAPDH mRNA, are determined by normalizing the respective HBV mRNA transcript levels to GAPDH mRNA for each sample. Briefly, 100 ng of total RNA is used to synthesize cDNA using High Capacity cDNA Reverse Transcription Kit (Life Technologies, Carlsbad, Calif.) according to manufacturer instructions. Quantitative PCR amplifications of regions within HBV antigens HBsAg, HBcAg, HbxAg, and GAPDH is then performed using Power SYBR Green PCR Master Mix (Life Technologies) and the primer sets listed in Table 1. Standard real-time PCR conditions are used: initial denaturation at 95° C. for 10 min followed by 40 cycles of 95° C. for 15 sec and 60° C. for 1 min.

TABLE 1

Primer sets for RT-qPCR

| HBV Antigen | Primer | Sequence (5'-3') |
|---|---|---|
| HBsAg | HBsAg_fwd | ATGTTGCCCGTTTGTCCTCT |
|  | HBsAg_rev | CCGTCCGAAGGTTTGGTACA |
| HBxAg | HBxAg_fwd | CGTCCTTTGTTTACGTCCCG |
|  | HBxAg_rev | AGTCCGCGTAAAGAGAGGTG |
| HBcAg | HBcAg_fwd | CCACCAAATGCCCCTATCCT |
|  | HBcAg_rev | ATTGAGACCTTCGTCTGCGA |
| GAPDH | GAPDH_fwd | ACACCATGGGGAAGGTGAAG |
|  | GAPDH_rev | GTGACCAGGCGCCCAATA |

Levels of inhibition of HBV transcripts at regions corresponding to HBV antigens HBsAg, HBcAg and HbxAg, relative to levels of GAPDH mRNA, for each shmiR of the disclosure (expressed individually, or as part of a triple construct), is determined at various MOIs.

Example 6—Knockdown of HBV Transcripts in HepG2.2.15 Cells Using HBV shmiR AdV Vectors Single and triple shmiR or shRNA AdV vectors were prepared by subcloning the ddRNAi expression constructs described in Example 1 (i.e., ddRNAi constructs designated HBV-shmiR1 to HBV-shmiR16, HBV-shRNA1-HBV-shRNA16, HBV-shmiRx3-v1, HBV-shmiRx3-v2 and HBV-shRNAx3-v1) into a adenovirus (AdV) construct for virus production (Vector Biolabs, Malvern Pa.).

To test the efficacy of shmiR AdV vectors described herein to knockdown expression of HBV genes, HepG2.2.15 are infected with shmiR AdV vectors of the disclosure and inhibition of HBV gene expression is assayed.

HepG2.2.15 is a sub-cell line of the HepG2 human hepatocellular carcinoma cell line which stably harbors the complete HBV genome (serotype ayw, genotype D). HepG2.2.15 cells express all HBV viral RNA and proteins, produces viral genomes, and secrete virus-like particles. HepG2.2.15 cells are maintained in the RPMI1640 medium supplemented with 4% fetal bovine serum, 4 mM glutamine, penicillin (100 U/mL), and streptomycin (100 µg/mL) and propagated in a 37° C. humid incubator in an atmosphere of 5% $CO_2$.

HepG2.2.15 cells were infected with the HBV shmiR AdV vectors or HBV shRNA AdV vectors in cell suspension and cultured on multi-well plates. Each well contained a suspension of approximately $1.25 \times 10^5$ HepG2.2.15 cells and one of the single or triple HBV shmiR AdV vectors, or one of the single or triple HBV shRNA AdV vectors, at MOI-100. Following transduction, cells were cultured at 37° C. at 5% $CO_2$ for 3-7 days and harvested for total RNA isolation using Qiagen miRNeasy mini kit (Valencia, Calif.) at 3, 4, 5, and 6 days post-transfection.

Total RNAs were quantified using the NanoDrop 1000 Spectrophotometer (Thermo Scientific) and then diluted to a working concentration of 10 ng/µl.

Figure 3A:
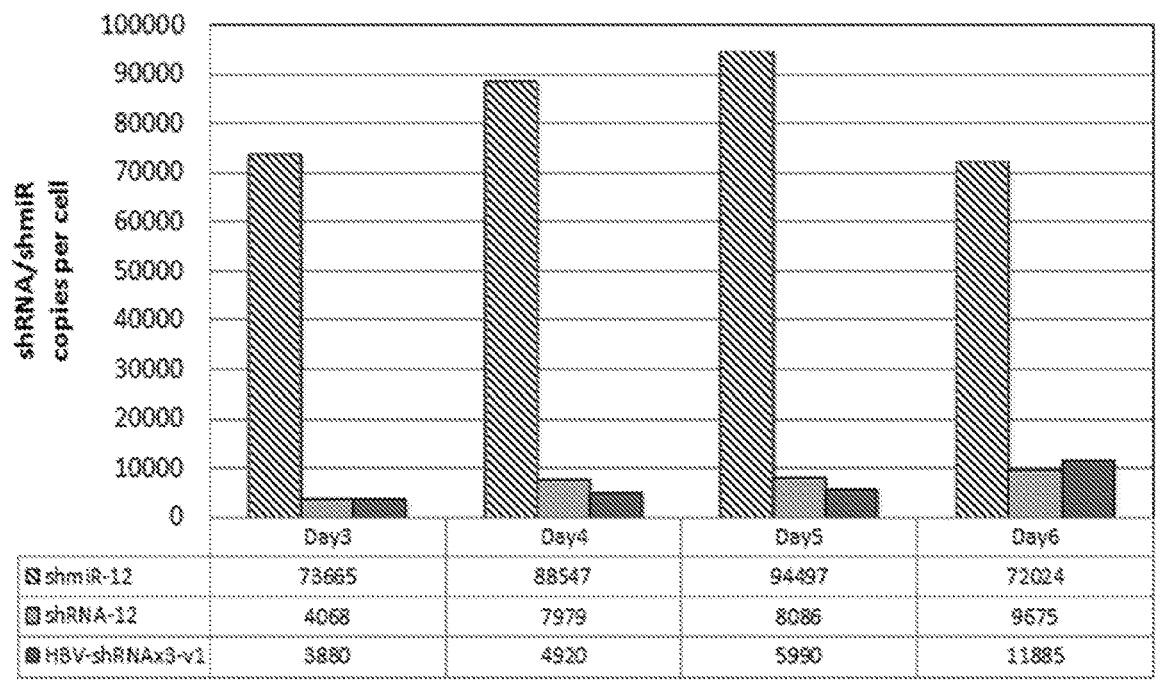
FIG. 3 illustrates the level of expression of RNAi effector molecules, expressed as copies per cell, in HepG2.2.15 cells transduced with ddRNAi agents: (A) shows the relative levels of expression of effector sequences for (i) shmiR-12 expressed as a single construct, (ii) shRNA-12 expressed as a single construct, and (iii) shRNA-12 expressed as part of HBV-shRNAx3-v1, at day 3, 4, 5 and 6 post transduction; and (B) shows the relative levels of expression of effector sequences for (i) shmiR-15 expressed as a single construct, (ii) shRNA-15 expressed as a single construct, and (iii) shRNA-15 expressed as part of HBV-shRNAx3-v1, at day 3, 4, 5 and 6 post transduction.
Figure 3B:
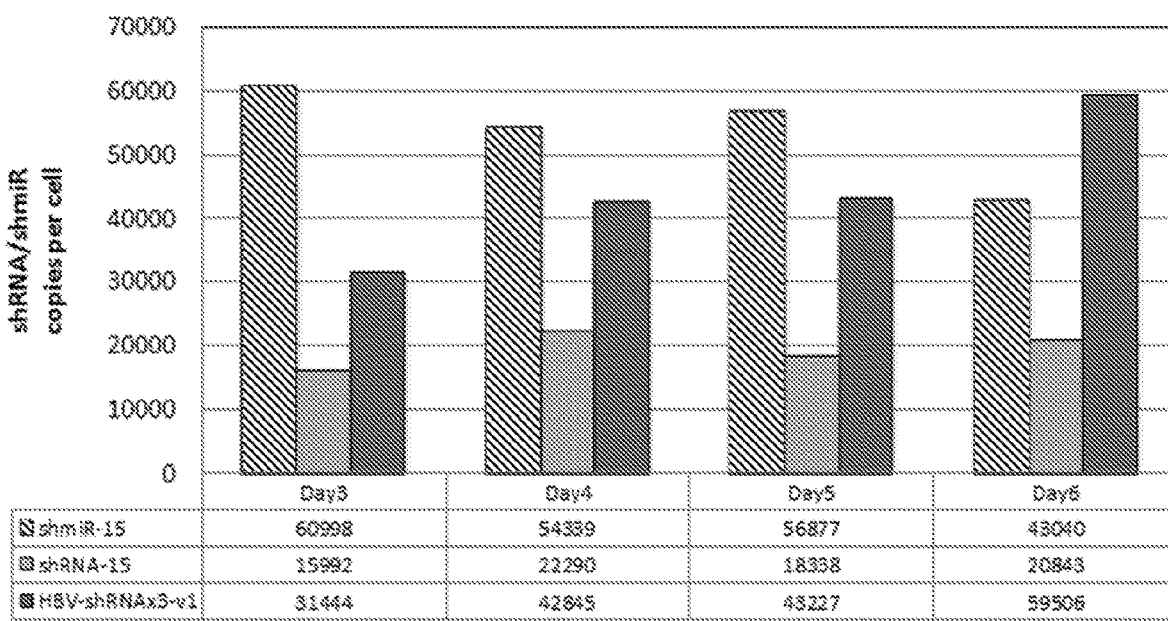

RNAi effector molecules expressed as copies per cell were determined for shmiR-12 and shmiR-15 (FIGS. 3A and 3B, respectively) when expressed in HepG2.2.15 cells from single or triple HBV shmiR AdV vector(s) using Qiagen's miScript PCR system (designed to quantitate RNA effector molecules processed from shmiR or shRNA). ShmiR expression was compared to levels of effector RNAi molecules induced by corresponding shRNAs in the context of single and triple constructs. For each RT-qPCR analysis, 50 ng of total RNA was converted into cDNA using Qiagen's miScript II RT kit. Quantitative PCR of effector RNAi molecules was carried out using Qiagen miScript SYBR green PCR kit with custom primers designed for the respective RNAi molecules using the following real-time PCR conditions: initial denaturation at 95° C. for 15 min followed by 40 cycles of 94° C. for 15 sec, 55° C. for 30 sec and 70° C. for 30 sec. Results demonstrated that the levels of effector RNAi molecule against regions of the HBV genome expressed by shmiRs-12 and shmiR-15 are higher than the corresponding shRNAs i.e., shRNA-12 and shRNA-15 respectively (FIG. 3).

Levels of inhibition of HBV transcripts at regions corresponding to HBV antigens HBsAg, HBcAg and HbxAg, relative to levels of GAPDH mRNA, were determined according to the method described in Example 5.

Figure 4A:
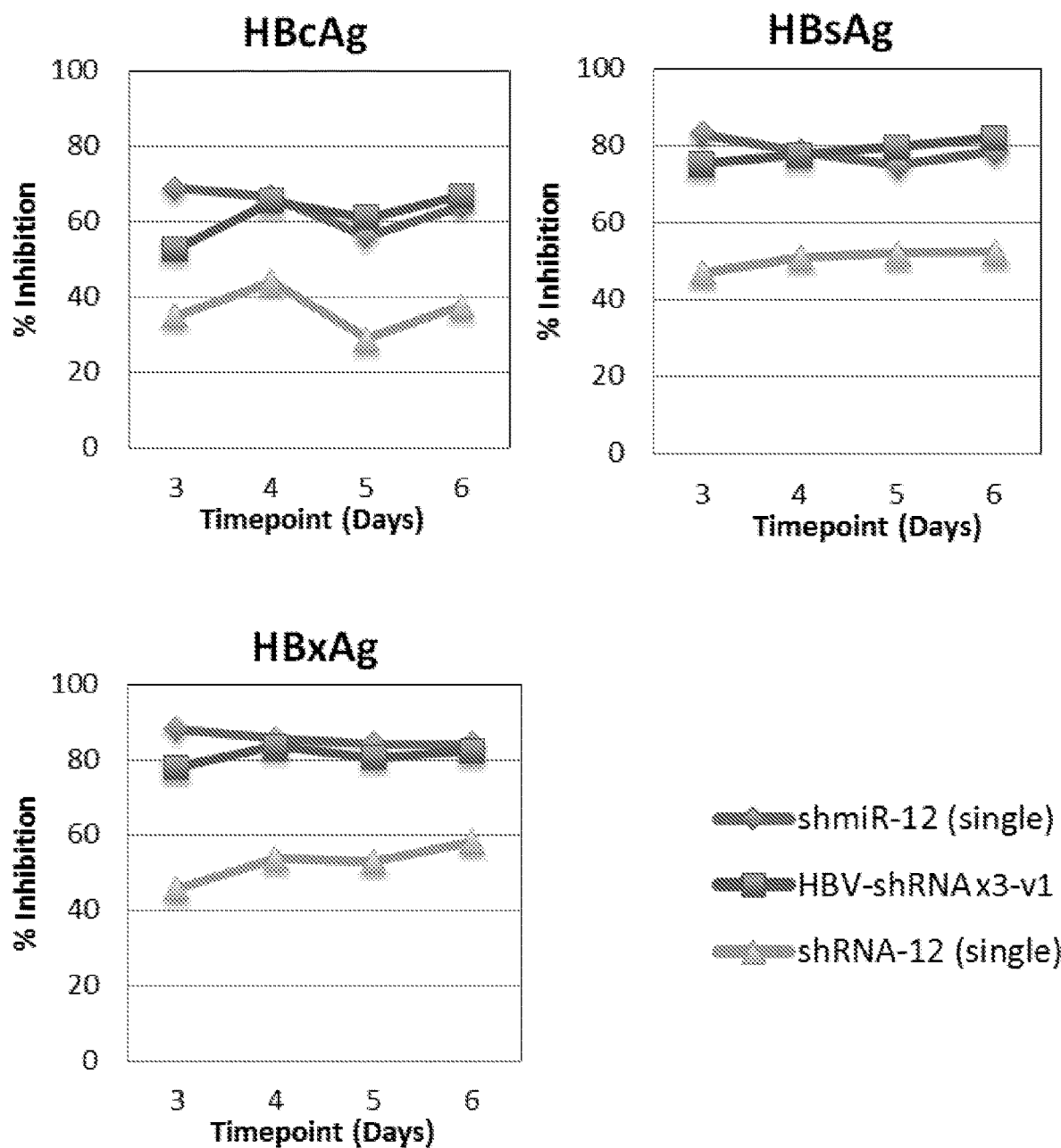
FIG. 4 illustrates the level of inhibition of HBV RNA transcripts at regions corresponding to HBV antigens HBsAg, HBcAg and HbxAg, relative to levels of GAPDH mRNA, in HepG2.2.15 transduced with HBV AdV Vectors (MOI=100) expressing (A) shmiR-12 or the corresponding shRNA as part of a single or triple construct, or (B) shmiR-15 or the corresponding shRNA as part of a single or triple construct, at 3 to 6 days post-transduction.
Figure 4B:
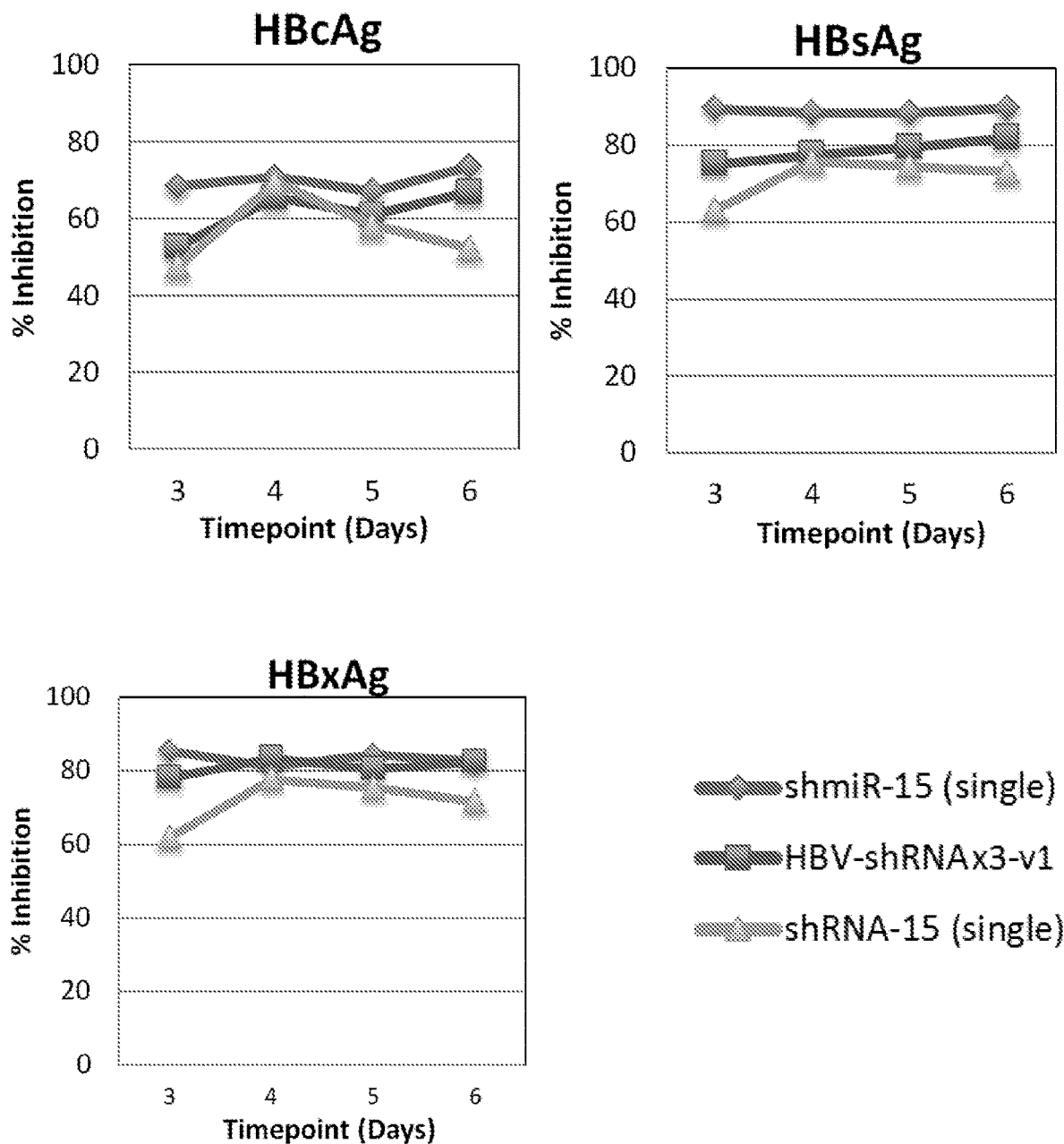

Levels of inhibition of HBV transcripts at regions corresponding to HBV antigens HBsAg, HBcAg and HbxAg, relative to levels of GAPDH mRNA, for each shmiR of the disclosure (expressed individually, or as part of a triple construct), was determined at an MOI of 100 at 3, 4, 5 and 6 days after infection with HBV shmir or shRNA AdV vectors. As shown in FIGS. 4A and B, shmiR-12 and shmiR-15 showed greater silencing of HBV RNAs compared to the corresponding shRNA expressing constructs.

Example 7—Generation of Self-Complementary AAV-Based Plasmid Constructs and Viruses Expressing HBV shmiRs Self-complementary adeno-associated virus type 2 (scAAV2) plasmids expressing three shmiRs of the disclosure are generated by subcloning the triple HBV shmiR ddRNAi constructs of Example 1 into a scAAV2 backbone.

Briefly, the triple HBV shmiR ddRNAi constructs of Example 1 (i.e., ddRNAi constructs designated HBV-shmiRx3-v1 and HBV-shmiRx3-v2) are cloned into a pAAV2 vector backbone to produce vectors designated pAAV-HBV-shmiRx3-v1 and pAAV-HBV-shmiRx3-v2, respectively. An AAV viral plasmid control expressing a non-targeting shmiR (pAAV-control-shmiR) may also be produced.

Recombinant pseudotyped AAV vector stocks are then generated using a AAV8 capsid. Briefly, HEK293T cells are cultured in roller bottles in Dulbecco's modified Eagle's medium, supplemented with 10% FBS, and incubated at 37° C. and 5% $CO_2$. Each of the pAAV-triple HBV shmiR viral plasmids (pAAV-HBV-shmiRx3-v1 and pAAV-HBV-shmiRx3-v2) and a pAAVhelpercap8 plasmid (pDP8r) is complexed with polyethyleneimine (PEI) according to the manufacturer's instructions. Double-transfections are then performed with one of the pAAV-triple HBV shmiR viral plasmids (pAAV-HBV-shmiRx3-v1 and pAAV-HBV-shmiRx3-v2) and pDP8r in the HEK293T cells. The HEK293T cells are cultured for a period of 72 hours at 37° C. and 5% $CO_2$, after which time the cells are lysed and scAAV shmiR-expressing particles for each of the viral plasmids are purified by iodixanol (Sigma-Aldrich) step-gradient ultracentrifugation. The number of vector genomes is determined using Taqman quantitative polymerase chain reaction (Q-PCR) with primers and probe designed against a region between expression cassettes.

For viral plasmids designated pAAV-HBV-shmiRx3-v1, pAAV-HBV-shmiRx3-v2 and pAAV-control-shmiR, the corresponding scAAV8 viral preparations are designated scAAV-HBV-shmiRx3-v1, scAAV-HBV-shmiRx3-v2 and scAAV-control-shmiR, respectively.

Single stranded adeno-associated virus (ssAAV) plasmids expressing the three shmiRs of the disclosure are also generated by subcloning the triple HBV shmiR ddRNAi constructs of Example 1 into a ssAAV vector backbone.

Figure 5:
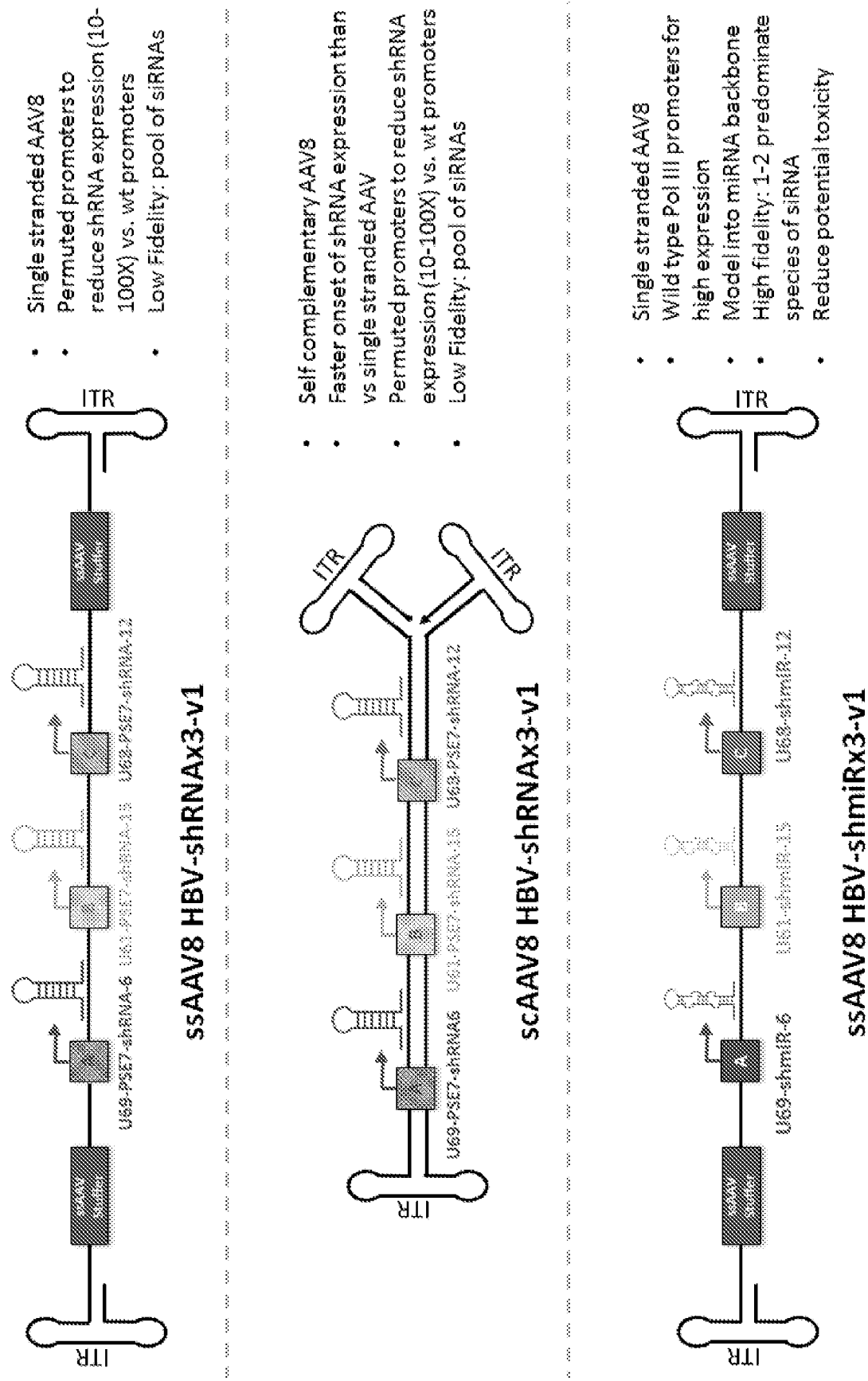
FIG. 5 provides construct diagrams for ssAAV8-HBV-shRNAx3-v1, scAAV8-HBV-shRNAx3-v1 and ssAAV8-HBV-shmiRx3-v1.

Example 8—Generation of Self-Complementary and Single Stranded AAV8-Based Plasmid Constructs and Viruses Expressing HBV shmiRs or shRNAs A single-stranded adeno-associated virus type 2 (ssAAV2) plasmid expressing three shmiRs of the disclosure was generated by subcloning the triple HBV shmiR ddRNAi construct of Example 1 designated HBV-shmiRx3-v1 into a ssAAV8 backbone. Similarly, ssAAV8 and self-complementary adeno-associated virus type 2 (scAAV2) plasmids expressing three shRNAs corresponding to the shmiRs of HBV-shRNAx3-v1 were generated by subcloning the triple HBV shRNA ddRNAi construct of Example 1 designated HBV-shRNAx3-v1 into a ssAAV2 or scAAV2 backbone. The DNAs were designed to express as recombinant AAV single stranded DNA genomes, as shown in FIG. 5.

Recombinant pseudotyped AAV vector stocks were then generated for the each of the AAV2 plasmids using a commercially obtained AAV8 capsid (Vector Biolabs, Malvern Pa.; Nationwide Children's Hospital, Columbus Ohio; Powell Gene Therapy Center, University of Florida) in accordance with the methods described in Example 7. The pseudotyped AAV vector stocks were designated ssAAV8-HBV-shmiRx3-v1, sAAV8-HBV-shRNAx3-v1 and scAAV8-HBV-shRNAx3-v1, respectively.

Example 9—Inhibition of HBV Parameters In Vivo

The in vivo effect of the scAAV shmiR-expressing particles designated scAAV-HBV-shmiRx3-v1 and scAAV-HBV-shmiRx3-v2 on (i) expression of HBV viral transcripts, (ii) extracellular HBsAg and HBeAg, (iii) extracellular and intracellular HBV DNA, and (iv) formation of cccDNA, is determined in a PXB mouse model infected de novo with HBV inoculum.

Methods

The scAAV shmiR-expressing particles designated scAAV-HBV-shmiRx3-v1 and scAAV-HBV-shmiRx3-v2 are prepared in accordance with Example 7.

Chimeric PXB mice (PXB-mice®) are obtained from PhoenixBio. All mice are housed individually at 23±5° C. and a humidity of 55±25% humidity, exposed to 12 hours-light/dark cycles and fed and watered ad libitum throughout the experiment.

PXB mice are inoculated with HBV genotype C and incubated for 4 weeks to allow baseline HBV infection to establish. To determine baseline HBV infection, blood is taken from mice at days −28, −21, −14 and −7 (i.e., 0, 7, 14 and 21 days post inoculation, respectively), from which human albumin (h-Alb) concentration and serum concentrations of HBV DNA, HBsAg and HBeAg can be determined.

Blood is collected from animals under anesthesia at each time point e.g., by isoflurane anesthesia (Escain®, Mylan, Osaka, Japan) via the retro-orbital plexus/sinus using Intramedic™ Polyethylene Tubing (Becton, Dickinson and Company, NJ, USA).

From the blood collected, 2 µL of whole blood is diluted in saline and blood h-Alb concentration is measured by latex agglutination immunonephelometry (LZ Test "Eiken" U-ALB, Eiken Chemical Co., Ltd., Tokyo, Japan) using a clinical chemistry analyzer (BioMajesty™ Series JCA-BM6050, JEOL Ltd., Tokyo, Japan).

Remaining whole blood is centrifuged to separate serum for HBV DNA quantification, HBsAg and HBeAg analysis.

To measure serum HBV DNA, HBV DNA is extracted from 5 µL of serum using the SMITESTEX-R&D Nucleic Acid Extraction Kit (MEDICAL & BIOLOGICAL LABORATORIES CO., LTD., Nagoya, Japan). The purified DNA is then dissolved in 20 µL nuclease-free water (Ambion). Serum from an HBV-infected PXB-mouse is used as an HBV DNA standard. Synthetic HBV DNA is used to determine the concentration of the HBV DNA standard which is then used in quantification of the serum HBV DNA level. The HBV DNA is extracted from the HBV DNA standard and used for real-time PCR after appropriate dilution. The range of the standard used may be between, for example, $4.0E^{+04}$ and $2.0E^{+09}$ copies/mL.

Real-time PCR is then performed to measure serum HBV DNA concentration e.g., using the TaqMan Fast Advanced Master Mix (Applied Biosystems, Thermo Fisher Scientific Inc.) and ABI Prism 7500 sequence detector system (Applied Biosystems). The PCR reaction mixture is added into 5 µL of the extracted DNA. The initial activation of uracil-N-glycosylase at 50° C. for 2 minutes is followed by the polymerase activation at 95° C. for 20 seconds. Subsequent PCR amplification consists of 53 cycles of denaturation at 95° C. for 3 seconds and annealing and extension at 60° C. for 32 seconds per cycle in an ABI 7500 sequence detector. The average serum HBV DNA level is calculated from the values of two separate wells.

The primers and probes used for real time PCR are as follows:

| Identification | Target Location | Dye | Sequence Information 5' Nucleotides 3' | Dye |
|---|---|---|---|---|
| Forward primer | 166-186 | n/a | CACATCAGGATTCCTAGGACC (SEQ ID NO: 158) | n/a |
| Reverse primer | 344-325 | n/a | AGGTTGGTGAGTGATTGGAG (SEQ ID NO: 159) | n/a |
| TaqMan probe | 242-267 | 6-FAM | CAGAGTCTAGACTCGTGGTGGACTTC (SEQ ID NO: 160) | TAMRA |

Serum HBsAg and HBeAg concentrations are determined using ChemiLuminescence ImmunoAssay (CLIA) e.g., as developed by Abbott (ARCHITECT® SYSTEM).

Animals will only be included for subsequent treatment experiment if they met the following criteria:

(i) weigh 15 g or more at day −1 (i.e., day 27 post HBV inoculation);

(ii) have a serum HBV DNA concentration of at least $1.0E^{+6}$ copies/mL at day −7 (i.e., day 21 post HBV inoculation); and (iii) have a h-Alb measurement of 10 mg/mL or more at day −7 (i.e., day 21 post HBV inoculation).

Mice in which baseline HBV infection is established and which meet the criteria above are placed into treatment groups. To minimise variance between groups, the group composition may be randomised based on the arithmetic mean values for body weight and geometric mean values for blood h-Alb concentration and serum HBV DNA concentration.

The treatment groups are as follows:

Group 1: a single 200 μl bolus of physiological saline only;

Group 2: a single 200 μl bolus of physiological saline containing 2.0E+13 (vg/kg) ssAAV-HBV-shmiRx3-v1 viral particles delivered to the tail vein by IV injection; and Group 3: a single 200 μl bolus of physiological saline containing 2.0E+13 (vg/kg) scAAV-HBV-shmiRx3-v2 viral particles delivered to the tail vein by IV injection.

(Eppendorf Co., Ltd., Tokyo, Japan). The concentration of DNA solution is adjusted to 20 ng/μL using Nuclease-free water.

Real-time PCR to measure liver HBV cccDNA concentration is then performed using the TaqMan Fast Advanced Master Mix and ABI Prism 7500 sequence detector system. Briefly, the PCR reaction mixture is added into 5 μL of the extracted DNA. The PCR reaction is conducted based on the Takkenberg's condition. The initial activation of uracil-N-glycosylase at 50° C. for 2 minutes is followed by the polymerase activation at 95° C. for 20 seconds. Subsequent 55 cycles of PCR amplification is then conducted at 95° C. for 3 seconds and 60° C. for 32 seconds per cycle e.g., in an ABI 7500 sequence detector. The average HBV cccDNA level is calculated from the values of the two separate wells. A plasmid containing the HBV full-genome sequence is used as a standard sample for HBV cccDNA quantification. The range of the standard used may be between $1.0E^{+02}$ and $1.0E^{+05}$ copies/100 ng DNA.

The primers and probes used for real time PCR are as follows:

| Identification | Target Location | Dye | Sequence Information 5' Nucleotides 3' | Dye |
|---|---|---|---|---|
| Forward primer | 1545-1563 | n/a | CTCCCCGTCTGTGCCTTCT (SEQ ID NO: 161) | n/a |
| Reverse primer | 1900-1883 | n/a | GCCCCAAAGCCACCCAAG (SEQ ID NO: 162) | n/a |
| TaqMan probe | 1602-1628 | 6-FAM | CGTCGCATGGARACCACCGTGAACGCC (SEQ ID NO: 163) | TAMRA |

All mice are anesthetised with 2-4% isoflurane immediately prior to treatment.

Following administration of the treatment (day 0), animals are then incubated for a further 56 days. During this time blood is taken on a weekly basis for 8 weeks (at days 7, 14, 21, 28, 35, 42, 49 and 56 post treatment), and serum concentrations of extracellular HBsAg, extracellular HBeAg and extracellular HBV DNA determined by real time PCR, using the methodologies described.

After the completion of blood sampling on Day 56, all the surviving animals are kept under isoflurane anesthesia and sacrificed by cardiac puncture and exsanguination.

Once sacrificed, whole livers are harvested from mice and weighed. A slice of liver of 3 to 5 mm in thickness is obtained from left lateral lobe and cut into cubes approximately 1 to 2 mm on a side. These liver cubes are transferred into a labelled tube and immersed in RNAlater® solution (Ambion, Thermo Fisher Scientific Inc., Waltham, Mass., USA) as quickly as possible. The liver samples are incubated in ≥5 volumes of RNAlater® overnight at 4° C. to allow the solution to penetrate the tissue. After the incubation, the RNAlater® solution is removed and the liver pieces are stored at −80° C. for subsequent quantification of hepatic HBV DNA levels.

To determine the level of hepatic HBV DNA following treatment, HBV DNA is extracted from frozen RNAlater®-preserved liver tissue using the DNeasy® Blood & Tissue Kits (Qiagen K. K., Tokyo, Japan). The DNA is dissolved in 200 μL nuclease-free water, after which the concentration of the DNA solution is determined using BioPhotometer 6131

Example 10—Inhibition of HBV Parameters in a Chimeric Mouse Model

The in vivo effect of the anti-HBV shmiR or shRNA-expressing AAV particles (as illustrated in FIG. 5) was determined in a PXB chimeric mouse model infected de novo with HBV inoculum. Inhibition of various HBV parameters was assessed: (i) expression of HBV viral transcripts, (ii) extracellular HbsAg, HBcAg and HBeAg, (iii) extracellular and intracellular HBV DNA, and (iv) formation of cccDNA.

Figure 6:
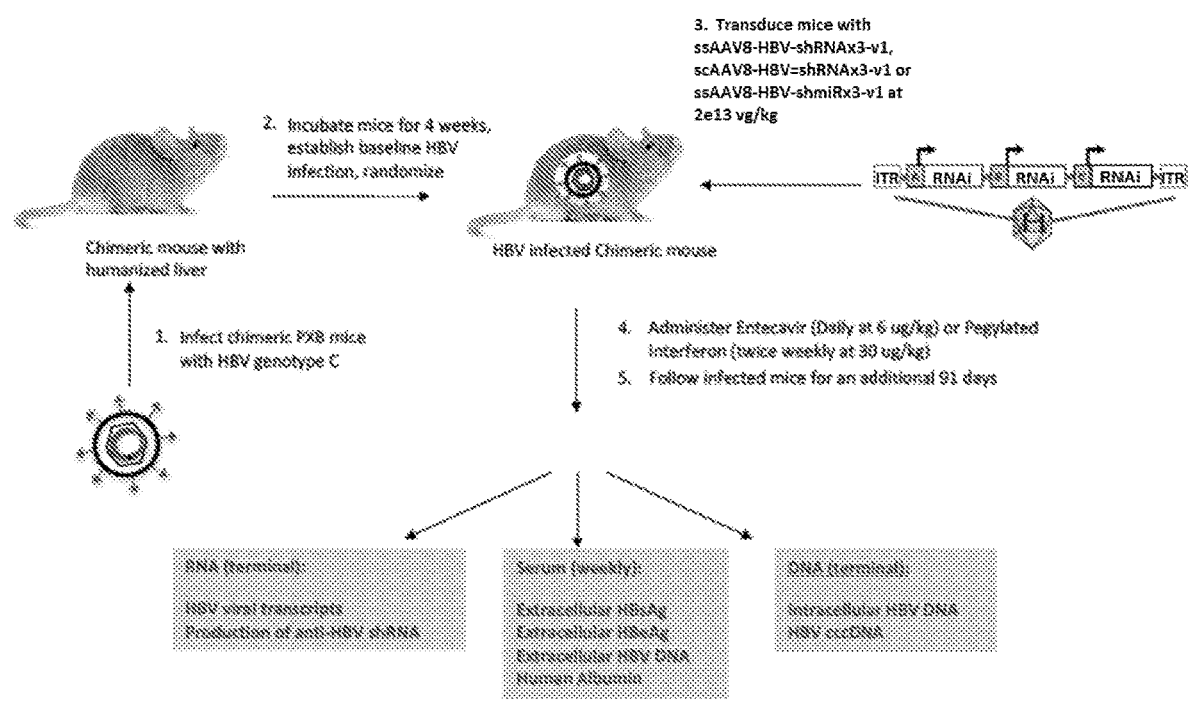
FIG. 6 provides a flow diagram for the in vivo efficacy study performed in the PhoenixBio (PXB) Chimeric mouse model using ssAAV8-HBV-shRNAx3-v1, scAAV8-HBV-shRNAx3-v1 and ssAAV8-HBV-shmiRx3-v1.

The anti-HBV shmiR or shRNA-expressing AAV8 particles described in Example 8 were tested in the PXB chimeric mouse model (FIG. 6). The theee anti-HBV AAV8 particles tested were as follows:

(1) a ssAAV8 containing HBV-shRNAx3-v1 (ssAAV8-HBV-shRNAx3-v1);

(2) a scAAV8 containing HBV-shRNAx3-v1 (scAAV8-HBV-shRNAx3-v1); and (3) a ssAAV8 containing HBV-shmiRx3-v1 (ssAAV8-HBV-shmiRx3-v1).

This in vivo study assessed the activity of single doses of ssAAV8-HBV-shRNAx3-v1, scAAV8-HBV-shRNAx3-v1 and ssAAV8-HBV-shmiRx3-v1 in the PXB mouse model when administered as monotherapy or when used in combination with HBV standard of care agents like entecavir (ETV) or pegylated interferon (PEG-IFN).

Methods

Chimeric PXB mice (PXB-mice®) were obtained from PhoenixBio. All mice were housed individually at 23±5° C. and a humidity of 55±25% humidity, exposed to 12 hours-light/dark cycles and fed and watered ad libitum throughout the experiment. Measurement of human serum albumin approximately 10 weeks after hepatocyte transplantation was used to ensure that the starting livers were comprised of at least 80% human hepatocytes. All chimeric animals passing this threshold of human hepatocyte composition were infected with HBV genotype C and incubated for 4 weeks to allow baseline HBV infection to establish. To determine baseline HBV infection, blood was taken from mice at days −28, −21, −14 and −7 (i.e., 0, 7, 14 and 21 days post inoculation, respectively), from which human albumin (h-Alb) concentration and serum concentrations of HBV DNA, HBsAg and HBeAg were determined. These permit detection of liver damage in test animals—no adverse reactions were detected.

Blood was collected from animals under anesthesia at each time point e.g., by isoflurane anesthesia (Escain®, Mylan, Osaka, Japan) via the retro-orbital plexus/sinus using Intramedic™ Polyethylene Tubing (Becton, Dickinson and Company, NJ, USA). From the blood collected, 2 µL of whole blood was diluted in saline and blood h-Alb concentration measured by latex agglutination immunonephelometry (LZ Test "Eiken" U-ALB, Eiken Chemical Co., Ltd., Tokyo, Japan) using a clinical chemistry analyzer (BioMajesty™ Series JCA-BM6050, JEOL Ltd., Tokyo, Japan).

Remaining whole blood was centrifuged to separate serum for HBV DNA quantification, HbsAg, HBcAg and HBeAg analysis. To measure serum HBV DNA, HBV DNA was extracted from 5 µL of serum using the SMITESTEX-R&D Nucleic Acid Extraction Kit (MEDICAL & BIOLOGICAL LABORATORIES CO., LTD., Nagoya, Japan). The purified DNA was then dissolved in 20 µL nuclease-free water (Ambion). Serum from an HBV-infected PXB-mouse was used as an HBV DNA standard. Synthetic HBV DNA was used to determine the concentration of the HBV DNA standard which was then used in quantification of the serum HBV DNA level. The HBV DNA was extracted from the HBV DNA standard and used for real-time PCR after appropriate dilution. The range of the standard used may be between, for example, 4.0E4 and 2.0E9 copies/mL.

Real-time PCR was then performed to measure serum HBV DNA concentration e.g., using the TaqMan Fast Advanced Master Mix (Applied Biosystems, Thermo Fisher Scientific Inc.) and ABI Prism 7500 sequence detector system (Applied Biosystems). The PCR reaction mixture was added into 5 µL of the extracted DNA. The initial activation of uracil-N-glycosylase at 50° C. for 2 minutes was followed by the polymerase activation at 95° C. for 20 seconds. Subsequent PCR amplification consisted of 53 cycles of denaturation at 95° C. for 3 seconds and annealing and extension at 60° C. for 32 seconds per cycle in an ABI 7500 sequence detector. The average serum HBV DNA level was calculated from the values of two separate wells.

The primers and probes used for real time PCR were as follows:

| Identification | Target Location | Dye | 5' Nucleotides 3' | Dye |
|---|---|---|---|---|
| Forward primer | 166-186 | n/a | CACATCAGGATTCCTAGGACC (SEQ ID NO: 158) | n/a |
| Reverse primer | 344-325 | n/a | AGGTTGGTGAGTGATTGGAG (SEQ ID NO: 159) | n/a |
| TaqMan probe | 242-267 | 6-FAM | CAGAGTCTAGACTCGTGGTGGACTTC (SEQ ID NO: 160) | TAMRA |

Serum HBsAg and HBeAg concentrations were determined using ChemiLuminescence ImmunoAssay (CLIA) e.g., as developed by Abbott (ARCHITECT® SYSTEM).

Animals were only included for subsequent treatment if they met the following criteria:
  (i) weighed 15 g or more at day −1 (i.e., day 27 post HBV inoculation);
  (ii) had a serum HBV DNA concentration of at least $1.0E^{+6}$ copies/mL at day −7 (i.e., day 21 post HBV inoculation); and
  (iii) had a h-Alb measurement of 10 mg/mL or more at day −7 (i.e., day 21 post HBV inoculation).

Mice in which baseline HBV infection was established and which met the criteria above were placed into treatment 12 groups with each group comprised of either 4 or 5 mice. To minimise variance between groups, the group composition was randomised based on the arithmetic mean values for body weight and geometric mean values for blood h-Alb concentration and serum HBV DNA concentration.

The treatment groups were as follows:

| Group | Strain | No. of mice (ID) | Test compound | Dose Level* | Conc.** | Volume (mL/kg) | Route | Frequency |
|---|---|---|---|---|---|---|---|---|
| 1 | PXB (HBV C-infected) | 5 (101-105) | Control Vehicle | 0 | 0 | 200 µl total | i.v. | Single, Day 0 |
| 2 | PXB (HBV C-infected) | 4 (201-204) | ETV | 0.006 | 0.0006 | 10 | p.o. | QD, for 91 days Days 0 to 90 |
| 3 | PXB (HBV C-infected) | 4 (301-304) | Pegasys | 0.03 | 0.003 | 10 | s.c. | BIW, for 13 weeks every 1$^{st}$ and 4$^{th}$ days of week |
| 4 | PXB (HBV C-infected) | 5 (401-405) | BB-101 | 2.00E+13 | TBP*** | 200 µl total | i.v. | Single, Day 0 |

-continued

| Group | Strain | No. of mice (ID) | Test compound | Dose Level* | Conc.** | Volume (mL/kg) | Route | Frequency |
|---|---|---|---|---|---|---|---|---|
| 5 | PXB (HBV C-infected) | 5 (501-505) | BB-101 | 2.00E+13 | TBP*** | 200 µl total | i.v. | Single, Day 0 |
|  |  |  | ETV | 0.006 | 0.0006 | 10 | p.o. | QD, for 91 days Days 0 to 90 |
| 6 | PXB (HBV C-infected) | 5 (601-605) | BB-101 | 2.00E+13 | TBP*** | 200 µl total | i.v. | Single, Day 0 |
|  |  |  | Pegasys | 0.03 | 0.003 | 10 | s.c. | BIW, for 13 weeks every 1$^{st}$ and 4$^{th}$ days of week |
| 7 | PXB (HBV C-infected) | 5 (701-705) | BB-102 | 2.00E+13 | TBP*** | 200 µl total | i.v. | Single, Day 0 |
| 8 | PXB (HBV C-infected) | 5 (801-805) | BB-102 | 2.00E+13 | TBP*** | 200 µl total | i.v. | Single, Day 0 |
|  |  |  | ETV | 0.006 | 0.0006 | 10 | p.o. | QD, for 91 days Days 0 to 90 |
| 9 | PXB (HBV C-infected) | 5 (901-905) | BB-102 | 2.00E+13 | TBP*** | 200 µl total | i.v. | Single, Day 0 |
|  |  |  | Pegasys | 0.03 | 0.003 | 10 | s.c. | BIW, for 13 weeks every 1$^{st}$ and 4$^{th}$ days of week |
| 10 | PXB (HBV C-infected) | 4 (1001-1004) | BB-103 | 2.00E+13 | TBP*** | 200 µl total | i.v. | Single, Day 0 |
| 11 | PXB (HBV C-infected) | 4 (1101-1104) | BB-103 | 2.00E+13 | TBP*** | 200 µl total | i.v. | Single, Day 0 |
|  |  |  | ETV | 0.006 | 0.0006 | 10 | p.o. | QD, for 91 days Days 0 to 90 |
| 12 | PXB (HBV C-infected) | 4 (1201-1204) | BB-103 | 2.00E+13 | TBP*** | 200 µl total | i.v. | Single, Day 0 |
|  |  |  | Pegasys | 0.03 | 0.003 | 10 | s.c. | BIW, for 13 weeks every 1$^{st}$ and 4$^{th}$ days of week |

*mg/kg for ETV and Pegasys; vg/kg for BB-101, BB-102 and BB-103
**mg/mL for ETV and Pegasys
***To be prepared on the day of dosing based on the bodyweight to achieve the target dose level. For final concentrations, please see Appendix 3.
n/a: Not applicable HBV-infected mice treated with saline served as the negative controls. Groups treated with standard of care agents against HBV served as positive controls: entecavir was administered daily at 6 µg/kg or pegylated interferon was given twice weekly at 30 µg/kg. For the anti-HBV ddRNAi treatment groups, ssAAV8-HBV-shRNAx3-v1, scAAV8-HBV-shRNAx3-v1 or ssAAV8-HBV-shmiRx3-v1 was administered once at a dose of 2×10E+13 vg/kg by a low pressure tail vein injection at Day 0. Co-treated animals started daily ETV at Day 1 or were dosed the first time with PEG-IFN on Day 4

All mice were anesthetised with 2-4% isoflurane immediately prior to treatment.

Following administration of the treatment (day 0), animals were then incubated for a further 91 days. During this time blood was taken on a weekly basis for 13 weeks (at days 7, 14, 21, 28, 35, 42, 49, 56, 63, 70, 77, 84, and 91 post treatment) and serum concentrations of extracellular HBV DNA (viral titer) and extracellular HBsAg were measured. HBeAg levels were measured every other week through Day 70 and then weekly thereafter until the conclusion of the 91 day experiment.

After the completion of blood sampling on Day 91, all the surviving animals were kept under isoflurane anesthesia and sacrificed by cardiac puncture and exsanguination. Once sacrificed, whole livers were harvested from mice and weighed. A slice of liver of 3 to 5 mm in thickness was obtained from left lateral lobe and cut into cubes approximately 1 to 2 mm on a side. These liver cubes were transferred into a labelled tube and immersed in RNAlater® solution (Ambion, Thermo Fisher Scientific Inc., Waltham, Mass., USA) as quickly as possible. The liver samples were incubated in ≥5 volumes of RNAlater® overnight at 4° C. to allow the solution to penetrate the tissue. After the incubation, the RNAlater® solution was removed and the liver pieces were stored at −80° C. for subsequent quantification of the various hepatic HBV DNA and RNAs as well as expression levels of recombinant AAV derived shRNA or shmiR RNAs.

To determine the level of hepatic HBV DNA following treatment, HBV DNA was extracted from frozen RNAlater®-preserved liver tissue using the DNeasy® Blood & Tissue Kits (Qiagen K. K., Tokyo, Japan). The DNA was dissolved in 200 µL nuclease-free water, after which the concentration of the DNA solution was determined using BioPhotometer 6131 (Eppendorf Co., Ltd., Tokyo, Japan). The concentration of DNA solution was adjusted to 20 ng/µL using Nuclease-free water.

Real-time PCR to measure liver HBV cccDNA concentration was then performed using the TaqMan Fast Advanced Master Mix and ABI Prism 7500 sequence detector system. Briefly, the PCR reaction mixture was added into 5 µL of the extracted DNA. The PCR reaction was conducted based on the Takkenberg's condition. The initial activation of uracil-N-glycosylase at 50° C. for 2 minutes was followed by the polymerase activation at 95° C. for 20 seconds. Subsequently 55 cycles of PCR amplification was then conducted at 95° C. for 3 seconds and 60° C. for 32 seconds per cycle e.g., in an ABI 7500 sequence detector. The average HBV cccDNA level was calculated. A plasmid containing the HBV full-genome sequence was used as a standard sample for HBV cccDNA quantification. The range of the standard used may be between 1.0E+02 and 1.0E+05 copies/100 ng DNA.

The primers and probes used for real time PCR were as follows:

|  | Target |  | Sequence Information |  |
|---|---|---|---|---|
| Identification | Location | Dye | 5' Nucleotides 3' | Dye |
| Forward primer | 1545-1563 | n/a | CTCCCCGTCTGTGCCTTCT (SEQ ID NO: 161) | n/a |
| Reverse primer | 1900-1883 | n/a | GCCCCAAAGCCACCCAAG (SEQ ID NO: 162) | n/a |
| TaqMan probe | 1602-1628 | 6-FAM | CGTCGCATGGARACCACCGTGAACGCC (SEQ ID NO: 163) | TAMRA |

Real-time PCR was used to quantitate the liver production of anti-HBV effector RNAi molecules and inhibition of HBV mRNA transcript as described in Examples 5 and 6. Results:

For brevity, only the key data points obtained for scAAV8-HBV-shRNAx3-v1 and ssAAV8-HBV-shmiRx3-v1 is presented.

Figure 7:
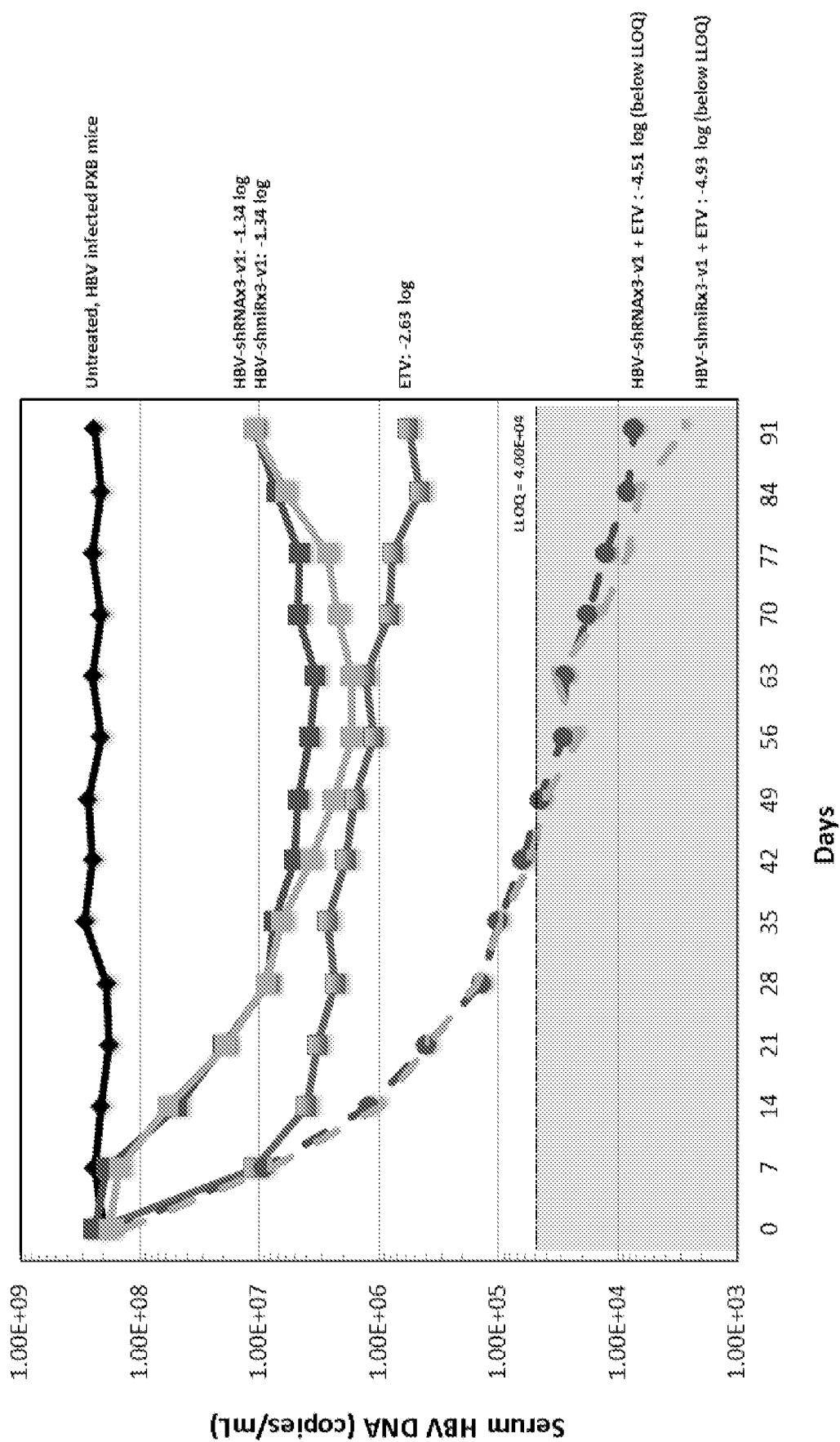
FIG. 7 illustrates that serum HBV DNA levels were reduced in mice treated with a single dose of scAAV8-HBV-shRNAx3-v1 or ssAAV8-HBV-shmiRx3-v1 as a monotherapy or in combination with Entecavir, whereas virus titers in saline treated control animals remained relatively constant over the course of the 91 day study.

The virus titer in saline treated animals remained relatively constant over the 13 weeks of the experiment (FIG. 7) at greater than 1E+08 HBV DNA copies/ml. A treatment arm consisting only of daily ETV resulted in in a 2.63 log drop in serum HBV DNA levels. Dosed in the absence of other anti-viral drugs, ssAAV8-HBV-shmiRx3-v1 and scAAV8-HBV-shRNAx3-v1 resulted in corresponding maximum drop of serum HBV DNA levels at 2.17 log and 1.87 log reduction, respectively. However, a modest rebound of HBV DNA levels was noted following 63 days of treatment. Yet, in combination with daily entecavir, a single dose of ssAAV8-HBV-shmiRx3-v1 and scAAV8-HBV-shRNAx3-v1 dropped the serum HBV DNA levels below 3.72 log, the lower limit of quantification (LLOQ) for the assay. Although it is difficult to accurately quantify HBV DNA levels, it appears that the reduction in viral burden continued to diminish until the end of the 91 day experiment.

Figure 8:
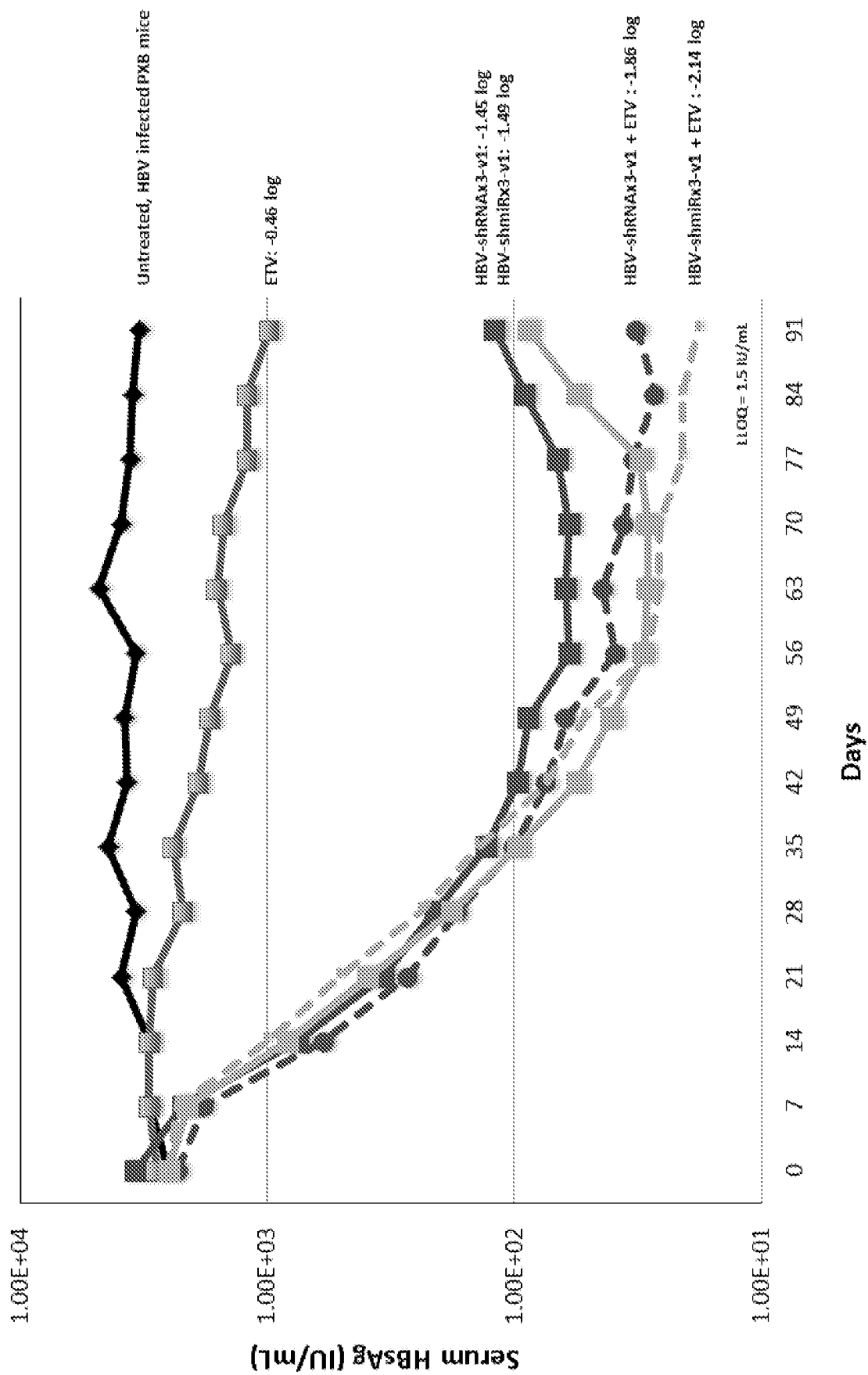
FIG. 8 illustrates that serum HBsAg antigen levels were reduced in mice treated with a single dose of scAAV8-HBV-shRNAx3-v1 or ssAAV8-HBV-shmiRx3-v1 as a monotherapy or in combination with Entecavir, whereas serum HBsAg antigen levels in saline treated control animals remained relatively constant over the course of the 91 day study.

The s-antigen (HBsAg) is a known contributor to immunosuppression and HBV chronicity. It is believed that the high levels of HBsAg expression that occur in active infection are problematic towards achieving a cure. A "cure" is often defined by the seroconversion of HBV infected patients defined by the expression of anti-HBsAg antibodies. Treatment of the infected chimeric mice with either ssAAV8-HBV-shmiRx3-v1+ETV or scAAV8-HBV-shRNAx3-v1+ETV dropped HBsAg levels by 2.14 log and 1.86 log respectively (FIG. 8). Treatment with ETV as a monotherapy only dropped HBsAg levels by 0.46 log.

Figure 9:
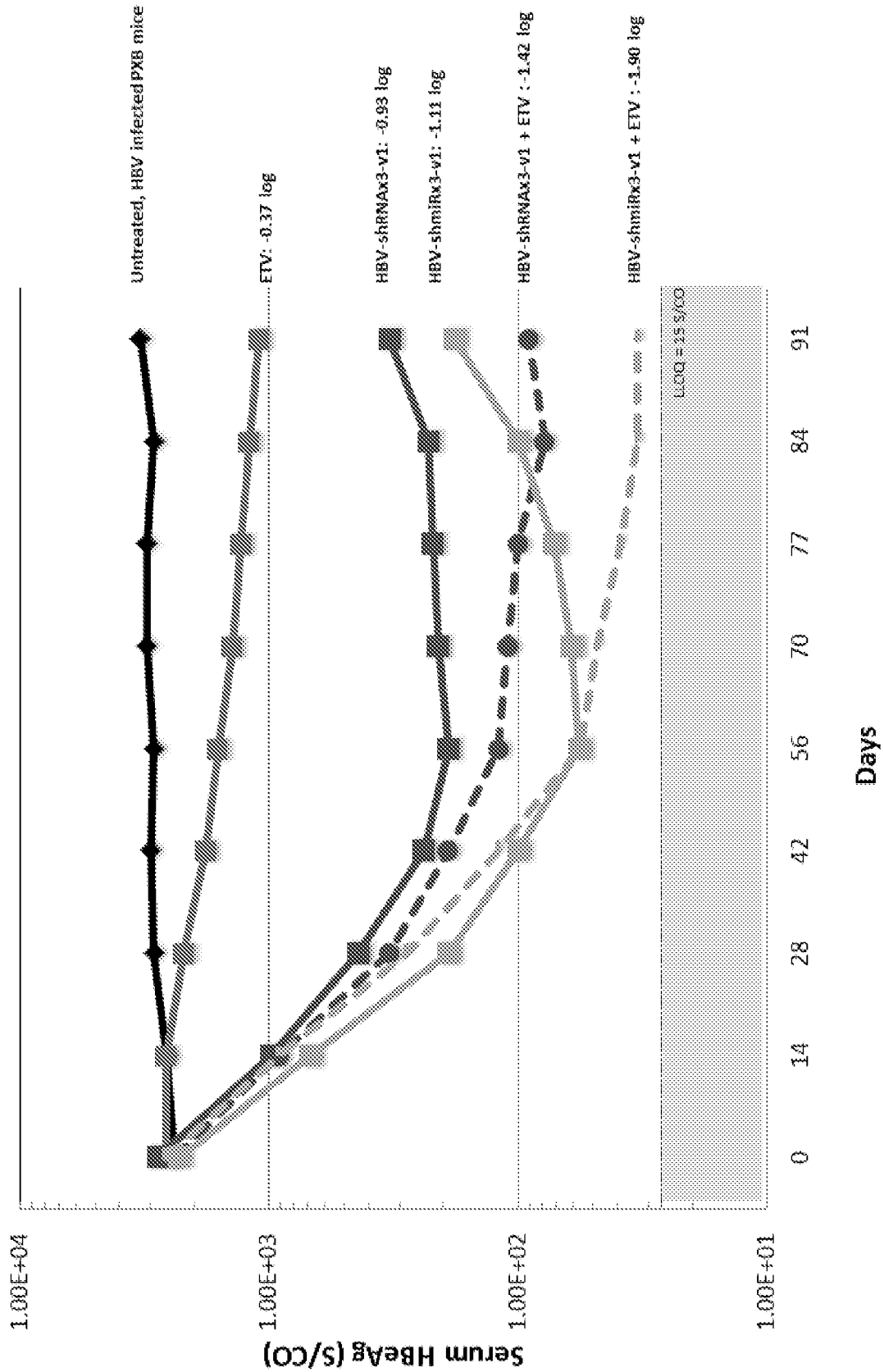
FIG. 9 illustrates that serum HBeAg antigen levels were reduced in mice treated with a single dose of scAAV8-HBV-shRNAx3-v1 or ssAAV8-HBV-shmiRx3-v1 as a monotherapy or in combination with Entecavir, whereas animals treated with Entecavir only showed a slight drop in serum HBeAg antigen levels (i.e., 0.37 log) and HBeAg antigen levels in saline treated control animals remained relatively constant over the course of the 91 day study.

Treatment with ssAAV8-HBV-shmiRx3-v1+ETV dropped HBeAg levels by 1.90 log, and treatment with scAAV8-HBV-shRNAx3-v1+ETV dropped HBeAg levels by 1.42 log. Treatment with entecavir only dropped HBsAg levels by 0.37 log (FIG. 9).

Figure 10:
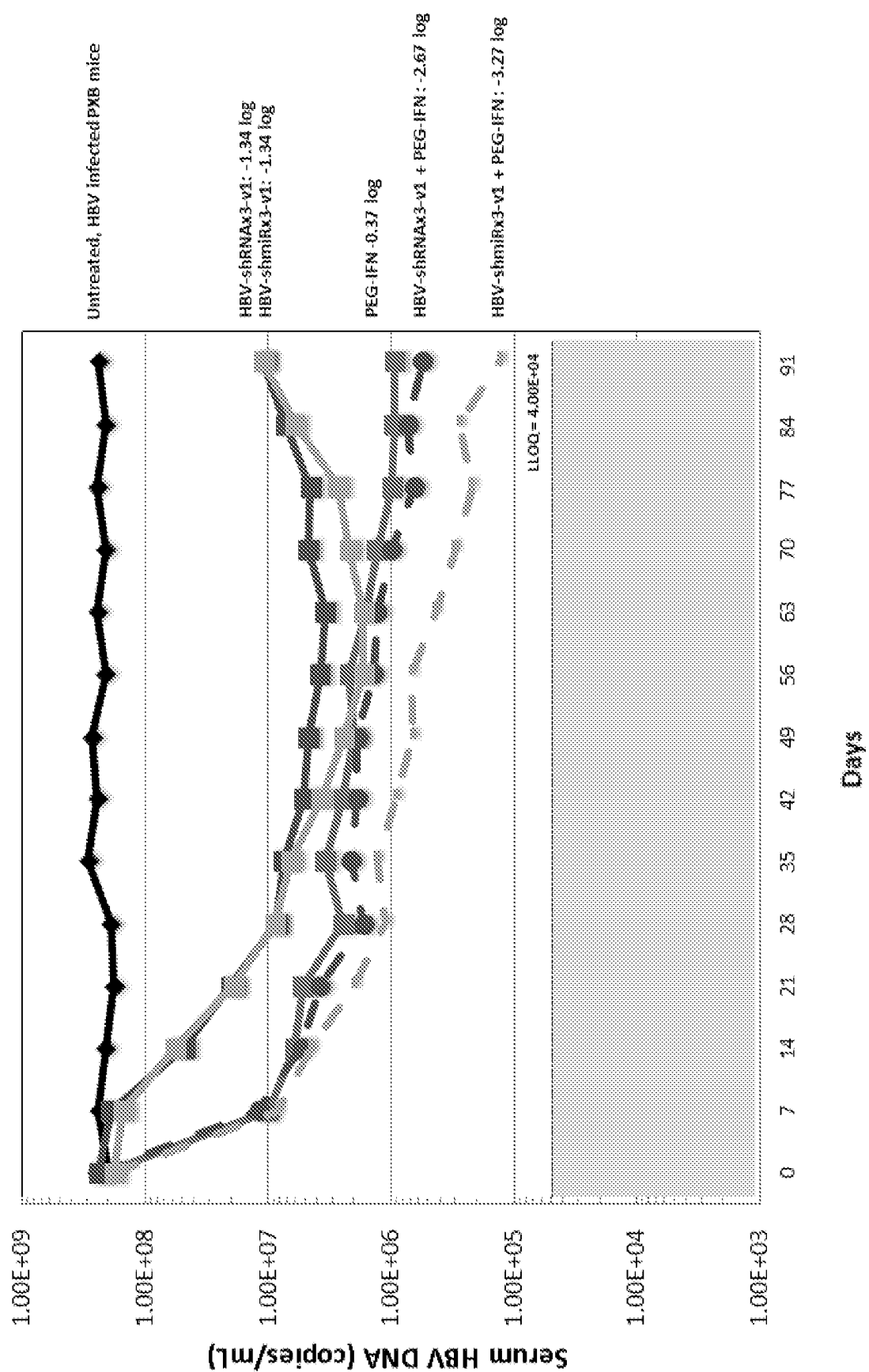
FIG. 10 illustrates that serum HBV DNA levels dropped significantly in mice treated with a single dose of scAAV8-HBV-shRNAx3-v1 or ssAAV8-HBV-shmiRx3-v1 as a monotherapy or in combination with pegylated interferon (where the pegylated interferon is administered twice daily), whereas serum HBV DNA levels in saline treated control animals remained relatively constant over the course of the 91 day study.

In addition to co-treatment with ETV, this study tested combinations of either scAAV8-HBV-shRNAx3-v1 or ssAAV8-HBV-shmiRx3-v1 when co-administered with PEG-IFN. A single administration of either scAAV8-HBV-shRNAx3-v1 or ssAAV8-HBV-shmiRx3-v1 on top of a regimen consisting of pegylated interferon given twice weekly resulted in a significant decrease in HBV serum DNA levels at 2.67 and 3.27 log respectively (FIG. 10).

At the conclusion of 91 days of drug treatment, the mice were sacrificed, the livers harvested and DNA and RNA were purified from these tissues to explore a number of hepatocyte parameters. For instance, as an RNA interference agent, ssAAV8-HBV-shmiRx3-v1 is expected to reduce levels of the HBV viral transcripts present in the cells.

Figure 11A:
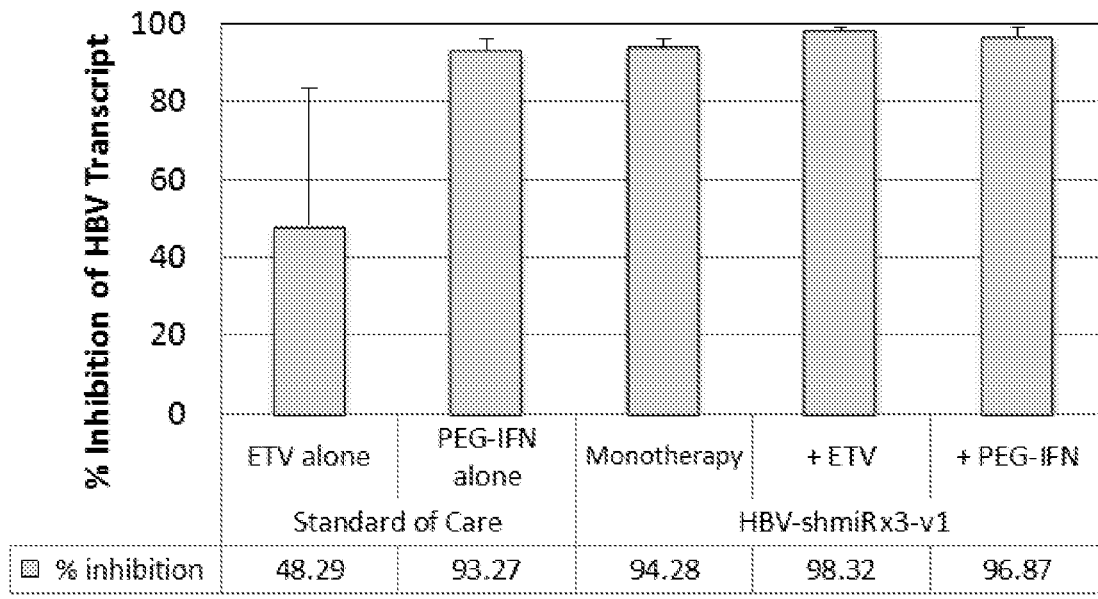
FIG. 11 illustrates that HBV RNA levels were reduced in mice treated with pegylated interferon as a monotherapy, or a single dose of ssAAV8-HBV-shmiRx3-v1 as a monotherapy or in combination with Entecavir or pegylated interferon, whereas HBV RNA levels were only modestly reduced when Entecavir was administered alone. (A)-(C) show HBV RNA levels for transcript corresponding to shmiR-6, shmiR-15 and shmiR-12, respectively.
Figure 11B:
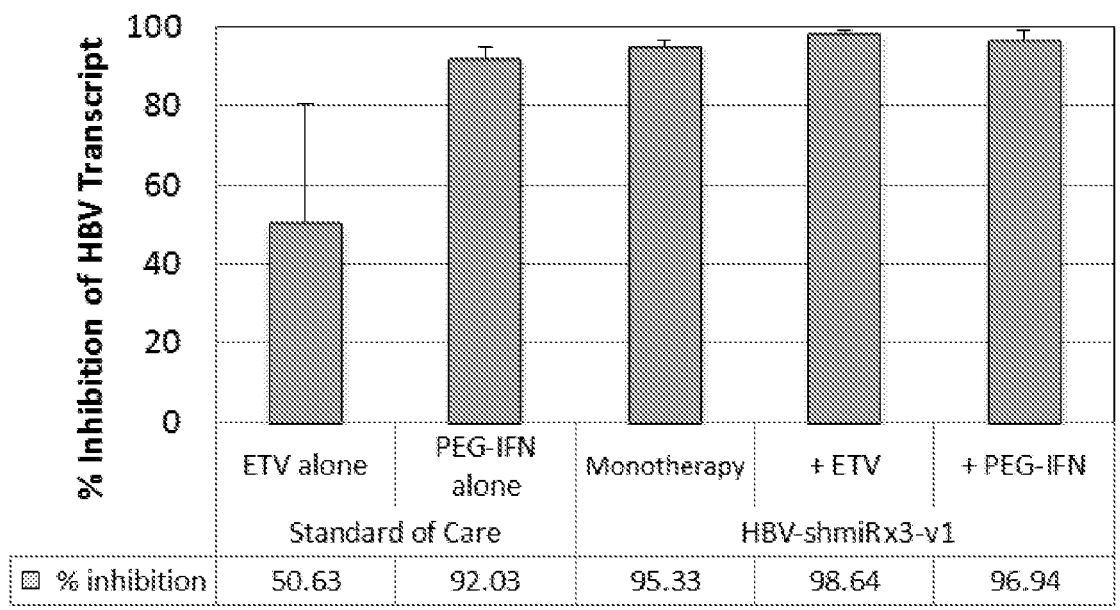
Figure 11C:
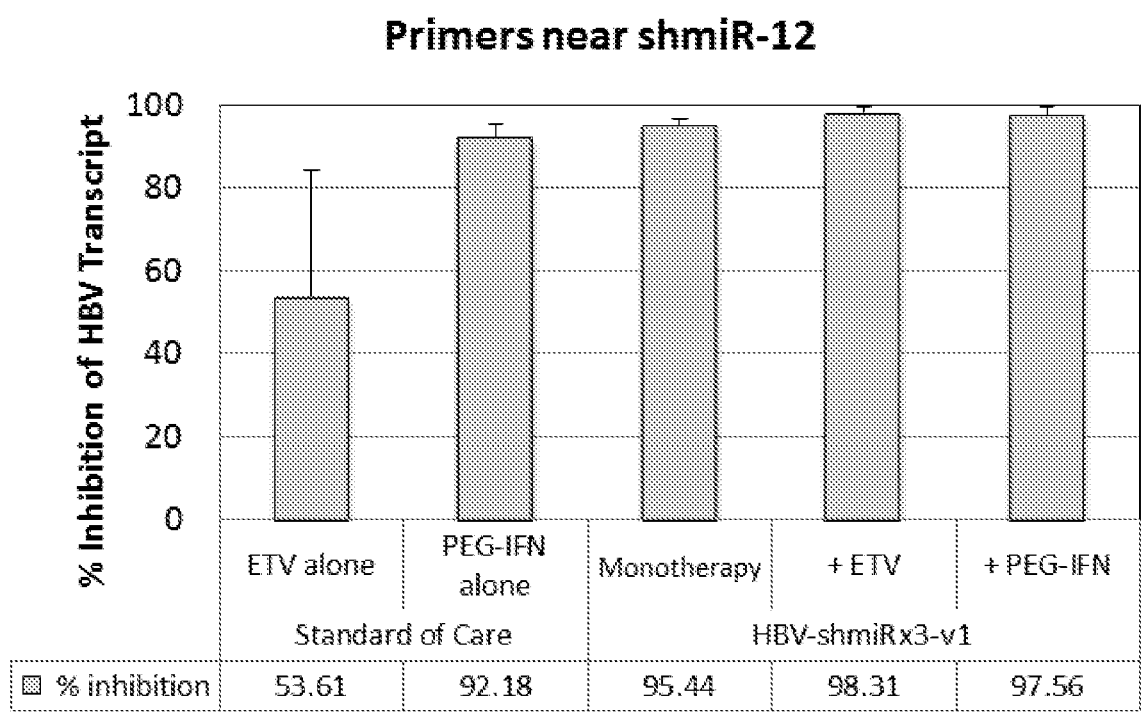

Using primer/probe sets that are located near each of the RNAi-induced cleavage sites, the levels of HBV RNA was assessed by RT-QPCR (FIG. 11). Although pegylated interferon had strong levels of activity as a monotherapy, the impact of entecavir was on HBV RNA levels was modest, achieving roughly a 50% reduction through 13 weeks of treatment. As a monotherapy, ssAAV8-HBV-shmiRx3-v1 had robust suppression of viral RNA resulting in greater than 94% reduction of the HBV transcripts. A combination of ssAAV8-HBV-shmiRx3-v1 with either of the two anti-viral agents further boosted the ability to inhibit viral RNA with suppression levels reaching as high as 98.6%.

Figure 12:
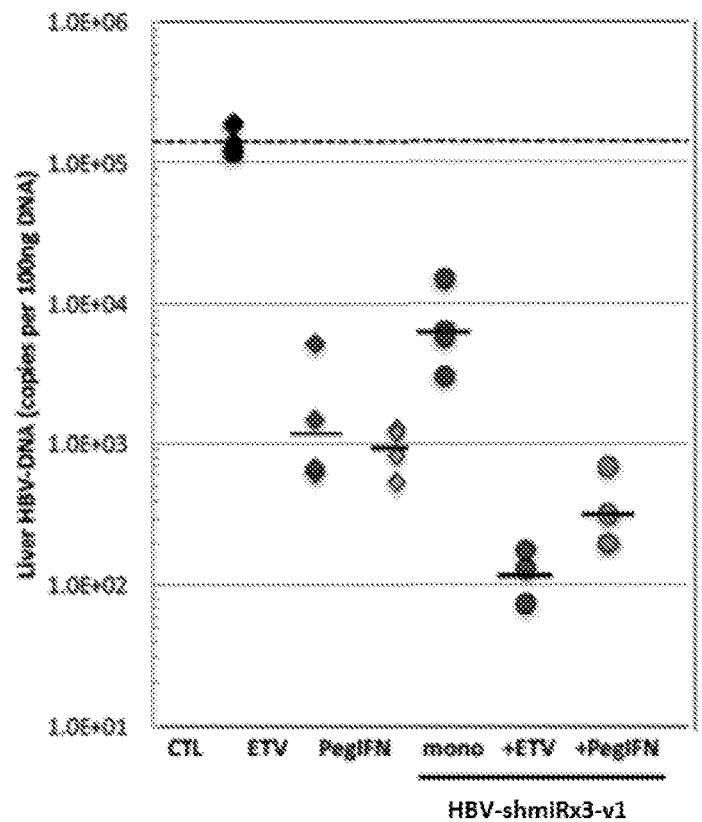
FIG. 12 illustrates that both intracellular HBV DNA and cccDNA levels were reduced in livers of mice treated with a single dose of ssAAV8-HBV-shmiRx3-v1 as a monotherapy or in combination with Entecavir or pegylated interferon.
Figure 12:
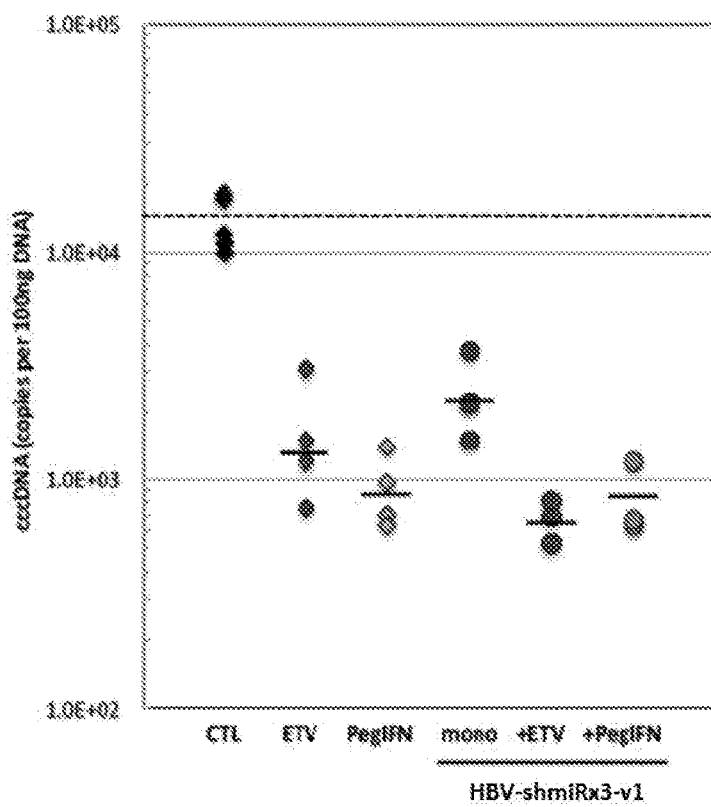

Intracellular HBV DNA, as well as cccDNA, was also assessed from the liver samples using quantitative PCR. Treatment with either entecavir or pegylated interferon alone was able to drop intracellular DNA levels by 2 logs (FIG. 12, left panel). Yet, a single addition of ssAAV8-HBV-shmiRx3-v1 into the treatment regimen further reduced intracellular DNA levels by 3 logs. Although RNA interference does not directly attack the intracellular HBV DNA, it is likely that a reduction of the RNA and corresponding transcripts reduce the ability of the reverse transcription process to covert the pgRNA template into the DNA intermediate leading to its reduction. Indeed, while a modest reduction of cccDNA occurred of slightly more than a one log reduction with ETV, the addition of ssAAV8-HBV-shmiRx3-v1 did not significantly cause further reduction of cccDNA levels (FIG. 12, right panel).

Figure 13:
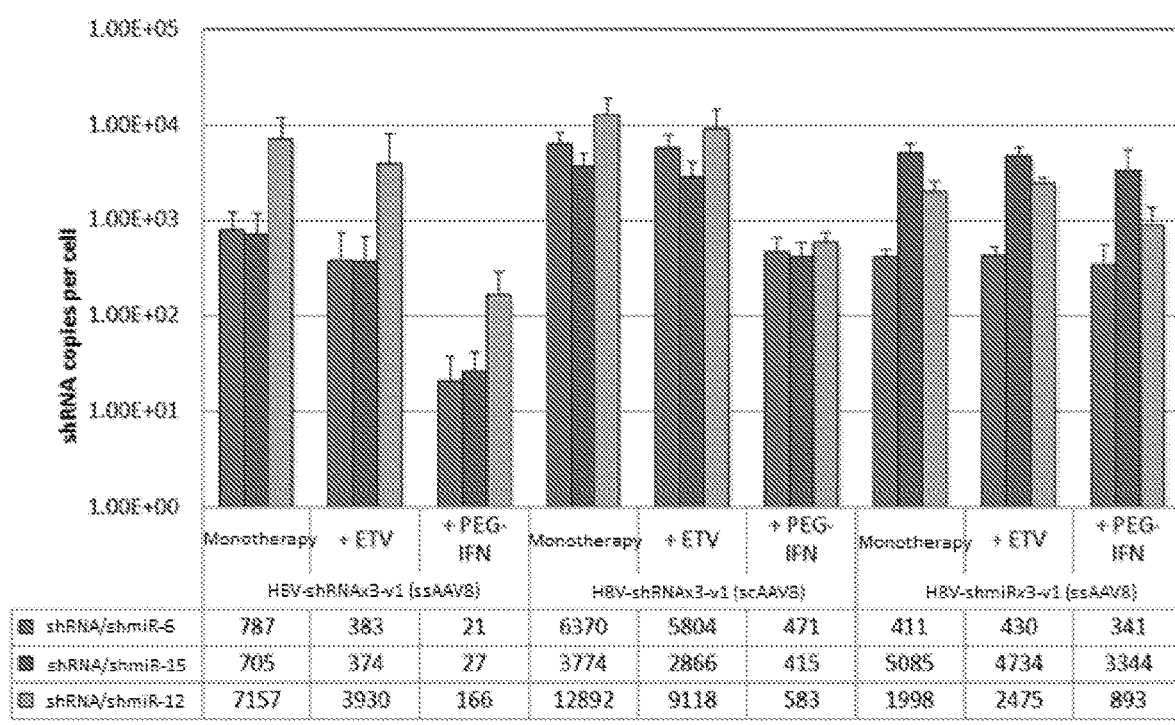
FIG. 13 illustrates the level of expression of RNAi effector molecules, expressed as copies per cell, in liver tissue obtained from mice treated with ssAAV8-HBV-shRNAx3-v1, scAAV8-HBV-shRNAx3-v1 or ssAAV8-HBV-shmiRx3-v1 as a monotherapy or in combination with Entecavir or pegylated interferon.
Figure 14:
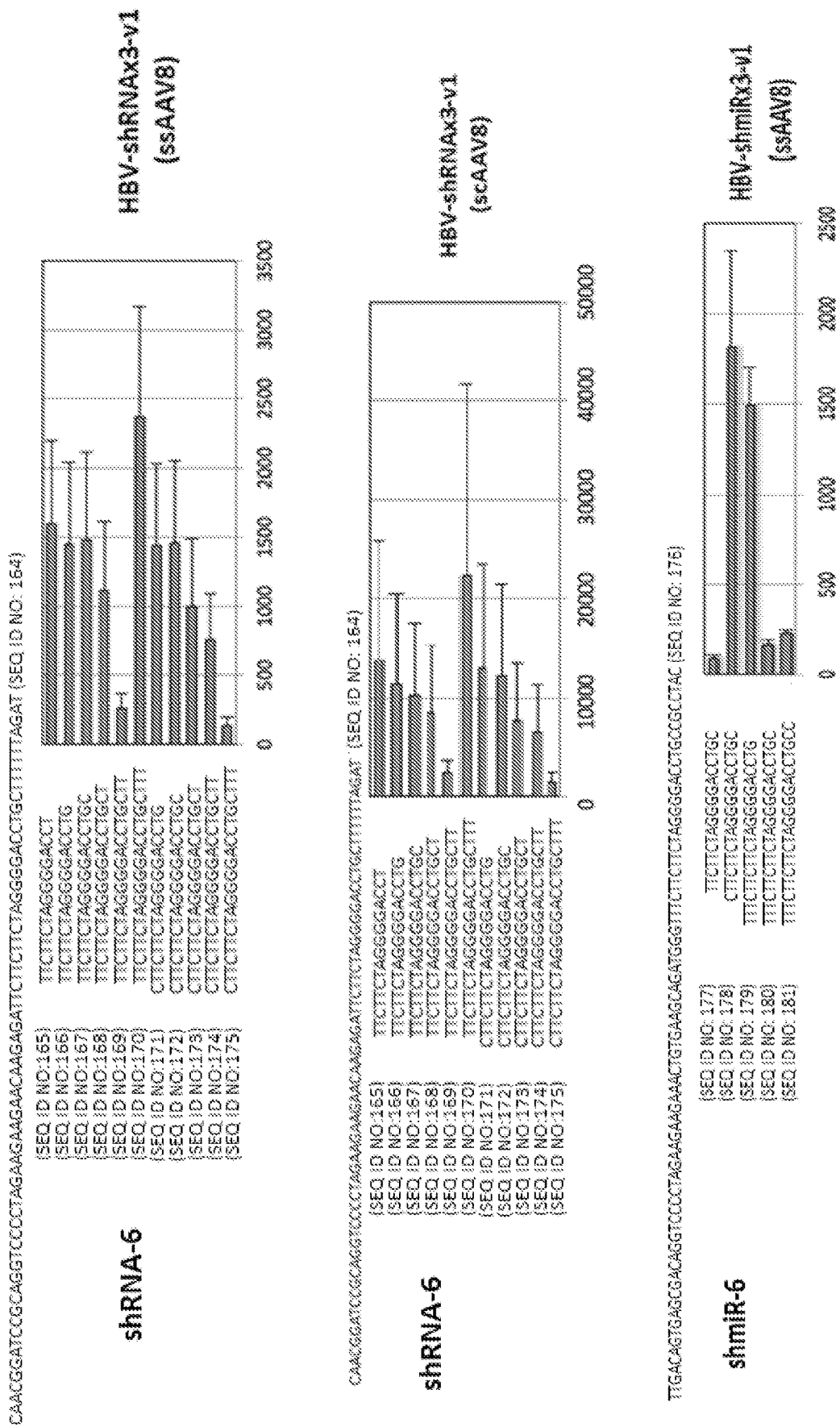
FIG. 14 illustrates the predominant shRNA-6/shmiR-6 effector sequence species and numbers of same produced from ssAAV8-HBV-shRNAx3-v1, scAAV8-HBV-shRNAx3-v1 and ssAAV8-HBV-shmiRx3-v1 in liver tissue obtained from PXB mice, as determined by next generation sequencing (NGS).
Figure 15:
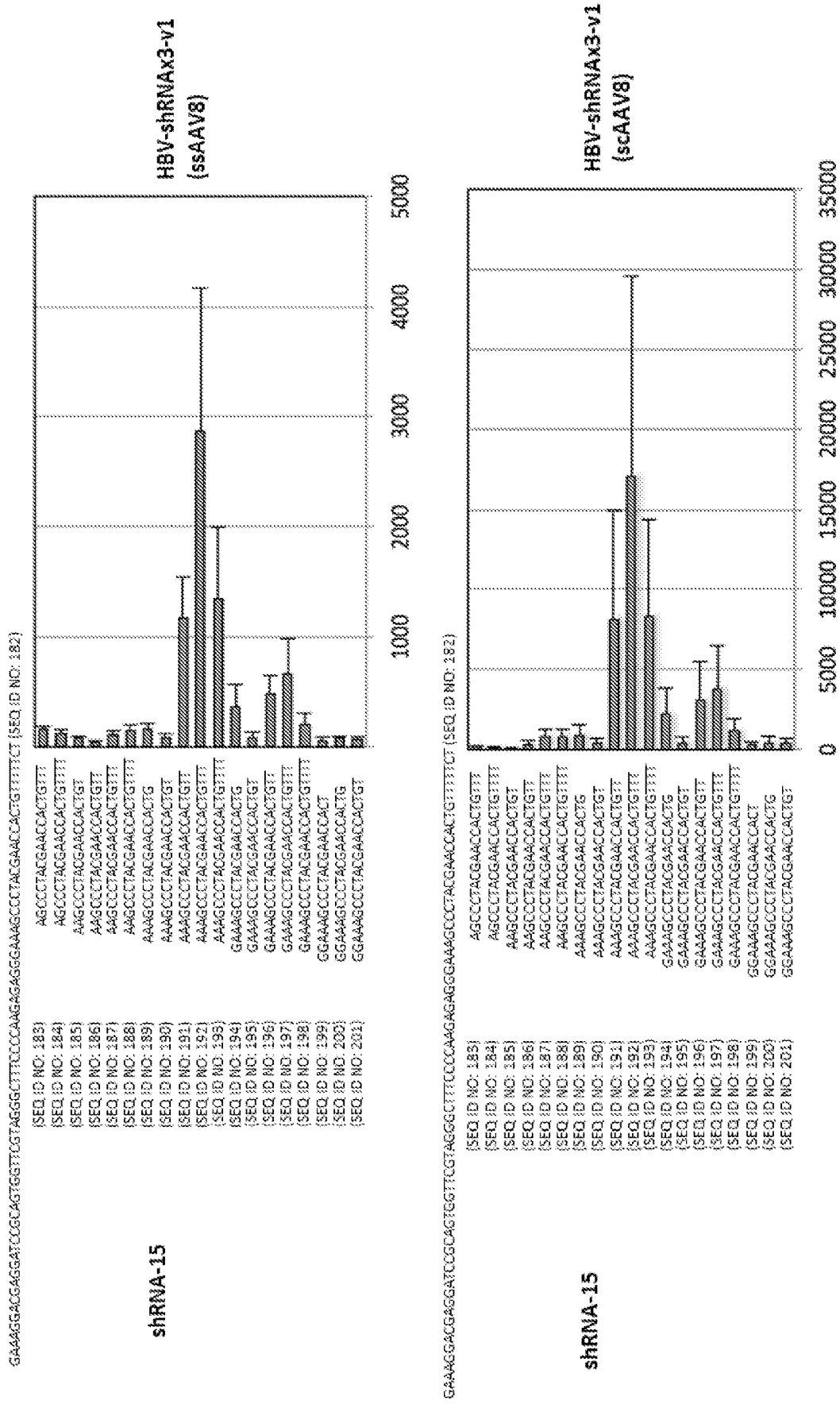
FIG. 15 illustrates the predominant shRNA-15/shmiR-15 effector sequence species and numbers of same produced from ssAAV8-HBV-shRNAx3-v1, scAAV8-HBV-shRNAx3-v1 and ssAAV8-HBV-shmiRx3-v1 in liver tissue obtained from PXB mice, as determined by next generation sequencing (NGS).
Figure 15:
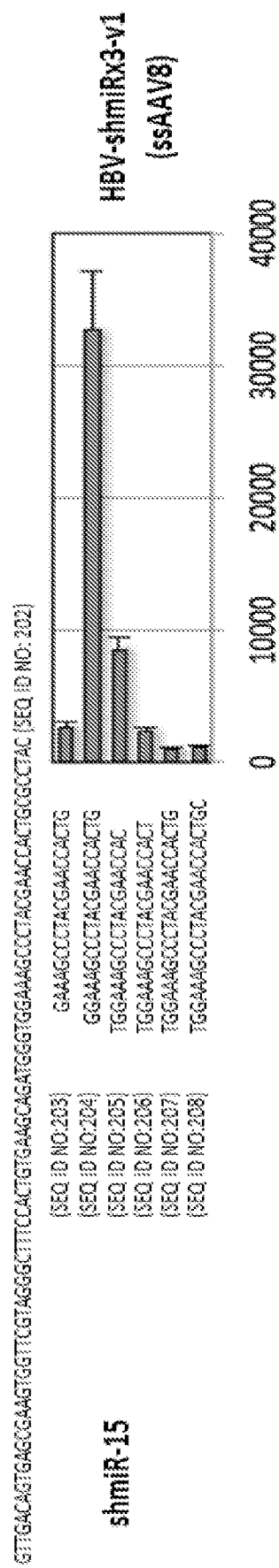
Figure 16:
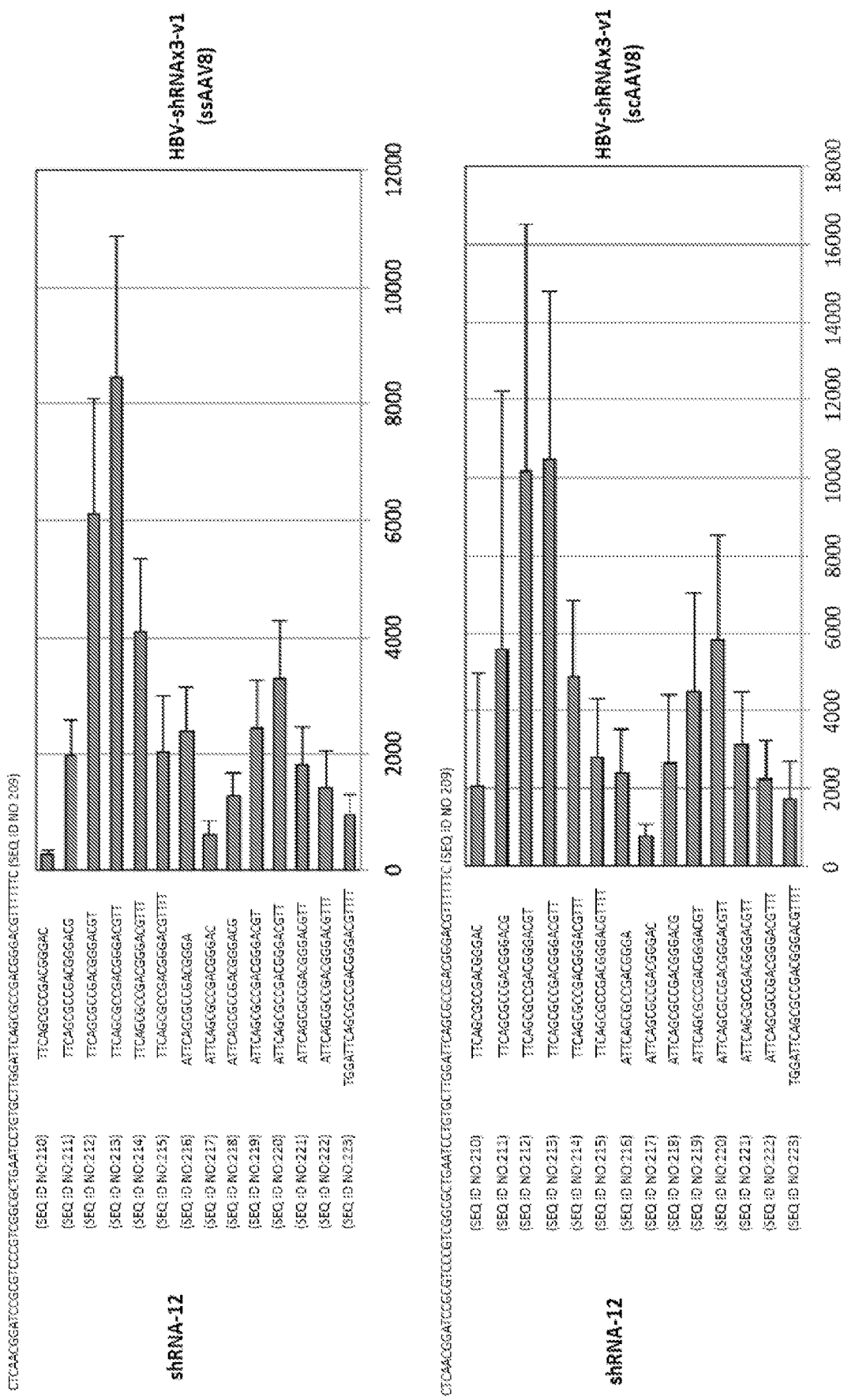
FIG. 16 illustrates the predominant shRNA-12/shmiR-12 effector sequence species and numbers of same produced from ssAAV8-HBV-shRNAx3-v1, scAAV8-HBV-shRNAx3-v1 and ssAAV8-HBV-shmiRx3-v1 in liver tissue obtained from PXB mice, as determined by next generation sequencing (NGS).
Figure 16:
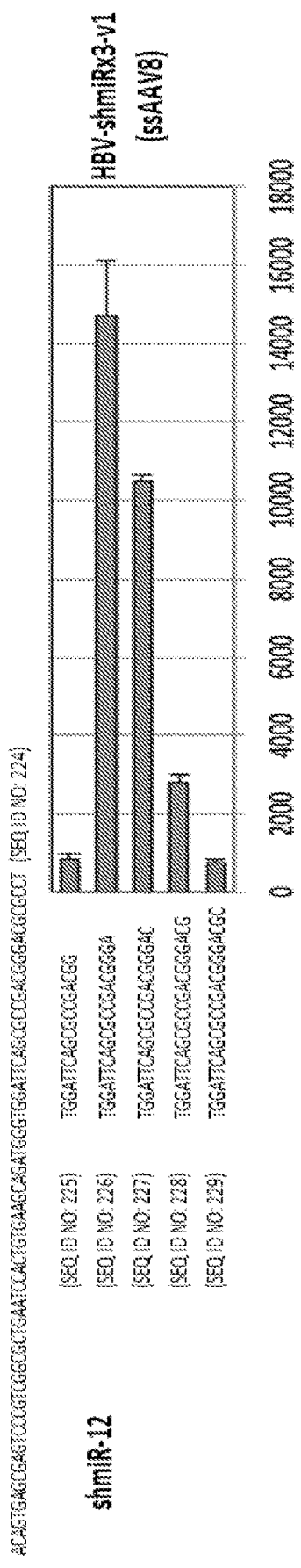

Expression of RNAi effector molecules from liver tissues of PXB mice was also determined via RT-QPCR (FIG. 13) and next-generation sequencing (NGS, FIG. 14-16). NGS data show that the number of predominate RNAi effector species is limited to 2 to 3 when produced from a shmiR (ssAAV8-HBV-shmiRx3-v1). The number of effector species is increased dramatically when produced from shRNA (ssAAV8-HBV-shRNAx3-v1 and scAAV8-HBV-shRNAx3-v1). As a shmiR precursor, the small RNA transcript enters the RNAi pathway upstream where Drosha performs the first cleavage and defines one end of the RNAi duplex. This end contains characteristic 2nt 3' overhang, which is presented as an optimal substrate for dicer, which cleaves the loop to produce the final siRNA duplex. Processing by drosha and dicer are very precise, and as such, only minimal number of sequences is found through deep sequencing. First generation shRNA, on the other hand, rely on transcriptional terminators (ie., polyT) built within the sequence to define one end of the RNAi duplex. This mechanism is imprecise and produce overhangs with 2 to 5 nt 3' overhangs which is not optimal for dicer mediated cleavage. As a result of the low fidelity cleavage by dicer, a larger number of species is observed through deep sequencing. More importantly, this broad distribution of effector species produced from shRNA (as compared to shmiRs) can diminish activity of desired species and the unwanted production of ineffective anti-HBV RNAi molecules can increase the chances of off target effects.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. A nucleic acid comprising a DNA sequence which encodes a short hairpin micro-RNA (shmiR), said shmiR comprising:
    an effector sequence of at least 17 nucleotides in length;
    an effector complement sequence;
    a stemloop sequence; and
    primary micro RNA (pri-miRNA) backbone;
    wherein the effector sequence is substantially complementary to a RNA transcript set forth in SEQ ID NO: 4;
    and wherein the shmiR inhibits or reduces expression of one or more Hepatitis B virus (HBV) genes in a cell by more than 60% relative to a cell in which the shmiR is absent.

2. The nucleic acid according to claim 1, wherein the shmiR is selected from the group consisting of:
    a shmiR comprising an effector sequence which is substantially complementary to the sequence set forth in SEQ ID NO:22 with the exception of 1, 2, 3, 4, 5 or 6 base mismatches, provided that the effector sequence is capable of forming a duplex with a sequence set forth in SEQ ID NO:22;
    a shmiR comprising an effector sequence set forth in SEQ ID NO:21 and an effector complement sequence which is substantially complementary to the sequence set forth in SEQ ID NO:21 and capable of forming a duplex therewith; and
    a shmiR comprising an effector sequence set forth in SEQ ID NO:21 and an effector complement sequence set forth in SEQ ID NO:22.

3. The nucleic acid according to claim 1, wherein the shmiR comprises, in a 5' to 3' direction:
    (a) a 5' flanking sequence of the pri-miRNA backbone;
        the effector complement sequence;
        the stemloop sequence;
        the effector sequence; and
        a 3' flanking sequence of the pri-miRNA backbone; or
    (b) a 5' flanking sequence of the pri-miRNA backbone;
        the effector sequence;
        the stemloop sequence;
        the effector complement sequence; and
        a 3' flanking sequence of the pri-miRNA backbone.

4. The nucleic acid according to claim 1, wherein:
    (a) the stemloop sequence is the sequence set forth in SEQ ID NO: 75; and/or
    (b) the pri-miRNA backbone is a pri-miR-30a backbone.

5. The nucleic acid according to claim 3, wherein:
    (a) the 5' flanking sequence of the pri-miRNA backbone is set forth in SEQ ID NO: 76 and the 3' flanking sequence of the pri-miRNA backbone is set forth in SEQ ID NO: 77; and/or
    (b) wherein the shmiR comprises a sequence set forth in SEQ ID NO: 48.

6. The nucleic acid according to claim 1, wherein the DNA sequence which encodes the shmiR is set forth in SEQ ID NO: 64.

7. A DNA-directed RNA interference (ddRNAi) construct comprising the nucleic acid according to claim 1.

8. The ddRNAi construct according to claim 7, comprising:
    (a) a nucleic acid comprising a DNA sequence encoding a shmiR comprising an effector sequence comprising or consisting of the sequence set forth in SEQ ID NO: 21 and an effector complement sequence comprising or consisting of the sequence set forth in SEQ ID NO: 22; and a nucleic acid comprising a DNA sequence encoding a shmiR comprising an effector sequence comprising or consisting of the sequence set forth in SEQ ID NO: 33 and an effector complement sequence comprising or consisting of the sequence set forth in SEQ ID NO: 34;

(b) a nucleic acid comprising a DNA sequence encoding a shmiR comprising an effector sequence comprising or consisting of the sequence set forth in SEQ ID NO: 21 and an effector complement sequence comprising or consisting of the sequence set forth in SEQ ID NO: 22; and a nucleic acid comprising a DNA sequence encoding a shmiR comprising an effector sequence comprising or consisting of the sequence set forth in SEQ ID NO: 39 and an effector complement sequence comprising or consisting of the sequence set forth in SEQ ID NO: 40; or (c) a nucleic acid comprising a DNA sequence encoding a shmiR comprising an effector sequence comprising or consisting of the sequence set forth in SEQ ID NO: 21 and an effector complement sequence comprising or consisting of the sequence set forth in SEQ ID NO: 22;

a nucleic acid comprising a DNA sequence encoding a shmiR comprising an effector sequence comprising or consisting of the sequence set forth in SEQ ID NO: 39 and an effector complement sequence comprising or consisting of the sequence set forth in SEQ ID NO: 40; and a nucleic acid comprising a DNA sequence encoding a shmiR comprising an effector sequence comprising or consisting of the sequence set forth in SEQ ID NO: 33 and an effector complement sequence comprising or consisting of the sequence set forth in SEQ ID NO: 34.

9. The ddRNAi construct according to claim 7, comprising:

(a) (i) a nucleic acid encoding a shmiR comprising or consisting of an effector sequence which is substantially complementary to a RNA transcript comprising the sequence set forth in SEQ ID NO: 4; and (ii) a nucleic acid encoding a shmiR comprising or consisting of an effector sequence which is substantially complementary to a RNA transcript comprising the sequence set forth in SEQ ID NO: 9; or (b) (i) a nucleic acid encoding a shmiR comprising or consisting of an effector sequence which is substantially complementary to a RNA transcript comprising the sequence set forth in SEQ ID NO: 4; (ii) a nucleic acid encoding a shmiR comprising or consisting of an effector sequence which is substantially complementary to a RNA transcript comprising the sequence set forth in SEQ ID NO: 9; and (iii) a nucleic acid encoding a shmiR comprising or consisting of an effector sequence which is substantially complementary to a RNA transcript comprising the sequence set forth in SEQ ID NO: 40.

10. The ddRNAi construct according to claim 9, said ddRNAi construct comprising:

(a) (i) a nucleic acid comprising a DNA sequence encoding a shmiR comprising or consisting of the sequence set forth in SEQ ID NO:48;

(ii) a nucleic acid comprising a DNA sequence encoding a shmiR comprising or consisting of the sequence set forth in SEQ ID NO:57; and (iii) a nucleic acid comprising a DNA sequence encoding a shmiR comprising or consisting of the sequence set forth in SEQ ID NO:54; or (b) (i) a nucleic acid comprising a DNA sequence comprising or consisting of the sequence set forth in SEQ ID NO:64;

(ii) a nucleic acid comprising a DNA sequence comprising or consisting of the sequence set forth in SEQ ID NO:73; and (iii) a nucleic acid comprising or consisting of the sequence set forth in SEQ ID NO:70; or (c) (i) a nucleic acid comprising a DNA sequence encoding a shmiR comprising or consisting of the sequence set forth in SEQ ID NO:48; and (ii) a nucleic acid comprising a DNA sequence encoding a shmiR comprising or consisting of the sequence set forth in SEQ ID NO:54; or (d) (i) a nucleic acid comprising a DNA sequence comprising or consisting of the sequence set forth in SEQ ID NO:64;

and (ii) a nucleic acid comprising a DNA sequence comprising or consisting of the sequence set forth in SEQ ID NO:70.

11. The ddRNAi construct according to claim 7, comprising a RNA pol III promoter upstream of the or each nucleic acid encoding a shmiR.

12. The ddRNAi construct of claim 11, wherein the or each RNA pol III promoter is selected from a U6 and a H1 promoter.

13. The ddRNAi construct of claim 12, wherein the or each RNA pol III promoter is a U6 promoter selected from a U6-9 promoter, a U6-1 promoter and U6-8 promoter.

14. The ddRNAi construct according to claim 13, said ddRNAi construct comprising:

(a) (i) U6-9 promoter upstream of a nucleic acid comprising or consisting of the sequence set forth in SEQ ID NO:64;

(ii) U6-1 promoter upstream of a nucleic acid comprising or consisting of the sequence set forth in SEQ ID NO:73; and (iii) U6-8 promoter upstream of a nucleic acid comprising or consisting of the sequence set forth in SEQ ID NO:70; or (b) (i) U6-9 promoter upstream of a nucleic acid comprising or consisting of the sequence set forth in SEQ ID NO:64; and (ii) U6-8 promoter or H1 promoter upstream of a nucleic acid comprising or consisting of the sequence set forth in SEQ ID NO:70.

15. An expression vector comprising the ddRNAi construct of claim 7.

16. The expression vector of claim 15, wherein the expression vector is a (i) plasmid, (ii) minicircle, or (iii) a viral vector selected from the group consisting of an adeno-associated viral (AAV) vector, a retroviral vector, an adenoviral (AdV) vector and a lentiviral (LV) vector.

17. A composition comprising a DNA Directed RNA interference (ddRNAi) construct according to claim 7 and one or more pharmaceutically acceptable carriers, excipients or diluents.

18. A method of treating Hepatitis B virus (HBV) infection in a subject, said method comprising administering to the subject a therapeutically effective amount of a composition according to claim 17.

19. The method according to claim 18, wherein the subject is suffering from acute HBV infection.

20. The method according to claim 18, wherein the subject is suffering from chronic HBV infection.

21. The method of claim 18, wherein treating HBV infection comprises one or more of the following:
   (i) reducing Hepatitis B viral load in a subject infected with HBV;
   (ii) reducing severity of symptoms associated with HBV infection in a subject suffering therefrom;
   (iii) reducing the infectivity of HBV in a subject infected therewith; and/or
   (iv) inhibiting or reducing expression of one or more HBV genes.

22. The method according to claim 18, wherein the composition is administered together with a further therapeutic agent for treatment of HBV infection.

23. The method according to claim 22, wherein the further therapeutic agent for treatment of HBV infection is selected from the group consisting of entecavir, tenofovir, lamivudine, adefovir and pegylated interferon.

* * * * *

SEQUENCE LISTING

<160> NUMBER OF SEQ ID NOS: 237

<210> SEQ ID NO 1
<211> LENGTH: 20
<212> TYPE: RNA
<213> ORGANISM: Hepatitis B virus

<400> SEQUENCE: 1
cauccugcug cuaugccuca                                               20

<210> SEQ ID NO 2
<211> LENGTH: 23
<212> TYPE: RNA
<213> ORGANISM: Hepatitis B virus

<400> SEQUENCE: 2
uuugcugacg caaccccac ugg                                            23

<210> SEQ ID NO 3
<211> LENGTH: 20
<212> TYPE: RNA
<213> ORGANISM: Hepatitis B virus

<400> SEQUENCE: 3
aagccuccaa gcugugccuu                                               20

<210> SEQ ID NO 4
<211> LENGTH: 28
<212> TYPE: RNA
<213> ORGANISM: Hepatitis B virus

<400> SEQUENCE: 4 gcagguccc uagaagaaga acucccuc                                       28

<210> SEQ ID NO 5
<211> LENGTH: 23
<212> TYPE: RNA
<213> ORGANISM: Hepatitis B virus

<400> SEQUENCE: 5
caagguaugu ugcccguuug ucc                                           23

<210> SEQ ID NO 6
<211> LENGTH: 20
<212> TYPE: RNA
<213> ORGANISM: Hepatitis B virus

<400> SEQUENCE: 6 cucgugugg acuucucuca                                                20

<210> SEQ ID NO 7
<211> LENGTH: 23
<212> TYPE: RNA
<213> ORGANISM: Hepatitis B virus

<400> SEQUENCE: 7

```
cucguguuac aggcgggguu uuu                                           23

<210> SEQ ID NO 8
<211> LENGTH: 29
<212> TYPE: RNA
<213> ORGANISM: Hepatitis B virus

<400> SEQUENCE: 8
ccgugugcac uucgcuucac cucugcacg                                     29

<210> SEQ ID NO 9
<211> LENGTH: 22
<212> TYPE: RNA
<213> ORGANISM: Hepatitis B virus

<400> SEQUENCE: 9
uacgucccgu cggcgcugaa uc                                            22

<210> SEQ ID NO 10
<211> LENGTH: 19
<212> TYPE: RNA
<213> ORGANISM: Hepatitis B virus

<400> SEQUENCE: 10
aaaugccccu aucuuauca                                                19

<210> SEQ ID NO 11
<211> LENGTH: 21
<212> TYPE: RNA
<213> ORGANISM: Artificial Sequence
<220> FEATURE:
<223> OTHER INFORMATION: shmiR-1 effector

<400> SEQUENCE: 11
ugaggcauag cagcaggaug c                                             21

<210> SEQ ID NO 12
<211> LENGTH: 20
<212> TYPE: RNA
<213> ORGANISM: Artificial Sequence
<220> FEATURE:
<223> OTHER INFORMATION: shmiR-1 effector complement

<400> SEQUENCE: 12
cauccugcug cuaugccuca                                               20

<210> SEQ ID NO 13
<211> LENGTH: 21
<212> TYPE: RNA
<213> ORGANISM: Artificial Sequence
<220> FEATURE:
<223> OTHER INFORMATION: shmiR-2 effector

<400> SEQUENCE: 13 caguggggu ugcgucagca a                                              21

<210> SEQ ID NO 14
<211> LENGTH: 20
<212> TYPE: RNA
<213> ORGANISM: Artificial Sequence
<220> FEATURE:
<223> OTHER INFORMATION: shmiR-2 effector complement

<400> SEQUENCE: 14
```

-continued ugcugacgca accccacug    20

<210> SEQ ID NO 15
<211> LENGTH: 21
<212> TYPE: RNA
<213> ORGANISM: Artificial Sequence
<220> FEATURE:
<223> OTHER INFORMATION: shmiR-3 effector

<400> SEQUENCE: 15
aaggcacagc uuggaggcuu g    21

<210> SEQ ID NO 16
<211> LENGTH: 20
<212> TYPE: RNA
<213> ORGANISM: Artificial Sequence
<220> FEATURE:
<223> OTHER INFORMATION: shmiR-3 effector complement

<400> SEQUENCE: 16
aagccuccaa gcugugccuu    20

<210> SEQ ID NO 17
<211> LENGTH: 21
<212> TYPE: RNA
<213> ORGANISM: Artificial Sequence
<220> FEATURE:
<223> OTHER INFORMATION: shmiR-4 effector

<400> SEQUENCE: 17
gaguucuucu ucuaggggac c    21

<210> SEQ ID NO 18
<211> LENGTH: 20
<212> TYPE: RNA
<213> ORGANISM: Artificial Sequence
<220> FEATURE:
<223> OTHER INFORMATION: shmiR-4 effector complement

<400> SEQUENCE: 18
guccccuaga agaagaacuc    20

<210> SEQ ID NO 19
<211> LENGTH: 21
<212> TYPE: RNA
<213> ORGANISM: Artificial Sequence
<220> FEATURE:
<223> OTHER INFORMATION: shmiR-5 effector

<400> SEQUENCE: 19
gagggaguuc uucuucuagg g    21

<210> SEQ ID NO 20
<211> LENGTH: 20
<212> TYPE: RNA
<213> ORGANISM: Artificial Sequence
<220> FEATURE:
<223> OTHER INFORMATION: shmiR-5 effector complement

<400> SEQUENCE: 20
ccuagaagaa gaacucccuc    20

<210> SEQ ID NO 21
<211> LENGTH: 21
<212> TYPE: RNA
<213> ORGANISM: Artificial Sequence

```
<220> FEATURE:
<223> OTHER INFORMATION: shmiR-6 effector

<400> SEQUENCE: 21
uucuucuucu aggggaccug c                                              21

<210> SEQ ID NO 22
<211> LENGTH: 20
<212> TYPE: RNA
<213> ORGANISM: Artificial Sequence
<220> FEATURE:
<223> OTHER INFORMATION: shmiR-6 effector complement

<400> SEQUENCE: 22
cagguccccu agaagaagaa                                                20

<210> SEQ ID NO 23
<211> LENGTH: 21
<212> TYPE: RNA
<213> ORGANISM: Artificial Sequence
<220> FEATURE:
<223> OTHER INFORMATION: shmiR-7 effector

<400> SEQUENCE: 23
acaaacgggc aacauaccuu g                                              21

<210> SEQ ID NO 24
<211> LENGTH: 20
<212> TYPE: RNA
<213> ORGANISM: Artificial Sequence
<220> FEATURE:
<223> OTHER INFORMATION: shmiR-7 effector complement

<400> SEQUENCE: 24
aagguauguu gcccguuugu                                                20

<210> SEQ ID NO 25
<211> LENGTH: 21
<212> TYPE: RNA
<213> ORGANISM: Artificial Sequence
<220> FEATURE:
<223> OTHER INFORMATION: shmiR-8 effector

<400> SEQUENCE: 25
uugagagaag uccaccacga g                                              21

<210> SEQ ID NO 26
<211> LENGTH: 20
<212> TYPE: RNA
<213> ORGANISM: Artificial Sequence
<220> FEATURE:
<223> OTHER INFORMATION: shmiR-8 effector complement

<400> SEQUENCE: 26
ucguggugga cuucucucaa                                                20

<210> SEQ ID NO 27
<211> LENGTH: 21
<212> TYPE: RNA
<213> ORGANISM: Artificial Sequence
<220> FEATURE:
<223> OTHER INFORMATION: shmiR-9 effector

<400> SEQUENCE: 27
aaaccccgcc uguaacacga g                                              21
```

```
<210> SEQ ID NO 28
<211> LENGTH: 20
<212> TYPE: RNA
<213> ORGANISM: Artificial Sequence
<220> FEATURE:
<223> OTHER INFORMATION: shmiR-9 effector complement

<400> SEQUENCE: 28
ucguguuaca ggcggggulu                                              20

<210> SEQ ID NO 29
<211> LENGTH: 21
<212> TYPE: RNA
<213> ORGANISM: Artificial Sequence
<220> FEATURE:
<223> OTHER INFORMATION: shmiR-10 effector

<400> SEQUENCE: 29
ugcagaggug aagcgaagug c                                            21

<210> SEQ ID NO 30
<211> LENGTH: 20
<212> TYPE: RNA
<213> ORGANISM: Artificial Sequence
<220> FEATURE:
<223> OTHER INFORMATION: shmiR-10 effector complement

<400> SEQUENCE: 30
cacuucgcuu caccucugca                                              20

<210> SEQ ID NO 31
<211> LENGTH: 21
<212> TYPE: RNA
<213> ORGANISM: Artificial Sequence
<220> FEATURE:
<223> OTHER INFORMATION: shmiR-11 effector

<400> SEQUENCE: 31
gauucagcgc cgacgggacg a                                            21

<210> SEQ ID NO 32
<211> LENGTH: 20
<212> TYPE: RNA
<213> ORGANISM: Artificial Sequence
<220> FEATURE:
<223> OTHER INFORMATION: shmiR-11 effector complement

<400> SEQUENCE: 32
cgucccgucg gcgcugaauc                                              20

<210> SEQ ID NO 33
<211> LENGTH: 21
<212> TYPE: RNA
<213> ORGANISM: Artificial Sequence
<220> FEATURE:
<223> OTHER INFORMATION: shmiR-12 effector

<400> SEQUENCE: 33
ggauucagcg ccgacgggac g                                            21

<210> SEQ ID NO 34
<211> LENGTH: 20
<212> TYPE: RNA
<213> ORGANISM: Artificial Sequence
<220> FEATURE:
<223> OTHER INFORMATION: shmiR-12 effector complement
```

-continued

<400> SEQUENCE: 34
gucccgucgg cgcugaaucc                                               20

<210> SEQ ID NO 35
<211> LENGTH: 21
<212> TYPE: RNA
<213> ORGANISM: Artificial Sequence
<220> FEATURE:
<223> OTHER INFORMATION: shmiR-13 effector

<400> SEQUENCE: 35
ugauaagaua ggggcauuug g                                             21

<210> SEQ ID NO 36
<211> LENGTH: 20
<212> TYPE: RNA
<213> ORGANISM: Artificial Sequence
<220> FEATURE:
<223> OTHER INFORMATION: shmiR-13 effector complement

<400> SEQUENCE: 36
caaaugcccc uaucuuauca                                               20

<210> SEQ ID NO 37
<211> LENGTH: 21
<212> TYPE: RNA
<213> ORGANISM: Artificial Sequence
<220> FEATURE:
<223> OTHER INFORMATION: shmiR-14 effector

<400> SEQUENCE: 37
ugaggcccac ucccauaggu a                                             21

<210> SEQ ID NO 38
<211> LENGTH: 20
<212> TYPE: RNA
<213> ORGANISM: Artificial Sequence
<220> FEATURE:
<223> OTHER INFORMATION: shmiR-14 effector complement

<400> SEQUENCE: 38
accuauggga gugggccuca                                               20

<210> SEQ ID NO 39
<211> LENGTH: 21
<212> TYPE: RNA
<213> ORGANISM: Artificial Sequence
<220> FEATURE:
<223> OTHER INFORMATION: shmiR-15 effector

<400> SEQUENCE: 39
ggaaagcccu acgaaccacu g                                             21

<210> SEQ ID NO 40
<211> LENGTH: 20
<212> TYPE: RNA
<213> ORGANISM: Artificial Sequence
<220> FEATURE:
<223> OTHER INFORMATION: shmiR-15 effector complement

<400> SEQUENCE: 40
agugguucgu agggcuuucc                                               20

<210> SEQ ID NO 41

```
<211> LENGTH: 21
<212> TYPE: RNA
<213> ORGANISM: Artificial Sequence
<220> FEATURE:
<223> OTHER INFORMATION: shmiR-16 effector

<400> SEQUENCE: 41
gggcaacggg guaaagguuc a                                              21

<210> SEQ ID NO 42
<211> LENGTH: 20
<212> TYPE: RNA
<213> ORGANISM: Artificial Sequence
<220> FEATURE:
<223> OTHER INFORMATION: shmiR-16 effector complement

<400> SEQUENCE: 42
gaaccuuuac cccguugccc                                                20

<210> SEQ ID NO 43
<211> LENGTH: 107
<212> TYPE: RNA
<213> ORGANISM: Artificial Sequence
<220> FEATURE:
<223> OTHER INFORMATION: shmiR-1 sequence

<400> SEQUENCE: 43
gguauauugc uguugacagu gagcgacauc cugcugcuau gccucaacug ugaagcagau    60
ggguugaggc auagcagcag gaugccgccu acugccucgg acuucaa                107

<210> SEQ ID NO 44
<211> LENGTH: 107
<212> TYPE: RNA
<213> ORGANISM: Artificial Sequence
<220> FEATURE:
<223> OTHER INFORMATION: shmiR-2 sequence

<400> SEQUENCE: 44
gguauauugc uguugacagu gagcgaugcu gacgcaaccc ccacugacug ugaagcagau    60
gggucagugg ggguugcguc agcaacgccu acugccucgg acuucaa                107

<210> SEQ ID NO 45
<211> LENGTH: 107
<212> TYPE: RNA
<213> ORGANISM: Artificial Sequence
<220> FEATURE:
<223> OTHER INFORMATION: shmiR-3 sequence

<400> SEQUENCE: 45
gguauauugc uguugacagu gagcgaaagc cuccaagcug ugccuuacug ugaagcagau    60
ggguaaggca cagcuuggag gcuugcgccu acugccucgg acuucaa                107

<210> SEQ ID NO 46
<211> LENGTH: 107
<212> TYPE: RNA
<213> ORGANISM: Artificial Sequence
<220> FEATURE:
<223> OTHER INFORMATION: shmiR-4 sequence

<400> SEQUENCE: 46
gguauauugc uguugacagu gagcgagucc ccuagaagaa gaacucacug ugaagcagau    60 ggguugaguuc uucuucuagg ggacccgccu acugccucgg acuucaa               107
```

```
<210> SEQ ID NO 47
<211> LENGTH: 107
<212> TYPE: RNA
<213> ORGANISM: Artificial Sequence
<220> FEATURE:
<223> OTHER INFORMATION: shmiR-5 sequence

<400> SEQUENCE: 47
gguauauugc uguugacagu gagcgaccua gaagaagaac ucccucacug ugaagcagau    60
gggugaggga guucuucuuc uagggcgccu acugccucgg acuucaa               107

<210> SEQ ID NO 48
<211> LENGTH: 107
<212> TYPE: RNA
<213> ORGANISM: Artificial Sequence
<220> FEATURE:
<223> OTHER INFORMATION: shmiR-6 sequence

<400> SEQUENCE: 48
gguauauugc uguugacagu gagcgacagg uccccuagaa gaagaaacug ugaagcagau    60
ggguuucuuc uucuagggga ccugccgccu acugccucgg acuucaa               107

<210> SEQ ID NO 49
<211> LENGTH: 107
<212> TYPE: RNA
<213> ORGANISM: Artificial Sequence
<220> FEATURE:
<223> OTHER INFORMATION: shmiR-7 sequence

<400> SEQUENCE: 49
gguauauugc uguugacagu gagcgaaagg uauguugccc guuguacug ugaagcagau     60 ggguacaaac gggcaacaua ccuugcgccu acugccucgg acuucaa               107

<210> SEQ ID NO 50
<211> LENGTH: 107
<212> TYPE: RNA
<213> ORGANISM: Artificial Sequence
<220> FEATURE:
<223> OTHER INFORMATION: shmiR-8 sequence

<400> SEQUENCE: 50
gguauauugc uguugacagu gagcgaucgu gguggacuuc ucucaaacug ugaagcagau    60
ggguuugaga gaaguccacc acgagcgccu acugccucgg acuucaa               107

<210> SEQ ID NO 51
<211> LENGTH: 107
<212> TYPE: RNA
<213> ORGANISM: Artificial Sequence
<220> FEATURE:
<223> OTHER INFORMATION: shmiR-9 sequence

<400> SEQUENCE: 51
gguauauugc uguugacagu gagcgaucgu guuacaggcg ggguuuacug ugaagcagau    60
ggguaaaccc cgccuguaac acgagcgccu acugccucgg acuucaa               107

<210> SEQ ID NO 52
<211> LENGTH: 107
<212> TYPE: RNA
<213> ORGANISM: Artificial Sequence
<220> FEATURE:
<223> OTHER INFORMATION: shmiR-10 sequence

<400> SEQUENCE: 52
```

```
gguauauugc uguugacagu gagcgacacu ucgcuucacc ucugcaacug ugaagcagau        60
ggguugcaga ggugaagcga agugccgccu acugccucgg acuucaa                    107

<210> SEQ ID NO 53
<211> LENGTH: 107
<212> TYPE: RNA
<213> ORGANISM: Artificial Sequence
<220> FEATURE:
<223> OTHER INFORMATION: shmiR-11 sequence

<400> SEQUENCE: 53
gguauauugc uguugacagu gagcgacguc ccgucggcgc ugaaucacug ugaagcagau        60
gggugauuca gcgccgacgg gacgacgccu acugccucgg acuucaa                    107

<210> SEQ ID NO 54
<211> LENGTH: 107
<212> TYPE: RNA
<213> ORGANISM: Artificial Sequence
<220> FEATURE:
<223> OTHER INFORMATION: shmiR-12 sequence

<400> SEQUENCE: 54
gguauauugc uguugacagu gagcgagucc cgucggcgcu gaauccacug ugaagcagau        60
ggguggauuc agcgccgacg ggacgcgccu acugccucgg acuucaa                    107

<210> SEQ ID NO 55
<211> LENGTH: 107
<212> TYPE: RNA
<213> ORGANISM: Artificial Sequence
<220> FEATURE:
<223> OTHER INFORMATION: shmiR-13 sequence

<400> SEQUENCE: 55
gguauauugc uguugacagu gagcgacaaa ugccccuauc uuaucaacug ugaagcagau        60
ggguugauaa gauaggggca uuuggcgccu acugccucgg acuucaa                    107

<210> SEQ ID NO 56
<211> LENGTH: 107
<212> TYPE: RNA
<213> ORGANISM: Artificial Sequence
<220> FEATURE:
<223> OTHER INFORMATION: shmiR-14 sequence

<400> SEQUENCE: 56
gguauauugc uguugacagu gagcgaaccu augggagugg gccucaacug ugaagcagau        60
ggguugaggc ccacucccau agguacgccu acugccucgg acuucaa                    107

<210> SEQ ID NO 57
<211> LENGTH: 107
<212> TYPE: RNA
<213> ORGANISM: Artificial Sequence
<220> FEATURE:
<223> OTHER INFORMATION: shmiR-15 sequence

<400> SEQUENCE: 57
gguauauugc uguugacagu gagcgaagug guucguaggg cuuccacug ugaagcagau         60 ggguggaaag cccuacgaac cacugcgccu acugccucgg acuucaa                    107

<210> SEQ ID NO 58
<211> LENGTH: 107
<212> TYPE: RNA
<213> ORGANISM: Artificial Sequence
```

```
<220> FEATURE:
<223> OTHER INFORMATION: shmiR-16 sequence

<400> SEQUENCE: 58
gguauauugc uguugacagu gagcgagaac cuuuaccccg uugcccacug ugaagcagau      60 ggguggggcaa cggggguaaag guucacgccu acugccucgg acuucaa                 107

<210> SEQ ID NO 59
<211> LENGTH: 107
<212> TYPE: DNA
<213> ORGANISM: Artificial Sequence
<220> FEATURE:
<223> OTHER INFORMATION: DNA sequence coding for shmiR-1

<400> SEQUENCE: 59
ggtatattgc tgttgacagt gagcgacatc ctgctgctat gcctcaactg tgaagcagat      60
gggttgaggc atagcagcag gatgccgcct actgcctcgg acttcaa                   107

<210> SEQ ID NO 60
<211> LENGTH: 107
<212> TYPE: DNA
<213> ORGANISM: Artificial Sequence
<220> FEATURE:
<223> OTHER INFORMATION: DNA sequence coding for shmiR-2

<400> SEQUENCE: 60
ggtatattgc tgttgacagt gagcgatgct gacgcaaccc ccactgactg tgaagcagat      60
gggtcagtgg gggttgcgtc agcaacgcct actgcctcgg acttcaa                   107

<210> SEQ ID NO 61
<211> LENGTH: 107
<212> TYPE: DNA
<213> ORGANISM: Artificial Sequence
<220> FEATURE:
<223> OTHER INFORMATION: DNA sequence coding for shmiR-3

<400> SEQUENCE: 61
ggtatattgc tgttgacagt gagcgaaagc ctccaagctg tgccttactg tgaagcagat      60
gggtaaggca cagcttggag gcttgcgcct actgcctcgg acttcaa                   107

<210> SEQ ID NO 62
<211> LENGTH: 107
<212> TYPE: DNA
<213> ORGANISM: Artificial Sequence
<220> FEATURE:
<223> OTHER INFORMATION: DNA sequence coding for shmiR-4

<400> SEQUENCE: 62
ggtatattgc tgttgacagt gagcgagtcc cctagaagaa gaactcactg tgaagcagat      60
gggtgagttc ttcttctagg ggacccgcct actgcctcgg acttcaa                   107

<210> SEQ ID NO 63
<211> LENGTH: 107
<212> TYPE: DNA
<213> ORGANISM: Artificial Sequence
<220> FEATURE:
<223> OTHER INFORMATION: DNA sequence coding for shmiR-5

<400> SEQUENCE: 63
ggtatattgc tgttgacagt gagcgaccta gaagaagaac tccctcactg tgaagcagat      60
gggtgaggga gttcttcttc tagggcgcct actgcctcgg acttcaa                   107
```

```
<210> SEQ ID NO 64
<211> LENGTH: 107
<212> TYPE: DNA
<213> ORGANISM: Artificial Sequence
<220> FEATURE:
<223> OTHER INFORMATION: DNA sequence coding for shmiR-6

<400> SEQUENCE: 64
ggtatattgc tgttgacagt gagcgacagg tccctagaa gaagaaactg tgaagcagat      60
gggtttcttc ttctagggga cctgccgcct actgcctcgg acttcaa                 107

<210> SEQ ID NO 65
<211> LENGTH: 107
<212> TYPE: DNA
<213> ORGANISM: Artificial Sequence
<220> FEATURE:
<223> OTHER INFORMATION: DNA sequence coding for shmiR-7

<400> SEQUENCE: 65
ggtatattgc tgttgacagt gagcgaaagg tatgttgccc gtttgtactg tgaagcagat      60
gggtacaaac gggcaacata ccttgcgcct actgcctcgg acttcaa                 107

<210> SEQ ID NO 66
<211> LENGTH: 107
<212> TYPE: DNA
<213> ORGANISM: Artificial Sequence
<220> FEATURE:
<223> OTHER INFORMATION: DNA sequence coding for shmiR-8

<400> SEQUENCE: 66
ggtatattgc tgttgacagt gagcgatcgt ggtggacttc tctcaaactg tgaagcagat      60
gggtttgaga gaagtccacc acgagcgcct actgcctcgg acttcaa                 107

<210> SEQ ID NO 67
<211> LENGTH: 107
<212> TYPE: DNA
<213> ORGANISM: Artificial Sequence
<220> FEATURE:
<223> OTHER INFORMATION: DNA sequence coding for shmiR-9

<400> SEQUENCE: 67
ggtatattgc tgttgacagt gagcgatcgt gttacaggcg gggtttactg tgaagcagat      60
gggtaaaccc cgcctgtaac acgagcgcct actgcctcgg acttcaa                 107

<210> SEQ ID NO 68
<211> LENGTH: 107
<212> TYPE: DNA
<213> ORGANISM: Artificial Sequence
<220> FEATURE:
<223> OTHER INFORMATION: DNA sequence coding for shmiR-10

<400> SEQUENCE: 68
ggtatattgc tgttgacagt gagcgacact tcgcttcacc tctgcaactg tgaagcagat      60
gggttgcaga ggtgaagcga agtgccgcct actgcctcgg acttcaa                 107

<210> SEQ ID NO 69
<211> LENGTH: 107
<212> TYPE: DNA
<213> ORGANISM: Artificial Sequence
<220> FEATURE:
<223> OTHER INFORMATION: DNA sequence coding for shmiR-11

<400> SEQUENCE: 69
```

```
ggtatattgc tgttgacagt gagcgacgtc ccgtcggcgc tgaatcactg tgaagcagat    60
gggtgattca gcgccgacgg gacgacgcct actgcctcgg acttcaa                 107
```

<210> SEQ ID NO 70
<211> LENGTH: 107
<212> TYPE: DNA
<213> ORGANISM: Artificial Sequence
<220> FEATURE:
<223> OTHER INFORMATION: DNA sequence coding for shmiR-12

<400> SEQUENCE: 70

```
ggtatattgc tgttgacagt gagcgagtcc cgtcggcgct gaatccactg tgaagcagat    60
gggtggattc agcgccgacg ggacgcgcct actgcctcgg acttcaa                 107
```

<210> SEQ ID NO 71
<211> LENGTH: 107
<212> TYPE: DNA
<213> ORGANISM: Artificial Sequence
<220> FEATURE:
<223> OTHER INFORMATION: DNA sequence coding for shmiR-13

<400> SEQUENCE: 71

```
ggtatattgc tgttgacagt gagcgacaaa tgcccctatc ttatcaactg tgaagcagat    60
gggttgataa gatagggggca tttggcgcct actgcctcgg acttcaa                107
```

<210> SEQ ID NO 72
<211> LENGTH: 107
<212> TYPE: DNA
<213> ORGANISM: Artificial Sequence
<220> FEATURE:
<223> OTHER INFORMATION: DNA sequence coding for shmiR-14

<400> SEQUENCE: 72

```
ggtatattgc tgttgacagt gagcgaacct atgggagtgg gcctcaactg tgaagcagat    60
gggttgaggc ccactcccat aggtacgcct actgcctcgg acttcaa                 107
```

<210> SEQ ID NO 73
<211> LENGTH: 107
<212> TYPE: DNA
<213> ORGANISM: Artificial Sequence
<220> FEATURE:
<223> OTHER INFORMATION: DNA sequence coding for shmiR-15

<400> SEQUENCE: 73

```
ggtatattgc tgttgacagt gagcgaagtg gttcgtaggg ctttccactg tgaagcagat    60
gggtggaaag ccctacgaac cactgcgcct actgcctcgg acttcaa                 107
```

<210> SEQ ID NO 74
<211> LENGTH: 107
<212> TYPE: DNA
<213> ORGANISM: Artificial Sequence
<220> FEATURE:
<223> OTHER INFORMATION: DNA sequence coding for shmiR-16

<400> SEQUENCE: 74

```
ggtatattgc tgttgacagt gagcgagaac ctttaccccg ttgcccactg tgaagcagat    60
gggtgggcaa cggggtaaag gttcacgcct actgcctcgg acttcaa                 107
```

<210> SEQ ID NO 75
<211> LENGTH: 18
<212> TYPE: RNA

```
<213> ORGANISM: Artificial Sequence
<220> FEATURE:
<223> OTHER INFORMATION: Stemloop

<400> SEQUENCE: 75
acugugaagc agaugggu                                                    18

<210> SEQ ID NO 76
<211> LENGTH: 26
<212> TYPE: RNA
<213> ORGANISM: Artificial Sequence
<220> FEATURE:
<223> OTHER INFORMATION: miR-30a backbone 5' flanking sequnece

<400> SEQUENCE: 76
gguauauugc uguugacagu gagcga                                           26

<210> SEQ ID NO 77
<211> LENGTH: 22
<212> TYPE: RNA
<213> ORGANISM: Artificial Sequence
<220> FEATURE:
<223> OTHER INFORMATION: miR-30a backbone 3' flanking sequnece

<400> SEQUENCE: 77
cgccuacugc cucggacuuc aa                                               22

<210> SEQ ID NO 78
<211> LENGTH: 47
<212> TYPE: RNA
<213> ORGANISM: Artificial Sequence
<220> FEATURE:
<223> OTHER INFORMATION: shRNA-1 sequence

<400> SEQUENCE: 78
cauccugcug cuaugccuca caagagauga ggcauagcag caggaug                    47

<210> SEQ ID NO 79
<211> LENGTH: 47
<212> TYPE: RNA
<213> ORGANISM: Artificial Sequence
<220> FEATURE:
<223> OTHER INFORMATION: shRNA-2 sequence

<400> SEQUENCE: 79
gcugacgcaa cccccacugg caagagacca gugggguug cgucagc                     47

<210> SEQ ID NO 80
<211> LENGTH: 47
<212> TYPE: RNA
<213> ORGANISM: Artificial Sequence
<220> FEATURE:
<223> OTHER INFORMATION: shRNA-3 sequence

<400> SEQUENCE: 80
aagccuccaa gcugugccuu ugugcuuaag gcacagcuug gaggcuu                    47

<210> SEQ ID NO 81
<211> LENGTH: 49
<212> TYPE: RNA
<213> ORGANISM: Artificial Sequence
<220> FEATURE:
<223> OTHER INFORMATION: shRNA-4 sequence

<400> SEQUENCE: 81
gguccccuag aagaagaacu ccaagagaga guucuucuuc uaggggacc                  49
```

```
<210> SEQ ID NO 82
<211> LENGTH: 49
<212> TYPE: RNA
<213> ORGANISM: Artificial Sequence
<220> FEATURE:
<223> OTHER INFORMATION: shRNA-5 sequence

<400> SEQUENCE: 82
cccuagaaga agaacucccu ccaagagaga gggaguucuu cuucuaggg          49

<210> SEQ ID NO 83
<211> LENGTH: 49
<212> TYPE: RNA
<213> ORGANISM: Artificial Sequence
<220> FEATURE:
<223> OTHER INFORMATION: shRNA-6 sequence

<400> SEQUENCE: 83 gcagguccccc uagaagaaga acaagagauu cuucuucuag gggaccugc          49

<210> SEQ ID NO 84
<211> LENGTH: 49
<212> TYPE: RNA
<213> ORGANISM: Artificial Sequence
<220> FEATURE:
<223> OTHER INFORMATION: shRNA-7 sequence

<400> SEQUENCE: 84
caagguaugu ugcccguuug ucaagagaac aaacgggcaa cauaccuug          49

<210> SEQ ID NO 85
<211> LENGTH: 47
<212> TYPE: RNA
<213> ORGANISM: Artificial Sequence
<220> FEATURE:
<223> OTHER INFORMATION: shRNA-8 sequence

<400> SEQUENCE: 85
cucguggugg acuucucuca caagagauga gagaagucca ccacgag            47

<210> SEQ ID NO 86
<211> LENGTH: 49
<212> TYPE: RNA
<213> ORGANISM: Artificial Sequence
<220> FEATURE:
<223> OTHER INFORMATION: shRNA-9 sequence

<400> SEQUENCE: 86
cucguguuac aggcggggu uugugcuuaa accccgccug uaacacgag          49

<210> SEQ ID NO 87
<211> LENGTH: 49
<212> TYPE: RNA
<213> ORGANISM: Artificial Sequence
<220> FEATURE:
<223> OTHER INFORMATION: shRNA-10 sequence

<400> SEQUENCE: 87
gcacuucgcu ucaccucugc acaagagaug cagaggugaa gcgaagugc          49

<210> SEQ ID NO 88
<211> LENGTH: 49
<212> TYPE: RNA
<213> ORGANISM: Artificial Sequence
<220> FEATURE:
```

<223> OTHER INFORMATION: shRNA-11 sequence

<400> SEQUENCE: 88
acgucccguc ggcgcugaau cugugcuuga uucagcgccg acgggacgu        49

<210> SEQ ID NO 89
<211> LENGTH: 49
<212> TYPE: RNA
<213> ORGANISM: Artificial Sequence
<220> FEATURE:
<223> OTHER INFORMATION: shRNA-12 sequence

<400> SEQUENCE: 89
cgucccgucg gcgcugaauc cugugcuugg auucagcgcc gacgggacg        49

<210> SEQ ID NO 90
<211> LENGTH: 45
<212> TYPE: RNA
<213> ORGANISM: Artificial Sequence
<220> FEATURE:
<223> OTHER INFORMATION: shRNA-13 sequence

<400> SEQUENCE: 90
aaaugccccu aucuuaucau gugcuuugau aagauagggg cauuu        45

<210> SEQ ID NO 91
<211> LENGTH: 51
<212> TYPE: RNA
<213> ORGANISM: Artificial Sequence
<220> FEATURE:
<223> OTHER INFORMATION: shRNA-14 sequence

<400> SEQUENCE: 91
auaccuaugg gagugggccu cacaagagau gaggcccacu cccauaggua u        51

<210> SEQ ID NO 92
<211> LENGTH: 51
<212> TYPE: RNA
<213> ORGANISM: Artificial Sequence
<220> FEATURE:
<223> OTHER INFORMATION: shRNA-15 sequence

<400> SEQUENCE: 92
cagugguucg uagggcuuuc cccaagagag ggaaagcccu acgaaccacu g        51

<210> SEQ ID NO 93
<211> LENGTH: 51
<212> TYPE: RNA
<213> ORGANISM: Artificial Sequence
<220> FEATURE:
<223> OTHER INFORMATION: shRNA-16 sequence

<400> SEQUENCE: 93
gaaccuuuac cccguugccc ggcaagagac cgggcaacgg gguaaagguu c        51

<210> SEQ ID NO 94
<211> LENGTH: 47
<212> TYPE: DNA
<213> ORGANISM: Artificial Sequence
<220> FEATURE:
<223> OTHER INFORMATION: DNA sequence coding for shRNA-1

<400> SEQUENCE: 94
catcctgctg ctatgcctca caagagatga ggcatagcag caggatg        47

```
<210> SEQ ID NO 95
<211> LENGTH: 47
<212> TYPE: DNA
<213> ORGANISM: Artificial Sequence
<220> FEATURE:
<223> OTHER INFORMATION: DNA sequence coding for shRNA-2

<400> SEQUENCE: 95
gctgacgcaa cccccactgg caagagacca gtgggggttg cgtcagc                    47

<210> SEQ ID NO 96
<211> LENGTH: 47
<212> TYPE: DNA
<213> ORGANISM: Artificial Sequence
<220> FEATURE:
<223> OTHER INFORMATION: DNA sequence coding for shRNA-3

<400> SEQUENCE: 96
aagcctccaa gctgtgcctt tgtgcttaag gcacagcttg gaggctt                    47

<210> SEQ ID NO 97
<211> LENGTH: 49
<212> TYPE: DNA
<213> ORGANISM: Artificial Sequence
<220> FEATURE:
<223> OTHER INFORMATION: DNA sequence coding for shRNA-4

<400> SEQUENCE: 97
ggtcccctag aagaagaact ccaagagaga gttcttcttc tagggacc                   49

<210> SEQ ID NO 98
<211> LENGTH: 49
<212> TYPE: DNA
<213> ORGANISM: Artificial Sequence
<220> FEATURE:
<223> OTHER INFORMATION: DNA sequence coding for shRNA-5

<400> SEQUENCE: 98
ccctagaaga agaactccct ccaagagaga gggagttctt cttctaggg                  49

<210> SEQ ID NO 99
<211> LENGTH: 49
<212> TYPE: DNA
<213> ORGANISM: Artificial Sequence
<220> FEATURE:
<223> OTHER INFORMATION: DNA sequence coding for shRNA-6

<400> SEQUENCE: 99
gcaggtcccc tagaagaaga acaagagatt cttcttctag gggacctgc                  49

<210> SEQ ID NO 100
<211> LENGTH: 49
<212> TYPE: DNA
<213> ORGANISM: Artificial Sequence
<220> FEATURE:
<223> OTHER INFORMATION: DNA sequence coding for shRNA-7

<400> SEQUENCE: 100
caaggtatgt tgcccgtttg tcaagagaac aaacgggcaa cataccttg                  49

<210> SEQ ID NO 101
<211> LENGTH: 47
<212> TYPE: DNA
<213> ORGANISM: Artificial Sequence
<220> FEATURE:
<223> OTHER INFORMATION: DNA sequence coding for shRNA-8
```

```
<400> SEQUENCE: 101
ctcgtggtgg acttctctca caagagatga gagaagtcca ccacgag         47

<210> SEQ ID NO 102
<211> LENGTH: 49
<212> TYPE: DNA
<213> ORGANISM: Artificial Sequence
<220> FEATURE:
<223> OTHER INFORMATION: DNA sequence coding for shRNA-9

<400> SEQUENCE: 102
ctcgtgttac aggcggggtt ttgtgcttaa accccgcctg taacacgag       49

<210> SEQ ID NO 103
<211> LENGTH: 49
<212> TYPE: DNA
<213> ORGANISM: Artificial Sequence
<220> FEATURE:
<223> OTHER INFORMATION: DNA sequence coding for shRNA-10

<400> SEQUENCE: 103
gcacttcgct tcacctctgc acaagagatg cagaggtgaa gcgaagtgc       49

<210> SEQ ID NO 104
<211> LENGTH: 49
<212> TYPE: DNA
<213> ORGANISM: Artificial Sequence
<220> FEATURE:
<223> OTHER INFORMATION: DNA sequence coding for shRNA-11

<400> SEQUENCE: 104
acgtcccgtc ggcgctgaat ctgtgcttga ttcagcgccg acgggacgt       49

<210> SEQ ID NO 105
<211> LENGTH: 49
<212> TYPE: DNA
<213> ORGANISM: Artificial Sequence
<220> FEATURE:
<223> OTHER INFORMATION: DNA sequence coding for shRNA-12

<400> SEQUENCE: 105
cgtcccgtcg gcgctgaatc ctgtgcttgg attcagcgcc gacgggacg       49

<210> SEQ ID NO 106
<211> LENGTH: 45
<212> TYPE: DNA
<213> ORGANISM: Artificial Sequence
<220> FEATURE:
<223> OTHER INFORMATION: DNA sequence coding for shRNA-13

<400> SEQUENCE: 106
aaatgcccct atcttatcat gtgctttgat aagatagggg cattt           45

<210> SEQ ID NO 107
<211> LENGTH: 51
<212> TYPE: DNA
<213> ORGANISM: Artificial Sequence
<220> FEATURE:
<223> OTHER INFORMATION: DNA sequence coding for shRNA-14

<400> SEQUENCE: 107
atacctatgg gagtgggcct cacaagagat gaggcccact cccataggta t    51

<210> SEQ ID NO 108
<211> LENGTH: 51
```

```
<212> TYPE: DNA
<213> ORGANISM: Artificial Sequence
<220> FEATURE:
<223> OTHER INFORMATION: DNA sequence coding for shRNA-15

<400> SEQUENCE: 108
cagtggttcg tagggctttc cccaagagag ggaaagccct acgaaccact g        51

<210> SEQ ID NO 109
<211> LENGTH: 51
<212> TYPE: DNA
<213> ORGANISM: Artificial Sequence
<220> FEATURE:
<223> OTHER INFORMATION: DNA sequence coding for shRNA-16

<400> SEQUENCE: 109
gaacctttac cccgttgccc ggcaagagac cgggcaacgg ggtaaaggtt c         51

<210> SEQ ID NO 110
<211> LENGTH: 21
<212> TYPE: RNA
<213> ORGANISM: Artificial Sequence
<220> FEATURE:
<223> OTHER INFORMATION: shmiR-17 effector

<400> SEQUENCE: 110
gggaaagccc uacgaaccac a                                          21

<210> SEQ ID NO 111
<211> LENGTH: 20
<212> TYPE: RNA
<213> ORGANISM: Artificial Sequence
<220> FEATURE:
<223> OTHER INFORMATION: shmiR-17 effector complement

<400> SEQUENCE: 111
gugguucgua gggcuuuccc                                            20

<210> SEQ ID NO 112
<211> LENGTH: 21
<212> TYPE: RNA
<213> ORGANISM: Artificial Sequence
<220> FEATURE:
<223> OTHER INFORMATION: shmiR-18 effector

<400> SEQUENCE: 112
ggggaaagcc cuacgaacca c                                          21

<210> SEQ ID NO 113
<211> LENGTH: 20
<212> TYPE: RNA
<213> ORGANISM: Artificial Sequence
<220> FEATURE:
<223> OTHER INFORMATION: shmiR-18 effector complement

<400> SEQUENCE: 113
ugguucguag ggcuuucccc                                            20

<210> SEQ ID NO 114
<211> LENGTH: 21
<212> TYPE: RNA
<213> ORGANISM: Artificial Sequence
<220> FEATURE:
<223> OTHER INFORMATION: shmiR-19 effector

<400> SEQUENCE: 114
```
uggaaagccc uacgaaccac a                                      21

<210> SEQ ID NO 115
<211> LENGTH: 20
<212> TYPE: RNA
<213> ORGANISM: Artificial Sequence
<220> FEATURE:
<223> OTHER INFORMATION: shmiR-19 effector complement

<400> SEQUENCE: 115
gugguucgua gggcuuucca                                        20

<210> SEQ ID NO 116
<211> LENGTH: 21
<212> TYPE: RNA
<213> ORGANISM: Artificial Sequence
<220> FEATURE:
<223> OTHER INFORMATION: shmiR-20 effector

<400> SEQUENCE: 116
gaaagcccua cgaaccacug a                                      21

<210> SEQ ID NO 117
<211> LENGTH: 20
<212> TYPE: RNA
<213> ORGANISM: Artificial Sequence
<220> FEATURE:
<223> OTHER INFORMATION: shmiR-20 effector complement

<400> SEQUENCE: 117
cagugguucg uagggcuuuc                                        20

<210> SEQ ID NO 118
<211> LENGTH: 21
<212> TYPE: RNA
<213> ORGANISM: Artificial Sequence
<220> FEATURE:
<223> OTHER INFORMATION: shmiR-21 effector

<400> SEQUENCE: 118
aaagcccuac gaaccacuga a                                      21

<210> SEQ ID NO 119
<211> LENGTH: 20
<212> TYPE: RNA
<213> ORGANISM: Artificial Sequence
<220> FEATURE:
<223> OTHER INFORMATION: shmiR-21 effector complement

<400> SEQUENCE: 119
ucagugguuc guagggcuuu                                        20

<210> SEQ ID NO 120
<211> LENGTH: 21
<212> TYPE: RNA
<213> ORGANISM: Artificial Sequence
<220> FEATURE:
<223> OTHER INFORMATION: shmiR-22 effector

<400> SEQUENCE: 120
aaagcccuac gaaccacugc a                                      21

<210> SEQ ID NO 121
<211> LENGTH: 20
<212> TYPE: RNA
<213> ORGANISM: Artificial Sequence

```
<220> FEATURE:
<223> OTHER INFORMATION: shmiR-22 effector complement

<400> SEQUENCE: 121
gcagugguuc guagggcuuu                                               20

<210> SEQ ID NO 122
<211> LENGTH: 21
<212> TYPE: RNA
<213> ORGANISM: Artificial Sequence
<220> FEATURE:
<223> OTHER INFORMATION: shmiR-23 effector

<400> SEQUENCE: 122
gggauucagc gccgacggga c                                             21

<210> SEQ ID NO 123
<211> LENGTH: 20
<212> TYPE: RNA
<213> ORGANISM: Artificial Sequence
<220> FEATURE:
<223> OTHER INFORMATION: shmiR-23 effector complement

<400> SEQUENCE: 123
ucccgucggc gcugaauccc                                               20

<210> SEQ ID NO 124
<211> LENGTH: 21
<212> TYPE: RNA
<213> ORGANISM: Artificial Sequence
<220> FEATURE:
<223> OTHER INFORMATION: shmiR-24 effector

<400> SEQUENCE: 124
cgggauucag cgccgacggg a                                             21

<210> SEQ ID NO 125
<211> LENGTH: 20
<212> TYPE: RNA
<213> ORGANISM: Artificial Sequence
<220> FEATURE:
<223> OTHER INFORMATION: shmiR-24 effector complement

<400> SEQUENCE: 125
cccgucggcg cugaaucccg                                               20

<210> SEQ ID NO 126
<211> LENGTH: 21
<212> TYPE: RNA
<213> ORGANISM: Artificial Sequence
<220> FEATURE:
<223> OTHER INFORMATION: shmiR-25 effector

<400> SEQUENCE: 126
uggauucagc gccgacggga c                                             21

<210> SEQ ID NO 127
<211> LENGTH: 20
<212> TYPE: RNA
<213> ORGANISM: Artificial Sequence
<220> FEATURE:
<223> OTHER INFORMATION: shmiR-25 effector complement

<400> SEQUENCE: 127
ucccgucggc gcugaaucca                                               20
```

```
<210> SEQ ID NO 128
<211> LENGTH: 21
<212> TYPE: RNA
<213> ORGANISM: Artificial Sequence
<220> FEATURE:
<223> OTHER INFORMATION: shmiR-26 effector

<400> SEQUENCE: 128
gauucagcgc cgacgggacg a                                              21

<210> SEQ ID NO 129
<211> LENGTH: 20
<212> TYPE: RNA
<213> ORGANISM: Artificial Sequence
<220> FEATURE:
<223> OTHER INFORMATION: shmiR-26 effector complement

<400> SEQUENCE: 129
cgucccgucg gcgcugaauc                                                20

<210> SEQ ID NO 130
<211> LENGTH: 21
<212> TYPE: RNA
<213> ORGANISM: Artificial Sequence
<220> FEATURE:
<223> OTHER INFORMATION: shmiR-27 effector

<400> SEQUENCE: 130
auucagcgcc gacgggacgu a                                              21

<210> SEQ ID NO 131
<211> LENGTH: 20
<212> TYPE: RNA
<213> ORGANISM: Artificial Sequence
<220> FEATURE:
<223> OTHER INFORMATION: shmiR-27 effector complement

<400> SEQUENCE: 131
acgucccguc ggcgcugaau                                                20

<210> SEQ ID NO 132
<211> LENGTH: 21
<212> TYPE: RNA
<213> ORGANISM: Artificial Sequence
<220> FEATURE:
<223> OTHER INFORMATION: shmiR-28 effector

<400> SEQUENCE: 132
auucagcgcc gacgggacgc a                                              21

<210> SEQ ID NO 133
<211> LENGTH: 20
<212> TYPE: RNA
<213> ORGANISM: Artificial Sequence
<220> FEATURE:
<223> OTHER INFORMATION: shmiR-28 effector complement

<400> SEQUENCE: 133
gcgucccguc ggcgcugaau                                                20

<210> SEQ ID NO 134
<211> LENGTH: 107
<212> TYPE: RNA
<213> ORGANISM: Artificial Sequence
<220> FEATURE:
<223> OTHER INFORMATION: shmiR-17 sequence
```

```
<400> SEQUENCE: 134
gguauauugc uguugacagu gagcgagugg uucguagggc uuucccacug ugaagcagau     60 ggguggaaa gcccuacgaa ccacacgccu acugccucgg acuucaa                  107

<210> SEQ ID NO 135
<211> LENGTH: 107
<212> TYPE: RNA
<213> ORGANISM: Artificial Sequence
<220> FEATURE:
<223> OTHER INFORMATION: shmiR-18 sequence

<400> SEQUENCE: 135
gguauauugc uguugacagu gagcgauggu ucguagggcu uucccacug ugaagcagau     60 ggguggggaa agcccuacga accaccgccu acugccucgg acuucaa                 107

<210> SEQ ID NO 136
<211> LENGTH: 107
<212> TYPE: RNA
<213> ORGANISM: Artificial Sequence
<220> FEATURE:
<223> OTHER INFORMATION: shmiR-19 sequence

<400> SEQUENCE: 136
gguauauugc uguugacagu gagcgagugg uucguagggc uuccaacug ugaagcagau     60 ggguuggaaa gcccuacgaa ccacacgccu acugccucgg acuucaa                 107

<210> SEQ ID NO 137
<211> LENGTH: 107
<212> TYPE: RNA
<213> ORGANISM: Artificial Sequence
<220> FEATURE:
<223> OTHER INFORMATION: shmiR-20 sequence

<400> SEQUENCE: 137
gguauauugc uguugacagu gagcgacagu gguucguagg gcuuucacug ugaagcagau    60
gggugaaagc ccuacgaacc acugacgccu acugccucgg acuucaa                 107

<210> SEQ ID NO 138
<211> LENGTH: 107
<212> TYPE: RNA
<213> ORGANISM: Artificial Sequence
<220> FEATURE:
<223> OTHER INFORMATION: shmiR-21 sequence

<400> SEQUENCE: 138
gguauauugc uguugacagu gagcgaucag ugguucguag gcuuuacug ugaagcagau     60 ggguaaagcc cuacgaacca cugaacgccu acugccucgg acuucaa                 107

<210> SEQ ID NO 139
<211> LENGTH: 107
<212> TYPE: RNA
<213> ORGANISM: Artificial Sequence
<220> FEATURE:
<223> OTHER INFORMATION: shmiR-22 sequence

<400> SEQUENCE: 139
gguauauugc uguugacagu gagcgagcag ugguucguag gcuuuacug ugaagcagau     60 ggguaaagcc cuacgaacca cugcacgccu acugccucgg acuucaa                 107

<210> SEQ ID NO 140
```

```
<211> LENGTH: 107
<212> TYPE: RNA
<213> ORGANISM: Artificial Sequence
<220> FEATURE:
<223> OTHER INFORMATION: shmiR-23 sequence

<400> SEQUENCE: 140
gguauauugc uguugacagu gagcgauccc gucggcgcug aaucccacug ugaagcagau    60 ggguggauu cagcgccgac gggaccgccu acugccucgg acuucaa                 107

<210> SEQ ID NO 141
<211> LENGTH: 107
<212> TYPE: RNA
<213> ORGANISM: Artificial Sequence
<220> FEATURE:
<223> OTHER INFORMATION: shmiR-24 sequence

<400> SEQUENCE: 141
gguauauugc uguugacagu gagcgacccg ucggcgcuga aucccgacug ugaagcagau    60 ggucgggau ucagcgccga cgggacgccu acugccucgg acuucaa                 107

<210> SEQ ID NO 142
<211> LENGTH: 107
<212> TYPE: RNA
<213> ORGANISM: Artificial Sequence
<220> FEATURE:
<223> OTHER INFORMATION: shmiR-25 sequence

<400> SEQUENCE: 142
gguauauugc uguugacagu gagcgauccc gucggcgcug aauccaacug ugaagcagau    60
ggguuggauu cagcgccgac gggaccgccu acugccucgg acuucaa                107

<210> SEQ ID NO 143
<211> LENGTH: 107
<212> TYPE: RNA
<213> ORGANISM: Artificial Sequence
<220> FEATURE:
<223> OTHER INFORMATION: shmiR-26 sequence

<400> SEQUENCE: 143
gguauauugc uguugacagu gagcgacguc ccgucggcgc ugaaucacug ugaagcagau    60 ggguugauuca gcgccgacgg gacgacgccu acugccucgg acuucaa                107

<210> SEQ ID NO 144
<211> LENGTH: 107
<212> TYPE: RNA
<213> ORGANISM: Artificial Sequence
<220> FEATURE:
<223> OTHER INFORMATION: shmiR-27 sequence

<400> SEQUENCE: 144
gguauauugc uguugacagu gagcgaacgu cccgucggcg cugaauacug ugaagcagau    60
ggguauucag cgccgacggg acguacgccu acugccucgg acuucaa                107

<210> SEQ ID NO 145
<211> LENGTH: 107
<212> TYPE: RNA
<213> ORGANISM: Artificial Sequence
<220> FEATURE:
<223> OTHER INFORMATION: shmiR-28 sequence

<400> SEQUENCE: 145
gguauauugc uguugacagu gagcgagcgu cccgucggcg cugaauacug ugaagcagau    60
```

```
ggguauucag cgccgacggg acgcacgccu acugccucgg acuucaa              107
```

<210> SEQ ID NO 146
<211> LENGTH: 107
<212> TYPE: DNA
<213> ORGANISM: Artificial Sequence
<220> FEATURE:
<223> OTHER INFORMATION: DNA sequence coding for shmiR-17

<400> SEQUENCE: 146

```
ggtatattgc tgttgacagt gagcgagtgg ttcgtagggc tttcccactg tgaagcagat   60
gggtgggaaa gccctacgaa ccacacgcct actgcctcgg acttcaa                107
```

<210> SEQ ID NO 147
<211> LENGTH: 107
<212> TYPE: DNA
<213> ORGANISM: Artificial Sequence
<220> FEATURE:
<223> OTHER INFORMATION: DNA sequence coding for shmiR-18

<400> SEQUENCE: 147

```
ggtatattgc tgttgacagt gagcgatggt tcgtagggct ttccccactg tgaagcagat   60
gggtggggaa agccctacga accaccgcct actgcctcgg acttcaa                107
```

<210> SEQ ID NO 148
<211> LENGTH: 107
<212> TYPE: DNA
<213> ORGANISM: Artificial Sequence
<220> FEATURE:
<223> OTHER INFORMATION: DNA sequence coding for shmiR-19

<400> SEQUENCE: 148

```
ggtatattgc tgttgacagt gagcgagtgg ttcgtagggc tttccaactg tgaagcagat   60
gggttggaaa gccctacgaa ccacacgcct actgcctcgg acttcaa                107
```

<210> SEQ ID NO 149
<211> LENGTH: 107
<212> TYPE: DNA
<213> ORGANISM: Artificial Sequence
<220> FEATURE:
<223> OTHER INFORMATION: DNA sequence coding for shmiR-20

<400> SEQUENCE: 149

```
ggtatattgc tgttgacagt gagcgacagt ggttcgtagg gctttcactg tgaagcagat   60
gggtgaaagc cctacgaacc actgacgcct actgcctcgg acttcaa                107
```

<210> SEQ ID NO 150
<211> LENGTH: 107
<212> TYPE: DNA
<213> ORGANISM: Artificial Sequence
<220> FEATURE:
<223> OTHER INFORMATION: DNA sequence coding for shmiR-21

<400> SEQUENCE: 150

```
ggtatattgc tgttgacagt gagcgatcag tggttcgtag ggctttactg tgaagcagat   60
gggtaaagcc ctacgaacca ctgaacgcct actgcctcgg acttcaa                107
```

<210> SEQ ID NO 151
<211> LENGTH: 107
<212> TYPE: DNA
<213> ORGANISM: Artificial Sequence
<220> FEATURE:

<223> OTHER INFORMATION: DNA sequence coding for shmiR-22

<400> SEQUENCE: 151
ggtatattgc tgttgacagt gagcgagcag tggttcgtag ggctttactg tgaagcagat      60
gggtaaagcc ctacgaacca ctgcacgcct actgcctcgg acttcaa                  107

<210> SEQ ID NO 152
<211> LENGTH: 107
<212> TYPE: DNA
<213> ORGANISM: Artificial Sequence
<220> FEATURE:
<223> OTHER INFORMATION: DNA sequence coding for shmiR-23

<400> SEQUENCE: 152
ggtatattgc tgttgacagt gagcgatccc gtcggcgctg aatcccactg tgaagcagat      60
gggtgggatt cagcgccgac gggaccgcct actgcctcgg acttcaa                  107

<210> SEQ ID NO 153
<211> LENGTH: 107
<212> TYPE: DNA
<213> ORGANISM: Artificial Sequence
<220> FEATURE:
<223> OTHER INFORMATION: DNA sequence coding for shmiR-24

<400> SEQUENCE: 153
ggtatattgc tgttgacagt gagcgacccg tcggcgctga atccgactg tgaagcagat       60 gggtcgggat tcagcgccga cgggacgcct actgcctcgg acttcaa                  107

<210> SEQ ID NO 154
<211> LENGTH: 107
<212> TYPE: DNA
<213> ORGANISM: Artificial Sequence
<220> FEATURE:
<223> OTHER INFORMATION: DNA sequence coding for shmiR-25

<400> SEQUENCE: 154
ggtatattgc tgttgacagt gagcgatccc gtcggcgctg aatccaactg tgaagcagat      60
gggttggatt cagcgccgac gggaccgcct actgcctcgg acttcaa                  107

<210> SEQ ID NO 155
<211> LENGTH: 107
<212> TYPE: DNA
<213> ORGANISM: Artificial Sequence
<220> FEATURE:
<223> OTHER INFORMATION: DNA sequence coding for shmiR-26

<400> SEQUENCE: 155
ggtatattgc tgttgacagt gagcgacgtc ccgtcggcgc tgaatcactg tgaagcagat      60
gggtgattca gcgccgacgg gacgcgcct actgcctcgg acttcaa                   107

<210> SEQ ID NO 156
<211> LENGTH: 107
<212> TYPE: DNA
<213> ORGANISM: Artificial Sequence
<220> FEATURE:
<223> OTHER INFORMATION: DNA sequence coding for shmiR-27

<400> SEQUENCE: 156
ggtatattgc tgttgacagt gagcgaacgt cccgtcggcg ctgaatactg tgaagcagat      60
gggtattcag cgccgacggg acgtacgcct actgcctcgg acttcaa                  107

<210> SEQ ID NO 157
<211> LENGTH: 107
<212> TYPE: DNA
<213> ORGANISM: Artificial Sequence
<220> FEATURE:
<223> OTHER INFORMATION: DNA sequence coding for shmiR-28

<400> SEQUENCE: 157
ggtatattgc tgttgacagt gagcgagcgt cccgtcggcg ctgaatactg tgaagcagat    60
gggtattcag cgccgacggg acgcacgcct actgcctcgg acttcaa                 107

<210> SEQ ID NO 158
<211> LENGTH: 21
<212> TYPE: DNA
<213> ORGANISM: Artificial Sequence
<220> FEATURE:
<223> OTHER INFORMATION: HBV forward primer

<400> SEQUENCE: 158
cacatcagga ttcctaggac c                                              21

<210> SEQ ID NO 159
<211> LENGTH: 20
<212> TYPE: DNA
<213> ORGANISM: Artificial Sequence
<220> FEATURE:
<223> OTHER INFORMATION: HBV reverse primer

<400> SEQUENCE: 159
aggttggtga gtgattggag                                                20

<210> SEQ ID NO 160
<211> LENGTH: 26
<212> TYPE: DNA
<213> ORGANISM: Artificial Sequence
<220> FEATURE:
<223> OTHER INFORMATION: HBV TaqMan probe

<400> SEQUENCE: 160
cagagtctag actcgtggtg gacttc                                         26

<210> SEQ ID NO 161
<211> LENGTH: 19
<212> TYPE: DNA
<213> ORGANISM: Artificial Sequence
<220> FEATURE:
<223> OTHER INFORMATION: HBV cccDNA forward primer

<400> SEQUENCE: 161
ctccccgtct gtgccttct                                                 19

<210> SEQ ID NO 162
<211> LENGTH: 18
<212> TYPE: DNA
<213> ORGANISM: Artificial Sequence
<220> FEATURE:
<223> OTHER INFORMATION: HBV cccDNA reverse primer

<400> SEQUENCE: 162
gccccaaagc cacccaag                                                  18

<210> SEQ ID NO 163
<211> LENGTH: 27
<212> TYPE: DNA
<213> ORGANISM: Artificial Sequence
<220> FEATURE:

<223> OTHER INFORMATION: HBV cccDNA TaqMan probe

<400> SEQUENCE: 163
cgtcgcatgg araccaccgt gaacgcc                27

<210> SEQ ID NO 164
<211> LENGTH: 69
<212> TYPE: DNA
<213> ORGANISM: Artificial Sequence
<220> FEATURE:
<223> OTHER INFORMATION: shRNA-6 DNA sequence with flanking region

<400> SEQUENCE: 164
caacggatcc gcaggtcccc tagaagaaga acaagagatt cttcttctag gggacctgct    60
tttttagat                                                            69

<210> SEQ ID NO 165
<211> LENGTH: 16
<212> TYPE: DNA
<213> ORGANISM: Artificial Sequence
<220> FEATURE:
<223> OTHER INFORMATION: shRNA-6 effector species 1

<400> SEQUENCE: 165
ttcttctagg ggacct                16

<210> SEQ ID NO 166
<211> LENGTH: 17
<212> TYPE: DNA
<213> ORGANISM: Artificial Sequence
<220> FEATURE:
<223> OTHER INFORMATION: shRNA-6 effector species 2

<400> SEQUENCE: 166
ttcttctagg ggacctg                17

<210> SEQ ID NO 167
<211> LENGTH: 18
<212> TYPE: DNA
<213> ORGANISM: Artificial Sequence
<220> FEATURE:
<223> OTHER INFORMATION: shRNA-6 effector species 3

<400> SEQUENCE: 167
ttcttctagg ggacctgc                18

<210> SEQ ID NO 168
<211> LENGTH: 19
<212> TYPE: DNA
<213> ORGANISM: Artificial Sequence
<220> FEATURE:
<223> OTHER INFORMATION: shRNA-6 effector species 4

<400> SEQUENCE: 168
ttcttctagg ggacctgct                19

<210> SEQ ID NO 169
<211> LENGTH: 20
<212> TYPE: DNA
<213> ORGANISM: Artificial Sequence
<220> FEATURE:
<223> OTHER INFORMATION: shRNA-6 effector species 5

<400> SEQUENCE: 169
ttcttctagg ggacctgctt                20

<210> SEQ ID NO 170
<211> LENGTH: 21
<212> TYPE: DNA
<213> ORGANISM: Artificial Sequence
<220> FEATURE:
<223> OTHER INFORMATION: shRNA-6 effector species 6

<400> SEQUENCE: 170
ttcttctagg ggacctgctt t                                              21

<210> SEQ ID NO 171
<211> LENGTH: 18
<212> TYPE: DNA
<213> ORGANISM: Artificial Sequence
<220> FEATURE:
<223> OTHER INFORMATION: shRNA-6 effector species 7

<400> SEQUENCE: 171
cttcttctag gggacctg                                                  18

<210> SEQ ID NO 172
<211> LENGTH: 19
<212> TYPE: DNA
<213> ORGANISM: Artificial Sequence
<220> FEATURE:
<223> OTHER INFORMATION: shRNA-6 effector species 8

<400> SEQUENCE: 172
cttcttctag gggacctgc                                                 19

<210> SEQ ID NO 173
<211> LENGTH: 20
<212> TYPE: DNA
<213> ORGANISM: Artificial Sequence
<220> FEATURE:
<223> OTHER INFORMATION: shRNA-6 effector species 9

<400> SEQUENCE: 173
cttcttctag gggacctgct                                                20

<210> SEQ ID NO 174
<211> LENGTH: 21
<212> TYPE: DNA
<213> ORGANISM: Artificial Sequence
<220> FEATURE:
<223> OTHER INFORMATION: shRNA-6 effector species 10

<400> SEQUENCE: 174
cttcttctag gggacctgct t                                              21

<210> SEQ ID NO 175
<211> LENGTH: 22
<212> TYPE: DNA
<213> ORGANISM: Artificial Sequence
<220> FEATURE:
<223> OTHER INFORMATION: shRNA-6 effector species 11

<400> SEQUENCE: 175
cttcttctag gggacctgct tt                                             22

<210> SEQ ID NO 176
<211> LENGTH: 80
<212> TYPE: DNA
<213> ORGANISM: Artificial Sequence
<220> FEATURE:

<223> OTHER INFORMATION: shmiR-6 DNA sequence with flanking region

<400> SEQUENCE: 176
ttgacagtga gcgacaggtc ccctagaaga agaaactgtg aagcagatgg gtttcttctt    60
ctaggggacc tgccgcctac                                                80

<210> SEQ ID NO 177
<211> LENGTH: 18
<212> TYPE: DNA
<213> ORGANISM: Artificial Sequence
<220> FEATURE:
<223> OTHER INFORMATION: shmiR-6 effector species 1

<400> SEQUENCE: 177
ttcttctagg ggacctgc                                                  18

<210> SEQ ID NO 178
<211> LENGTH: 19
<212> TYPE: DNA
<213> ORGANISM: Artificial Sequence
<220> FEATURE:
<223> OTHER INFORMATION: shmiR-6 effector species 2

<400> SEQUENCE: 178
cttcttctag gggacctgc                                                 19

<210> SEQ ID NO 179
<211> LENGTH: 21
<212> TYPE: DNA
<213> ORGANISM: Artificial Sequence
<220> FEATURE:
<223> OTHER INFORMATION: shmiR-6 effector species 3

<400> SEQUENCE: 179
tttcttcttc tagggggacct g                                             21

<210> SEQ ID NO 180
<211> LENGTH: 22
<212> TYPE: DNA
<213> ORGANISM: Artificial Sequence
<220> FEATURE:
<223> OTHER INFORMATION: shmiR-6 effector species 4

<400> SEQUENCE: 180
tttcttcttc tagggggacct gc                                            22

<210> SEQ ID NO 181
<211> LENGTH: 23
<212> TYPE: DNA
<213> ORGANISM: Artificial Sequence
<220> FEATURE:
<223> OTHER INFORMATION: shmiR-6 effector species 5

<400> SEQUENCE: 181
tttcttcttc tagggggacct gcc                                           23

<210> SEQ ID NO 182
<211> LENGTH: 75
<212> TYPE: DNA
<213> ORGANISM: Artificial Sequence
<220> FEATURE:
<223> OTHER INFORMATION: shRNA-15 DNA sequence plus flanking region

<400> SEQUENCE: 182
gaaaggacga ggatccgcag tggttcgtag ggctttcccc aagagaggga aagccctacg    60
aaccactgtt tttct                                                    75

<210> SEQ ID NO 183
<211> LENGTH: 20
<212> TYPE: DNA
<213> ORGANISM: Artificial Sequence
<220> FEATURE:
<223> OTHER INFORMATION: shRNA-15 effector species 1

<400> SEQUENCE: 183
agccctacga accactgttt                                               20

<210> SEQ ID NO 184
<211> LENGTH: 21
<212> TYPE: DNA
<213> ORGANISM: Artificial Sequence
<220> FEATURE:
<223> OTHER INFORMATION: shRNA-15 effector species 2

<400> SEQUENCE: 184
agccctacga accactgttt t                                             21

<210> SEQ ID NO 185
<211> LENGTH: 19
<212> TYPE: DNA
<213> ORGANISM: Artificial Sequence
<220> FEATURE:
<223> OTHER INFORMATION: shRNA-15 effector species 3

<400> SEQUENCE: 185
aagccctacg aaccactgt                                                19

<210> SEQ ID NO 186
<211> LENGTH: 20
<212> TYPE: DNA
<213> ORGANISM: Artificial Sequence
<220> FEATURE:
<223> OTHER INFORMATION: shRNA-15 effector species 4

<400> SEQUENCE: 186
aagccctacg aaccactgtt                                               20

<210> SEQ ID NO 187
<211> LENGTH: 21
<212> TYPE: DNA
<213> ORGANISM: Artificial Sequence
<220> FEATURE:
<223> OTHER INFORMATION: shRNA-15 effector species 5

<400> SEQUENCE: 187
aagccctacg aaccactgtt t                                             21

<210> SEQ ID NO 188
<211> LENGTH: 22
<212> TYPE: DNA
<213> ORGANISM: Artificial Sequence
<220> FEATURE:
<223> OTHER INFORMATION: shRNA-15 effector species 6

<400> SEQUENCE: 188
aagccctacg aaccactgtt tt                                            22

<210> SEQ ID NO 189
<211> LENGTH: 19
<212> TYPE: DNA

<213> ORGANISM: Artificial Sequence
<220> FEATURE:
<223> OTHER INFORMATION: shRNA-15 effector species 7

<400> SEQUENCE: 189
aaagccctac gaaccactg                                                    19

<210> SEQ ID NO 190
<211> LENGTH: 20
<212> TYPE: DNA
<213> ORGANISM: Artificial Sequence
<220> FEATURE:
<223> OTHER INFORMATION: shRNA-15 effector species 8

<400> SEQUENCE: 190
aaagccctac gaaccactgt                                                   20

<210> SEQ ID NO 191
<211> LENGTH: 21
<212> TYPE: DNA
<213> ORGANISM: Artificial Sequence
<220> FEATURE:
<223> OTHER INFORMATION: shRNA-15 effector species 9

<400> SEQUENCE: 191
aaagccctac gaaccactgt t                                                 21

<210> SEQ ID NO 192
<211> LENGTH: 22
<212> TYPE: DNA
<213> ORGANISM: Artificial Sequence
<220> FEATURE:
<223> OTHER INFORMATION: shRNA-15 effector species 10

<400> SEQUENCE: 192
aaagccctac gaaccactgt tt                                                22

<210> SEQ ID NO 193
<211> LENGTH: 23
<212> TYPE: DNA
<213> ORGANISM: Artificial Sequence
<220> FEATURE:
<223> OTHER INFORMATION: shRNA-15 effector species 11

<400> SEQUENCE: 193
aaagccctac gaaccactgt ttt                                               23

<210> SEQ ID NO 194
<211> LENGTH: 20
<212> TYPE: DNA
<213> ORGANISM: Artificial Sequence
<220> FEATURE:
<223> OTHER INFORMATION: shRNA-15 effector species 12

<400> SEQUENCE: 194
gaaagcccta cgaaccactg                                                   20

<210> SEQ ID NO 195
<211> LENGTH: 21
<212> TYPE: DNA
<213> ORGANISM: Artificial Sequence
<220> FEATURE:
<223> OTHER INFORMATION: shRNA-15 effector species 13

<400> SEQUENCE: 195
gaaagcccta cgaaccactg t                                                 21

<210> SEQ ID NO 196
<211> LENGTH: 22
<212> TYPE: DNA
<213> ORGANISM: Artificial Sequence
<220> FEATURE:
<223> OTHER INFORMATION: shRNA-15 effector species 14

<400> SEQUENCE: 196
gaaagcccta cgaaccactg tt                                          22

<210> SEQ ID NO 197
<211> LENGTH: 23
<212> TYPE: DNA
<213> ORGANISM: Artificial Sequence
<220> FEATURE:
<223> OTHER INFORMATION: shRNA-15 effector species 15

<400> SEQUENCE: 197
gaaagcccta cgaaccactg ttt                                         23

<210> SEQ ID NO 198
<211> LENGTH: 24
<212> TYPE: DNA
<213> ORGANISM: Artificial Sequence
<220> FEATURE:
<223> OTHER INFORMATION: shRNA-15 effector species 16

<400> SEQUENCE: 198
gaaagcccta cgaaccactg tttt                                        24

<210> SEQ ID NO 199
<211> LENGTH: 20
<212> TYPE: DNA
<213> ORGANISM: Artificial Sequence
<220> FEATURE:
<223> OTHER INFORMATION: shRNA-15 effector species 17

<400> SEQUENCE: 199
ggaaagccct acgaaccact                                             20

<210> SEQ ID NO 200
<211> LENGTH: 21
<212> TYPE: DNA
<213> ORGANISM: Artificial Sequence
<220> FEATURE:
<223> OTHER INFORMATION: shRNA-15 effector species 18

<400> SEQUENCE: 200
ggaaagccct acgaaccact g                                           21

<210> SEQ ID NO 201
<211> LENGTH: 22
<212> TYPE: DNA
<213> ORGANISM: Artificial Sequence
<220> FEATURE:
<223> OTHER INFORMATION: shRNA-15 effector species 19

<400> SEQUENCE: 201
ggaaagccct acgaaccact gt                                          22

<210> SEQ ID NO 202
<211> LENGTH: 81
<212> TYPE: DNA
<213> ORGANISM: Artificial Sequence
<220> FEATURE:

<223> OTHER INFORMATION: shmiR-15 DNA sequence plus flanking region

<400> SEQUENCE: 202
gttgacagtg agcgaagtgg ttcgtagggc tttccactgt gaagcagatg ggtggaaagc    60
cctacgaacc actgcgccta c                                              81

<210> SEQ ID NO 203
<211> LENGTH: 20
<212> TYPE: DNA
<213> ORGANISM: Artificial Sequence
<220> FEATURE:
<223> OTHER INFORMATION: shmiR-15 effector species 1

<400> SEQUENCE: 203
gaaagcccta cgaaccactg                                                20

<210> SEQ ID NO 204
<211> LENGTH: 21
<212> TYPE: DNA
<213> ORGANISM: Artificial Sequence
<220> FEATURE:
<223> OTHER INFORMATION: shmiR-15 effector species 2

<400> SEQUENCE: 204
ggaaagccct acgaaccact g                                              21

<210> SEQ ID NO 205
<211> LENGTH: 20
<212> TYPE: DNA
<213> ORGANISM: Artificial Sequence
<220> FEATURE:
<223> OTHER INFORMATION: shmiR-15 effector species 3

<400> SEQUENCE: 205
tggaaagccc tacgaaccac                                                20

<210> SEQ ID NO 206
<211> LENGTH: 21
<212> TYPE: DNA
<213> ORGANISM: Artificial Sequence
<220> FEATURE:
<223> OTHER INFORMATION: shmiR-15 effector species 4

<400> SEQUENCE: 206
tggaaagccc tacgaaccac t                                              21

<210> SEQ ID NO 207
<211> LENGTH: 22
<212> TYPE: DNA
<213> ORGANISM: Artificial Sequence
<220> FEATURE:
<223> OTHER INFORMATION: shmiR-15 effector species 5

<400> SEQUENCE: 207
tggaaagccc tacgaaccac tg                                             22

<210> SEQ ID NO 208
<211> LENGTH: 23
<212> TYPE: DNA
<213> ORGANISM: Artificial Sequence
<220> FEATURE:
<223> OTHER INFORMATION: shmiR-15 effector species 6

<400> SEQUENCE: 208
tggaaagccc tacgaaccac tgc                                            23

<210> SEQ ID NO 209
<211> LENGTH: 69
<212> TYPE: DNA
<213> ORGANISM: Artificial Sequence
<220> FEATURE:
<223> OTHER INFORMATION: shRNA-12 DNA sequence plus flanking region

<400> SEQUENCE: 209
ctcaacggat ccgcgtcccg tcggcgctga atcctgtgct tggattcagc gccgacggga    60
cgttttttc                                                           69

<210> SEQ ID NO 210
<211> LENGTH: 17
<212> TYPE: DNA
<213> ORGANISM: Artificial Sequence
<220> FEATURE:
<223> OTHER INFORMATION: shRNA-12 effector species 1

<400> SEQUENCE: 210
ttcagcgccg acgggac                                                  17

<210> SEQ ID NO 211
<211> LENGTH: 18
<212> TYPE: DNA
<213> ORGANISM: Artificial Sequence
<220> FEATURE:
<223> OTHER INFORMATION: shRNA-12 effector species 2

<400> SEQUENCE: 211
ttcagcgccg acgggacg                                                 18

<210> SEQ ID NO 212
<211> LENGTH: 19
<212> TYPE: DNA
<213> ORGANISM: Artificial Sequence
<220> FEATURE:
<223> OTHER INFORMATION: shRNA-12 effector species 3

<400> SEQUENCE: 212
ttcagcgccg acgggacgt                                                19

<210> SEQ ID NO 213
<211> LENGTH: 20
<212> TYPE: DNA
<213> ORGANISM: Artificial Sequence
<220> FEATURE:
<223> OTHER INFORMATION: shRNA-12 effector species 4

<400> SEQUENCE: 213
ttcagcgccg acgggacgtt                                               20

<210> SEQ ID NO 214
<211> LENGTH: 21
<212> TYPE: DNA
<213> ORGANISM: Artificial Sequence
<220> FEATURE:
<223> OTHER INFORMATION: shRNA-12 effector species 5

<400> SEQUENCE: 214
ttcagcgccg acgggacgtt t                                             21

<210> SEQ ID NO 215
<211> LENGTH: 22
<212> TYPE: DNA

```
<213> ORGANISM: Artificial Sequence
<220> FEATURE:
<223> OTHER INFORMATION: shRNA-12 effector species 6

<400> SEQUENCE: 215
ttcagcgccg acgggacgtt tt                                              22

<210> SEQ ID NO 216
<211> LENGTH: 17
<212> TYPE: DNA
<213> ORGANISM: Artificial Sequence
<220> FEATURE:
<223> OTHER INFORMATION: shRNA-12 effector species 7

<400> SEQUENCE: 216
attcagcgcc gacggga                                                    17

<210> SEQ ID NO 217
<211> LENGTH: 18
<212> TYPE: DNA
<213> ORGANISM: Artificial Sequence
<220> FEATURE:
<223> OTHER INFORMATION: shRNA-12 effector species 8

<400> SEQUENCE: 217
attcagcgcc gacgggac                                                   18

<210> SEQ ID NO 218
<211> LENGTH: 19
<212> TYPE: DNA
<213> ORGANISM: Artificial Sequence
<220> FEATURE:
<223> OTHER INFORMATION: shRNA-12 effector species 9

<400> SEQUENCE: 218
attcagcgcc gacgggacg                                                  19

<210> SEQ ID NO 219
<211> LENGTH: 20
<212> TYPE: DNA
<213> ORGANISM: Artificial Sequence
<220> FEATURE:
<223> OTHER INFORMATION: shRNA-12 effector species 10

<400> SEQUENCE: 219
attcagcgcc gacgggacgt                                                 20

<210> SEQ ID NO 220
<211> LENGTH: 21
<212> TYPE: DNA
<213> ORGANISM: Artificial Sequence
<220> FEATURE:
<223> OTHER INFORMATION: shRNA-12 effector species 11

<400> SEQUENCE: 220
attcagcgcc gacgggacgt t                                               21

<210> SEQ ID NO 221
<211> LENGTH: 22
<212> TYPE: DNA
<213> ORGANISM: Artificial Sequence
<220> FEATURE:
<223> OTHER INFORMATION: shRNA-12 effector species 12

<400> SEQUENCE: 221
attcagcgcc gacgggacgt tt                                              22
```

```
<210> SEQ ID NO 222
<211> LENGTH: 23
<212> TYPE: DNA
<213> ORGANISM: Artificial Sequence
<220> FEATURE:
<223> OTHER INFORMATION: shRNA-12 effector species 13

<400> SEQUENCE: 222
attcagcgcc gacgggacgt ttt                                           23

<210> SEQ ID NO 223
<211> LENGTH: 24
<212> TYPE: DNA
<213> ORGANISM: Artificial Sequence
<220> FEATURE:
<223> OTHER INFORMATION: shRNA-12 effector species 14

<400> SEQUENCE: 223
tggattcagc gccgacggga cgtt                                          24

<210> SEQ ID NO 224
<211> LENGTH: 75
<212> TYPE: DNA
<213> ORGANISM: Artificial Sequence
<220> FEATURE:
<223> OTHER INFORMATION: shmiR-12 DNA sequence plus flanking region

<400> SEQUENCE: 224
acagtgagcg agtcccgtcg gcgctgaatc cactgtgaag cagatgggtg gattcagcgc   60
cgacgggacg cgcct                                                    75

<210> SEQ ID NO 225
<211> LENGTH: 18
<212> TYPE: DNA
<213> ORGANISM: Artificial Sequence
<220> FEATURE:
<223> OTHER INFORMATION: shmiR-12 effector species 1

<400> SEQUENCE: 225
tggattcagc gccgacgg                                                 18

<210> SEQ ID NO 226
<211> LENGTH: 20
<212> TYPE: DNA
<213> ORGANISM: Artificial Sequence
<220> FEATURE:
<223> OTHER INFORMATION: shmiR-12 effector species 2

<400> SEQUENCE: 226
tggattcagc gccgacggga                                               20

<210> SEQ ID NO 227
<211> LENGTH: 21
<212> TYPE: DNA
<213> ORGANISM: Artificial Sequence
<220> FEATURE:
<223> OTHER INFORMATION: shmiR-12 effector species 3

<400> SEQUENCE: 227
tggattcagc gccgacggga c                                             21

<210> SEQ ID NO 228
<211> LENGTH: 22
<212> TYPE: DNA
```

```
<213> ORGANISM: Artificial Sequence
<220> FEATURE:
<223> OTHER INFORMATION: shmiR-12 effector species 4

<400> SEQUENCE: 228
tggattcagc gccgacggga cg                                        22

<210> SEQ ID NO 229
<211> LENGTH: 23
<212> TYPE: DNA
<213> ORGANISM: Artificial Sequence
<220> FEATURE:
<223> OTHER INFORMATION: shmiR-12 effector species 5

<400> SEQUENCE: 229
tggattcagc gccgacggga cgc                                       23

<210> SEQ ID NO 230
<211> LENGTH: 20
<212> TYPE: DNA
<213> ORGANISM: Artificial Sequence
<220> FEATURE:
<223> OTHER INFORMATION: HBsAg_fwd

<400> SEQUENCE: 230
atgttgcccg tttgtcctct                                           20

<210> SEQ ID NO 231
<211> LENGTH: 20
<212> TYPE: DNA
<213> ORGANISM: Artificial Sequence
<220> FEATURE:
<223> OTHER INFORMATION: ccgtccgaaggtttggtaca

<400> SEQUENCE: 231
ccgtccgaag gtttggtaca                                           20

<210> SEQ ID NO 232
<211> LENGTH: 20
<212> TYPE: DNA
<213> ORGANISM: Artificial Sequence
<220> FEATURE:
<223> OTHER INFORMATION: HBxAg_fwd

<400> SEQUENCE: 232
cgtcctttgt ttacgtcccg                                           20

<210> SEQ ID NO 233
<211> LENGTH: 20
<212> TYPE: DNA
<213> ORGANISM: Artificial Sequence
<220> FEATURE:
<223> OTHER INFORMATION: HBxAg_rev

<400> SEQUENCE: 233
agtccgcgta aagagaggtg                                           20

<210> SEQ ID NO 234
<211> LENGTH: 20
<212> TYPE: DNA
<213> ORGANISM: Artificial Sequence
<220> FEATURE:
<223> OTHER INFORMATION: HBcAg_fwd

<400> SEQUENCE: 234
ccaccaaatg cccctatcct                                           20
```

```
<210> SEQ ID NO 235
<211> LENGTH: 20
<212> TYPE: DNA
<213> ORGANISM: Artificial Sequence
<220> FEATURE:
<223> OTHER INFORMATION: HBcAg_rev

<400> SEQUENCE: 235
attgagacct tcgtctgcga                                                   20

<210> SEQ ID NO 236
<211> LENGTH: 20
<212> TYPE: DNA
<213> ORGANISM: Artificial Sequence
<220> FEATURE:
<223> OTHER INFORMATION: GAPDH_fwd

<400> SEQUENCE: 236
acaccatggg gaaggtgaag                                                   20

<210> SEQ ID NO 237
<211> LENGTH: 18
<212> TYPE: DNA
<213> ORGANISM: Artificial Sequence
<220> FEATURE:
<223> OTHER INFORMATION: GAPDH_rev

<400> SEQUENCE: 237
gtgaccaggc gcccaata                                                     18
```